US011971411B2

(12) United States Patent
Huttenhower et al.

(10) Patent No.: US 11,971,411 B2
(45) Date of Patent: Apr. 30, 2024

(54) COMPOSITIONS AND METHODS FOR SCREENING AND IDENTIFYING CLINICALLY AGGRESSIVE PROSTATE CANCER

(71) Applicants: DANA-FARBER CANCER INSTITUTE, INC., Boston, MA (US); PRESIDENT AND FELLOWS OF HARVARD COLLEGE, Cambridge, MA (US)

(72) Inventors: Curtis Huttenhower, Boston, MA (US); Travis Gerke, Tampa, FL (US); Christopher Sweeney, Waban, MA (US); Lorelei Mucci, Newton, MA (US); Gwo-Sho Mary Lee, Newton, MA (US); Daniela Bornigen, Tostedt (DE); Xiaodong Wang, Stoughton, MA (US); Svitlana Tyekucheva, Boston, MA (US); Kristina Jordahl, Seattle, WA (US)

(73) Assignees: DANA-FARBER CANCER INSTITUTE, INC., Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 434 days.

(21) Appl. No.: 16/071,289

(22) PCT Filed: Jan. 20, 2017

(86) PCT No.: PCT/US2017/014362
§ 371 (c)(1),
(2) Date: Jul. 19, 2018

(87) PCT Pub. No.: WO2017/127696
PCT Pub. Date: Jul. 27, 2017

(65) Prior Publication Data

US 2020/0041515 A1 Feb. 6, 2020

Related U.S. Application Data

(60) Provisional application No. 62/280,994, filed on Jan. 20, 2016.

(51) Int. Cl.
*C12Q 1/68* (2018.01)
*G01N 33/574* (2006.01)

(52) U.S. Cl.
CPC .................. *G01N 33/57434* (2013.01); *G01N 2333/4703* (2013.01); *G01N 2800/54* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 2009/0170715 | A1 | 7/2009 | Glinsky | |
| 2010/0055705 | A1* | 3/2010 | Wilson | G01N 33/57484 435/6.14 |
| 2012/0028264 | A1* | 2/2012 | Shak | C12Q 1/6886 435/6.1 |
| 2014/0303002 | A1* | 10/2014 | Shak | G16B 25/00 506/2 |
| 2015/0159161 | A1 | 6/2015 | Krieg et al. | |
| 2015/0247208 | A1* | 9/2015 | Stone | C12Q 1/6886 506/9 |
| 2016/0312294 | A1* | 10/2016 | Walker | C07K 16/18 |

FOREIGN PATENT DOCUMENTS

| | | | | |
|---|---|---|---|---|
| WO | WO-2012058689 A2 * | 5/2012 | | C12Q 1/6883 |
| WO | WO 2015/087088 A2 | 6/2015 | | |

OTHER PUBLICATIONS

Dhanasekaran et al. Delineation of prognostic biomarkersin prostate cancer. Nature ;2001;412:822-826. (Year: 2001).*
Glinsky et al.Gene expression profiling predicts clinical outcome of prostate cancer. J Clin Invest.; 2004; 113(6):913-923. (Year: 2004).*
Zhu et al. Prognostic value of ZFP36 and SOCS3 expressions in human prostate cancer. Clin Transl Oncol; 2016 ; 18:782-791(online Nov. 2015). (Year: 2016).*
Taylor et al. A Pathogenetic Role for TNFa in the Syndrome of Cachexia, Arthritis, and Autoimmunity Resulting from Tristetraprolin (TTP) Deficiency. Immunity, 1996; 4: 445-454. (Year: 1996).*
Guo et al. Post-transcriptional regulatory network of epithelial-to-mesenchymal and mesenchymal-to-epithelial transitions. Journal of Hematology & Oncology; 2014; 7: 1-19. (Year: 2014).*
Glinsky et al. J Clin Invest.; 2004; 113(6):913-923. (Year: 2004).*
Zhu et al. Clin Transl Oncol; 2016 (online Nov. 2015); 18:782-791. (Year: 2015).*
Glinsky, et al. "Gene expression profiling predicts clinical outcome of prostate cancer", Journal of Clinical Investigation, BMJ Group, GB, vol. 113, No. 6, Mar. 1, 2004.
Zhu, et al., "Prognostic value of ZFP36 and SOCS3 expressions in human prostate cancer", clinical and Translational Oncology, Springer Italia SRL, Italy, Spain, vol. 18, No. 8, Nov. 13, 2015.

(Continued)

*Primary Examiner* — Jehanne S Sitton
(74) *Attorney, Agent, or Firm* — Mueting Raasch Group

(57) ABSTRACT

The present invention provides methods for screening and diagnosing prostate cancer based on a correlation between cancer cell growth, cancer lethality or recurrence and the expression level of ZFP36 or NEDD9 and PTEN in conjunction with ZFP36. The disclosure also provides methods for screening and diagnosing prostate cancer based on a correlation between cancer lethality and the genotype of rs1910301 SNP. Also provided are methods for treating prostate cancer comprising providing a treatment or monitoring based on the expression level of ZFP36, the expression level of NEDD9, and the expression level of ZFP36 in conjunction with PTEN levels or the genotype of rs1910301 SNP.

12 Claims, 18 Drawing Sheets

Specification includes a Sequence Listing.

(56) References Cited

OTHER PUBLICATIONS

Chandran, et al., "Gene expression profiles of prostate cancer reveal involvement of multiple molecular pathways in the metastatic process", BMC Cancer, Biomed Central, London, GB, vol. 7, No. 1, Apr. 12, 2007.

Supplementary European Search Report dated Aug. 9, 2019 in related European Application No. 17742021.3 (11 pages).

International Search Report with Written Opinion from PCT/US17/14362 dated May 23, 2017.

Barret et al. (2009) "NCBI GEO: archive for high-throughput functional genomic data," Nucleic Acids Res. (Database issue):D885-90.

Breitkreutz et al. (2008) "The BioGRID Interaction Database: 2008 update," Nucleic Acids Res. (Database issue):D637-40.

Griffiths-Jones (2006) "miRBase: the microRNA sequence database," Methods Mol Biol.342:129-38.

Jia et al. (2011) "dmGWAS: dense module searching for genome-wide association studies in protein-protein interaction networks," Bioinformatics. Jan. 1, 2011;27(1):95-102.

Kerrian et al. (2007) "IntAct—open source resource for molecular interaction data," Nucleic Acids Res.35 (Database issue):D561-5.

Matys et al. (2006) "TRANSFAC and its module TRANSCompel: transcriptional gene regulation in eukaryotes," Nucleic Acids Res. 34(Database issue):D108-10.

Parkinson et al. (2009) "ArrayExpress update—from an archive of functional genomics experiments to the atlas of gene expression," Nucleic Acids Res. 37(Database issue):D868-72.

Robertson et al. (2006) "cisRED: a database system for genome-scale computational discovery of regulatory elements," Nucleic Acids Res. 34(Database issue):D68-73.

Sboner et al. (2010) "Molecular sampling of prostate cancer: a dilemma for predicting disease progression," BMC Med Genomics. 3:8.

Setlur et al. (2008) "Estrogen-dependent signaling in a molecularly distinct subclass of aggressive prostate cancer," J Natl Cancer Inst. 100(11):815-25.

Pallares et al, "Immunohistochemical analysis of PTEN in endometrial carcinoma: a tissue microarray study with a comparison of four commercial antibodies in correlation with molecular abnormalities", *Modern Pathology*, 18:719-727, 2005.

Ausubel et al., *Current Protocols in Molecular Biology*, John Wiley & Sons, Inc. (2003). Cover page, Forward, Editors, and table of contents (32 pages).

D. N. Glover; *DNA Cloning: A Practical Approach, vol. I*, IRL Press: United Kingdom, GB (1985). Cover page, back cover, Abstract, and table of contents (5 pages).

D. N. Glover; *DNA Cloning: A Practical Approach, vol. II*, IRL Press: United Kingdom, GB (1985). Cover page and book review summary (2 pages).

R. I. Freshney, *Animal Cell Culture: A Practical Approach*, IRL Press: United Kingdom, GB (1986). Cover Page and bibliography (2 pages).

D. V. Goeddel; *Methods in Enzymology: Gene Expression Technology (vol.* 185), Academic Press: San Diego, CA (1990). Cover page, title page and table of contents (10 pages).

B. D. Hames and S. J. Higgins, *Transcription and Translation: A Practical Approach*, IRL Press: Michigan (1984). Cover Page and bibliographic information (2 pages).

B. D. Hames and S. J. Higgins, *Nucleic Acid Hybridisation: A Practical Approach*, IRL Press: McLean, VA (1985). Cover Page and table of contents (2 pages).

M. J. Gait, *Oligonucleotide Synthesis: A Practical Approach*, IRL Press: United Kingdom, GB (1984). Cover page, table of contents, and back cover (3 pages).

B. V. Perbal, *A Practical Guide to Molecular Cloning*, Wiley: California (1984). Cover page, review, and bibliographic information (3 pages).

Sambrook et al.; *Molecular Cloning: A Laboratory Manual, Second Edition*, Cold Spring Harbor Laboratory Press: New York (1989). Cover page, copyright page, and table of contents (33 pages).

Taylor et al., "Integrative Genomic Profiling of Human Prostate Cancer." *Cancer Cell*. Jul. 13, 2010, 18(1):11-22. 10.1016/j.ccr.2010.05.026.

Woodward, *Immobilized Cells and Enzymes: A Practical Approach*, IRL Press: United Kingdom, GB (1986). Cover page and table of contents (3 pages).

* cited by examiner

Positive Regulation
of NFkB

Gene: ZFP36
log2(RPKM+1) - scaled to mean
4
2
0
-2
-4
-6
log2(RPKM+1)
10
8
6
4
2
PCa
CRPC
NEPC

SEQUENCE LISTING

<160> NUMBER OF SEQ ID NOS: 17

<210> SEQ ID NO 1
<211> LENGTH: 2566
<212> TYPE: DNA
<213> ORGANISM: Homo sapiens

<400> SEQUENCE: 1

```
agcctgactt cagcgctccc actctcggcc gacacccctc atggccaacc gttacaccat     60
ggatctgact gccatctacg aggtgagtcc ccgccgcacg gcatccccgg tacctgcatg    120
cctgagtccg agtccccacc tctctagcgc cgcaaactcc agcccgggac gcttgcctcc    180
cttctccaac tggggctccc tagcgccgcg ccctccagcc tggggcccct gcctcccgct    240
cagaccagct tggtgatttg gaggtgaaaa tggaacccgc gacacccggc tcttcgctca    300
aacatgggtg gggcggccca tgcaagtgga aagtcggaga acttttctca gaccgaggct    360
gcctggaggc ggaagtggcc cccatacctg gctcacccct agtcgttgct gagggcgtgg    420
ttttgcgcgg aggcgtctct ggggctgaag tctcagggtg gggggatccg acttctgtct    480
ctccagtccc tgaccgtaga gacagagaac cctaaaaccg aagcaatccg gacttccagg    540
tcaactttgc ccggtttctc cagttgtgaa actggagatc ccgacgcgtg ggtcatatcc    600
ggggaggaca agagacccaa aattgggaaa cagtggtgcg ccctgacttc ggggtccccc    660
tcttggtcca gccggggaag ccgggattcc tgggtccctc gggataaggc ctcggtggtg    720
ggtaaactca gaacctccaa ctctgggttc ctggcatccg gaacccaggg gtttctgcgg    780
gcgggtgggg ctcaggcggg gagcccacaa accggcctgg caagctctag ttccctgcag    840
ctggggtggg gcgtcgccct gcattttcag gtgccttaac cgacccattt ccgcagagcc    900
tcctgtcgct gagccctgac gtgcccgtgc catccgacca tggagggact gagtccagcc    960
caggctgggg ctcctcggga ccctggagcc tgagcccctc cgactccagc ccgtctgggg   1020
```

```
tcacctcccg cctgcctggc cgctccacca gcctagtgga gggccgcagc tgtggctggg   1080
tgcccccacc ccctggcttc gcaccgctgg ctccccgcct gggccctgag ctgtcaccct   1140
cacccacttc gcccactgca acctccacca ccccctcgcg ctacaagact gagctatgtc   1200
ggaccttctc agagagtggg cgctgccgct acggggccaa gtgccagttt gcccatggcc   1260
tgggcgagct gcgccaggcc aatcgccacc ccaaatacaa gacggaactc tgtcacaagt   1320
tctacctcca gggccgctgc ccctacggct ctcgctgcca cttcatccac aaccctagcg   1380
aagacctggc ggccccgggc caccctcctg tgcttcgcca gagcatcagc ttctccggcc   1440
tgccctctgg ccgccggacc tcaccaccac caccaggcct ggccggccct tccctgtcct   1500
ccagctcctt ctcgccctcc agctccccac caccacctgg ggaccttcca ctgtcaccct   1560
ctgccttctc tgctgcccct ggcacccccc tggctcgaag agaccccacc ccagtctgtt   1620
gcccctcctg ccgaagggcc actcctatca gcgtctgggg gcccttgggt ggcctggttc   1680
ggacccccte tgtacagtcc ctgggatccg accctgatga atatgccagc agcggcagca   1740
gcctgggggg ctctgactct cccgtcttcg aggcgggagt tttgcacca ccccagcccg   1800
tggcagcccc ccggcgactc cccatcttca atcgcatctc tgtttctgag tgacaaagtg   1860
actgcccggt cagatcagct ggatctcagc ggggagccac gtctcttgca ctgtggtctc   1920
tgcatggacc ccagggctgt ggggacttgg gggacagtaa tcaagtaatc cccttttcca   1980
gaatgcatta acccactccc ctgacctcac gctggggcag gtccccaagt gtgcaagctc   2040
agtattcatg atggtggggg atggagtgtc ttccgaggtt cttgggggaa aaaaaattgt   2100
agcatattta agggaggcaa tgaaccctct cccccacctc ttccctgccc aaatctgtct   2160
cctagaatct tatgtgctgt gaataatagg ccttcactgc cctccagtt tttatagacc   2220
tgaggttcca gtgtctcctg gtaactggaa cctctcctga gggggaatcc tggtgctcaa   2280
attaccctcc aaaagcaagt agccaaagcc gttgccaaac cccacccata aatcaatggg   2340
ccctttattt atgacgactt tatttattct aatatgattt tatagtattt atatatattg   2400
ggtcgtctgc ttcccttgta tttttcttcc tttttttgta atattgaaaa cgacgatata   2460
attattataa gtagactata atatatttag taatatatat tattacctta aaagtctatt   2520
tttgtgtttt gggcattttt aaataaacaa tctgagtgta agctgg                  2566
```

```
<210> SEQ ID NO 2
<211> LENGTH: 1752
<212> TYPE: DNA
<213> ORGANISM: Homo sapiens

<400> SEQUENCE: 2

agcctgactt cagcgctccc actctcggcc gacacccctc atggccaacc gttacaccat     60
ggatctgact gccatctacg agagcctcct gtcgctgagc cctgacgtgc ccgtgccatc    120
cgaccatgga gggactgagt ccagcccagg ctggggctcc tcgggaccct ggagcctgag    180
cccctccgac tccagcccgt ctggggtcac ctcccgcctg cctggccgct ccaccagcct    240
agtggagggc cgcagctgtg gctgggtgcc cccacccct ggcttcgcac cgctggctcc    300
ccgcctgggc cctgagctgt caccctcacc cacttcgccc actgcaacct ccaccacccc    360
ctcgcgctac aagactgagc tatgtcggac cttctcagag agtgggcgct gccgctacgg    420
ggccaagtgc cagtttgccc atggcctggg cgagctgcgc caggccaatc gccaccccaa    480
atacaagacg gaactctgtc acaagttcta cctccagggc cgctgcccct acggctctcg    540
```

```
ctgccacttc atccacaacc ctagcgaaga cctggcggcc ccgggccacc ctcctgtgct    600

tcgccagagc atcagcttct ccggcctgcc ctctggccgc cggacctcac caccaccacc    660

aggcctggcc ggcccttccc tgtcctccag ctccttctcg ccctccagct ccccaccacc    720

acctggggac cttccactgt caccctctgc cttctctgct gcccctggca ccccccctggc    780

tcgaagagac cccaccccag tctgttgccc ctcctgccga agggccactc ctatcagcgt    840

ctgggggccc ttgggtggcc tggttcggac cccctctgta cagtccctgg gatccgaccc    900

tgatgaatat gccagcagcg gcagcagcct ggggggctct gactctcccg tcttcgaggc    960

gggagttttt gcaccacccc agcccgtggc agcccccccgg cgactcccca tcttcaatcg   1020

catctctgtt tctgagtgac aaagtgactg cccggtcaga tcagctggat ctcagcgggg   1080

agccacgtct cttgcactgt ggtctctgca tggaccccag ggctgtgggg acttggggga   1140

cagtaatcaa gtaatcccct tttccagaat gcattaaccc actcccctga cctcacgctg   1200

gggcaggtcc ccaagtgtgc aagctcagta ttcatgatgg tgggggatgg agtgtcttcc   1260

gaggttcttg gggaaaaaaa aattgtagca tatttaaggg aggcaatgaa ccctctcccc   1320

cacctcttcc ctgcccaaat ctgtctccta gaatcttatg tgctgtgaat aataggcctt   1380

cactgcccct ccagttttta tagacctgag gttccagtgt ctcctggtaa ctggaacctc   1440

tcctgagggg gaatcctggt gctcaaatta ccctccaaaa gcaagtagcc aaagccgttg   1500

ccaaacccca cccataaatc aatgggccct ttatttatga cgactttatt tattctaata   1560

tgattttata gtatttatat atattgggtc gtctgcttcc cttgtatttt tcttcctttt   1620

tttgtaatat tgaaaacgac gatataatta ttataagtag actataatat atttagtaat   1680

atatattatt accttaaaag tctatttttg tgttttgggc atttttaaat aaacaatctg   1740

agtgtaagct gg                                                        1752
```

<210> SEQ ID NO 3
<211> LENGTH: 332
<212> TYPE: PRT
<213> ORGANISM: Homo sapiens

<400> SEQUENCE: 3

```
Met Ala Asn Arg Tyr Thr Met Asp Leu Thr Ala Ile Tyr Glu Ser Leu
1               5                   10                  15

Leu Ser Leu Ser Pro Asp Val Pro Val Pro Ser Asp His Gly Gly Thr
            20                  25                  30

Glu Ser Ser Pro Gly Trp Gly Ser Ser Gly Pro Trp Ser Leu Ser Pro
        35                  40                  45

Ser Asp Ser Ser Pro Ser Gly Val Thr Ser Arg Leu Pro Gly Arg Ser
    50                  55                  60

Thr Ser Leu Val Glu Gly Arg Ser Cys Gly Trp Val Pro Pro Pro Pro
65                  70                  75                  80

Gly Phe Ala Pro Leu Ala Pro Arg Leu Gly Pro Glu Leu Ser Pro Ser
                85                  90                  95

Pro Thr Ser Pro Thr Ala Thr Ser Thr Thr Pro Ser Arg Tyr Lys Thr
            100                 105                 110

Glu Leu Cys Arg Thr Phe Ser Glu Ser Gly Arg Cys Arg Tyr Gly Ala
        115                 120                 125

Lys Cys Gln Phe Ala His Gly Leu Gly Glu Leu Arg Gln Ala Asn Arg
    130                 135                 140

His Pro Lys Tyr Lys Thr Glu Leu Cys His Lys Phe Tyr Leu Gln Gly
145                 150                 155                 160
```

```
Arg Cys Pro Tyr Gly Ser Arg Cys His Phe Ile His Asn Pro Ser Glu
                165                 170                 175

Asp Leu Ala Ala Pro Gly His Pro Pro Val Leu Arg Gln Ser Ile Ser
            180                 185                 190

Phe Ser Gly Leu Pro Ser Gly Arg Arg Thr Ser Pro Pro Pro Pro Gly
        195                 200                 205

Leu Ala Gly Pro Ser Leu Ser Ser Ser Ser Phe Ser Pro Ser Ser Ser
    210                 215                 220

Pro Pro Pro Pro Gly Asp Leu Pro Leu Ser Pro Ser Ala Phe Ser Ala
225                 230                 235                 240

Ala Pro Gly Thr Pro Leu Ala Arg Arg Asp Pro Thr Pro Val Cys Cys
                245                 250                 255

Pro Ser Cys Arg Arg Ala Thr Pro Ile Ser Val Trp Gly Pro Leu Gly
            260                 265                 270

Gly Leu Val Arg Thr Pro Ser Val Gln Ser Leu Gly Ser Asp Pro Asp
        275                 280                 285

Glu Tyr Ala Ser Ser Gly Ser Ser Leu Gly Gly Ser Asp Ser Pro Val
    290                 295                 300

Phe Glu Ala Gly Val Phe Ala Pro Pro Gln Pro Val Ala Ala Pro Arg
305                 310                 315                 320

Arg Leu Pro Ile Phe Asn Arg Ile Ser Val Ser Glu
                325                 330


<210> SEQ ID NO 4
<211> LENGTH: 199051
<212> TYPE: DNA
<213> ORGANISM: Homo sapiens

<400> SEQUENCE: 4

acacatacat atgccactca catccgacgt gtgtggttgc tcagtaggga aatgcttaca      60

gctgcctcta gaagcaagtc cgctcgctgc atggagaggg aaacatgagc atgcagcagg     120

actagctgtc acctcccgcc cgcctgccca gagagggcca gagcgtcggg gaggcaagat     180

gatccaccag cggttccatc ctacacttgg gtgagttctc agccacttgc tgtggcctgt     240

gggagaggag ggactcattc aggctcctac ttcctgagtt ggtgccagac atctggtggt     300

gtttccccac tgtgaacact cctcaactgg ggcagggagg acctccacat gccccagaag     360

aggaatgagt gactcccggt ctccaagttg acctggaggt gctggtttta gtgcaacatt     420

caaaccagca tgatttctac ttatgaaatt gttctgggta gatgcttcct ggtgtgtaag     480

tacatggccc ctcccctctt cctactgtcg tcagagagct tacctgacag caactaagct     540

tttatttttc ctgaattatt tcagtacttc aaagtgtggg ccgtcactta ttctttatgg     600

tggattagaa tcatttacgt ccttttcagc ctctttggac atgagtcctg actggcgaga     660

aatggtgact gaggattgga ttctgtgcgt gtcctatccc tgtagtcatt aggatcatct     720

ccaaggggct gaggacaagt gacagcacac tgtgttctcc ctgtccatag tgagccgccc     780

aagagctcca cccttacttt tctctatgtt tattctttca cttagcccat tcattcattt     840

cttccttcat tcattcattc aattgccttt cttccaccaa ggacttgagg caaatttttt     900

atcttgctga aattttttca aaatgaagac catctgtaat cataaagggg acaatcgttc     960

tgaaagggtt atacataatt ctaagctatg cagagatcgg ccaccaatct tttccctttg    1020

cttgtgttga gaagtgagag taggcgctct agtcatttaa actcctgcat ggggagtccc    1080

tccttcccct gcccagaagc tggtttccca cccagcatgg ggtgtgaaga gcaattgtcc    1140
```

```
atgacagaat actgggaatc tgccaaatag ttttcttctt tgtttctgtt ttcttccaag   1200
cttggttact ttcgaggaca ttcctggttc taagaatgcg gaaagtggag ttggtggaaa   1260
agaaaggatg tgaaatcagt gtttagctag cgctccacca tttcttgtta atcggttagt   1320
ttatttaaca gctatttagt ggctgtcact ttgtacgtca ccacttaaac aagatagctg   1380
ggcacggtgg tgtatgccta tagtcccggc tatgcaggag gctaaggcgg gaggattgct   1440
ggagcccagg aggtcgaggc tgcagtgagc tatgattgca ccactgcact gcagcttggg   1500
tgacagagtg agatcctgtc tcaagaagaa gaagaagaag aagaagaaga cgatgactag   1560
gaagatataa aagcagaggt gtaggagagg acaggctgta agggtcacat gatgtaattc   1620
ccggtgcctc ttcctctaca cgtaaataag ggaaaagagc tatcttgaat ggctgtggta   1680
aggattagat tgaatagcaa acatttaagc atctggcaga gaaggggtat ccgaagtagt   1740
cagtgtcctg cctccctcct ccaggcctca ctgtgactga gctggctgct gacaacctga   1800
gtctttatct catgacctga gagctttctc caagccacac agggacaact gtaattgccc   1860
aaagggcaga cgaaaattcc cagaaatgaa ctcctcaaag gctgtaaata ttccagctcc   1920
ctcagtcttg agtggaataa tctacacgga atcaagctcc agttgcccac agtggcgggg   1980
cccttcatgg cttctctcct tccctggata ctccttcact ccccatcaat gcttcctggg   2040
atcatttctt aaactacatg tcctcgaact ctgcattggg gtctacttct gggggaaccc   2100
aagctaagac caccggccac ctactactgt aggtacttaa agagtttagt cgtctgtttt   2160
ccaatgatca gctccatctc catttgacct tagactctga gttttgattt cccacatatc   2220
cattcaaggg ttgtagtggg ggaagatcct cctcctcctc ttctggattt ggcttggaga   2280
aagggcacag gcacagcatg gagagcacct taggcttgac atgtctccat gcaaacccgc   2340
acagcacgaa gatgcgtcct actgcaaatg accttcactt tgtcctgctt atctgtcacc   2400
ttcacaactc atttgatgaa aatttctgaa gtgtggaaca caaataggag aattttatat   2460
agcacaagat acatagatag agcatgaaat cacattgaac ctgatcttaa agctactcta   2520
actcttggct ccttactgtt ttaacaagag aaagtcgatc tgaggctagg agccatcaac   2580
aggcactggt agctagctac aaattaatag catggcttta ttttcctgta tttgcttttt   2640
atggttacct tatattaaac cacaacggcc tgttttttttt ttaatttgta ggaatggtat   2700
aaacatttct tttaaaatat aaatctttaa gttttaaaaa agtgaattta ttattactat   2760
tattattttt gagacaaagt ctcactctgt cacccaggct agagtgcagt gtggctcact   2820
gcaacttctg cctcccaggt tcaagtgatt ctcttgcctc agcctcccaa gtagctggga   2880
ttgcaggtgc ccaccatcac acctggctaa tttttgtgtt tttagtagag atggggtttc   2940
accatgttgg ccaagctggt ctcgaactcc tgacctcagg tgacccgccc accttagcct   3000
cccaaagtgc tgggattaca ggcatgagcc actgcgcccg gcccaaaagt gagttaattt   3060
aaagaaaaaa acgttgctga cagtcctgac agcacacaga atatggcaaa ccctggaaaa   3120
tggggtttga ttaagagaag actaggaaag ccccactaga acgcaggctc ctcaagggca   3180
tggctgcatc tcccagtgcc ttccacccag ggcctgcctg gcctgtgcca ctgggctgga   3240
attgtatgga ttttggatat cccaggaagc aggggtccaa gctgcccttg ttagctacag   3300
gctttttttgg tcttcaaaat atacaacttc actttgccca cagtggctcc caaacgtccc   3360
agcagtgatg cagggtagta tagacaccta aaaatgggta caacacaagc tccattgtat   3420
ggtagttcca ccctaagtaa gaatccatga ggctccgatg taactcagca atgtgagctg   3480
```

```
aggggacggg tggaggtatt tcttcatctg cattcctttt cacttttgct tcagattaga   3540
agctctggtt cgtgaaggtc tgtaattcac ttaactagag gtcaatgaat gataaatttt   3600
tttgaacagc tacaaaaccc tctactttcc aaggaaagtg atacatgagg gtgaataatt   3660
tagataaatt tagcttgaaa aaatttttaa atattgtaac attttatact acaaaaaagt   3720
atatataagg tatccatata ttctaaataa tcataggaat aaaaacataa atacacatcc   3780
acctgttacc ccactaccca accctgaaag cctgctgtgt gcccctaaac aattgtatcc   3840
ttctctccca atgcccactg ggttggtcta tgtttgtgtg gctataaata cctgaggctg   3900
ggtaatctgc aaagaaaaaa ggtttaattg gctcatggtt ctgcaggctg tataggaagc   3960
atggtgctgg catctgcttc tggtgaggcc tctggaagct tacagtcatg gtgaaagatg   4020
aagggggagc cagcatcaca tggcaagagt gggagcaaga aagctgggag gtgccacact   4080
cttttaaaca atcagatctt ttttttgaga cagaatctca ctctgtcacc caggctggag   4140
tgcagtggtg caatcttggc ttgccgcaac ctccacttcc tgggttcaag tgattctcct   4200
gcctcagcct cctgagtagc tgggattaca cgtgcatgcc accacaccca gcaaaatttt   4260
gtatttttag cagagatgga gttttgtcat gttggccagg ctggtcttga gctcctgacc   4320
tcaggtgatc cacccacctc agcctcccaa agtgctgggg ttacaggcat gagccactgc   4380
gcctggccta aacaaccaga tctcatgtaa actaattgaa gaagaactca ctcatcacca   4440
gatagatggt gttaattcat tcataaggga tccacccgca tgctccaata cctcccacta   4500
gatcccacct ccaaaattgg ggatcacatt tcaacatgag acttggaggg gacaaatgtt   4560
taaaccatat cattctgccc ctggcttccc aaatctgatg tccttctcac attgcaaaat   4620
acaatcatct tctcccagta gtctcccgaa gtctgaattg attccagcat caagtacaaa   4680
gtcgtgtctc atctaagact caaatctgtc cacctatgag actctaaagt caaaacaagt   4740
tagttacttc caaggtacaa tgatggtaca gatattgggc aaacattacc attccaaaag   4800
ggagaaattg gccaaaagaa agggtatagg ggccccacac aaatctgaaa cctagcaggg   4860
tagtcattaa atcttaaagg tccaaaatac aatctccttt gactccaagt cctacattta   4920
gggcacactg ttataacagt ggactcctaa ggccttgagc agctctggcc ctgtggcttt   4980
gcaggatgca gcccacatgg ctgctctcat gggtttaagt tgagtgcttg ttgcttttcc   5040
agttaaaggg tgcaagctgc cagtgaatct gctattctgg gttctagagg gtggcagccc   5100
cctttccgca gctccactag gtagtgccct ggtggggact ctgtgtagga gctccaaccc   5160
cacatttccc ctggcatttt cctagtagag tttttctgtg gggcctctgc ctctgcagta   5220
ggcttctgcc tgagcaccca ggctttccca tacatcctct ggaatctagg tggaagccac   5280
caagccttct tcacacttgc gttctgagca tctgcagact taaccccatg tggcaatcac   5340
caaggcttat ggcttgtgtc ctccagaact gtggccagag ctgtacctgg gccccttga    5400
gctgaggctg aagccagagt ctgaagctca gcagggcagt agggccctgg gcctggcccc   5460
tgaaaccatt cttttctcct aagcctctgg gcctttgatg ggaggggctg tcctcaagat   5520
ttttgaaatg cctttggagg gtttttgcct tgtcttggat attggcttcc ttttagttat   5580
gctcatctct ctagcaagtg aatgtttcac aacctgcttg gattctttct ctaccacaga   5640
gccaggctgc aaattttaca aacttttaca ctctgtttcc cttttaaata taaatttcaa   5700
tgttaagtca cttctttgct cccatatctg atttaggttg ctggaagtag ccaagtcacc   5760
tcttgaatgc tttgctgctt agaaatttcc tctactaggt agcctgggtc atcactctta   5820
agttcaaact tccacagatc cctagagcat acagtgcaac caagttcttt gttagggcat   5880
```

```
aataagaatg accccattcc atttcccaaa aactttctca tttccatctg agacctcatc   5940
agccagaact tcactgtcca tatctgtatc agtattttgg tcacaaccat ttaaccagtc   6000
tctaagaagt tccaaacttt ccctcatctt cctgtctttt tctgagtcct ttaaactctt   6060
ccagcctctc ccttaccccg ttccaaagtc acttccacat tttcagttat ctttatagca   6120
atgctccact tctcagtacc aattttcaat tttctgtgtt agtccgtttt gcatcactat   6180
aaagaaatac ccaaggctgg gtaatttata aagaaaaaaa gtggggaccg ggcacggtgg   6240
ctcacgccag taatcccagc actttgggag gccgagacgg gcggatcacg aggtcaggag   6300
atcgagacca ccctggctaa cacagtgaaa gcccgtctct actaaaaata caaaaaatta   6360
gctgggtgtg gtgacgggcg cctgtagtcc cagctactca ggaggctaag gcaggagaat   6420
ggcatgaacc cgggaggcgg agcttgcagt gagccgagat cacgccactg cactccagcc   6480
tgagtgatag agtgagactc cgtctcaaaa aaaagaaaga aaaaagaaaa aagggttgat   6540
tgacttatgg ttctgcaggg tatacagaaa gcatggtgct ggcatctgct tcgggtgagg   6600
cctcaggaag gttacaatca tggcggaagg aggagccagc atatgacatg gcaagagaga   6660
gagaaaagga cagaagggag aggtcccaga gtcctttaaa caaccagatc ttgggtgcgt   6720
taactgagtg aaaactcact caccatcaaa gggacagcac taagccactc atgagggatc   6780
tgcccccata atccaatacc tcctactagg ccccacctct aacactgtgg atcacatttc   6840
agcgtgagat ttggaggaga caaacatcca aattatatca cctaccacaa aaggaactat   6900
tgtcttaaaa ttttgttagt cattccctta ctttactttt tgattggcct cctaggtcta   6960
agtgtatgca tagacatata tgcataggta tatatacaat ttgcatatag tcaatttctg   7020
cctgtttggg aactgtaagt aaatataatc atacataagc attcttccaa gacttgctct   7080
agggtcaaca tgatatttct gagtgttatc catgttgatg ccaagagatg ttgataattc   7140
attttcacag ctgtatagta tcctattgca tgaatgtatg acagtctatc atttctatca   7200
gttggcagtg ctaagtcatt gacaaaaatg atggttcaga gttaggattt caagaaggca   7260
caattgccac caaatttatc cctgtttcat gcacaaacta cttgagcaga gaagtgaaaa   7320
ttttgcctca agttagaagc aggttttagc taggggacat caaaggaggg aaggggtctt   7380
aaatgggaga ggaagaaagg gctaaagtga ctccccaaga ttaaaaaata aaaacaaaaa   7440
gaaaaaaaag aatcttcctg gacagacaat ttgtgactgg gctagcccat gctgattgtg   7500
ggcaaattaa ggctttcact ctcactgtca cttcccctcc agataagccc ttggggaaaa   7560
gttctatatg aatacttaat ttacaaaagt attgttcccc agaccagcag attgggttcc   7620
atgaaggtcc atcactttgc ttgatcctga agagaaccaa atttcatata gtgctcatct   7680
ataagcttcc tattgatgta tttttatat tcaccttttt ctatagcata tgcgactatg   7740
cagctaccac acagttatca aatagtagtg tccatgaacc tttagtaacc tttgactagt   7800
ttccatgact ctgaaattcc ccacccacag cttcacttgt aaagagtgga aatatttaga   7860
ggaagtgaga ctatcagcag ctcagcctca ccatgggaag cattttctcc tcaaagcaca   7920
gtagtatgct ggtgccttct gtcacactat caggacatgg ctttagcaag tacagtgtcc   7980
tctcagcacc tgttcctcat gcaggtgctt tgcatcatat aatcgtcgaa acattaagga   8040
agtaatgctc tttgtcactc caccggagtg gagaagttaa agtcaagagt gtacttcagg   8100
ggttgtatca ctggtttggc tttagtagtt gtgaggtctt gatgggtgag agtgatccct   8160
ggcaaatgac atatattgat tgattcattg agtgagcaaa ggagtaaggt gggtgtatta   8220
```

```
gggttctcca gacaaacaga accaatggaa tgtgtgtgtg tatatatata catatatata   8280
tagagagaga gagagagaga gagatttatt ttatgaagtt ggttcacaca attatggaga   8340
ctggcaagtc caaaatcagc aaggcaggct ggcaagctgg agatcaggga agaactgaca   8400
ttgctacttg agtccgaagg cactctgcta gctgaattcc ttcttgctct gtggatgtcg   8460
ctctttttc tattaaggcc ttcaactgat tggaggccca cctacattat ggaaggtcat   8520
ttgttttgct caaagcctac tcatttaaat gttaatcttt taaagaagat agctttgcag   8580
tgacatccag aagaatgttt gatcaatatc taggtacctt ggcttagcca agttaacacg   8640
taaaattaac catctcagat actgtatcca tttcagaaaa taatttagta gatattaata   8700
tttattgaac atctgttaag gactctgtat gggccaggca ccatattagg tgctggggat   8760
tcagcaggaa agccagccag acaaaatccc tattttcaag aagcttacat atggaagggt   8820
ggaggtttga gtaattaaaa cactcgcagt agttttcatg ccttcaagaa gcactgcaga   8880
tacaactcaa gtcaatcaaa tccattctcc catatacata tggtattggg gtatagtgaa   8940
aagaggaaca gaggttctga cttcctggac tttgtcttct actgaggacc tcaggtctaa   9000
attatatgat gaccatagac acattttaac aattatatac aacatgttat tcattatgta   9060
gctttcaaaa gcacatataa ttcagttata aaggatgatg aaaattaaca aattgcatac   9120
aattgtatta aaaataaagt gacaaaggta ttttgtacat gattatttca ttttcttcat   9180
gagttttttt tttttaattt ttatggcaaa acagttcaag gaaccactta acgaaggtgt   9240
ttgatttcaa aagaattgat ttgggaagac agaactgctt gatgatgtct gtttctttgt   9300
tagctttaag taactggttt actcaattgg cctcttcctt cattgtgttt tggagttttt   9360
ttgactgaag caaagacaag cattaaaaat aaagacattg gtttatgttg tttagaactg   9420
agaatccatt taaaaaaaat gaattggagt atctatgcca gattgctctt acatgatata   9480
tgtggccatg ggcagaggag ggttgcattc ttaatttatg ccctgaaaga atatcaggct   9540
tatttctcaa aaggaaaaat acaaatggca agcaggtata tgaataggtg ctcaacatca   9600
ctgatcctca gagaaatgca aatcaaaact acaatgagat atcatttcac cacagttaaa   9660
atggcttata tgcaaaagtc aggcaataac aaattctact gaggatgtga agaaaaggga   9720
accctcatat actgttagtg ggaatgtaaa ttagtataac cactgtggag aacagtttgg   9780
aggttcctca aaaaactaaa aatagagctg tcatatgatc cagcaatccc actcacatat   9840
acccaaaaga aaggaaatca atatattaaa gacatatctg cagtcctgtg tttattgcag   9900
cactcttcac aagtgccaag atttggaaga aacctaagtg tccatcaaca aataaatgga   9960
taaaggaaat gtggtacata tacacaatgg agtactattc acccataaaa aagaatgaga  10020
tccagtcatt tgcagcaaca tggatggaac tagtggtcat tatgttaagt gaaataaacc  10080
aggcacagaa agacaaattt cacatgttct cacttacttg tgggagctaa aaattaaaat  10140
aattgaactc ataaagacag acaatagagg gatggttacc aggggctggg aagggtagcg  10200
ttgtgggtgg gggggattat ggggggcagg taggggagat agataatgag tacaagtcat  10260
agaaagaatg agtaagacct agtatttgct agcacaacag gatgaccgta gtcgaaaata  10320
atttaattgt acattaaaaa ataactaaaa tattgtaatt ggattgtttg taacacagag  10380
gataaatgct tgaggtgatg gagaccccat gtaccctgat gtgattatta cacattgcat  10440
gcctgtatca aaacatctca tataacccat aaatatatac acctactatg tatccactga  10500
attttttttaa aaagaaaaaa aacagccttt aattagaata tttgcatgtc acaggctagg  10560
gctaataatc caattaaagt tttaggtaag ggctggagga cacagggatg tgtagcacac  10620
```

```
gttgatgtac ctcaaagagg ggaattcttc taagaaagcg tcatcacgat ttctcacctg  10680
ttatctacaa ccttcaaccc attgctctaa aaaatcttac atttgagttg aagaaagaac  10740
aaatacgttt gtaaaacaaa aatcacattt aaaaaatagc taaatatgtt gctaagtgaa  10800
agaagccaat ctgaaaaagc tgtatattgt atgattctaa ctagaacgtt ctggaaaaga  10860
taaaactagg gtaccagtaa aaagatcagg ggttcccagg gactgcaagg agggagggat  10920
gaataggtga ggcatggaag atttgagggc agtgaaagtc ctctgcgtga tacgatagtg  10980
gtagaagcgt gtcactgtgc atttgcccaa tcccatagaa tgtacaccac caggtgcgaa  11040
ccctactgtc aactatagac ttggggtcat aatgatgtgt caatgcaggt ttattgattg  11100
tagcaaatgt gccagtctgt ggagggaggt cgacagtggg agagcctgtg tgcatgtggg  11160
agcaggaggt atatgggaaa tctctgtacc tttttctcaa ttttgctgtg aacccaaaag  11220
tgctctaaaa aatagtcttt ttttaaaagg agctaagtgg cctctttgat gttcccccag  11280
aaggccaaga aagtgcccaa caccggacgt ttgcactgac agtccctctg cctggaagga  11340
ccttctggga gatccctgcc aggctccgtc cccttcctca ttcagctctg ggccacaagt  11400
cacccaatcc gccagccctc cctcacatgc catgcaaaat ggccacgggg tcacctctgt  11460
caccctcccc gttgtcacct gtcctcaaca ccacccgacg ccgtgcagac tgacgtactg  11520
gcttatggtc tgtttctgcc tctgaaccgt tggctccgtg ggtgggtgaa ggacgttatt  11580
ttgtcccctg ctgtgttctt ggcacatggg aggtgctgga gggacatctg ctgaaggaac  11640
gagtgagtga gccagtgagt ggatcatcca gtgagcgtga gggacgggtg ctaccaggca  11700
gggaaagaag ctctctgtaa gcagggaagc ctgctcagaa gtgaagctgg tatggccctt  11760
gcaaaacggg aaggacacag aaaagcatga ggagattgtg aggggaagaa aaggcggctt  11820
gaggagagcc ttgtgcacct agtgggtcgg tgagggaacc atttggactg gaatgcaggt  11880
cttgggagga caggggtggg agccgtcctc cagccgtgtg tgcgtgctgt aggcaaaggc  11940
agacttttcc tcaggaaagc aaatttggat ccgctccagc atttgaataa cagcctgatt  12000
gaaaaacaaa gctctactct acatagcaga gcaaagaatg gttttggtca gagcattttt  12060
caaagacaat gttcctcact tcttgcttca gcataggaaa acgtcagcag agcttcggtg  12120
cagcgtttta ctctaagcag gcctgtgatt caggggctgg cctccttggg ttcccacaag  12180
catgatttag cagagagatg tgtctatttc atcattaaac gaaatgttcc ttagggaaaa  12240
gactctttat atacctcagt tgacatccct aatgatattc cctgaatacc cagttagaga  12300
agtgttagcc tcttctatgt catactttct atctgctgag taatttcttt cttaattgca  12360
cagaagagcc acttggccca acactcccta tttgagttcg acctagcaga gatttctttc  12420
ttttgaggct atgtgaaatg cagttgagca tgatattgaa aacatgaaca caatccaaaa  12480
gtccatcagt agggtcctta ttacaatttg gcaatccaca ctttggaata ctgtgctact  12540
ggtgaaaaag aagaaagagg atatacacaa agatatgaaa agatgtgaat caaatacaaa  12600
gcaacaaatg caaaagaaca tacagtacaa gcccattttt atctatctca ttgtagaata  12660
aaagtctagc aaaatataga ctcccaaata tttttaaatg ttttgggatt gggtttataa  12720
gacaggttca ctttctgcag tagacattgt ctgtctttag atatttaaaa atgagtttac  12780
gttgctttgt gattgaaaac tggctcaaat tttaaaaact ctgtgtgtgt acacgtgcac  12840
aatcactcat gcatgccagg ttgtgtagta cacaggagca atggttggag aaatggggag  12900
ttcctaataa aatttaacag taggaatgtg tttttaagat tattttactt aaaaataata  12960
```

-continued

```
attcttctcc cctcgtcagg cttatctttt gaccattttt gttttggctt gttttcttgt  13020
tttgttaatt tgttaataaa taattgataa aaataaatgg caaagcaaaa aaaaagttct  13080
aagcaatgta agaaagtcat ggcatactct ctaaggagat tctttctctg cagcatggga  13140
acattcacaa agcaactatc aagcaacata agttggggaa atgatcatca gggttcagga  13200
aatggacaga ttcaagaagg ttggagtgct taagagagaa ccaactgcct gagttcaaat  13260
ccaacctgta ccacccacct gccatgtgct attgagcaaa ttactttact tttctgtttc  13320
tctgtttctc atctgcacaa aggaggtaat aagagcccta cctcaccggt ggttttgaag  13380
gttttatgag tcaatggatg attttgaatg ttacatgagt caacacacac acagcaccta  13440
aagtggtatc tgacacatta agtgctcaat acatattagc tagtgggagg aagaggagga  13500
gagggaatga gttttcataa aagagaaggg atgtaaagaa tgagtagggt ttgacagaaa  13560
aaagaattcc agaagatcaa gaaaaaaaca aaacccaaag gcttatagga tacatgaaat  13620
gatccagtta aattcacccc aacctctgta aagaaagccg aaatgatatt tcatgactag  13680
atgataaaca taagcagata tgtacaagca ctcaaatgaa atagaaggag ggttttttaa  13740
agttagcttt cctttattat tctgtagacc cttctgtgtg tcagtcatca gtcaacaaat  13800
tcgtatggag ctacgtggtg gtgtagctcc caccagcatg gaactttttc caagtgggtt  13860
taaagttgga aaaccatggc gatcatttgt tttattgtgt gttgattagt agcgtatcca  13920
agagttgtgg tagttacttc ggtgtgactc attcaggaat agaagaaaga ttcattgtat  13980
tactcttaaa atataaacaa ttcttaattt ttctgtgcta atgaagaacc acaggaataa  14040
atatagttga tagattaaat tatgtttatt ttattttatc tgtaaattaa gcaaatcttc  14100
attgttttgc ctttttgaaa cttttctcca tctgtttggg tttctgggta ccccccagcc  14160
ctggtgtctt cttcccagct tgcaaacagc catcagggcc caagggcaag gggagaagcc  14220
actgagggcc agactgcgca cagtagcttc caagcaggcc ctgggtaatt gagttgcttg  14280
accttggcaa gcacagaacc agcctcatcc acgaaaacac gaaaaacaca tgtgactagg  14340
tgctgagact gatgcttttg atcaccagcc ctgaccacac tgaagagccc ttttaagaac  14400
caaggtccag tctcatacaa tcccgagagt tcagacaaaa aggccaaaat tccatagctc  14460
tgccggactt atttgcaagg ggtgctgtgt agaaggtgcc gaaatggcta gtagctaggt  14520
ttaagcaatt acagtcacta gttggttcaa agggatgcca ttcactcctg gaatcctgct  14580
gtcaatgatt gagctaggga gtttggtctc cagggaagag ttaaacatta gacaggaacc  14640
attacaaaac tttccactaa aaataagttc cttgtaagag aagttgagag acttgctaat  14700
tgcagcttac tctaaaccta atgacagtct gtatcatttg caaagaaagc acaggatgtg  14760
tgaatgatgg tgagggaagt ggggagtctt ggcagataga tctgactctg atagatgcag  14820
ttggtcctct agactagtga tccattttgg agtaaactgc attgggagac tgatcaaatt  14880
tcctttctcc aggattctta ccaacagtaa agactgataa aacacatttg tgctgctgtg  14940
tttttcaaaa gctcggccat ataataactt taacagactc cctaaatttc aaacatttcc  15000
ttgatgtagg atgatcacaa tagaaaggaa tgttattctc atccagccat cggtaagctt  15060
ttgtcttcct taatcccaga aactaaatca ctggctacct cagaggctct gacctaaatc  15120
ttaattgatg cccactgcac tttcagacca ctgtgtgtga ttttaaccag acaaaccaag  15180
gaggaaggat taatgaagaa agcctaatat tttgaccaat catagagtcc actgcagtgc  15240
cctttccatt ttaattgagc tttatacggt tctcctctcg aggtaaccct cctttcttaa  15300
tgttcagtac agcaaaaact aatctaggtt ttctttttaa tgtttgattt atctcttcaa  15360
```

```
tcttggtgct aggtaacaac attggatcaa aatattaaca gccaagattt agatattatt  15420
ttacaattaa cacagcacat tgactcatat tatttcactt tcacagtggt cctggggcat  15480
gtttattgta tctcccactc tacagatagt gaaactgagg agatcacggt gggaaagatg  15540
acgtaactca catgaagttg ggcaactgat cagatgacac agctaggact gaagcctggg  15600
tcccctaagt catttgctta gagctcattc aatgacgagg caactccttg ctgtgcatcc  15660
tttcagcaca cgttgttggt gtgaagacgc tggttttcat cagactaaaa tgcatcttac  15720
ttcaagatag gcagtttctg ttttggtttc cacctctcat acattgcttt taaagtgcca  15780
acctctaatg gctatcccat gagaaaatct actgtaagta tgaagtgacc ctttggtact  15840
accagttttt catcctaaat cccttttctt tcttctttct tttcctttct ctctttcttt  15900
ctttttttctt tctttcttcc tttctttttc ttttttcttt cttcttttat ttctctctct  15960
ctctgtcttg ctccccctttt ctttctttct tcatttcttt ctttctttct ctctgtcttt  16020
ctcctttctt tctttctctt tctttctttc tttccttcct tccttccttc cttccttctt  16080
tctcagactc tcactctgtc acccacgcac aatctcggct cactgcaacc tctgcctccc  16140
aggttcaagt gattctcctg cttcagcctg ctgagtagct ggggttacag gcacatgcca  16200
ccacacccgg ttacttttttg tagttttaat agagactggg tttcaccttg ttggtcaggc  16260
tggtctcaaa ctcctgacct catgatctgc ccaccttggc ctcccaaagt gctgggatta  16320
caggtgtgag ccaccacgcc cagcctcttt cttttttttga ctgtgtctct tgctctgtca  16380
ctcaggctgg agtgcagtag cacaatctcg gctcacggca acctctgcct cctgggctca  16440
agtgattctc cagcctcagc cccccgagta gttgggtcta cagatgcatg ccatcacatc  16500
cacctaattt ttgtattttt agtagagaca gggtttcacc atgttggcca ggctagtctt  16560
gaattcctga gctcaaagtg atccgcccac ctcggcctcc caaagtgctg ggattacagg  16620
cgtgagccac tgcgcccggc cccattttat tttctttctt ctttttcttg gcatttgtta  16680
tgatcaagcc tttttttttaa gtactgaata tccatggact ccttccagtt ttacctcatc  16740
aaaatgtgct tgcagggaag gatttggtct tgttgatttc aattaatgta actccaagcc  16800
accactcttc tgctattcac cttttaatct atatttctta ctatacataa gaagctttgc  16860
ttctctactt atttcaagga gtgtagggtg aagatgaggt ttttaaatca cggtatcttt  16920
cttcagtcct ttcctccaaa ttctacacgt agatgtactg tgcttcagcc aacttatctc  16980
taactaggac attcagatct actaactaag ctatgactta ttataggcag gcggtcagca  17040
ggaagagctg ttttttttttg aaagtaggac aagaataggt ctatggaatg ttggggtcac  17100
ttggtttcct caatggaaag aaacgggatg tttctgcatt aactagaaca cttgaaaggt  17160
agggaggggt gagggtgatt gagaaatgat ttcaacaaac agaacattaa gtactctgtt  17220
tgtcagacag cgtgttccca tctggggggt gagtggcaga aaacatagtc gccatcatga  17280
gaagagctcc cctaaatctg cccacccacc tccaactctt gctccagtca gtttttctga  17340
atgcccagcc tgctacactg accctcaccg ctcttacccc ggtgccaggg tgagagaggc  17400
cagggatcag gtaaggaaag aggagaggaa atgcagaggc tccatttggc ttataaagga  17460
actgtaccat aatagttatt attgtttaaa aaaatagcat gacatccatt ctatttctct  17520
ccctcttctt caaagatatt tcagcctcag ggactttctg cttgttagtg ggatggcgaa  17580
aaatgcatga tagatttcta gttagtaggt agaagggacg ggagattaca tcctaataca  17640
gtagagtaac tatgttttat tgagcactta atatgtactg agtgaacaca cctgctttga  17700
```

-continued

```
ttcacaacca cttaatgagg gaactttgga gcctccttaa gggttacaag caaaagctgt  17760
ggagtcagct tgcctgggtt caaatcctag ttgtgccatg tacctgctgt gtggccttgg  17820
tatagttact taacctctcc atgaatcagc ttcctcacct taaaatggag ataattataa  17880
tgtcacacac ctttgggggg aattcccaag gccacccccca ggttcaatga ctcattagga  17940
ggacccacag gattcatcat agagacatgc ccacagctaa gttctattac ctcaaagaca  18000
aatcagaatc agcaaagggg aaagcaacag aagaaaccag acatgagcta ccaagagtcc  18060
tctcctaggg gagtcacaca ggacatactt aactcctcca gcaacgagtt atgacaggta  18120
tgaaatgttg tctactaggg aagctcagta gatacttagt gccagagttt tgatttggag  18180
ctggtcactt agacaccctc tgtctggcat gtacacaaat tccagactcc cagaaggaaa  18240
gcaggtgttc agcataaacc atgttgtttg cacacacagt taagtcacag tgagccactc  18300
atatcacgga ccagcaggaa cccctcacat gttcccagat gccagccaag ggccagcctt  18360
gcaagcagga ttgagacagc agtctcagac ctgctatgtg aactctttac tgcttgctac  18420
cttttgattg ttgtgagatt acataaggta atatatatat ctgttgctta caacagtgcc  18480
taatttgtgg gaagccctac agattttttt agcccttact attatgcaga aaaaaaaata  18540
ctcaggttta gaatgactac acagtcaaaa tggaacaaac tggaatctga attcacatat  18600
ccccaaaaaa ggttcatgca tctattcaca tcaccctaac atgagcaaag tagcatcctt  18660
cttcaaaccg taactgggga tgttgttggt gggtccctcc cttttcaggt tcagagaaga  18720
tggagccttt cattccagtt gtgttctgaa gacagagctt cttggagcta taagcaccat  18780
taggttgctt ctttctcagg ttaaaccact cagagtgcat ttatggtctg gtacttaatg  18840
ccccacatga gcatatttca gacttccccc ccattccatg aggcttgctt tgttgatgtc  18900
cttcattttt caggatacgt atccacaaat ccataagaat tttcttccat aagatctaga  18960
tagtgaatca tctcgccgta attgaaatca tcccattgta aaccattttt aggcttaaaa  19020
aaaatctgac aaagaaattt ctcccaccta cttctcccaa tgcaaagtag ttaatcaatc  19080
tctttaatca tgggattacc tctatcttat ctttcaccag gttttctggt ctttggttat  19140
gtcagtgggc agggcagcag agtgtccaat agctagctgt gaatgctaag caactgtagt  19200
agatgccaaa tcagttgcac caccaaagtc tatgcattga aatgaagtca ttgactgcaa  19260
ccaatttaga tatcttttag tatttttttt ttcaaagacg gatttcaaaa tgggaacagg  19320
gctagaagaa tcctttcaat tttaagttaa aaattatgca tcatcaatgc agattgccat  19380
atggttgtag agtaagatga aacagagtct tagagcaata gtttatttca gcattagcat  19440
tgttagttgt tagacatctg tcccttccaa taaatgaaga ttttgtaaac ttcttagtca  19500
tttctgtccc catagatcca agaatagaat tcacacatgg tgactgttta ttaaaggtct  19560
gctccattaa cactcaaatg ctaatgcact tccacttaat aaaagagctt catctttggg  19620
tctggcagct catgacatat cccaagtgag taggtgacta tttcctggat gactatagtc  19680
aacgcagtgc cagattttga cacctacaca aatatctccc tttggtgaga aaagcaagca  19740
agagttatag tgaaagaata gtgtgactgc agttaatacc ataatttgaa gaacaaataa  19800
tggcatctat aaaaaaataa gatgtgaagc tcatagaata taagaatcaa agtgctcatg  19860
gtagccctgg ttgctactag ctgagtctac acatgctaat aaatggcaga agacatgaaa  19920
aggcaaagca agaggcagaa cacacagaag agagagaaag agagggatga aaatggaatt  19980
atgtcagtgt actcataagt ttggactgct agaaccgagt actatagact aggcggcttg  20040
taaacatcat atgtttattt cttacagttc tggagactaa cattctgaaa tagggtgcct  20100
```

gttgaggccc tcctctgggt tgcagattgc tgccttctca ttgtattctc acatggcagc 20160
aaaagaggta gagagctctc tgggatctct ttcataacgg cactacatcc attcaggagg 20220
attcaccctc atgatgtaat cacctctcaa agccctcccc tcctatcacc atcacattgc 20280
gggttgggac ttcaacatat aaatttgggg gtgatacaag cattcagttc attgcaagca 20340
gcacagcaca attcatgaag actttttctt tctatgcaat ctcccaaata ttccttgaat 20400
atctgtacct ctgcctttgc tcagactaat ttcttctttt tctccatatg ccaggctcag 20460
ctcacatacc acctacttct tgaacacccc agcccatctc agccccccat gctttctccc 20520
tcctacaaac tcctagagct tccattgtga tgctgaatgt tgttctttag ggtcgcaatt 20580
agattgtata ggtgttcttc ttgtactcct aagtttctta aataaaaatg acatggtttt 20640
tgttctctca tcagctataa gcatttccta accatctgct gtgaataggg atgatatagt 20700
ttaggttttt gtccccaccc aaaaatctca tgttgaattg taatctccag tgctgaaggt 20760
ggggcctggt aggaggtgtt tggatcatgg tggtgcatcc ctcatggctt ggtgctgtat 20820
ttgtgatagt gaggtcttgt gagatctggt tgtgtaaaag tgtatggtac ctcccccctg 20880
ccccttgaca ctctgtctgt ctctcttgct cctgctttca ccatgtgacg tacctgctcc 20940
tactctacct tccgccatga ttgtaagcct cctgagacct ccccagaagc agaagcctct 21000
gagctttctg taaagcctgc agaaccgtga gccaatttaa cccagtctcg ggcatttcct 21060
tatagcagtg caagaatgcc ctaatacaga agataaagag gatatgatct agagtttggc 21120
tggactttaa ccagagcccc catccctaca actctgaccc cctgacactg ctgtctgagc 21180
acacagctgt cctttagcac ctttagcctt gttttcttat ttccagaaca agctgcatat 21240
ttctggagac cattcctcca ctatttcact ttttgaataa agcttaagtg caccaaaagt 21300
aaatggcaat aagaaaaatg taccatacat gcctcacaca catgtacgct cacagtcata 21360
cacacaaaca agctgataca ttagttttac tttggctcac ctctagaatc tgggtggaca 21420
gtctgctcta tgccttttct gttctttctc ttccattgtc cgcagaatat gaggaccaaa 21480
gtgctcattg ttgtttcttg aattctgcat gtaggcaagg agtggtagcc ttccctgatg 21540
tattagtcag ttctcacact gctataaaga aatacctgag actgggtaat ttataaagaa 21600
aagaggttta attggcccac ggttctgcag gctatacagg aagcatgatg ctggcagctg 21660
ctcagcttct ggggaggcct caggaaactt tcaatcatag cagaaggtga aaggggagaa 21720
agctcatctt ccatgactgg agcaggagga agagagagag cagggaggtg ctctctcacc 21780
aaccagatct catgagaact cactcactat caggagaaca gcaaccaggg aaaaatctgc 21840
ccccatgata caatcacctc ccaccaggcc ccacctgcaa cattgggaat tacattttga 21900
catgagattt gggtggggac acagaggaaa ccatgtcacc tggctaagtg gtgaccacac 21960
agttctcacc tgtgtgtggg ttattcactt tctgctcttc cctaagactc tccttaaatt 22020
cctggcagac tcttgctcat gctctccttt gggagttctt cttctgctct acaatgcttt 22080
ctgcatttga accctttcct catatgtcac accctcttca ccctaatggg ggtttatttt 22140
gcttgatcac tctttaatcc atctgtactt tccctttga gtggcaccca agactgagcc 22200
tcgttccaat agcagtgccc tggaaccaca gatttgggag ctgaatagga ctgtcatctc 22260
tttgctgtgt cacacactag tgatggaagc ctgcagaatt ctcccacaga tggacagttt 22320
agttatgaat cccacaccaa cttctgctca tcaaacatcc tcctttcatg atataggcag 22380
aaatttcaga agattatttg ataatgcctt gttttatttt tttgacacaa ctgtcaacca 22440

```
cgccacttca agatgtggtt tgtccctcat ggcatgaaac aggtctcaaa cgacttgcta  22500
tctggcaaca aaatggtaca ccaacacatt aaactccttc aacaggagaa catcttcatg  22560
acaaagacag tggttcgcag gttggacacc aatcttatag gatgggtttc cttggagttc  22620
agggttaaca acatgtggca acttgtttgg gatattatga aagagaaaag tattctattc  22680
tgccttaacc atggcggaag cagcccttga ggagctgctg tcatgacttc cagtcatcct  22740
tctaaaggaa gatgtctaga agaatgtggg gcaaaagtga agtttgtaca gagaatgaga  22800
ggaacttaca gataactttg aactggcata tctgtagtta tctctattaa tgtgaattta  22860
caaaaagtta actagtgaaa tagggacaga taggcatttg ttctctgaag ccatttgggt  22920
atgtcttcat aatcccagga cattgggcag aggcttcctc tatcctctta ctcagagaaa  22980
tccaaatatg gcaaatgatc cctgtagctt cctgggcaaa ggcccatttg cttctgattc  23040
tttcaagggt aaacaggaag gctttataga aagcttcagc ttgtttctcc aagagtttcc  23100
taacacagag ataaatacat accttcccct gacatctctc caccctgccc acgtgaaacc  23160
cttgctggct ctctgtctct gtaacccctc tagcctttcc tttctggggg acttgccagc  23220
ttgctactcc acctggagaa cagaacagga tggagtagaa caggaatttt caattctctc  23280
ctttatatac agaagctctc tcaagtctct ctaagctttt cagacttaac gtgtctccta  23340
caaaatattt gttcctgact caccactaag aagatgaact ttaagaattg cacagtttgc  23400
ctctccccca tgataatatg catagctaag ccacagcaag gctaccttc tcattcttgc  23460
tgcctgccga tggtgtgatc ttagcccctc tctcagtatt tgaatttcct cggtctttat  23520
gaatggtaag agttgtttaa gtctctcctt gcaacactcc gccacccacc attcatccca  23580
taatctttca catggaagac tgcatgtatt ttgtaaaacc agggggaaaa gtcctgattc  23640
taaatcaaga ggcaattatt aagagtggca cgcaggtcat ttttcttcct tcctccaacc  23700
accctgtcaa ccaccacccg ccatgttcac aaaagcctcc aaggctacct acaagaaaat  23760
acccagcttt cctctagggt gacttgactc ttcaaactgc ttctcagtgg aaaacttttt  23820
aaacgctccg ttttatttat tctctaacag ttttcctgtt aactaggttt ggaggtgttt  23880
tctgaaacat gaatgccatt aatccaacac caaaaagatt ccagaacttt ccagggcaca  23940
catggccaag ccttccagac cagtttgcac tggaggagcg ttctgcactg gcaggcgttt  24000
ctgcagcttc tgacatcagg gaaaaggtgt tattcctaca gtgctgctga cgttatgtaa  24060
cagcagagcc attgcttttt tttttttttt tttttttttt ttgacggagt cttgctctgt  24120
cgccaggctg ggagtgcagt ggcgtgatct cagctcactg caacctccgc cttccggatt  24180
caagcgattc ccctgcctca gcctcccgag tagctgggac tacaggcatg cagcacgcac  24240
gcccggctaa tttttgtat tttagtagag acggggtttc accatgttgg ccaggatgat  24300
ctcgatctcc tgacctcgtg atccgcccgc cttggcctcc caaagtgctg agattacagg  24360
cgtgagccac catgcggccc catagcttct ttagttgaat ggctgcctct ggaggcggga  24420
cccacaggga ctgcctgggt ggaagaaagg cagggaaggc tgctttcact catcaccgca  24480
gactcactgc cattcagcta ggccgatctt gtagaactga cgtagaaaag attacttctc  24540
cataagtata ggttctggtc agaaccaaac tctctttcca aggactgctt cctgcctgtt  24600
tgtgcacaca tcttgttttc ttagggtcat tgggactgaa tactaattaa tcgaggtctg  24660
catgatcagc accgaagcaa gcgcctgaaa agagagtgaa tcttttttaa aagttacttt  24720
attatttgta tttattttct gggtgttgtt tctgattcca agtagttaca taaaagttgc  24780
aaagccagtt aaacaccctc tgaatgttcc tgcagaactt ggactgggcg ctccctattt  24840
```

```
agaggttaat aatggtcagt ggctttctct tcctttctaa ctttatttgg ggtgtgccta 24900
gccttgagat ctgggttgtg gccatgaata ggtctctgta gtccaagaaa catttctcag 24960
actacggaag atgtgtggaa agacagtgcc aagctgcctg ccgctgtggc agcaccaacg 25020
gagaagaaaa acaagccaaa ggatgcgggt gtgatcaggg cctgcgcagg ggttggagtg 25080
gtcatttggg gcttccagag ggataatgac aagtttatcc acaggagtaa agggttagag 25140
cagccagaag acgcttgtgt aatgtcccag caaatcaatt taaagactta aatatgacaa 25200
catgctaaag aaagcctgga aggaattggt gggtgaaaag gaaatctgcc ggccttcaaa 25260
agtgaaaaac gaagcaaaat ggagctccaa aaaatggtgg ctcaacgaga ccccagtggg 25320
cttggctaga ggctccggaa cagaaggcct cagtcacctc attgtattca gcacagtctc 25380
taaagctgag agcaggaaat cctgttgccc cacccatgtc ctcagctgag gtcccatgag 25440
acaatattcc ttagatacca gcagaaactt ttcttacatg cgaaggggtg taattcacaa 25500
tattctttag aaagatggtt gaaaggtcac gtcattcagg ccataaaaca tttatccaca 25560
catttattca tcaataattt actgagtgct ataccagggg gaggggaaag ggtggggggg 25620
gtgggttatg atgatgccaa cgattaaaga gaccagtcaa gacactcaag tgagcctgtg 25680
gtctaaaatg atgctactga aggtggcaga tgcccacctg ggagtatctt aggaatgcaa 25740
attccagccc cgcccagcct tactgaaaca gaaaccctgg gggtggtgcc cagccatctg 25800
tgttttaaca agctttcctg atgcacggaa aatttaagat gtatgggaac atggtgtctc 25860
aaacaatgat gtgtcctggc catttgcgag atgtgtggaa agtaatatat tattaatgat 25920
agttagcata ccgacatttg tgaataattt atatgtatgt cacctgcaaa gattttgtaa 25980
aaatacagat ccctggctcc acccaattcc aacggagtag aaatatccag gtgtggcagg 26040
cagtatttag ttttaagact tcccaggtga ctcttaggat ccgtcaggtg tgggaaccag 26100
tggtctataa gagccatttg ccccataaca aagagaaaaa atcatggaat tctagagggt 26160
ggtccctcgg agagcaggtt tccccactcc cctaacaaat gttaggcaga tctcaattga 26220
aacacataca agagaaactc caactgcagc agaaatggag tggaggttgc ttcatacttt 26280
cctttctgca gtggctgttg cagctcttag taaaaatcta gagctctcgg ccgggcatgg 26340
tggctcacgc ctgcaatccc aggactttgg gaggccaagg tgggcagatc acgaggtcag 26400
gagatcgaga ccatcctggc taacacggtg aaaccccgtc tctactaaaa aatacaaaaa 26460
attagccggg cgtggtggcg ggtgcctgta gtcccagcta ctggggaggc tgaggcagga 26520
gaatggtgtg aacacaggag gcggagcttg cagtgagcgg agatcgcgcc actgccctcc 26580
agcctgggcg acagagcgag actctgtctc aaaaaaataa ttaaaaaaaa aaacctaaag 26640
ctctcaaaaa tatggtttga aaagcatgga tgtttctatc accacctcct cctcctgcca 26700
catacgcccc attcattgat gaagaaacca aggctcagaa aagtaaaatg acctgaaaac 26760
atgtgactga ccattcaggt ctgcccaaga ctaaaggcat cccagaaatt agagcgttca 26820
gttttaaaac agggacagtc ccagaccaac caggatgaat tcgtcaccct aggtcggaga 26880
cttcacgaca cccacagttc ttgcgttttg gctgatttat tattgttgtt gttgttgcta 26940
ttataccata ttactgcaag aagaattcaa attactattg gtttttaatt tttttttaaa 27000
tttttctagc cccttgagaa gttcttacta aattactatg gtttcctttt aaaaaccata 27060
tttgttttta ttccctcatt ccagaaggat ttaagggagt aataccctta ttttatgtgt 27120
tttgaaatac ttgtaagtat tctaaaatac tctggactat tcctgtgtcc atgtctcctc 27180
```

```
tatctgactt cagacccacc ataccatatg cattttctct ttggcttcca tatatttgtg  27240
tgatgtttgc tatggcacct actgtgccct actgagatct gtgtattagt cagaactctt  27300
tagcttgcca gtaaaagaaa acaaaaggat ggagtatgtc agcttgggta gcagaaaaga  27360
gcttcaggca caagtggata caggggctcc acctcatcag gacatggtcc ctctttgaac  27420
ccatagcaag atggtcacat gcagctccac acacccgcat cctcccagca acccagctga  27480
cggcatcttg tccccagtag cttttgtaaa agtccctagg atgaactctg tttgggctga  27540
cttgtgctat gacccttccc taaaccagtt gcagccccca ggacaatgga atactctgat  27600
tgtccagact gtggccatgc acccacccct ggcaccaggg tctaagaaga gagaaatgca  27660
agtctcccaa aagaaagtca aaagatggtt cctagaagca gaggaggaac agatgctggg  27720
taggtgaaaa cagcaaatgt ccatggtagt cttaaacagt tcaagagggc tgaccaactg  27780
attggctgat gcacgggcaa cagcatgcag ctccatgtct tcctctatcc ccactctgct  27840
gagatctagg tactattttc ccctgaaaca ctaggttgca agactccaag gtcaccattg  27900
tcagttctaa ttttgaagac acgcaccaca tttagctgaa gctagcagca gccccagaac  27960
ccatgggact ccatccgaaa aatgataagc cctttgctgg gctcccaaat atggagctcc  28020
tgagagtgag gagctggtga ctcatgttct ctgtgctttg gttgccccca cgttttccag  28080
ctgggttggt gacgtgggac tcagtacttt cttcaatgcg tcctgtacac aaagaataaa  28140
tagccccaga gctctttctt tttcttcctg cctttcttcc tgtaattcat tctcagccca  28200
actcagcttt gttcaaacca cagtatttca cattgcctgg caagttctga cacagctgct  28260
tgctttattc tttcagtctt ctgttaagcc agaggtaaag ttataccttg tggctaattt  28320
ttagtctgta aaccttatcc cttgttcaag ccgaaatctt agattaatca gcatgaaaat  28380
gccagctccc ccaagaccgt tgaattatgg cccccatcac tcttcctgcc ctgacattca  28440
tttgagtccc tttcaacttt tacaagttgt tttctcttat ccatgagcaa ggtggtggct  28500
tgggcctttt taggcaattt tcttttcttc ttaatcacct gcccctattc catccaatct  28560
atttcaattt ctatataatc atgtaataca tctctaattt gagtcaccag gttttccacg  28620
ttaaaggtgg gctttaggaa tgtttatttt acaaactaat agaacttcca gtcctatgga  28680
ctctaactag tagtggggcc actgtgtcag cttcccagag ctgctgttac aaagtaccat  28740
aaactgggtg gcttcagatg acagaaatag attttcttac agttctggag gccagcagtc  28800
tgaaatcaag gtgctggcag ggccacgctc tttctgaacc ttcaagggga ggatccttcc  28860
ttgcctcttt cagcttccag cagccccggg cattcctggg cttgtggcag catctctcac  28920
acctgtgcct ccatcttcac agggccgcct tctccctctg cgtctctttc acacagagtt  28980
ctcttcccct tttacaaaaa cagcagtcat attgtatcag ggctcacctt catgacctca  29040
tcttaacttg atgaaatctg caaagatctt atttccaaat aaagtcacat tcgcaggtgc  29100
aaggagatag gactcccaca taccctttca tggggaagga agacacaatt caacccctag  29160
cagccaggaa agagaaaaac agggacagaa aaataactct ttgatcttgg tcaaccaaaa  29220
aggggatcct gatgttctca gaggatgttc acccagaaag agcctgggac cccgacagga  29280
acatctggag atggaggcga aagcctagca gcaaaggtga tcgctcaaga gggcaggaga  29340
atccactgga gggcaaaagc caaggacaca tttgtgcttg aagagcctac tgtgtgccac  29400
atgtgctttt atcccattga atcctcaaat aactctgcca aagagttgct attattcttt  29460
tttaatacat ggagaaactg aggctctgat taaataatga gacccagatt ataagtagaa  29520
aagcgagatc atgattgcta ttaccgctgt cacttctgtt tttaataggc attggatctc  29580
```

```
ttgtgctact atacaccaag gatgttacct gtattaactg agatcttcac agctcacaaa  29640
gctagatatt gatggcctta tagagatgaa gaaacagaag ctcaaagagt ttcaatcact  29700
tgcctgaagt cacacaagta ttacataatt cagccaaaat ttaaactctg gtctttctga  29760
ctggcaggac cattccttac catgatgcca tgttgctggt ggacattagg gtatctaaac  29820
tagggtagtc ctagcttcag agaaagaagc tgtataaaga aaccaaatga ttatgcttga  29880
ggcttaacca aagcaatata aaaagtgtat gttctcaggg gaatgggcaa aacagaagag  29940
aaaaaggccg gccaccgagc ggctgtgggt gaatgagtta accaaagagc aaatgtctga  30000
gttggatcat gaaacagcag atcaagtggg ctcagtgtct gtaaacatct acactgccca  30060
tgaggacaag atctgtatgc tccatctaca cccagaggct gaaggaatgc ctgtggtgta  30120
gacaactcac ttttctagag aaatggagaa gggattagac atgttaaccc tgaagaaaag  30180
gaaacttggg gtagggtagg ctcagaaagt cttcagaggt tgggaacgtg gcccatgaaa  30240
gagcagggag actggaaagg gaccctgcct gtggaggcag ctctgggccc cacttgaaca  30300
cacacgggtg aaccacttga cccaccttac agtgaaagaa gctggcacct gtggaccact  30360
ggagaaacct cagtagccat ctggtgttcc ccaatgactg tgttgctcac aaccctcaag  30420
agtcctttgt tgcttttgga attgtagggc tggcaagatg tcttcaccca ctgctagatt  30480
catggctgag gcccctataa tgaaggacag atgaacaaga gaagaacata caaacgcata  30540
gaatataagt tttacatgac acagaagcct ttgaggggaa atgaagaacc agagaaacag  30600
ggaaacctgt gtatttgcta tgctcgattg gatgaagagt ggacagtcat ggagaggcat  30660
gaccgagcaa agcgggtgat aacctggagg gaatgtcacc acatctgttg gctcagattc  30720
tcctctgtgt ccttgtgtct tcagaaaaag gatgttcctt tcctctgagt atgcgggcat  30780
cactcacacc agggtccaat gtcctacttc aggggaaagt caggaaatcc ttcctgggac  30840
tgatgaccgg cctcagagag aagggtagaa caagggaagg tgagagtggc ctttctgctt  30900
ttgctgtttt ctcaaatgcc aattttctat tttcaggggc aatatgtcct gaaccccatc  30960
aggatgaagc cccagctcca tgaagcccct cttgaactgg tccatcctac tgttccagtc  31020
tcagctccct ctgctccagg ccttgaactt cacattccag cctggggact cctggcagtt  31080
ccctaaatat gcaaagagct cagctttctt tcctggtcct ggtcctggtc acttggccct  31140
ctctgtctct cccttccttc ttcccatctc tcttcctttc tggctcatgt ccctcgcaca  31200
tgctgtaaac tcttcctgga acatctccct tccacctgtg aatctcttgc cagctcactt  31260
cttttctccc tttaagaatc cacttctcaa aagaaaatgg caactctgtg aggtgataga  31320
aatgctgatt cgcttgatca ttgtggcgtc cacaatgtat atataaaaca agttgtacac  31380
attaccatgt ataaatttgt gtttgtcgat tatatgtcaa gaaagacaag gaggtgtgga  31440
aagactgcac ctctgtcaag acgcctttct gaccaccccc cgaccctggt tgacactccc  31500
tgacatgagc ccccgagtgt ttacctacgc tatgtgtatc agggcatccc gaccacttgc  31560
tcactcacct gtctccccac tgtgaggtca gcggcagggc cttgttcagt gtcttagtca  31620
tatcccctcc agcacccacc atgacctctg gcactaagta ggggctcaat aagccaatca  31680
ttgtgttgat gtaccagtga cattgaggga agaccaagct cgccgacctc taagatcctg  31740
tccactctga gagtctgtga gtctgtattt ctgctcccac agttagtcac ggaggaagtt  31800
gccaaagcag atgatgagac ttctgtttgg ggttgcccag gtctgcctgg cctttgcaat  31860
ttgtaatcag gtcctttgaa agagaaactg aactgagaga aaaacacagt ttggatgagg  31920
```

```
caagagttgc aaaataatga gttatgtaat ggtgatggtg gcctgtggta gcatctttgg  31980
ccctgcccag atgatacaag actttgtatg tataccettg agcatggcca aaaggacaat  32040
tgtcaaaacc acggcttaag tgttcaaaag cctcttttcc cataagatgt tgcctcttga  32100
ggtcagactg aaatcctgta cctgtaataa tttcctcctt aggactggat gtacatgaaa  32160
agattggaga tatatatgta ccttttttat atgccatgta aatggtataa cccttgcact  32220
ctttggccat taacagccaa ttgtcaatta gtttattgtg tattagatca aactgtattg  32280
cccaggccag ctcctgaaga actgtgaact atgaacatct cagcctagaa ggataatgtg  32340
accttcaatt tgcacaccat ccattgtctc tttcaaacta agagcctctc taagctagat  32400
aggccaagga ttattttttt aacttttatt ttaggttcag gggtacatat acaggtttgt  32460
tacataggta acctcatgtc atgagggatt ttgtatagat tatttggtga cccaggtact  32520
aaacctagta cccattagtt gttttttctg ctcctctccc tcctctcacc ctccaccctc  32580
agttagttcc cagtgtgtgt tgtttcccca catctatcca tgtgttctta ttatttagct  32640
cccacttata agtaagaaca tgcagtgttt ggtttttctgt tcccgattag tatgctgagg  32700
ataatggctt ccaattccat ccatgtttct gcaaagaaca tgctctcatt ctttaatatg  32760
gctgcatagc gttccatggt gtgtatgtac cacattttct ttatccagtc tatcattgat  32820
ggccattgtg gttgattcca tgtcttggct attgtgaata gtgctacaat aaacataaca  32880
tgtgcatgtg tctttatgat ggaatgattt ctatttcttt gggtatatac ccagtaatgg  32940
aattgctggg tcaaagggta tgtctgtctt taggcctttg agaaatcacc acgctgcttt  33000
ccacaatggt tgaactaatt tacactccca ccaatggtat ataagcattc ccttttctcc  33060
acaatcttgc aagcatctgt tatttttttta tttttgtta atagccattc tgactggtgt  33120
gagatagtat ctcattgtag ttttgatgtg cctttctcta atgattagtg gcattaagct  33180
tttttcatat gcttgttggt cacatgtatg tcttcttttg aaaagtgtct ttttatgtcc  33240
tttgccaaat ttttaatggc gttgtttttt cttgtaaatt tgttaaagtt tcttatgggt  33300
tctggatatt agacagatgt aagatgcata gtttgcaaat attttctccc attctgtagg  33360
tcgtctgttc cctatggtga tagtttcttt tgctgtgcag aagctcatta gtttaattag  33420
atcccatttg tcaatttttg cttttgttga gattgctttt ggcatctttg tcatgaaatc  33480
tttgccagtt cctaagccca gaatggtatt gcctaggttg tctttcaggg tttttatagt  33540
tttgggtttt acatttaact cttcagtcca tcttgagttg atttttgtat atagtataag  33600
gaagggatcc agtttcaatc ttctgtaaat gcctagccag ttattccagc accattattg  33660
aacaggactc ctttccctgt tgcttgtttt tgtcaacttt atcaaagatc agatgattgt  33720
aggtgcacag ctttatttct gagctctcta ttctgttcca ttggcctgcg tgtctgtttt  33780
tgtaccatgc tgttttggtt actgtagccc tgtagtatag tttgaagttg ggtagtgtgt  33840
tacctcccgc tttgttcttt taacttagga ttgctttggc aattcagact cttttttttgg  33900
ttccatacta atttttaaat agttttttct aattctgtga agaatgtcat tggtagtttg  33960
ataggaatag cattgaatct gtaaattgct ttgggcagta tgtccatttt aatgatgttg  34020
attctttcta tctatgagta tggaatattt ttctatttgt ttgtgtcatc tctgatttct  34080
ttgagcagtg ttttgtagtt ctcattgcag agatctttca cctccgtggt tagctgtttc  34140
ctaggtattt tattctcttt gtagcagttg ttaatgggat tgtgttctgc tctcagcttg  34200
actgttgttg gtgtatagga atgctcgtaa tttttgtaca tcaattttgt atcctgaaac  34260
tttgatgaag ttgcttatca gctcaaggag tgtttgggca gagactatgg ggttttctag  34320
```

```
ctataggatc atgtcatctg caaacagaga tagacttcct ctcttcctat ttggatgccc  34380
tttatttctt ctcttgcctg attgccctgg ccagagcttc caatactatg ttgcatagga  34440
gtggtgagag agggcatcct tgtcttgctc cagttttcaa ggggaatgct tccagctttt  34500
gcccattcag tgatgtgctg gctgtgagtt tgtcacagat ggctcttatt attttgaggt  34560
atgtttcttc agtacctagt ttgttgagag tttttaacat gaagggatgt tgaattttat  34620
tgaaagcttt ttcttcatct attgagatga tcacgtgggt cttgtcttta gttctatttg  34680
acccatcaca tttattgatt tgcacatgtt gaacaagcct tgagtcccag ggataaagcc  34740
tacttgattg tggttgatta gctttttgat ggctgctgga aaggtttgct agtattttgc  34800
tgagggctta tgcatcaatg ttcatcaagg atattggcct gaagtggtta tttttgtttg  34860
tttgttttgt tttgtttttc ttgttgtgtc tctgccaggt tttggtatca ggatgatgca  34920
ggcttcatag aatgagttgg gaaggagtcc ctcctcctca atttttggga acagtttcag  34980
taccagctct tctttgtaca tctggtagaa tttggttgtg aatccatctg gtccttggct  35040
tttttggtt tgtaggaggc tggggatttt tatcccagat ttataaataa agaaattgag  35100
tctcagagag aagtgacttg cccaaagttg cagctcatga aaataaaaag aagtggccag  35160
acatccgatc tttgtacccc agtgctcctc tccactttgt accccagtgc tcctctccac  35220
cctgcacctc ttgggcttgc tcttctggtg gaaacacaag gacctgaggt gaagctggag  35280
agtggagggg atggtggaga gggctgagga gagcaggctg gtgagttgtg ctttggggcc  35340
tcttagccca tggagataca tgaaggatga ggggaagggg ttggagcata gaaatggagt  35400
ttggggagca ggtaacagga gaagctggct gacctttcac aacacaaatt tcaggccagt  35460
cctgactaag atgctctggg ctgaagccaa ctgagcatga gctcccacag agaaaagagg  35520
tttgcacatc ctctccacat gggtgcccat gagccagccc cctactaagc acaaattcag  35580
ggttgctgcc ctaagcagct actggctgag tgatcaaagc aagtcaagag ccttgaaaag  35640
ttgaaagtgg ctgctcaacc agcagtcagt ccagatccta tctataactc cagtcctccc  35700
cagcccctc cttccccgat gagagtccag accagcctca aacagaaact atggagatga  35760
atcaaagaca gagccaagac atctttgcct gggaattcta gtgtatccat cataattggg  35820
tttattttac ccagtaaaga gagggctttc cactcacctc gggggggggg gcctccgagc  35880
cttcttataa cagtacaacg aaagtgaacc acagacattt gttcccttaa ttaacagcgt  35940
tgctcttttg ggtgggtctt gaactgttag cactggtctc ccacattctt tagtcagtta  36000
agggctgcca ccatcatgac atggaatagt aggactggga gaatgtactg aatcagtacc  36060
tagtgcagaa caaaaccctt ccatggaaca taaaaggtac aaatattaca ttcacagcca  36120
tgtttgttca ttcaaagagc atcttctgaa gactttctgt gtgccagaca ctgtccccag  36180
tgctggagaa aatagacaag atccctgtta tcatggagct tatatgctaa tggtggagac  36240
acaaaaaagc caaataaata aataaacacg ctagaccatg tcagagagtg gcaagtgcca  36300
tgaagaacct gaaaatgaga catggtgttg taggagatgc cttagatagg gaggtcctgg  36360
gggcagagta cctggaggtc tgagatcaga gcttttacgc aaacagagca ggtgcagaag  36420
ttgtgttcga ggaacaacca ggaggccagt tggcctgcaa ggcatgagcc agggaatggt  36480
ggtacaagat aaacttggaa attgtttatg ctctgtctct cacactgact tggccttcga  36540
tctcagctaa aatgctgctt tacttcctac tgtattggtg tttgcaacca atgcatgatg  36600
tgtcatgtac tttctactca gagaaaagtc ctctaccagt gttgatgagg gtgaaaagat  36660
```

```
cattcctact ccaggaagtc tctttggaaa cttggtggcg gaagacagga gagctaagag  36720
cagttcccat cttgtatgat ctaaggttcc cctggaagtg aagccacgat cccctgtagc  36780
tatcacagca tagggatgtg cggagatcct ggctccacat atagttggca ggaggtgagt  36840
ctcctttaag gtgttcaaat gtagcacaca cacacacaca ctctctctct ctcacctgct  36900
gtcttgctcg atgctccatc tcttctattg ctgtcctgag aaccaagaca gctccatgta  36960
caagtaactc aaaaccctga cactccctca cactgcccaa aacaagacac tgtcaaaata  37020
agtcacagat gtcacagttc cttgtcactc agttttcttg gcttagattt aaagcattaa  37080
atcagctcat cttcatctct cattccctag ccccagctct tccctgctga gttatctttg  37140
atattccctt gggtggattt cttctccctc cttcttctct aagaatctgt aagtttattt  37200
tctctcttac tctcactccc cttctcatcc tgcctcaccc cggtccctct ttctaagccc  37260
tcttctccac cgccctattc tagacaagat cttacaaaaa tacctttctt ccataatatc  37320
ttctctactt ccacaagaat tcccccagat tcctttcctt tttgttgaaa gggctgactc  37380
ctggcattta taattttaac cagcagaagg gcttgaaatg agaagtatga gtacttcgac  37440
tcttttccac acctgttccc aatctccact tttttttgaa tactgactct gtaatgggtg  37500
gagagtaggg gaaaagaaag agagatggga aaacaagaaa tgaaagggat ttttagtaat  37560
aaaagcaaat gaggagataa ggtaactgtg ttctgaacat cagggctgga gaggctgatg  37620
ctcatgatgg acacaggagg agaggcgcag tgctggctaa caacctggac acagcaccaa  37680
gcagattgta gtcacatgct aaagcatgtg ctatgccatc taggtgcagt agagatcagc  37740
cataggctgg agtttgcccc gaaggaggtg gcattgaggt cacacactgc agagtcatcc  37800
acatgacttt gtagattgga atcttatttt atcaactgct tacctgaaat aaacatgccc  37860
cacctgaaac ttaaatgcag cttgatcttt tctttggaag agtgtgatgc ttacgacagg  37920
aatgtgttgc catgggatgc tgctgatatt ttgtccacac tcctatctta gcctttcgcc  37980
actttgaagg tgccctcttt ctccaggata aacatcttca acaacgggga ctttccaaca  38040
gagtggacca ggtgaatttt tttaactctc tggaatttga tgttatgtga gatttctaac  38100
tgtggaattg cgctcacatt catgttagaa tattatgtct atcacatatt cttatcagca  38160
catttttgta gccagagatg tatgcaaccc aagtgtcatg agcccactac acctaagagt  38220
ttagacttac taattcactg aaaacttaaa agaggccagg atgtagtaga ttgcttggtg  38280
atagatagca gcctactcac cctgtctctt gagaaataac ttcacttctc tcccccttat  38340
cctaattctc taaaacagtc ctatcttcca atggataaag tacagacaga tatctggtta  38400
cctttattgt aaacatctat agttcaccca agagcctaga tgaagcacct cacatagcat  38460
gccaactgct ggcccgtgta tttagtctat gtttaatacc cttttactta ggtttcttgc  38520
cctgtaaatt ggaattagac taaaatctgg tgtcttgagt ttcacagcat attgagtttc  38580
acagtatgat tttagcctgt ctactcatct tatatctgat agcagtaaag aaggtaaatt  38640
cattcattca tatattcctt tattcattca ttcatgtaaa tttattgagc atgcattttg  38700
tgctaggcac tgttcttggt atggtccaca gctctgaaca taacaggcaa aagttcttgc  38760
ccaaatggaa gttacattct aggaggtaat ataaagcaag acaaaaatat ccagtgtgtt  38820
agacagagat atgtgctagg gagtagtgga gtagtggggt gcagttttaa atagggtact  38880
cagggaaagc ctcattgaga aggtactttt tttttttttt gagacagagc caccttctgt  38940
tgcccaggct agagtgcagt ggcgccatct ccactcactg caacctctgc ctcccagatt  39000
caagcaattc tcctgcctca gcctcctgag tagctgggat tacaggcgca tgacaccaca  39060
```

```
cccagctaat tttttgtact tttagtagaa acggggtttc accatgttag tcaggctggt  39120
ctcgaactcc tgacctcatg atccacccgc ctcagcctcc caaagtgctg ggattacaga  39180
cgtgagccac ggcactgggc cgaagttacc ttttttaagg tttttttttt cagccaatgt  39240
taccatggtg taatttatct tctgtaaaat tcccacattt taagtgtaca gatgagtggc  39300
ttttgactaa tgtatacatc cactacccta atcaagctac agaaaatttc catttccttg  39360
aaacgtccct ctttcttttt catatttagt ctcctactcc cactcaagct accacagata  39420
ctatttacat cattataggt tagtttttcc tgtcctagaa tttaatatgc aactatgcat  39480
gttaagtctt ttgaatgtgg cttcctttgg ttagttgaag ccatgttact gcatttatca  39540
gtcattattt ttttattact gagtctattg tatgaatgtt ttataatttg tttactcagt  39600
tacttattgt ttctattact cttcattctt tgtgtggttt cttcctggta ctattctctt  39660
tatactgaag aacatccttt agcattgcct gtagttcaga tctgcttgtg atgaatcttc  39720
tcagattttg cttatctgaa aatgtcttca tttcaccttc aattttgaag actattttta  39780
ttcaatttat atagaattct gtgtgaatag gatttttaca tctccaaaga tgttgtttca  39840
ttgtcttcta gcctctactg tttctgatga gcactagtaa taattcttaa ctttgttcct  39900
ctgtatgtgt ctttttcttt ggctgctttt aacattctac tttatcttca gtgttcagtc  39960
atttgactga tgtacttagg tggggcttcc tttatcttca tcttacttgg gcttcgtgga  40020
tttttaagtc atttttttaaa attttgggaa gctcttggcc actatttctt cagatatttt  40080
ttctgctctc tctctctctc tcctccttct gggacaccaa atagacgtaa gttagactgt  40140
ctgatattgt tccataggtc tttgaccctt tgttcatttt ttccttaata ttttttattt  40200
ctgttcttca gatttgatat tttctactgc tgtgtctcca acttcacttt ttcttctatc  40260
atctccaacc tgctggcaag ctcttccgat gaatgattca cttcaggcat tgcacaattc  40320
tagaatttcc atttgtttct ttttagggtt cccatttatc tactaaaaat tcctcattta  40380
ctcacaactt agggccattt gtctctaatt aattaatata ttttttgaat atatattgta  40440
aaacatatat gttttaatgt ctttattttc taaatccaac atttggtcca tcttagaata  40500
gttcctttgc tttcattttt tactatggat tacactaccc ttgtatggtt tttgttggtt  40560
tttatgtcta gtgatttatc attgaatact gggcattgtg aatgttacat tgtagaagct  40620
ctagctcagc actcttcaat agtacctgca atgaagaaag tgttctgtgt ctgcaccatc  40680
caataggaca gctgctggcc acatgtggct attgaacact tcaatgtgac tagtgtgact  40740
gaggaactca attttaattt taatctaaat gttcgcatat ttacacccag aacttctcaa  40800
cctctgttat actgtttcag tctcaacctc atagcagctg acatctggca agcctctgat  40860
ggttttccct gcacatatac agtcaagccc tcagccgtgg actgagggag gggcttccca  40920
tacgcatgca aggacttcta gggctttgtc tttgcacaga ttccagctat ttcagttgcc  40980
tcagattctg atccctgcct cttcagccca gcaagagtcc tgtgctctgc tcaaactcaa  41040
gtctccaggc agacagctgg actactgtgg ggctcacctc acactcccct ctccccattt  41100
ttgcagtctg gtgttgttta ttttccattg tctgaaaact atcttgcttc acataccttg  41160
tcctgttttc taattgttta caggagacga aatagtctga aactagtcat tccatcacag  41220
tcagtagcct gagaagtgtc ccttcaggtc ataatccaaa gaagattgtg ggataactaa  41280
ctaggggaag agagtttcaa acagggggac gtcaatggaa agggtgggag gcagaagcat  41340
gcctgcctga cttagaacgg tagggaggca acatggctga gcacgagagc taaggacaga  41400
```

-continued

```
gagagtagga cagtaggtca gagaggcatg gtggtgggaa agacactgtt tggcttcata  41460
ggccattatc tgcactctag cttttactct agtgagatga aaagtcattg gaaagtttgg  41520
ggccaagaac tgatttaggt tttaacagaa tcacactagc tcttggaaac acctccagga  41580
caaaagcagg gtgctgaatt agaaggccat tgagagaatc tattgactaa acttgcaaat  41640
ctaattaaaa ttctgaatta ttcaaggtcg atggctgagt ttttattcat ttcctagagt  41700
ttggggctca cgaggagaca ggtaccttag tgtggaagat cacatcatct gaagtctgat  41760
tggctgtgtg actttaggca agtgacttca actgtctttc tttatttcta tacaatggaa  41820
ataataagaa tacctattac ataaaagata ttatgacgat taaatgagat aattcctgtc  41880
aaattctcta aattatacct ggtgcatata attcctgtca aattctctaa attatacctg  41940
gtgcatatga agtaagcgtt ctacaaatgt taactattac tatctgagag gctgaatgtc  42000
tgatgattat tactgtaccc tgtggacatt gacattgatc tactctgtga ataaagggta  42060
ccacactcaa ttctgattct caagagatat gtgcaactgg catagaaaaa atatctcaaa  42120
aacaagactg aaggaaatta gagccaagta gaggtccatg ctgtcagctc ttgcataagg  42180
agggaaggct gaggcgttat tcattcaggc tgaggagatc tttgaagact attgagaggc  42240
aatgagttag ggtttgaaga atggattaga tacagagact gtggaaaggg aagggaattc  42300
tgaaggtcac ctgaacttgc ggccatcact aatgtttaaa gagcttctta aattcaaagt  42360
gaaaaattat gagttcaaca tggttattat ccccttaagc tcacatttgg aatcaaccat  42420
aagaagtagg atatcattac cgtacagctg aatggcttta ttaacttatt tttggaaatt  42480
agatgacaaa tgcaagcaca gtcttgttta acaagaagca tttcccagtt gtttctatga  42540
gaatttaaga aaggttctag aaatgcaaat agagagaacc cagtcaagtc ctgaaatctc  42600
agtgcagcag aattgagaaa gtgaataatg gcccacaggt cacaggaagg caatgaatac  42660
gctaatcaaa ggttgtgatt aatgaatgtt gtctcacatt tcatctggca taacatgtgt  42720
ccaattgatc atttttagca tagctcatca gaggagaaaa acttggtgaa atatgatctg  42780
gtggggcagg atgcaccagt tgcacaacag acataagctg ctccactttg gccacacctg  42840
tataaaacat gagaaaagta ggttttcata gaggttgagg catatctaac tacctcaagt  42900
agaaaaagag tatccattta tttaatgagg gagagagcag tggaaaggct cagcctcatc  42960
caggctgaga agtgattacc ttggaaatgc tgtttgtttt gattgagaaa gtcagctgag  43020
aatgtatttt aaataggcag aaaatatatc tatcaaagaa atactatgca gtcatcaaaa  43080
agaatgaggc atgtttggta ttttaatagt tatctccaat gtttataata aagtgataaa  43140
tgcaatatat agataattat atagtgtatg acaattatga gaaaaatgaa atgtacatct  43200
gcacatacat aaggttgcac acacaaagga tgcctctggg ggagggaaat tgggtagctg  43260
ggactgaaaa taaagataaa caggagactt atgtttcagt ctatatcttt tgaatttatt  43320
tgtatatgca cctagatcca gatagtttta tttctcggtt gaaaaaatta aaaaagaata  43380
ggaaaaaaga aaataacaac catagtttaa tttttttttt ttttttttga gacagagtct  43440
cgctctgtcg ccaggctgga gtacagtggc acaatctctg ctcactgcaa cttctgcctc  43500
ccaggttcaa gcaattctcc tgcctcagcc tcccaagtag ctgggattac aggcacacac  43560
cactacaccc agctaatttt tgtattttta gtagatatgg ggtttcacca tgttggccag  43620
gatggtctcg atctcttgac cttgtgatct gcctgccttg gcctcccaaa gtgctgggat  43680
tacaggtgtg agccactgcg ctcagcctaa tttaattttt aaaagagctg gaatgcgtcc  43740
attcctttcc catttgcaaa gggctccaga atcatcccag atgatggctt tcaaaatgat  43800
```

```
agttcaataa gggagattta ggataaagtg cttctttctg atgcttcact taagggtccc  43860
tgagagtatt agtttgctag ggctgttgtt aaaaaacaaa aacacaaact gagtgactta  43920
aacagcaaac atttattgtc tcccagttct ggagactaaa aggctgagat caagggtgtc  43980
aggaggattg gctcctttcg agggctgcaa gggagaacct gtggctctct cctaacttct  44040
ggtgtttgct ggccgtcttt ggcattcctt ggcttgtaga ggcatcaccc taatctctgc  44100
tttcatgttc atgtgtcact gtccttgtgt gcatgtgtgt ttatgtccaa attttccact  44160
tttataagga caccagtcat tggattaggg gtgtgctcta gtgacttcag gttaaccaat  44220
gacatctgca acaaccctat ttccagataa gatgacattc tgaggcactg gggcttagga  44280
cttcagcata agaatttgga ggggacagca ctcaactcat gacaccaagg gacacttacc  44340
cagagttaaa ctgcttactg aggggaggtt tttgctatgt gtctatgaag cacagatagt  44400
aacatgcatc tcctcatgcc cgagatgtat aaagtgaata cacgctggta tgattgaaaa  44460
ccttaatatt ttttaacgca ctaccatcct ctgaggaaag aagagagctt aaacttgctt  44520
aactaagaac aacagcttgt tggagcgata aatccatgaa acaaaactca gatcccctgc  44580
tcttccctcc ccatccatgc cagctaaagg catgtgcaca cagcaatgtt tattaaacac  44640
ctactgatgc ccgatactgc actgagagcc agggacggag ttggacagaa catcctcctg  44700
cccttcaggt ggagaaaaga cacataaaat aatgcaggca tgcactaagt gactatgctt  44760
cagtcaacaa cagaccgtat ataggaccgt ggtcccgcaa gactatgatg aagctgaaaa  44820
tttcctatca cctagtggca ttgtagccat cctaacatca cataataatg cattgctcac  44880
atgtttgtgg tgatgctggt gtcaacaaaa ctactgcatt gccacaacat ataattgtgt  44940
acagtctata atatttgatg atagtgaatt actattttac tagtttgttt ttactatagt  45000
atacttttaa tcattatttt agagtgtaca atttctcctt atttttaaaa attaacttta  45060
aaacagtctc aggcaagtcc ttcaggaagt attccagaag aaggcattgt tttgtttttg  45120
tttttgtttt tgagacagaa tctcactctg tcacccaggc tggagtgcag tggcatgatc  45180
tgggctcact gcaacctccg cctcctgggt tcaagagatt cctctgcctc agcctcctga  45240
gtagctggga ccacaggcat gctccaccac gtccagataa tttttgtatt tttagtagag  45300
acagggtttc aactattggc catgctggtc tcgtactcct gacctcatga tccgcctgcc  45360
tcagcctccc aaagtgctga gattacaggt gtgagccacc gcgcccagcc aagaaggcat  45420
tctaggagat ggcaggtccc tgtatgtcat tgcccctgaa gatcctccag cagggcaaga  45480
tgtggaggtg gaagacagca atactgctga tcctgacccc atgtagggct aggctaatac  45540
gtgttctagt gtctttcttt ttaattacaa aagagtaaag aagttttaat ttttcttaag  45600
tttataaagt agaagaagtt atagtaagct aagggtaatt tattattgga gtaagaaaaa  45660
ttgtttgata aatgtagtgt agcctaaatg tacagtattt ataaagtcta cagtagtgta  45720
cggtaatgtc cgaggccttc acattcactc actgactcac ccagagcaat ttccagtcct  45780
gcaagcacca ttcatggtag ctgctctata cagatgtgcc actttttacc ttttatatcc  45840
atattcatac tgaacatttt ctatgtttag gtaggaagta tttacataca caaatactta  45900
ccattgtgtt gccattgact acaatattca gtacagtgac atgctgtcta cttttgtagc  45960
ctaggagcaa taggctagac caaataacct gggtaagtag taggctctac catctgggtt  46020
tgtgtgagta cactctatgc actttgtaca attacaaaat catctaacaa tgcatttctc  46080
agaacacgtc cccatcgtca agtggcacat ggctataatt atatcactat agtatagtaa  46140
```

```
atgtagagcc atgaccaagg cagaaagaaa accgttaact ccacttggcg atgccaagga  46200
aggtggccta tgagaagtgt cataagagat gactgtgaaa ggctgactct gagggaggtg  46260
agggcaggag gaggtgacta gggaaaaggg agtcctgggg catgtcgtgt ctcaagcggg  46320
ggagcccaga cagactcctg gttaccagga atggagacag gagttggaag taaatctcaa  46380
gtgcagacga gcttctgaag gagcttatct tcagcctgag gatttgggac ttctttatcc  46440
tccaggaaac cctggaagat ttagaggagc cacttggtca gatttccttc tttgaaatat  46500
attagattgg tgcaaaagga attgtggttt gggactgtga attttagatc cttataacta  46560
gactcaaaca catctttatt aattcaaata ggaacaatta ctatcaacac atttttgcca  46620
atgagaaata agtttgttta ttcctgtagc ataaaggtct gtgctttggg attcaatgaa  46680
cacttggaaa gcattttctg cacactgctg gttgtggaag caaaaagttg ttgagatgct  46740
tgaagaagtg gtagtcggtt ggcgagaggt caggtgaata tggtgggtga ggcaaaactt  46800
tgtagcccaa ttcgctcaac ttttgaagca ttggttgtat gacgtgcagt cgggtgttgt  46860
tgtggagaag aatttgtccc tttttgttga ccaatgccag ctgcagccac tgcagttttc  46920
agtgcatctc attgatttgc tgagcagact tctcagatgt agtgatttcg ccaggattca  46980
gaaagctgta gtggatcaga ctggcagcag actaccaaac agtgaccatg accatatttt  47040
ggtgcaagtt tggctttgga aagtgctttg gagcttcttc tcggtccaac cactcacctg  47100
gtcgtcactc gttgttgtat aaaatccact tttcattgca tgtcacaatc cgatcaagaa  47160
atggttcatt gttgttgtgt ggaataagaa aagacaacac caccaaatgg tgattttttt  47220
ttactttcag tcaactcatg aggcacccac ttaccgagct tttcaccct ttgaatttgc  47280
ttcaaatgcc aaagaacagt agaacagtcg atgttaagtt cttcggcaac ttctcgtgta  47340
gttgtaagag gatcagcttt aatgattgct ctcaattggt cattgtcaac ttccaacagc  47400
tggccgccac actcctcatc tttaaggctc tcgtcctctt tgcaaaactt cttgaaccac  47460
cactgcactg tacatttgtt agtggttcct gggccgaatg tgttgttgat gttgccagtt  47520
gtctctgctg ctttacaact cattttgaac ttgaattaaa aaattgcttg aatttgcttt  47580
ttgtttaaca tcatttccat agtctaaaat aaacataaaa taaacagcaa gtagtaagtc  47640
attagcaaaa aaacataaag cgagaaatgc ccattaaaat gatgtataac ataaccacat  47700
ttatttaaga atgtattcca atatcaaaca gcaaattcca acaatgcaaa aatgcaatta  47760
acgtttgctc caacctaata ttttcagaga gaatgaataa tggggaaaga aactgaagag  47820
aaagtaacag gcaaggagat atttgcaggt gagaaaaaaa ttatgaccaa tagtctaaac  47880
agtggtagcg gtggcatgaa tagagaaaac aggggcaccc ttatcttgcc cgatttgtac  47940
aaattcagtt aattctattt taacttattt atttgtgtta tttttcagat gacaaaagat  48000
aatacatact cactgtaaaa aattttggat taaaacattt aaaatgtata aggaatacaa  48060
caaaatcgcc ccttaattac tcagaaataa gcattcttat taatgtttgt gtatcctatt  48120
aagttctttt caaaatcata tctatgtaca tatatagtca tttactcaga cttttataaa  48180
cagctttttc cactttatat atttccctat tagtaacttt atagaacttg atttttgatt  48240
gatgtgctat atttatttag ctaatctaga ggacagattt gaaaactgtt aaggaattat  48300
aaattgcagt aggaggtgat taattagctg atggggtatg agggaaagga aaaaaactga  48360
gcaaccccaa cttttgggct aaagcccttc tttttacagc tttcttcttg ttttggccag  48420
aactggaggg tccatcttgt gaaaaggagg tggcagaagg atctgtgaat atatgttaca  48480
ttcaacctca acgatggtga acataagcac tgttcagggc atgcagacac agccccaggt  48540
```

```
tcacaagctg ccagaacatt cattaaagtg gataaaatgg cctgcaatga aatcctcaaa  48600
ggatgtggta gataaagcaa atgccctcct aaacacagct gcaggctgcc aaaacccccca  48660
gccacacctg gtgagcattc tcagagagga gcaagtagag acagccttcc ctgccaggag  48720
ggagtccctc tccaggctgt gtggccctgg ctgtggtctc tgcacctgcc gcttgcctga  48780
tggctttctt gcattctggg agggcatgcc tgtccgagca cttcctctgc tcagtctttc  48840
catagcgaga ggaggaagag caagaggagt caatacctgt gaggcacaat aaatccaact  48900
gaggtgaata ataaagcgta ttcatttcca aaaacttaga agacaatgtt agggcagata  48960
ttgggaaaga aactgactaa ttgacccagg ctttcatttc aggctcagtt tggtttccat  49020
tgcctaacac aactctccta cgctcctgtg cctcttcaga aatggcttct gattgaaaca  49080
caacctgtgt cttttgattg attgggaact gaaagatgtt cctcttttaa tctcatggat  49140
ggaacccaat atatttcact ttcttctttg tgctgataga caaagcctcg gaaaaaaatg  49200
ctatttaaat aatagctttc actgacagta gactcatggg aaaattgtcc ttccttcctt  49260
ccctccctcc ctccctccct ccctcccttc cttccttcct tcctttttc cttccttcct  49320
ttttctgaag tgtatggacc attattgctt ttactttgtc ttatttggct tatgggaaac  49380
cgtgggactc ctcatatatc tatgtgctga gctgacataa gggggactat taaccgcttc  49440
tatgcagcat ttattttgct gaagagaaaa catggagtgt ggctttgttg aaaagctccc  49500
catcattcac agttcactga aactcatcca ttcaatcatc aagcacagat ctacctctgc  49560
tccacttgtg cctgggatgg tgctagatgc tgagaacgtg ccattgccca catgttctca  49620
gcatctagca gaagaatcag ttccagagca cactcaccca gcttctggaa tctcacaggt  49680
tagttgggag gtcacttaaa tagaacacga cgtgtgctgt aaacaagtta agcacagagt  49740
gcaaaggagc atctaattca agagctgctt aggatggttt tgtagagaag gcatgtatga  49800
ttctaaaatg aaggcatggc acgtgcaagg ctgtggtgtt acaagagaac ttggagcatt  49860
tggagaagcg gacgtagcgc aatgtgaggc gagagatgag agtggtacat cctagcaagg  49920
aaactcccag tcttggaggt aatggagaac cattgatgaa ttttaaggat tttaagaata  49980
ggcataatgt agtcaaattc acactcagtg aagtagtcct tgaaccattg ttcactgcac  50040
cacatggtca cagtcttatt aagctgacag ttgaaagttt cattggaaaa caaacctggc  50100
agttcttgaa atggaaacat gaaggtaatg cagggcctac aactctaggt tgcaaaaaga  50160
tcaaggacat ttcatagatc ttgccttact tttcctctta gggcaaaaca cacattacaa  50220
agaccctcaa atgatgctca ctgttaccaa cattttttc taatcttaca tctttcatcc  50280
taaatgctca tgaaagacat gttgcttctg gttcaaactt gggccaatga caatgctttt  50340
catgtttgtt gacccaataa tcagccattg cactcaaaga cttagagcgg atcagtttaa  50400
aaacagctat tactgcattt gaactacagc tcccctccag ccctctgtat gtctgggctt  50460
gctgctgcca caggaaagct cctagttcta cccagggagg gattgtgttt ctcagcctgt  50520
ttcagcacca acccgtaaaa gctgcttatg tcaaatgtca gttaattgca aacttacccg  50580
tgaggtttaa ttgaccttat tccacaacaa gtgtggccat atgaaataaa cccaaagatt  50640
catgatcagg caggtctaag tgttgcattt tggagaatgg caaggggtcg tttttggaag  50700
gagatggagc acctcctatg ctaatctcat gagattagct ttaaacatct tcagtttcct  50760
ccagtcaata atttgttatg gaactgtcat tttacattta aacatttttt gaaccctttt  50820
atttttgcac cctttagcgt tgggataaaa aattcttaag tcatatctcc tccccactcc  50880
```

```
caccaccgcc acactgtttt atataatact tccttttact attttactgt tttaaattta  50940
tctaccttcc tgtccacacc ccccaccccc gcctcaccct gttgcttcag aaaaactcat  51000
gatttgtgga ggagtaaatg ctcacaacta tctattctct cagccctaca tctctctcaa  51060
cttgcgtctc tctggacaga acaattttta tctttttagc aattcttata ccgcagttcc  51120
ccttcactgc cataattctg gtgaactcac tgtttgagat cagtctccac tgttccccat  51180
ggagatcacc aaagccgata ctaccagaag ctcacatttg agccctgcag aacattgagg  51240
aaaagagcat tttgggtttg gtttgatttg tttcagctat tttttcccct ctctagaaac  51300
atgggtaggt ggagcttacc aggtgaggtt gctgactttc ttctctagag tctgtagagt  51360
agagtatcta cacaatattc catttgtgaa aatttgcaca atagactaga taaacaacgg  51420
attacggaga aaacagccct aatactcaga ccctaaagca gtgctaggtt aacaacaagg  51480
tgcttacttg cttggggtgc cagccaaagt cagaacaatg aggctttcat ggacttatcc  51540
agaattttat aactgataaa aagaaatcat tttatgtttt gtggtttagt attgctttaa  51600
tctgggttta tatatgggag gaggcaccaa aatatttcag tgcttgggga cttagactaa  51660
aagccacaag gaggaagaga aaaagcagga aacaggctgc cctttgtcac ggaccttgtc  51720
tttcctggca ctctttggct ctggttttca cagacatgag tctgatgaga atgctgagtg  51780
attggcttcc agtctcagca gagtgtatat gaggaaagaa agcactggtt gcctttgcta  51840
cgtctagcct atgtctccac ctcccccagt gtatcctagt tagcccctcc ccaagcttac  51900
cccctggtca ttctcacggg gtcctgtttt ttaccctagg cctcttagtg ctctctgttc  51960
ccgccaaaat atctttcaga tccgttagtc atattaaatt agcaacagct ctttacaagt  52020
taaaggtctt ctccctccca cagataatgt cataccaaca cgggttaaag tcttagctaa  52080
agaaggagtg tctaactttg gattctcagt cataaaccag tggaaaggac atctgactag  52140
ggggcaggtg atctcagtgc atctaagctc ccgctgtatg gactcgtgct gcctaacaga  52200
gtagctacca gttgcatggg acgattacaa tttaattaat taaaattaca taaaataaaa  52260
aactcactac ctcagtcaca ctggccacgt ttgacccact caataaccac atgtggctgg  52320
tagctcccac atcggacagc acagatactg atcatttctg gtctcacagg aagctcccca  52380
ttggatggtg caaatctaag taatttcctt cttggcttat gcaaaggcaa ggccctcccc  52440
agtgcagggt tgctcaggct tagcactatt gccatcttgg actggattct tctttgttgg  52500
gggtggggat gtcctgtgca ttataggatg tttagaagcc tccctggtct ctatccccta  52560
catgccagta acagccaccg cccccccccac ccagttgtgg cagtcaaaaa acatctcgag  52620
acattgctaa atgtccccta ggggacccct acactgaagt tggctggagc tctggggatc  52680
agggaggaca tctgcaagcg tgcttatgag ttgtaagctc taagagggga gggacattgc  52740
acagggcagg tcaggcacat tgtaagtgct cttaaaacat tacagttgag aagaatttca  52800
gagtaacatt tatagccaag aaagatattc ttcccccaac ttgggcattc ccttgatgtt  52860
aaattgtcct gtgcgtcaaa accctaaaga actgcaggga agcctataac cccaaaggaa  52920
ggcagagaaa ggtcctgggg gacaggttgt ggggtgagtt aacttattcc agccaaggtg  52980
aaggagttgc cccgggcttc actctgagac ttggagccta gtgtgctaag ctcccagttc  53040
ccaaagtgac cattcccacg ctgaatgtca ttactgcctc atcagcagct tgtcagctgt  53100
aatttctaat cccaagccgg gtctctcttc ccaggaccaa agtcataaag atgtttgccc  53160
ttgcacgggt gtttgacatg tgctaggcca tatttgtgca tttgtcttag ggccctcttg  53220
agggcttagc acttctctct gacccaggca agactttatg tgctgtgcat tcctcctgaa  53280
```

```
catgatgtca tgcttgtgcc tcaccatgga attctgcagc caggcactgg ggctcaagtc  53340
caaagacggg aagacttaaa aggctcaaac aagcaaatgt ttgtcattat ttaagatttt  53400
aagacaactg aattctgaaa tgtttatggt cctggcctcc tttgtgggtc atcaatgacc  53460
tcttcccttt taggaggtat ctcatggaga gggcgtcttg gcctgctccc ctctggggcc  53520
actaactcac accagagctg actcaaccat tccaggggaa gattggtaag aagtttattc  53580
accagacatg tctagctgaa atgaatgaaa tcaaactcag cagaagtcaa cacttagcac  53640
ggaaggcaaa gtagagacaa agggtcaccc ggctgctgca caccggcctt tagctttagc  53700
tcaagttgtt ctgctttaaa ggacaatgcc aatcatctca taagtaaatg aagacaatga  53760
ttcaacagtg ctgtcaagtt tgagagaaaa gagaagccat ccctacaccc aacacttaat  53820
atattgttag gcttggggtg ggttgcccag tgccttctgg gatgacctgt gctcttttct  53880
tttatccagg agcaattaga atcaatctgc ttcatctgga agttctgccc aagggtctgg  53940
caccatagga agttgtccag gattatttta accctgttac aggatccaag taattcctga  54000
tatgtatgaa tgtaaagccc attcttgtat tcagcgtttc tcagtggaga tacttttgac  54060
attttgggtg ggatgaatct tccttatggg agtgtctcca gcacacaaca gggcacagaa  54120
tgcaagtggt gtcctcctct ggtcattgtc acaaccatcc acccaccaat gcacgcactc  54180
ccaggcacca cgtggtgggt ggcactgccc ccactgagca cattgcaagc ttattgccac  54240
agaaactaga atgctagtac tacccatggg agcaggcagc aggcctgttc tttatttatt  54300
tcactctttg attctgcaga cctcagattt acccactgtt attgatctgt ggaaggcttt  54360
tgactgtcca ttttcccccct agggtgagct catataagtg gaagagaagc aaagagatag  54420
ctgttgcaca gctgttccat tcctgctccc tgttgatctc ctaatgttgt gaatacaccc  54480
taagaattct cccaggtgtg gattaagacg acttaagcca ggaggaaatt tgccccaagg  54540
caaagcatcc tcttttccct ctgcagaaac tttgtccagg caccctagca tgagggattg  54600
cctccccatc taacatcttc acacaggccc tcttgctgga cccacattaa tggacggcag  54660
cttctgactt ccagcaggcc ctctttcact ttccatcgtc tttctctgtc tgtgttttat  54720
agcatgaggc actgaagtta tcaggtgatc agagaagact agaactggat ataaaccaac  54780
agatcatcga gtaacgtggc tttcaacctc cagacttcga ggtctattga ctgtgaagat  54840
actggagggg actcaaaagc tattatcatt ttctaaaatg gtgtcagaac tgttcgatgt  54900
actttaaata ggactcacag gtgtattaaa atgtcaagtt ttcttttgcc taaaactgta  54960
tgaacgcggt gcaataactg gttatttcaa tgctgacaaa agttctgatt gacagaactt  55020
gcactcatta tatatcactc agtacctaat tgatatgata attttgaaat caggaagact  55080
gtggagagag attagtaaga ggtccttagt ggtaaaagga ctaaggaaat tgtagtccga  55140
ttgtctcttt cttcaaaagt tgaggcccag agatgttaag tgacttgctg acagttggat  55200
gattaatgcc ctagaactat ggtggccatg ccacaccagt acagtcccta tgtgctcctg  55260
ttgtcccagc atcatcacca gtaggaatcc ctgtcgctct caaaagaaat ccagtttgat  55320
taataagtta catggtcact ctacctaaaa cccaagtctc caactgccaa ttcatccctt  55380
ttctcaccac acaactctac ctctttctct ctttttcctg gttctcaaaa ttgtttctcc  55440
tatctgaatg catctcttat gttttcacaa gtaagtcatc ctcaaagttt gggcgactat  55500
aaatgacagc tccaaatcca gatggcctga accgtgggac cttttgttcc tgagtggagg  55560
gggaaggaag atggtacggg gcaggggcag ctgggcccca ggcaagccca gggccttgcc  55620
```

```
caagcctcag acagccaccc atgtgctcct gtgttctcag tgacaaaggc caggaggggc  55680
agagggaagc tggtgaattt ttatgattta aaaaatatga atccacactg gatagaaaaa  55740
aatacaatgt aaaacaccac ccatgccgct ctgaaagtct agaatgtcca ggtgactcca  55800
gaatggtgtt catagacttt ggcaatactt tgaaaacctc tgtgaacaat aaaagttaag  55860
catgagaaag aaaatatttc ccataagaaa atgtaaaccc ttttccttgt ctgccacatg  55920
gggccaaaca taccagtgtg tttaattggt agatcagtac cactctcaag aatttcttag  55980
atgccataaa cacagaatgc aattttggtg gagtcccaca gcaagctata atcatgagca  56040
gggaggacct gggttcagca gctgtgcttt attcctgtgt tgctttgaac tcacagcaga  56100
gctaaatacc cggctcataa gaccttctga taacaaagtc cagcggactt gggagaaact  56160
tggggttttt tttgttttgt ttttcctttt tttttttttt ttgagatgag gtttttgctc  56220
tgttgcccag gctagagtac agtggtaaga tctcggttca ctgcaacctc cgcctccagg  56280
gttcaagaga ttctcctgcc tcaacctccc aagtatctgg gattacaggc atgtgccacg  56340
acacctgtct aatttctgta tttttagtag agacggggtt tcgccatgtt ggccagactg  56400
atctcgaact cctggcctca ggtgatccgc ccgcctcggc ctcccaaagt gctgggatta  56460
caggcgttga gcctctgcac ccagccaaga aacttgttaa aatgaaaatt gggtctatgt  56520
agactgggag attaaaaatg actccttttt aatgtaagga actttgcttt actgtttcat  56580
taaaaggttt gccagtgcaa accgaaaatg taggagccct ttttcaaaag caggaacaaa  56640
aacaacctct gctgtgaaag gtactaaaat aaaagccgct ttttttcttc tgcagtctct  56700
cttttgactt gtcacaaggc ttttaaaatc attcttattc gctatttaat gccactctaa  56760
gtaaaggaaa attaaaattt taaattgtta gcatgaatct taccattcat ctttatattg  56820
tgcaaagcca gctttaaacg aaaatataag agcatttaat ttgtatgcta aattgttcca  56880
aatgatgcaa tttgcatatt tcattcttac cagaacagtg gaaaatgctg cacaaaacta  56940
attcaatgct tttatttcgc ttctcaataa tgcacattct tttttttttt ttttgagaca  57000
gagtccctct ctgtcaccca ggctggagtg cagtggcatg atctcagttc actgcaacct  57060
ctgcctcctg ggttcaaatg attctcatgc ttcagcctcc cgagtagctg ggattacagg  57120
cacccggcac cacaccctgc taatttttgt atttttagta gagacagggt tttgccatgt  57180
tggccaggct agtctcaaac tcctgacctc aggtgatcca ccacctcggc ctcccaaagt  57240
gctgggatta caggcgtaat ccaccgtgcc cggcctgata catgcacgtt ctatcaatgc  57300
tctctacctt tggcttactg acaagtaagg aagaatttaa aaaaggccta tgggttgcct  57360
tatctttcta tttctttctg tgtcttcatt ttcagtttaa gttgtttgca aatgcaaaga  57420
agtaacatga gtaagaaagg tcaaaccaag tttccttggt catatgtgtt tcttagaata  57480
ccactgctgc ctttgtgttt gaagcaagtt ttggttttca aatggaaagt gtggcctctc  57540
agggctgtca gtgtccctcc ccctccccag ctaactcatc atagacaaaa cacacttggg  57600
agtcacttag aagcttcatg aactcccaca cattgtgaat acaccagaat tctgagttca  57660
tggcgaatgc tccatgtgaa tagggtgaca agaaaggaca ggcacacgta tctcctgtgt  57720
ttctgctcat tccatgctgt ctcatcagaa gtcacttaca aaatacaagt ttcaagagga  57780
aattattaca attttaatac ggtggccgca gagcatgaaa cccatcaaga agtccttctg  57840
agcaccaagt cctatgcaag cacacaggtg acgtgccatg aagctggccc tgcacgtggg  57900
gtggcaccat gcatgaaaat ggtgaagaga tcccagggga tcgggcggtg cactgagaag  57960
gaacaccagg catccagacc tgcacacagg gcagtgtgca cagcaggagt ccagggcagc  58020
```

```
cagagattca ctaccagagg tacagcccga gagcacatgc catgccagga aagaggagac  58080
aggcagagac aggaagatca aagtggaggg agaaaagcca gattactggt taactaagac  58140
actcagccgg cagtgtcagg agagagccac aaaatgaagg caagggaatc acggaagcca  58200
gatactagca aaggggcatc ggaaaccagt ggccacgtgg ctctgatccc aagcactgag  58260
tgccctcccc ggcatccttg tggggctgtg aggttcgttt catgtgtctg gacgtggctc  58320
ctcagcgtgg tcttccagct cctctcatcc ctctaccctc ttggtaaaaa caagacatct  58380
tctaggagtg aggcaacctc cccgctgccc tgtagagagc cacacttctg cttttctagt  58440
gttctaagaa tgcttttcct gatttatcat cgttaagaat gggtgggaaa ctagctatgt  58500
tgaacatgtg acgtgcaagg tggttaatgg tgatccacca atgagcagga cgccaggacc  58560
ttgtgcaact gggagacttt gcaacaccac agcggaaggc tgtccctcag aggtttgtag  58620
ccacctaggg gcctccttct atcacccatg actaagtctt ctgcattagc ttagagcagt  58680
gtttttcagc cttgaaacca tgaacatttg gggccagaca gttttctgtt gtggaagact  58740
gtccagtgta ccgtaggatg tttagcagcc tctctggcct ctgttcactg catgctagta  58800
gcaacccccct ttccctaccc tgtgacaaaa atgtctccag acgttgctag atgctccctg  58860
tgggaaatca tcacccttgg tgagaacctg tgactttgag cccatgagcc ctgcagagga  58920
tcatgtctga gaggacgcca ctcccaccac atgctcttcc agctggaatg gttgtctttg  58980
cagtgcctgc ttttctgaaa gtgtctcttt attgctttgg cttccttcta gcactatatt  59040
ccccactcct gggcaagtta gtaaggcctg gggtatagt aaagtcactc agtgggcaag  59100
tctccttgct ctgtgttcat ccaaagagag ttagatcagc cttgaaagtc actgcaaaat  59160
atatatatcc tgaggcctac aaagattttt gtgagctcac cgtccctttg ctaactctct  59220
agggcactgt gtactactat gtagcaagag ctcaatgttt gccagccttg tcatatgttt  59280
tgtctctttt aatcttcaaa gagaaaaaaa taactcctat aacataacag cgtatctcct  59340
ataacttata aaaaattcct ataaagtagt attgactccc atgccgggaa ttaataagta  59400
acttgcccaa gaccacccag gtagtaaatg gatttgaact tgggtttttt ggctgctggt  59460
ctaagacctt ttctatcaat gcttccctgg cttcgtgcat gtaagaatca cctgtgggtg  59520
tttgcaaaca atgcaggtcc ccaggcctcg cccctagagc cttggtaggc aggtttagag  59580
caggccccaa gaatcgggat ttgaaacatc tgatgaaaca cgtcattccg gtaatgactg  59640
tgcaggtgac tgccccttga gtaacactga actccattat tctgtgcttc ctggcaaacc  59700
atcagggaag gagggaagga gaaaagagaa aagagaggag aagggttgag agagattgaa  59760
agcactcagg ctgatgcagg gttgagagga gctggtttcc tccttcctct ctcatccttg  59820
caggcttagc cacatgtctg acaatggcaa taccgtgtcc aaaactccac acccacgaga  59880
tgccccttga cctctcctgc ctctgtgtgt ttgggcagcc tgggtgtggg ttcccccagc  59940
tcagtcctca ggtgccagga ccaaagctcc catcagtgaa cctgactaat tcacaaagca  60000
tttctttttt tttttaagtt ctgggataca tgtgcagaat gtgcaggttt gttacacagg  60060
tatacgtgtg ccatggtggt ttgctgcacc tatcaacccg tcatctaggt tttaagcccc  60120
gcatgcatta gatatttgtc ctaatgctct cccttccctt gcccccggcc caccaacagg  60180
ccctgctatg tgatgtttcc ctccctgtgt tcacgtgttc ttattgttca gctcccactt  60240
atgagtgaga acatgtggtg tttggttttc tgttcctggg ttaattggct gaggatgatg  60300
atttccagct tcatccatgt ccctgtaaag gacatgaact tgttcatttt tacggctaca  60360
```

-continued

```
tagtattcca tggcgtatat gtgccacatt ttctttatcc agtctctcgt tgatgggcat  60420
caattcacaa agcacttgca tcagcttcat ttgattatgg aaattagccc actaacattg  60480
catttctttg ttcacagata ctttctaaaa tccttggcct tcgctagaga ctttcctgga  60540
aggtttgtct cccctggcta gatcatgaaa aacctggatc agccttaagt tggatatctg  60600
gtcacttttg cttttaaata gtctggcaaa gcaagaggta caacacatcc tggtttgatg  60660
tactttccag caaaaagtat tagcaaaaca ataataatat tcagagggct cagttcccag  60720
tagaattcag cacatactcc agatctcctg aggttcaggt ctagttgaag ggaaaggaat  60780
gactgagatg agtttgagtt tcagacttga gtttctccca gctcccttga gaggcaaaga  60840
aaatctgccg ataaacacga aacaaagctc attgtcctgc tacttgtttg caagcaattg  60900
tatgtctgtc ctgcagacct cactgggctc acggcatttt gaatagcttt ctgtgatgta  60960
acgcacacag gttttcactc acactatgcg cagggaattc agctctcgga gtcatgacta  61020
cgtcatcctt cacctctcaa accatcgctg ctggtggcct tcgcttttat ttgttaagct  61080
gtagcttcag gaaagagcca attccctccc tccctccctt ccttcctccc tccttccttc  61140
tttccctccc tccttccttc tttccctccc tccttccttc tttccctccc tccttccttc  61200
tgtccctccc ttcttccttc cttcctttct ttgcccctcc atttccctcc ctctttttct  61260
ttcattccct atctccctcc cttcattctc tctctctctg tcatggttaa caacacatgc  61320
ttcaacaggt ttttttttta acctcttaag aggtatatgg ttaaaaagtc tctttgctat  61380
tcctgtcttg tacctaagcc acctaccccc accccacccc tgccatacac acattcatac  61440
acacaagtaa accattggta ctgatttgat gtttttcctt ccaaagtgct ttcaatatat  61500
atgaaagcac atttgaatag atgttgtcag cccccaaatg acagcctgta aaacacagtg  61560
ctctgcatct tacacttttc actcaccatt atatcttaga gatctttcca aacgtaaaga  61620
ccttgtacat tcttttttat ggcatcatag tactccagtt gtatagatta gcatcattta  61680
tgtagccaat cctctattaa caaaaattca ggttgcttcc aatatgttgc tgtcaccaac  61740
aatgttgtag cacgtagccc tgcactatgt cttcctgcac atgtgccagt ctgtgtgcag  61800
cataaactcc tgaggatggc atttgaggat gagtggctgt atgcacctgc agtctggata  61860
gatacgaaca aatcgcttat cgtaggcacc gtgtggacct ctcttccacc aatagtgcaa  61920
cgggacctgg cagtccctat tgcaacaagt tcctgaggct ttcctgggat aagaaaaagg  61980
cgagagagta tagaaggtta tttaattaga agaccaggtt ccccctctca cttcccaagc  62040
cacaaccatc aaaattctca aacctgattc tttatgatac aacccaagaa agatatattt  62100
ttatttttaa aatcgtaacc taatgaatta ggattttttt gactgtgagt aacaaaatac  62160
agttcaactc agcttggcag tggactgggg gagaaagagc ggcagggcgt ggtcactgta  62220
agaagaagga cacatctcat ggtacagtag gcaggagtgc agccgtgctc ccaggaggga  62280
cagcatccag gagctgggag accacaggac agccaaggat acagggcctg tcacccattg  62340
ctgcttctat ttggatcttc tttcttgaaa tatttttttc ctctcttcta ttcaatcctc  62400
acaacaggta aaggtggaag ctcatagtga ccaaattcac agttggagac agactttgtg  62460
tgcatgtgtg catgttagtg tgtatgagtg tgtgagtgtg catgagtgcg tgagtgtatt  62520
tgcttgttag tgcaagtgtg caccagtgtg tgagtgtgca tgttagtgtg cgtgagtgtg  62580
catgttagtg tgcatgttag tgtgtgtgtg catgttagtg tgtgagtgtg catgtttgtg  62640
tgtgcatgtt tgtgtgagtg tccatgtttg tgtatgtgtg catgttagtg tgtggcatgt  62700
gtgagtgtgc atgttagtgt gtgtgtgtgt gagtgtgagt gtgcatggtt agtgtgtgcg  62760
```

```
ttagtgtgag tgcatattag tgtgtgtgtc cgcatgttag tgtgtgtccg catgttagtg  62820
tgagtgtgca tgttagtgtg tgtgtgcatg agtgtgtgat tatttgcttg ttagtgtgag  62880
tgtgtaccag tgtgtgtgta catgttagtg tgtgagtgtg catgtgtgac tgtatgtgag  62940
ggtgcatgag tgtgtgtgag tgtgagactt gtgtgtatgt tagtgtgcat gtgagtgtgc  63000
atgtgagtgt gtgggtgtgt gagagtgtga gtgcacagga tgcttttctg ctttgattcc  63060
ccattcccag aaaagggcgt tggccctgaa cttggggcca ggcacccagc ctgggccagg  63120
cagctgtgaa cagcagagct tggtcatgtt gtccaagctg aaatgtgggt cccgctgttc  63180
tgagtgggca gaagagccag gggaatcttt tcaagccgag cagatattcc acatggcatc  63240
tgcacaacca caaataaagt tgtttatctt tgtcacttta atattataac aaaagcatta  63300
taaaaacaag gcagaaacat aatgaactct aaggcccaat aaatctcttg gttaaatggc  63360
cctcgtggtt tctgaagtta tcccagaatg ggataatggc agaaatgaat taggtataaa  63420
ctggacaaat tctcacctct cctgttgttt cttttcagcc aatagtttcc taaaaactgg  63480
gttatcagag acgctctttt agagtaaaac aatttttttt ttttacattt ttaaaaacag  63540
agcttctctc caatgaatgt ccagaaagac catacatttc agggctggcc tacaggacat  63600
atttcaaagt gatgtgtaat gtcattttag aagagtgagc tgttttctgt tgtttttttt  63660
taacttaaag acaaaatggc cagggaaaaa gctgccaagt ctctgagtaa tcttattgag  63720
ggttcagctt tctaagtatg accttatgct agcaacagcc cctgagtaac aagaaaacaa  63780
gccaagctag gaagccttgt ttctatgaga cgaaatggta agacagcaaa gtctgaaggt  63840
gaattctaat tatgtaacat gagtgagtca tcaacgccgt cagcgatcac agacaatgat  63900
gcagtgaccc gccgtctccc cacacttgca aagcacagag gctgtgtttc tcatcccccg  63960
ctccacacct tcctctcacc cctccttcct tccttctttt ctatttttct cttttctttt  64020
ccattttgtg ctgcattact cagggttctc agaaccaata agatacacat atatatttag  64080
aaagtgattt cttgtaagaa cttggctcat gtgatcatgg aggcaggcag gtcccaagat  64140
ctgcagaatg agttggcaaa ctggggaccc aagagagctg atggtgtggt tcctgtctgc  64200
gtctgaggct ctggaaccca ggagagcgga tcacatagct ctagcacaaa ggccagcagg  64260
tttgagaccc aggaagatct gatatctcca tttaagtcca aaggtgagaa aaagccaatg  64320
ttctagttca aagacgacca agcaggagga tttctctctt gctcagggga aggtccacct  64380
ttttgttcta ttcaggcctt caactgattg aacaaggccc acctgcatcg ggagggccac  64440
ctgctttact caatttactg atttacacgt taatctcatt tcaaaacacc ctcagaacac  64500
ccagaataat gtttgcccaa atgtctggac atcctgtggc ctagtcaggt ggacgcatag  64560
aattaactat cacgtgtgcc ttcctgttct cgggtgcact ggccacgcat gctgtcaccc  64620
atttcccgtt tatcatcttt tctttacagc caagtttcta gaaagagaag tctagactgt  64680
ctgcagtttc tcatctctca ttcacaagtc aacccagcgg cagttggcgc ctgtccccat  64740
cattttcttg aaactgatct caagaatctg cataatctaa ttgtcaagtt ctttcctctg  64800
ttctttgtgt aataacgcac catcctgaat ctctccttca ggcctctctt ctctgtgcgg  64860
ccctctagga gtgatagtcc ccaggatcct accatcttcc tatctatctt tttttttttt  64920
aatttatttt tttgagacgg agcctcaccc tatagcccag gctggagtac tcactgctac  64980
ctccacctcc cagtttcaag caattctcct tcctcagcct cccgagtagc tgggatcaca  65040
ggcccgcacc cccataccca gctaattttt gtatttttag tagagacggg gtttcaccat  65100
```

-continued

```
gttggccagg ctggtctcaa actcctgacc tgaggtgatc tgcccgcctc ggcctctcag  65160
agtgctggga ttacaagtgt gagtcaccgt gcctggcccc ctatctcatt taacaagctc  65220
tgtctggcag atgttataag ctctcttgct ttaactgcca gctctaggct catgactata  65280
aaatctctgt cttcaacatt ctctctctct gaatctcaga cttgggatat ataactgctt  65340
acagattctc tccccattgg atagtctcca catgaaactg gaacttaaca tgccgcattc  65400
aaattcacca tttcccccgt agacttaatt cttaatttct tctttctcag aatgatacta  65460
gcatccatgc agtctccaga ggttttatcc aggagacatt tattaccaac ggctccgtct  65520
cccaccttgt aattcaaatc agttactatg ctctttcggt tctccttgct aaatatccat  65580
ttcctctcct cttcactgtc cctgtctcca gcttaatccg aaccttcctt ataattctca  65640
actggagtat agctttataa tggatttctc tccacctcca tttcaactgc cccttcaatg  65700
aattagtgac tattttcagt gtgattctta tgcaagaaaa tgtgatcgag ttaattccca  65760
ctgaaagcat ttccaagcct accccattgc ctttaggata caatatgaag acaattgcaa  65820
cagtccagga gagagactgt gagctaagac agaggcaact gagatggaga cacaggacag  65880
aatgaaggga gctgggagat cctacaagct agaaatgcca agaccccatt acccatgaga  65940
cgatcagacg tgggagtgag agtaaaggga gatgaaggaa atcctctcca tcctgacttt  66000
gatgataaag tgagtcatag tcttgttctc tgagctgggg aactctagat cctgactttc  66060
ctcaaagcaa acagcaagtg aacttacttg ggtggggcac cctgtctggg gaagcaaagc  66120
cttcaggaaa ctcaaaggtc tgcgtagaga tgaatcagag actcaataac gaagaaataa  66180
aaattaatac cagatgggtg aaggaggcag ttgaaagtcc ttgtaaatag tcagcatcca  66240
agagtgctgc agaagtggaa ggtgccacaa acaatgctct tctgccagga gattcctaaa  66300
aatctgctgg caaagaccag agaaagaatc agagccacgt gcccagcaag acattaccta  66360
agctcaaaag ggtttaaagg acttataacc ctgcctttta ccctcaatta tttcatgatc  66420
accaccatgc ccttttttcct ggtcaggtgg ttggcagtag tttggaatac cttgctgttt  66480
gtagaacatg ttaaagcatg aattatttgt tgctatgcct tctgggtgca tatttggatg  66540
ccctaacaga tgaactaata gctcttttca tctcactctc tttattgagt cttgcccatt  66600
tacaacaaag gagagacttg ttttgtagat ctttaaaaca cacctgagga ttttgaattc  66660
atttataagc caatcccctc cagtgatcat tcagtaagaa ccaaagtcat ttgcaaagct  66720
atacaccaac aacatttaaa ctggttaaat tgagccaaac cacccaattt ggctgttcag  66780
ccaaattcaa gtatgtccaa tgcattggga tattaaatcc ccaacaaatt cttctttggc  66840
atggcctgac aagatcactg gtatttattg gttgctttta tacaaatgga aagaaatata  66900
tcataaccaa aaagtttca caggcaacct cattagaatc ttgcatggga cccaagagtg  66960
ggctgaagaa cacagtcttt cctgccaaag agcagccttt tgctctgcaa gcaggtggct  67020
gatgggctgt tttatgaagg gtttaatgat ctctgtctgc cttagttacc taccaaaata  67080
aactgtgtga atcccaacgt ggtagaagga ctccctcatt aactgtcaag caaaatcttg  67140
gtagggctcc acagcctgag gaaataaagt tgctaaggaa gacaagtcag tgattctgta  67200
gtttctacag acctctgctt cagatactgt tagcagccca ggaagtagtt ctgttggctg  67260
cattgatcct gggcccagaa ttaccctaag gcagaaccat cagggagaca gagctagatc  67320
agtctccatt cccctaggac actactcatt tggcgacaag ctaaccagag agcttcactc  67380
aatttataat attcataact gataaaggcc ttttctggta tcccactaat tatatatcca  67440
ggttataacc taaataagat acaaaactga ggatgcattt ttgtctgatc tctttatttg  67500
```

```
atgcctgagg aaactgagac tcaggaatgg ctgaactgcc tgaagttgca cacctgagag  67560
tcgagcccag gtctcctgac ttgcaggcca cagttcttcc tgctgtgaat accatcatgt  67620
gctgccagct gcacatggtt gaatgggagt tacagaagtt tggaaaacct gggtcagata  67680
tcagactaga gaaacatcca aagagagata agaaaaaaca tagactggat ggtccacaag  67740
cctcagtgta ggaaatgaag tggattagcc aggaaatcag gaacctaggc tgttttgagg  67800
gggcataaaa gctgccttgc tcaatcatgc ttatttcaat ctatagagag aaacacccta  67860
caggcagaag acctgccatt tttacccatg cttggtccaa gagtacgcct tccttcatcc  67920
atatttctag ctttctcccc acccactcct ttctttggaa ggaagttatt ttcctttcct  67980
atcactgaaa attctaacag agccccactg agagtcttct tcatcctacg tcctcattta  68040
aagccaaatt ttactgagca cttactatgc accaggtgct gagctggggt aacaaagatg  68100
gagcagccac agttataatc cacaaggatc tcctcatcca aaggtcctgt ttatgtagag  68160
tgcttgcttg caccatgtgg acagtgagca tacttctaaa ccccaaatct caacatatgg  68220
tccaagaaaa gcctgctttt ctaatttgcg aatgttttat aagggtgtct ttaaaaggct  68280
tacaaattga attgtgttag taagtcctat aacaagttcc tttactagaa aaaaataaat  68340
tttattaaat caggattttt gagaaaaatc tgtgctgtgt gttctccaaa tccatatgtt  68400
ttaacttgta aaacctccct ataatcacag tctattgcag ttgggaagga tctgaaatgt  68460
cacctaatcc agaagatgta aattttttat tttttaacaa tgaaacaatt tttaaaaaca  68520
aatattaccg tgacttccaa aataataaaa gaattaaaat tggcaccttt ctcctaaaaa  68580
atgagcttgt ttactcttcc cgtcgcaaat gaggaaactg agatccaaag agagtgagag  68640
gtcaaaggtc tcaaagaaag ttacttgcag agtgagggta ggaacatagg atcctttcct  68700
attctctttc cacccatcca tccatccact catccatcca tccatccttc cattcaccca  68760
cccacccatc catctattca tctatccacc catctatcca tccatccacc cattcaccta  68820
tccatccacc catccatcta ttcattcatc tgccatccat ccatctatct acccactcat  68880
atatccatcc atccatcatt ccattcatcc acccacccac ccatccatct attcatctat  68940
ccatccatcc accccttcac ctatccatcc acccatccac catccatcta ctcagccatc  69000
catccactat ctatccaccc atccatccgt tcattaatcc acccatccat tcaacaatcc  69060
acccaatttt ctattcatcc atccatccat ccacccacca tctatctatt catttatcca  69120
tccatccatc catcatatat ctacccattg atccatccac ccatctagat attcatctat  69180
ctacccatcc accaaccatc catctattca tccatccatt catctaccca tccattcatc  69240
tacccatcca tctatctacc cactaatcca tctatccatc catccacttc acaaaccttc  69300
aataagtcct aggggtcctg cacttgaaaa acaggtagac agaggccaga ccatgcatgg  69360
ccttatgagt caccttaaga attttggaca ttgtcttaag aacaataaga aagacattgc  69420
agtacttttt gttttgcttg ggtttaggga ttttctttta aaaacatttt attgtagaat  69480
gtttcaaaag tagaaagagt agtatcaatt acctagcttc aataattctc agcacatgga  69540
aaaccttgtt ttacgtctcc ccactttccc caccccactg ggttattggc ctgcaaatac  69600
tcagtatgaa tcttcaaaag acaaagactc tttaaaaata tatatatata tatataatat  69660
atataatata aaattataat accattatca aacttaaaac atttccatag taattccata  69720
atattaaaat ttcattagct gactaaaaag tttagagatt gggaactcac atgacacagt  69780
tgacatttta gagacatcag ctctggctac agcatgaaga aagggttata gagagatgag  69840
```

```
ccaagtctca agggccaatg cagtaatcca gatgagaatg gaagtggcct gaacatgaca  69900
gcagtaggga cagagaggaa tggagaggta caagagcact gcaggaggca tcgtcgagag  69960
gacatcttga aagccatggg gaagatagac aatggaaacc attaggatga ggccatgggg  70020
aagatggaca atggaaacca ttaggatgag gcccagcatc tagtgtgggt ggtggtgcca  70080
ttcactgaga ggagaccaaa gctgaaaata tccatttgga ttaacagatg gggtgtgtct  70140
tttggagagg tggagcacag ggtgggagag gggcatcacg gggagctgtc cagggccagc  70200
tggagagaat gcttgggctg gagagacagg ttcaggagtc ctgaagctgt aggtggaaac  70260
tgaagttgtg gctgcaggtg gtgaaagtag aggaggctga ggacagaact ggaggctcag  70320
tgccatgatg ggaggtgaag agaaacaccc agacagacta gcaccaagga aagagcatca  70380
tttaaaaggg gaaacgtggt caatggtgtg aaatcttgca gagatgtcaa gtaaagtcag  70440
actcaaagtg ggccactggg tttaggaaaa aggatttaga gcaagggatg ttgggaagag  70500
cccggttggt gagggagaga aagcaagcac cagactgtca ccagtgaaaa cggaggaact  70560
ggaatttctt ctgcgcccga cccaaagtgc taggattaca ggcgtgagcc actgcacccg  70620
acccagtctg taatatttta ttatggcagc tctagcaaac taatacagcc aggcactgtg  70680
attaacatgt tacttccttc tttttattta atattcacaa acatctcatg aggtaagtgc  70740
tcctgtatct ccttttcttg atgaagagat tgaagcttag agagggaaac aaactaactt  70800
gcataagatg gaaaagtcag taagcagaat tctaatgcag tttcccaggg atgctgtcac  70860
aaagcaccac agactgcagg gcttaaacag aaatcgatcg tttcacagct cgggaggctg  70920
ggagagacca acgggtcggt agggttggtg gcttgagagg gctgtaagga aagaatctgc  70980
ccatgtttct tcatatcagc tttcctctcc gtattgctcc tctttataag gacatcagtc  71040
cagttggatg aggggcccac cctgctctag taggacctca tcttaactaa ttacatctgc  71100
aatgacttta tttccaaata aggtcccatt ctgagatact gggggttagg aatttaacat  71160
atgaatttgg gggtacacaa ttcaatcctc ctgccctgcc tggatgaagg ccgtgtgagc  71220
tgaaggactc agtcagctag gggaaaacct gacttcaggg tcttaaagga aaggggtgac  71280
tgctgggagc aagtcaggag agaggtcata tatggagaaa agtcccatag aaggcaagac  71340
aggatggcat tcagtggcag gtgacaggtg gagggattca cttgggcatg agaggacaca  71400
ttttccttat tgttacaagg atgagggaag gaaaaaggga tgagttgaaa tgtgaagtca  71460
atctgcagat gtggaggagg gaagttgagg aagttcattt cagagggcgc ctgctttctt  71520
tgtggagcag gtggggagac tgcctactga ggttaacagc agggtttaag attggggctc  71580
agaagaaaga cagcaaataa aaccagagac attgaaaaac atggggaaag tttgaaacat  71640
ccgctgtgta taaactgcaa cagcctgctg tttctagact aggccccatt caatgtagca  71700
ttgcagaaga taatctactc tcattttaat tagaaaaata ggagaagagg agggtgagct  71760
ggccagggaa ctacagaagg ctgcctgaca gtaacaaggg tctagatggc attggtggcc  71820
ctgaggttgc agtggcacca tctgcagggt gtgtggtttt gccagccatg ctcaatagct  71880
gggcgattga tgcagagtaa gtaaacagtt gagttcatcc aaagctgggc tttggccagg  71940
gcaatgcatt aaaaggacaa acggcaagga ggttgagcat attggcaaga ggagggtgaa  72000
gtagggaagc tcaggggttt cagtgggcag agagggaagt gggcatgtga ggaggctgtg  72060
gctatttctg ctgaagaggc ctgctcatgc cccttgcttt cggagcgcat ggctgttgct  72120
gcttcctgga ggaacagatg ctgccagatg tgccatacta atgagctgca ggctgacagg  72180
ctccccagat ggtctccctc ctctgcagtg gtcctgactg gtcccagctg ggcaattcag  72240
```

```
caatttgtgc tcagtgctgc cacaacgctc agagcatgct ctggggacac acacccctgt  72300
gaaaggatga ggttggtacc agctgccctc ctagtggcgt gtcgatgtat cccctggatc  72360
agtcagctca tttctctgtt actttaaaat gcagtatgga gtgactctgt ttacatcttg  72420
gattttattg ctgtaatctt ctaagactac caatcttccc ttagctgcca tatttcaaat  72480
aaaaactatg gatattatta taaatattat tgatattact attctatacc tctactgatg  72540
ttattagcag tcaacttgaa actccaagtt accatattca cttcagtatc ttcatataca  72600
aataaaggag aagaaaaacc cataaatgtt ttagaggggt ggtgacacac taatgttatt  72660
cctagtacaa aatggtcaac atttaaaaaa aatactaaac attgtcagaa gcaatgggag  72720
ctattatacc ttgttgatga gaatatcgat tgatacgacc actttggaaa cagtttggta  72780
ttttctgtta aagctgaaaa caaagcaggc aaggttctgt gagcctgtag tcccagctac  72840
tcaggaggct gaggcaagag aatcccttga ggcagcctgg gcaacacaaa gaaacaagga  72900
aggcaggaag gcagggaggg atggagggaa acctatcatc cagcaattcc acataaacac  72960
aacagaaaca gataaagatc tacgtagcat tattattcat aatgggctag tactggaaac  73020
aacacaattg tctgtgaaca ttattaatag gatggaaaaa tgttggcata tccatacagt  73080
ggaataccat acagcaatgc aaattacaaa ctacagctac aggcaataac acagatgcat  73140
tgctcaaacc taatgctgag tgggagaagc tgacacaaaa gatcatatgc tgtgatccat  73200
ttatccaaag tttaaaaaca ggggaagtca ctttattgta taggagtgcc aagtgacata  73260
gtaaagcaca gagaaaacta aggagggaat gacgagaaca gtccaggtag tcacctgtag  73320
gcaggcccac cgttaacaga caactggcac attcagtaat tgaggacaca taagtatact  73380
ttagacgctg ctttgcttat atacaaataa aaatctgcaa tatatatcat atggaattat  73440
tcttttcctt tgacatcact tcaaaatgta tattatctga ttcttatcat gagtttaaaa  73500
caaaggatca atgcctgata ttctcccaaa taataaatta tcaggattcc ttggagcatg  73560
acaaaaaaca attttttgtg gggcttaagg tagaagtaca gatggagaac tgcatattat  73620
gggtctaaat attgtaaaat tataaattaa actaacaagc tgttaaataa aagatgtccc  73680
ggccgggcgc ggtggctcac gcctgtaatc ccagcacttt gggaggctga ggtgggcgga  73740
tcacgaggta aggagattaa gaccatcctg gctaacacga tgaaaccccg tctctactaa  73800
aaatacaaaa aattagccca gcgtagtggc gggcgcctgt agtcccagct actcgggagg  73860
ctgaggcagg agaatggcgt gaacctggga ggcggagctt gcagtgagcc gagattgcgc  73920
cactgcactc cagcctgggt gacagagcca gacttcgtat caaaaaaaaa aaaaaaaaaa  73980
aaaaaaagat gtcccatcct cctacttgga caaatgtctc ttcatagtga cctgagaaac  74040
cacgttggac cttagaattc ttggactgct tgggtcttcc tgctgtaaca tgtgccacag  74100
gaagaagcca cccctagacc cagccatcta cccttatgcc ccagccctgc tccatcccat  74160
aacccaaggg ccttggtgct catatgtatc actcttgagc cctcaagtct accttcaccc  74220
atggcctttt acgaatatct gcttccaggc cccccgtcag gaataaggac ttaaggaaga  74280
gcccacaaag accaggaagt aggtttggaa tcgtctgaac aggaagtccc aatgtcctgg  74340
tccttggcac ggggtctaga aagggagaca tggatctcgg gtgggcatgg tctcttggcc  74400
ccacagacct ctttcccctt gagaaagttc atggctggag gacagccaga agcccaaaag  74460
cacaaggccc aacacagaga ccccggtgca tggggtaagg gtagtaccac cttaatggga  74520
aagagagggg ttgcactgga aagggctctt ggaaagcttc tggagtcctg gcagtactct  74580
```

```
atgtcttgac ctgggtggca gttaaattta taacaattta ttaagctata catttatttt  74640
atacagtttt ctatatgtgt gttatatttc ccagtaaaga attaatgaca tgtgtgtgtg  74700
tatatatata tatataattt ctggtactgt agtttatggt atccccatag acaaatcagc  74760
tctgagaggt tgtcttataa gcacagacac cttgggcagt taaaatgcct caaggtgtga  74820
gtacctaaag aagcaataga cagacagggc gctggaaacg cagtaaatct cccttttgtt  74880
tctccatcct gtgtggggcc aagacactgg ggtaaccaca catgggttca ggcagagcaa  74940
atgagtcatg ggcctgtgtc cccttgccta gccactgcaa gtgcctcaga ggaaaattcc  75000
tttttccccc ctcttagcca agactataaa tactgcgttt atcaaactga aattacagga  75060
ggctgttccc atcctggtag aagtgaaagg agaccaactc ccaattatcc tgtttggaaa  75120
ggagttctag gaggacttct cttcctccta agggcagctg cataggttca ttaatttttt  75180
tgctgagctt ctattatgtg ccagacactc ttcttatttt tctgcttccc cttttaaaac  75240
aacctcttac ttattcttga taggaaaaca ctgtcctttt acaaagattc acattaccaa  75300
ttctcaaaaa gatattcacg tgccccgtgt ggtttaaata tcagggtttt tctaaggata  75360
tataccccaa ctatagccta caaatacata cacatacata cacacacacc atctcaaaac  75420
agccttacag ctgcaagata ttgaaagaga gtgaaaaatt ggccagtact aactcaccga  75480
aagcccagtc catgtttttc ccaaaaaatc aaattctggg ctttgcatct aagctattta  75540
aaagccacat ttccaaaaca ctagtttttc tccttttctg gaaacaagaa aagcatatgg  75600
ctccagtgac cttcacaagc tgctggtaag aggtagagtc aggcacatct tgtggcttca  75660
aaatgataaa agtggtaaca tattaagttg gtataaaggg ggatggtggg gcctcaggga  75720
tgggagagta gaaaacaatc aatgaaatca atgacaagac taaaactgta ggttataggc  75780
aaggaaattt cactctcacc tctactatcc atacaaaaca tctggcaaac gtctacccat  75840
ctctcaagac tccacccaag attgaccttc ctttgtgccc tcaccagacc cactgcacat  75900
ttgacccgaa atgatgtaac attttattgt gctgtatttt tgtttgttca gtgagactgt  75960
gggatccttg aggacaggac tatattttat gtgtctttga agttccaact aaagcatagt  76020
aagaacccca taaatgcttt ctttgattgc atgaatgaat ggatgatgga ttccattcac  76080
aagactatgg atttggcttt tccagctgct atgatgcaac ccttaaatga tgaaaagcat  76140
ctcaattttt ttcagatctt accaaccttt ccatctctat ctcctgtttt cagattcagt  76200
aagctgtgag gtccgtaatg tcagacactg gcaaacatca tatgttcttc aagtagagtt  76260
atgaaaacga agaaactggt cagaagagta aaacgccgga attgtccttt ccaacatcca  76320
gagctgcatc attccttggg gcaaaatgtg gacaagggtg agtactgata gaaaaaaaca  76380
gacaatttgt gattcccctt tttccagttt gctcagccta aattctctgc aataataata  76440
caaatcatgt ttttttgtca tacgggcctg caactaacat ttggggaaaa tactgttaag  76500
tttagactgc cagattttgc tgttaggtga attttttaca tggatgcact gatgcccaca  76560
gggcatccta ttccatccag aaatctctgg ggaagcagtc ttctgggatg cagatagatt  76620
attccactta acataatggt gcccgagcaa gcctggaagt tacactcact gaactattca  76680
ttcagaagct gattgcccac gtttggaaat agccagttct tggtgccttg tttctctgtt  76740
tgccagtcac cttcaaccat tcaacttcca ttcggccatt cctcaagaaa atcaagttgg  76800
cctggagtag agtgtaggat gaaaataatc aatttttcta tctaaccaag gcttcctaaa  76860
ggttttatga aaattcagta gaagaaatga tatgtaattt tacctattag ttggcctcta  76920
aaagaggcag gcatcatcgc atggcatagt ggcattgagg gtcacaaaga tctgaatttt  76980
```

```
ggtccttgct tttctgttta gtagtagagt tgacctggag ccagtgacct gaccctttttg  77040
aatctctgtt tctgtgttta taaaatggtg acaggaagat tgttcagagg atgaaatgag  77100
aaaatgcaca tagagtaact catgctcaaa atgaaaaaag gtaaattccc ttatctattg  77160
agatcgatca actgttttct gtatctcaga gaatcaacca tcaactgcac acaaataaaa  77220
aagctctggg caccgtatca agccaagaac agcccaatct cctttctggg caaacgttcc  77280
aaggtaaata taataagaaa tgctttcttt aaataatttg ataagtaaca aaaggatttc  77340
cctggaaggc attaaaaaca agtttgattg tcatatcact gtgggttttt ttaattatat  77400
tttaagttct agggtacatg tgcaaaacgt gcaggtttgt tacataggta tacatgtgcc  77460
atgtgggttt gctgcaccca tcaattcatc atttacatta ggtatttctc ctaatgctat  77520
atctccccca ggcccccacc cactgacagg ccccggtgtg tgaggttccc caccctgtgt  77580
ccatgtgttc tcattgttca actcccacct atgagtgaga acatgcaatg tttggttttc  77640
tgtccttgtg atagtttgct tagaatgatg gtttccagct ttatccatgt ccctacaaag  77700
gacatgaact catccttttt tatgactgca tagtattcca tggtgtatat gtgccacatt  77760
ttctcaatcc agtctatcat tgatggatat ttgggttggt tccaagtctt tgctattgtg  77820
aatagtgccc caataaacat acgtgtgcat gtgtccttat agtagcatga tttataatcc  77880
tttgggtata tacccagtaa tgggatggct gggtcaaatg gtatttctag ttctagatcc  77940
ttgaggaacc gccacattgt cttccacaat ggttgaacca gtttacactc ccaccaacag  78000
tgtaaaaccc ttcctatttc tccacatcct ctccagcatc tgttgtttcc tgacttttta  78060
atgatggcca ttctaactgg tgtgagatag tatctcttg tggttttgat atgcatttct  78120
ctgatgacaa gtgatgagca tttttcata tgtctgttgg ctgcataaat gtcttctttt  78180
gagaagtgtc tgttcatatc ctttgcccac tttttgatgg ggttgtttgt ttatttcttg  78240
taaatttgtt taagttcttt gtagattctg aatattagcc ctttttcaga tgggtagact  78300
gcaaagattt tctcccattc tgtaggctgc ctgttcactc tgatggtagt ttcttttgct  78360
gtgcagaagc tctttagttt aattagatcc catttgtcta ttttggcttt tgttgccatt  78420
gcttttggta ttttagtcat gaagtccttg cccatgtcta tgtcctgaat ggtattgcct  78480
aggttttctt ttaggatttt tacagtgtta ggtcttacat ttaagtattt aatgcttcta  78540
gttaattttt atatacggtg taaagaaggg atccagtttc agctttctac atatggctag  78600
ccagttttcc cagcaccatt tattagatag ggaacccttt caatattgct tgtttttttc  78660
aggtttgcca aagttcagat ggttgtagat gtgtgatgtt atttctgagg cctctgttct  78720
gttccattga tctatatatc tgttttggta ccagtaccat gctgttttgg ttactctagc  78780
ttgtagtata gtttgaagtc aggtagcggg atgcctccag ctttgttctt ttaagtagtt  78840
ttttccaatt acgtaaagaa agtcaggtag cttgatggcg atgacactga atctataaat  78900
taccttggaa agtatggacg ttttcataat attgattctt cctatccatg aacatggaat  78960
gttcttccat ttgtttgtgt cctcttttat ttcattgagc agtggtttgt agttctcctt  79020
gaagagttcc ttcacgtccc ttgtaagttg gattcccagg tattttattc tttttgtagt  79080
aattgtgaat gggagttcac taatgatttg gctctctgtt tgtctattat tggtgtatag  79140
gaatgcttgt gatttttgca cattgatttt gtatcctgaa actttgctga agttgcttat  79200
tagcttaagg agattttggg ctgagacaat ggggttttct aaatatacaa tcatgtcatc  79260
tgcaagcagg gacaatttga cttcctcctt tcctaattga ataccctta tttctttctc  79320
```

```
ttacctgatt tccctagcca gaacttccaa cactatgttg aataggagtg gtgagagagg  79380
gcatccctgt cttgtgccgg ttttcaaagg gaatgcttcc agcttttgtc cattcagtat  79440
gatattggct gtgggtttgt cataaatagc tcttattatt ttgagatacg ttccaccaat  79500
acctatttta ttgagagttt ttagcatgaa gcgctgttga attttatcga aggccttttc  79560
tgcatctatt gagatgatca tgtggttttt gtcattggtt ctgtttatgt gatggattac  79620
atttacagat ttgtgtatgt tgaaccagcc ttgcatccca gggatgtagc caatgtgatc  79680
gtggtggata agctttttga tgtgctgctg gattcggttt gccagtattt tattgaggat  79740
ttttgcatca atgttcatca gggatatggc ctaaaattat cttttttttgt tgtgtctcta  79800
ccaggctttg gtatcaggat gattctagcc tcataaaatg agttagggag gattcccctt  79860
ttttctattg attgaaatag tttcagaagg aatggtacca gctcctcttt gtacctctgg  79920
tagaattcag ctgtgaatct gtctggtcct ggactttttt tggttggtag gctattaatt  79980
attgcctcaa tttcagagcc tgttattggt caatccagag attcaatttc ttcctggttt  80040
agtcttgaga gagtgtatgt gtccaggaat ttatccattt cttctagatt ttctagttta  80100
tttgcataga ggtgtttata gtattctctg atggtagttt gcatttctgt gggatcagtg  80160
gtgatatccc ctttatcatt ttttattgca tctatttgat tcttctctct tttctttttt  80220
attggtcttg ctagcagtct atctattttg ttgatctttt taaaaaaaca gctcctggat  80280
tcattgattt tttgaagggt tttttgtgtc tctctctcct tcagttctgc tctgatcttt  80340
gttatttctt gccttctgct agctgttgaa tttgtttgct cttgcttctc tagttctttt  80400
aattgtgatg ttagagtgtc gattttagat ctttcctgct ttctcttgta tgcatttagt  80460
gctataaatt tccctctaca cactgctcta aatgtatccc agagattctg gtgtgttgca  80520
tctttttttct cattggtttc aaagaacatc tttatttctg ccttcatttc gttacttacc  80580
cagtagtcat tcaggagcat gttgttcagt ttccatgtag ttgtgtggtt ttgagtgggt  80640
ttattaatcc tgagttctaa tttgattgca ctgtagtcag ggagagtttg ttgtggtttc  80700
tgttctttta catttgctga ggagtgcttt acttccaact aagtggtcaa ttttagaata  80760
agtgcaatgt ggtgctgaga agaatgtata ttctgttgat ttggggtgga gagttctgta  80820
gatgtctatt aggtctactt ggtgcagagc tgagttcaag ccctcgatat ccttgttaac  80880
cttctgtctc attgatctgt ctaatactga cagtggggtt ttaaagtctc ccattattat  80940
tgtgtgggag tctaagtctc tttgtagatc tctaaggact tgctttatga atctggttgc  81000
tcctgtattg ggtgcatata tatttaggat agttagctct tcttggtgaa ttgatcccct  81060
taccattatg tggtggcctt ctttgtctct tttgatcttt gttggtttaa agtctgtttt  81120
atcagagact aggattgtaa cccctgcttt tttttgcttt ccatttgttt ggtagatctt  81180
cctccatccc tttattttga gcctatgtgc gtctttgcac atgaaatggg tctcctgaat  81240
acagcacacc catgggtctt gactctttat ccaatttgcc agtccgtgac ttttaactgg  81300
ggcatttagc ccattttcac ttaagattaa tattgttatg tgtgaatttg atcctgtcat  81360
tttgatgtta gctcattatt ttgcctgtta attgatgcag tttcttcata gcatcaatgg  81420
tctttacaat ttggcatgtt tttgcagtgg ctagtaccag ttattccttt ccatgcttag  81480
tgcttccttc aggagctctt cttataaggc aggcctggta gtgacaaaat ctctcagcat  81540
ttgcttgtct ataaaggatt ttatttctcc ttcacttatg aagcttagtt tggctggata  81600
tgagattctg ggttgaaaat tcttttcttt aagaatgttg aatattggcc cccactctct  81660
tctggcttgt agggtttctg ccaacagatc cgctgttagt ctgatgggct tccctttgtg  81720
```

```
ggtaacccga cctttctctc tggctgccct taacattttt tctttcattt caaccttggt  81780
gaatctgaca attatgtgtc ttggggttac tcttcttgag gagtatcttt gtggtgttct  81840
ctgtatttcc tgaatttgaa tgttggcctg ccttgctagg ttgaggaagt tttccaggat  81900
aatatcctga agagtgtttt ccaacttgat tccattcttc ccgtcacttt caggtacacc  81960
aatcaaacgt agatttggtc ttttcttata gtcttatatt tcctggaggc tttgttcatt  82020
tccttttact cttttttct ctaaacttct cttcttgctt tatttcatta atttgatctt  82080
caatcactga tatcctttct tccacttgat cgaataggct attgaatctt gtgcatgagt  82140
catgaagttc tcatgccgtg gttttcagct ccatcaggtc atttaaggtc ttctctacac  82200
tgtttattct agttagccat tcatctaatc tttttcaag gtttttagct tccttgcaat  82260
gggttagaac atgctccttt agctcagaga agtttgttat cacagacctt ctgaagccaa  82320
cttctgtcaa ctcatcaaac tcattctctg tcccgttttg ttcctttgct ggtgaggggc  82380
tgcaatcctt tggaggagaa gaggcactct gtttttttgg aattttcagc ttttctgctc  82440
tggtttctcc ccatctttgt ggttttatct acctttggac tttgacattg gtgacctaca  82500
gatggagttt cggtgtggat gtccttttttg ttgatgttga tgctattcct ttccgtttgt  82560
tagttttcct tcttacagac ccctcagctt caggtctgtt ggagtttgct ggaggtctaa  82620
tccagaccct gtttgcctgg gtatcaccag cggaggctgc agaacagcaa atattgctgc  82680
ctgatccttc ctctggaagc ttcgtcccag gggggcactc acctgtttga ggtgtctgtt  82740
ggcccctact gggaagtgtt tcccagtcag gctacacagg ggtcaaggac ccacttgagg  82800
aggcagtctg tccgttcttg gagctcaaat gccatgctga gagaaccgct gctctcttca  82860
gagttgtcag acagggacgt ttaagtctgc agaagctgtc tgctgccttt tgttctccta  82920
tgccctgacc ccagaggtgg aatctgtaga agtagtaggc cttactgagc tgtggtgggc  82980
tctgcccagt ttgtacttcc tggcctcttt gttttcactg tgacactttg tttactcaag  83040
cctcagcaat ggcagatgcc cctccccccc tcaagctgca gcgttgcagg tcgatctcag  83100
actgcagcgc tagcagtgag caaggctctg tgggcgtggg acccactgag ccggcacagg  83160
agggtatctt cttgtctgct ggttgctaag actgtgggaa aagcacagta tttggtcagg  83220
agtgtactgt ttctccaggt acagtctgtc atggcttccc ttggctagga aagggaaata  83280
ccccaacccc ttgcatttcc ctgatgaggc aatgccccac cctgcttcag ctcaccctcc  83340
atgggctgca tccactgtcc aaccggtccc agtgagatga atcaggtgcc tcagttggaa  83400
atgcagaaat cacccatctt ctgcatcaat cttgctggga gctgcagact ggagctgttc  83460
ctattcgtcc atcttggaca atagcccgct tactgtgatg ttttaaggtc aaggtaatga  83520
cctcttaaca atcctcgcta gtactagatt ctatggcaaa agtctgtcac agaactggat  83580
acttcagagg cttccaccaa accaaattag taatccaaac tggaacaaac tatatttatt  83640
tgtgaattct caatccattc aatataaata ccaatttctc tatgaatagt gaaacaaaaa  83700
atgtctctct tctcattttt tatacctact cagccaacat tactaaactg agacaaaaac  83760
agagagatac agggagataa aacattccct gaagcaagtc agtatttcat tccagctgta  83820
actctgcaat taacattagt tctatggtat ttccaataca tgctgattct caacttttgg  83880
aattctaaac ctaaaaacca tataatttca ccacctcaat tttttaattt gctttagaat  83940
tatctatgtt gagtcaaaag ggcctttgag gtctttaatt tcatgacttc tgggtgattt  84000
tttcccccat tattaaactt tattttaact tttcatacac acagatacac acactcacac  84060
```

```
acacacatca cttcacacta cgcatacata tattcctact gctctttttc aggtaggatg  84120
ctggttaaaa atatggactg gggctgggtg cagtggctca tgcctgtaat cccagcactt  84180
tgggaggtca aggcgggcag ataagttgag gtcaggagtt cgagagcagc ctgaccaaca  84240
gagtgaaacc ccatctctac taaaaataga aaaattagct gggtgtagtg gtgcgcacct  84300
atagtaacag ctattcagaa ggctgaggca tgagaattgc ttgaacccca gaggcagagg  84360
ttgcagtgag ctgtgattgc accactgcac tccaacctag gcgacaaagc gagactctgt  84420
ctccaaaaaa aaaaaaagaa aagaaaaaaa aatacggact agaagccata ctgcctagtt  84480
tgaatcccag tcttgcctct attgagtaat agggccttga acaagttatt aaccctcttt  84540
gtgcctcagt ttcttcatct acaatatgag aatgagaata gtaccgacct caaagggttt  84600
gtgatgatta aacatgcatg ttgcttagaa ttgtgtttgg cacgtactaa gccctcaaaa  84660
gaagcttcct gagttttata gcacataaaa agtcaagtca gtgcagctaa aagaaatcat  84720
tgaagggaga agatgagaga cacagagcat aatgaaaggc ctggtgggag aatgagcctt  84780
gggaatctgg atggggctag acttggtcac tcacctgaac ttccttaagc tgtgattttt  84840
ctggttccag aggtgacaat gaagacacca tgagtgaagg catggacaga aaaattcact  84900
ggggaagcct gtgctaaact cataaatact cttaaaagta aaccccttac aagaagcctc  84960
agcaaataaa agcaagccct gagggaactg cactaatatc agtgtgagga ggaaggcgga  85020
gaggtctcct cacacctgga gagctgtccc tggctgcaga gaggctggca ccctgcagca  85080
ttcttttccc aggatggttc tgttttattt cattttcaaa gagctggtag ttaaacattt  85140
accattgctc cactgaagac aataaagaat aaaggggctg gctcagaaaa aaatgaaaac  85200
caaaaaaaaa aaaaaaacaaa acaaattaaa ctgcaaagct ttttcacctt tgcattaggg  85260
caggaagcct gcagccaggc atggcatgtt atagtttatc taaagaaaaa aagccaaatc  85320
ggctgggcgt ggtggctcac gcctataata ccagcacttt gggaggccga ggtgggtgga  85380
ccgcctgagg tcaggagttc aagactagcc tgggcaagat ggcgaaacca tgtctctact  85440
aaaaatacaa aaattagccg ggcatggtga tgtgcacctg taatcccagc tactccggag  85500
gctgaggcag gagaattgct tgaacccagg aggtgaaggt tgcagtgagc tcagatcacg  85560
ctactgcact ccagcatggg tgatagagca agactttgtc tcaaaaaaga gaaagaaaga  85620
aaagaaagga aggaaggaag gaaggaagga aggaaggaag gaaggaaggg aaaggaaagg  85680
aaaggaaagg aaaggaagga aggaaaggaa ggaaggaagg aagaaagaaa ggaaggaagg  85740
aaattttgcc attctttccc actaaatgca agttcactgc agttccaagg tacttatcca  85800
caccgtgtat ttacatctgc ctcaggtttg tagtaaatgc tgtaaacaga gagatgtgat  85860
gaagagaggt aatgcatatt ctttatcacc tctctaaaaa catgattatc ctgacctatt  85920
gtagggaata tgaaaacact atgtagtgag aattaccatc ctgcttcatt atacttaaaa  85980
gagaatttaa cctgttcaga tttctgagtt gttccttaag tataaaagtg aaagaatcag  86040
gatcaaaacg aagaacctct aaatccgcct attgtatctg cttgggctgc catgacaagg  86100
tatcacagag tgggggctta aacaacagaa atttattctc tcacagttct ggaggctgga  86160
agtccaagat aaggtgtctg cagggttgat ttctcctgaa gcctctctcc ttgacttgta  86220
gaccttcatc ttctccctgt gtggtcttcc ctctgtgggt ggctgtgtcc tcatctcctc  86280
ttcttataag gactcctgtc atattggatt agggcccacc catgtgacct cattttaact  86340
taattacttc tgtgaagacc ctatctctaa acacagtcac atttggagtt ccttggtgtt  86400
aaagtttcaa catgaatttg gggtgggggt cacaattcag tccatcacac acctaacgtg  86460
```

```
ggtgtaatgt gtctacagga acagtttgat tgagcaacac cacaggttgc attcccagag  86520
aagcaaattt tgagatggag attggcatgc tggaagtttg tggagagtgc tcctgggaaa  86580
ctgtcaaggc aagagaggaa gcaggattag gcagaggagg aagctgaaat caggataaag  86640
accccagcaa gtcacagagg ccctccaaag ctgggatgtc cttccatgtt gtctgaactg  86700
aggcaaggta gttggaagtt tatgcccctt cctagacagt cactgtaaac aggccacccg  86760
agggaggagg tgtgctgtgc ctcagctggg gacaatctca agaggggact ctgaagcaag  86820
ctgctaggtg ccaacccttc catagctgac agaatgattg actaagcctg aagtggggtg  86880
tcaggtcatg gaccccagtg tccactacaa atctgaaatt tactttcctc aagtgagtgg  86940
aaggacttac cattatcttc ttaagaaata tctcgcaccc tacagaatgg gagaaaatat  87000
ttgcaaacca tccatctgat aatgggttaa cagtcagaaa aataaaacgc actcatacaa  87060
taataacaat aaaacataat ctggctaaat aaatgggcag agaacctgaa aagacatttg  87120
tcaaaagaag acatacaaat ggccaagagg tacatacaaa ggtgtgcaat atcactaatt  87180
gtattagtct gttctcacac tgctaataaa gacctaccca agactgggta atttatatag  87240
aaaaagaggt ttaatggact caccattcca catggccggg gaggcctcac agtcaatgca  87300
gaaggcaaag gaggagcaaa ggcacgtctt tcatggcagc aggcaagaga gcttgtgtag  87360
tggaactgcc ctttacaaaa ccatcagatc ttgtgagact tactcactgc cataagaaca  87420
gcacgggaaa gacccgtccc catgattcaa ttacctccca ccagattcct ctcacaacat  87480
gtgggaatta tgggagatac aattcaagat gaggtttggg tggggacaca gccaaaccgt  87540
atcactaatc atcagggata tacagatcaa aaccataatg agatatcatc ttaccccagt  87600
tggctatcat caaaaacact aataagtgtt gtgaggatat gggaaaaggg aacccacgta  87660
tactgttggt aggaatgtaa actgatatat tagttcgttc ttacattgct ataaagaact  87720
acctaagact gggtaattta taaagaaaag aggtttgatg ggctcacagt tctgcaggcg  87780
gtacaggaaa catggctgca gaggcctcag gaaacttaga atcatggcag aagacaaaag  87840
ggaagccagc acatcctata tggctggaac aggagaggga gagagcaaag ggggaagtgc  87900
tacacactct caaacaacca gatctcatga gaacttactc actatcacga gaacagcaaa  87960
agggaaatcc acccccatga tccaacattt cccaccagac ccctccccca acactgaaga  88020
tcacaattca acatgagatt tgggtagaga catagagcca aaccatatta gctggtatag  88080
tcgttatgga acacagcatg caggttcctc aaaatttaaa aatacaatta tcatatgtag  88140
cagtaactcc acttctgggt atatatccaa aggaaatgaa atcagtacct caaagagttc  88200
tatgcacctc catgttcatt acaacattat tcacaatagc caggatatag aatcaaccta  88260
agtgttgatt ctactaatac atgagcagat aaagaaaatg tgatacacac acacacatac  88320
acacatacac acacacacac acttacacaa tggaattcta ttcagccttg aagaagaagg  88380
aagtcctgtc atttgtgaca atgtggatga acctggagga cattatgctg agtgaaataa  88440
gccaggcaca gaaagacaaa tactacatga tctcacttta tatatggcat ctaaaaaaga  88500
cagactcata gaagcagaaa gtagaactgt gcttaccagg ggttggggga ctgggaggat  88560
tggaaagatg ttggtcaaag agtacacatt ttcagttaca agatgaacaa gttttgggaa  88620
tctaataaat aacatggtga catggttaaa aatactgtat ttaatatata cttgaaactt  88680
gctaccacag tagatcttaa atattctcaa cacgcacaca cacacacata gacggtcatg  88740
gtgtgaggtg acagatattt caattagctt ggttgtggta attatttcac aatgtatatg  88800
```

```
tatatcaaag catcatgttg tacactgtaa ctatatacaa tttttatttg tcaaatatgc  88860
ttcgataaag ctgagagggg gggatagaaa acaaagaaat ttctcacaat gtctctcagt  88920
agatctaagg gtaacatatt aaaaactcga aaatatttgg cccaatcctg ggctgctaac  88980
atgggttagt ggaaaagtgc actgtggcgc cagaaaggtc tgggttcaaa tctctatctt  89040
gctgtttgct aatatttctt aacctctctg aacctccaat ttctcctgtg caaaatgaat  89100
ataataatac ccatcttatt ggactgttgc aagatttaaa caaaaaaaaa aacatagact  89160
tagattgtct agcaacaatg cttgacacaa agaaggcatt taaaaagcat ttgttccctt  89220
cccctttta cagcaaatag ttcattggca gtgaatgatt acaaactaca agtgtttctc  89280
aacttggagt ggtttctcaa gtatgtgact ggaaccacct gtagagattg ttaaactaca  89340
gatccctgga ccccacccca ttcttaatga atctagttca tgggttctag ggtggagccc  89400
aggaatgtat aattttagca agttccatgg atgtttctga tacccagaaa atcatgaagc  89460
cctctgcttg aggctgagct cagtaagaat attctttgta ttagaaccca gggaggtctg  89520
tgcttagagg atgcctgagg acatttgcac ctccctcctt gtcatgagtt ctgtggatgt  89580
acatctgcac atcacatcac agagacctct ctccattgca taaattctgt gtattccaaa  89640
actaaaacat gcataaatca catcagttat agactcaaac caattctcct ttttgagatg  89700
tcattttatt gagttataaa tcaccactaa aaggcaattt tgtgcagaca gaaattttac  89760
tggaggatgc agatcccctg agcttgtctg gaaaatgaga agcctattca aagacgaagt  89820
gtcctgctgg tggaagagtc attgggcctg caaagaggca tgtctggatg gaggtttaac  89880
tttttcattt caaccaaaca aaatggagcc cctcacccag atgggattgc tgaaggcttt  89940
ctgggtttga ttatgggtca caaagtccag ctgcattgca gaaattacac tgtcaagaag  90000
acgctgacca aggtccagaa aataaacagg agctgagatg cagaaagtga cctcgaagct  90060
taaacaggct ttcccatgcc taccagacgc ttttcttgat ttaacaccgg gtcatgtggt  90120
ttttcagtgt cttctgtggc tttcttttcc catagatggg cctcacttat tctaaaatat  90180
aaagctttgg gggtttcttg aaaatggcac tttcactcag taaaaataag tccagatgaa  90240
aaccttatct gtgggaatcc attctgaaga aggattaaag taagtctatt ttccccaaat  90300
gatcaataac cacccagacc taatcactat ctctgattac atgatgaaaa agattctgga  90360
agcagcacag caaaaatatg acaatgacag agaactcaaa ggtgaccctg tactcaccat  90420
ctccatgcag acatcacaag tgcagggatg agtaagccct ttagttggag atctatgttg  90480
ctaataacaa gacattctga gttttcttct tcttagtgag agagccttcc atgaccattt  90540
tcccatagtt tgcctttatt cgtttctaag aaactatttt tccagttttg accatggtgc  90600
tgtaacccac agaggcaccg ttacactgaa actatgcaac cctatctgtt aagtattatc  90660
caacgcccac ttgggttttc actggctcat ttagagaagc acctttgagt acaatatcca  90720
attaaacagt aggtttacat ggagtgcttc ctgctcgtgt taaaaatctc attctggccg  90780
ggcgcggtgg ctcacgcctg taatcccagc actttgggag cccgaggcag gttgatcacg  90840
aggtcaggag atcaagacca tcctggctac tacggtgaaa ccccgtctct actaaaaata  90900
caaaaaatta gctgggcttg gtggcaggtg cctgtagtcc cagctactgg ggaggctgag  90960
gcaggagaat ggcgtgaacc cgggaggcgg agcttgcagt gagcagagat tgtgccactg  91020
cactccagcc tgggcgacag agcgagactc cgtctcaaaa aaaaaaaaaa aaaaaaaaaa  91080
acctcattct atttctgccc tgtgctctgc cattccctag atacacagaa ttttggaccc  91140
agtagagcac cttcacgagg atagtgctgc agtgaaccgc agtagcaagg aaatcgtaca  91200
```

```
agctcagtgg ctcagcacaa cacactgttc tcactcgtgg tccagtcagg gactctcctg  91260
gacagctgtc ctcggggatc tgggtctctt ccatcatggg ctccagtatc tcggggcctt  91320
tcacttccag catgtgaaac actccgtctt cttcaagagg gagtgtgtgg gacatgttag  91380
ggagcaggct agaaagcaga gtacatcact tccactggca ctctaccgtc tagcactcaa  91440
tcgcatcatc aacctaaatc cgaagaaagc agggagatgt agagatgagc acagctgctg  91500
acagtgcctg cctcggagag atgttagctg cccctttctt tcaatccctt tttaaggttt  91560
tgcagttgag gcgactgaga ctcggaagac atgttaccca cagctagtca gtgacagccc  91620
agcgcagtgt tcacccaggg gcctcttgcc cacccttatt aattccaatt aatggataaa  91680
agggctcatt tggtctcgag gtacagctgg agctttgttt cctgctcttc tacgcaggac  91740
tccacggtga ggaggaggac gaccactctg ctgcaaaacc cgcagttcca gggcaatgcc  91800
tcttggtctg ggagctgcac agatgaatac ctcaaggagc aagtgccagt agccaaccgt  91860
aattatggga aatgcttctt ggctcctaag ggatataaaa ttactttggg gaaagtcaag  91920
gaaaatagaa acagaatacc ccataatgct ttatttggag gccagaagtc acatactaag  91980
gcttgtgttt tgtgtttgat tctgtcaaga gagcttaaaa ggtggagaca gcctttgggg  92040
ggaatgaagg tctggatggt atcagcctgg cttgcaagcg tcgctgtggc tcatgaaaac  92100
atatgtcttg aaaggttgtc ctgctcatag ttccgagcaa atgtgagaaa caacagaggc  92160
ttccaacaaa tacctgctaa agaatgagga aatggacaca ggcaaatagg caaatggagt  92220
ctccttaacg gaatcgtaag gctgtctgga ggtaatacga gtggaaagaa ctcctgtgtg  92280
aaaatctgca tgcatctttg cccccgtgga accgtctaca caagtgctaa tggaacagtt  92340
agttacatac ctattttttt aaactctgac tttaccatta cagaggttat atatctatag  92400
gatttttgc ctgaattttt agattttcac ctggagatct ggtatggaat aattaaatgc  92460
tgcatattgt ttctcttatt cttaaggatc ttggagaaat tatttaacag tctgagatct  92520
ccttctctcc ttccctaccc tccccacccc tgacctataa cagctaggga gagaaaataa  92580
atacaaataa tatctgctgg ccaggcacag tggctcacgc ctgtaatccc agcactttgg  92640
gaagctgagg caggcagatc atgaggtcag gagatcaaga ccatcctgtg taacatggtg  92700
aaacctcgtc tctactaaaa atacaaaaat tagccaggcg tggtggcagg tgcctgtagt  92760
cccagctact cgggaggctg aggcaggaga atggcgtgaa cccgggaggt gggggttgag  92820
gtgagccaag atcgcgccac tgcattccag cctgggcgaa atagcgagac tccatctcaa  92880
aaataaataa ataaaataaa ataaaatatc tgccatttgg ctgcaaagta tggtgctgat  92940
ttaacctgaa tattaccaca taaaatcaaa taacaataat aatagaaaat aggtttatag  93000
cagtaccaga attatattac ttaatttagc tgccttttcc caaaatataa tcacacttcc  93060
tagattttac aggtcagata taaaagagta cagtggaaga attcaatcac atgtgccttc  93120
attgttcact ttttcatctc aagctcttct tttcatgcta gctgttccag ctcttcaaaa  93180
aatgtttgtt cttgtgagtc agaaatattg tatccatttt attaacagcc tgtttgaagc  93240
caataagatg aatgcgtttg ctgagcatag gttagtttat ggcaaagtct ggactcaaat  93300
caatggcagg agaggagagg caagctagtt agatacctcc aaaggacttg gacataagga  93360
agatttcaga gttaaattag caaaatgcat acattcaata catacacact agtaaaacaa  93420
aatggctgca attagtcaat tatggaagta aaccaagaaa acatccatct gtctgtaaaa  93480
tagaagagtg tgggaacttc ttaaacttca gtcctgctga tctggggtat agtaatgagg  93540
```

```
aagatgaata tatggttgta agtcagtgag cagaatgcca agtggctgca ttgtgcctga  93600
ttggatgaaa tgttatccat gttatctgat tggatgaaag gtatgtgaac agaaggggct  93660
ggtcagccaa agaagcaaga aagaaggaga atcagagggt ctgaaagccc ctctagatgg  93720
caaagccctt ggacatggaa gcatctaaga aaaacatagt cttggcagtg ttgaccaaaa  93780
gtatggttcc ctttatgaga cgttccctgt tgtgagcaag agtgcctcaa gccattgaca  93840
gcagcattct aagatccatt aagagcactt gttctgatcc tgtggacacc aagcaacctt  93900
gtgataattt ggctcctcac atagtgagac tattggcagc tctgcctcaa cacattctgg  93960
tctacttgtc agttgtatag acgaatttaa ttatatctga cgtggtgtgc tgactccacc  94020
ctaagcacgc caacaaaatc acttttatga gcctaacaga ccttagacca gggtgtactc  94080
tttaaggtaa acaccaccct cggcatgcag ctggacaggc agtaatgttg cccagcaaca  94140
ccccaggcca cacgccatac gccacttgaa ctgcagctga accagcctgc gtaattttga  94200
ctgagccaca tataaagtca agatcaggat gttctaacaa catgaccacc tctagtgatc  94260
tgaccaaaca attgccatat cacaagccag gagcagtctg cagagtggag gaatggaaag  94320
aacctaaacc attttaacag gccatgtgcc aattttcaac tgtacccggg accccaccat  94380
agacagcttc atcaaagata tcaatgctgt tgacagagta atgttttcca ggttttatcc  94440
caccctactc agttgcagta attgttaggt gataaagaca gtgacagctc attacaaaat  94500
tcaacttcca gaagctggaa ggttaagtga cacctcttac ctgctgggtg atgggttagc  94560
gtcttaacct tatccttttg ctactctctg ccccaaactc caaccccatc tggaagcttg  94620
tgcacttgag gcagtagatt tcacatgaaa ccaagtcaga aggctttaca acagaccatt  94680
aagtaggaat gtgtaggaaa agtacgtaga ggagaatgga tgaaggggat gaagaatatt  94740
gcctaaaaac tcaagaccgt tatctgtagc ccttataaca ctttttattt atgtgttctg  94800
tgtgtgtgtg tgtgtgtgtg tgtggatttg tgcactactg taccttcata ccagcttgtc  94860
acacacgtat aaacctatgt ccacagacat taactacttg gtttttgttt tgttttgttt  94920
tgagatggag tctcgctctg ccacccagac tggcatacag tgacaccatt tcagctaact  94980
ccaacctcca cctaccaggt tcaagcaatt ctcctgcctc agcctcctga gcgtctggga  95040
ttacaggcac ctgccaccat gcctggctga tttttgtatt tttagtagag atggggtttt  95100
gccatgttgg ccaggctggt ctcgaactcc tgatatcaag tggatccgcc tgcctgggcc  95160
tcccaaagtg ctgagactaa aagcgtgagc caccgcgccc agcctacttg gcttctttaa  95220
acagctttat tgaggcataa ctgacatacg ataaactaca catactgaaa atataaatta  95280
ttttaatctg taattacacc tttatttttt aaaaaattgt gtgagcccaa ccagataacc  95340
atgaaaagtt ccatattaat gatgattgta ctgagtagag aagcctccaa ttaaagtaaa  95400
ttttgataac attgacatat atatatgcac tggtggaacc atcgccaaaa ccaagataac  95460
aaacacatcc atcacctcca gaagttttct catgcccctt tgtaatccca cctctgctgc  95520
ttcctacccc cagccccatt cctaggcaac cgttaatctg ctttctgtca ctatacatca  95580
gtttggatat tccagaaaat tatataaatg atacatatct tatataccct ttttctggct  95640
tcttatactc agaatagtta ctttgatttg tatctatgtt gtaatatgta tcaatagttc  95700
atttattttc attatggctg agtgttattc ttcatacgga tggaccacag tgtgtttatc  95760
cattcacctt tgatagatat ttggtttgtt cccagttggg ggcaattaga aataaaattc  95820
taaaaacatt tatgtaaaag ggtgtgcatg gcataggctt tcttttctct tggataaaaa  95880
tctaggaatc aatgactaga ttatatgatc agtgtattcc taacttccta agaaactgcc  95940
```

```
taactatgtt cccatcacca gtgtttgaga gttccagttc ctcctcaccc ttgccaacac  96000
attttatggt cagattttcc ttctaattct tgctattcta ataggtatgt agtggtacct  96060
tctagtggct ttaatttgca tttctctaat gactaatgat gttgagcatc ttttcatatg  96120
cttatttgtc atctgtgtgt gtcctcatta ataaaatgtc tggtcaaata ttttgtccat  96180
tttctatttg gtttgttttc ttattattca gtaatgagag tttcttatct attctggcta  96240
caattacttt atcagattta tatattgtaa acattttccg ccagtgtctg gcttgtcttc  96300
ttagtctaat aacaatgtct ttagaagagc aggtgttttt aatttttatg aagtcctatt  96360
tattaatttt ttcttttatg gattgtgctt ttggtgtggt aactaagaaa tccttgccta  96420
cccaaagtca caaacatttt ctcttatatt tttatagttt taggttttat atttatttct  96480
gatccacttt gaattaatat tcatataatg aaagatatga actgaagtgc actattttga  96540
atactgatat ccaagtgtac tagcaccatt tgttgaaaga actatgtttc tccactaaag  96600
tttctttgca cctttgtcaa aagtcagttg tccatatagg tgtgtaggcc tctttctatt  96660
ccacttatct atttgtcagt ctttaagcca atatcacatt gtcttgatta gtatagtttt  96720
gcaattcttg aaatccggca gtattaatcc tccaagtttg ttcttctttt ataaagattt  96780
ttgtttttga ggatttttgt tttgcttttt gtttgtgctg ttctaggtcc tttgtgtttc  96840
tatatgaagt tcagaatcga tttgttcatt tctacaaaaa aaagcctact gggcttttga  96900
ttggggtgat atcaaatcta taaatcaatt taggaagaac tgacatctta ccgatataag  96960
tctttggatt catgaacaca ttatatctct ccatttattt atatcttctt taatttttct  97020
caacagttgt tttatggttt ttggtgtaca gagaactgta caccaaaata tcatttctca  97080
gtatcaaagt attcaaagta catcacttct cagtatcaga ctgtcaggaa aatgatcaat  97140
ttccccttca agactgacaa gctaaaggca ccagaggctt aggcttctta cagcaacaca  97200
atgcagggac tataaaaagc aaacgatagc acctatttcc taaagtcacg aatgttaagt  97260
gagtttaaca tttatgcagt ttaacgtaac accggttgtg aaggtaaact gcctgggttc  97320
aaatcccagc tgcaccactt ataactgaat caccttggga aattcacagt ctctctagaa  97380
ctcagttttc tgatcagctt aatgcagaaa atactagcac ctccctcata agggtcttca  97440
taagaataaa ataagctcac taaagactta gaactattct tgtcatataa gaactaataa  97500
atattagtta tattaatata taaatcttag caagttttat attatattta ttatattaat  97560
atataaatat tagcaatcat tgttgatttt attattagta gcacttaaca tagtatttgg  97620
aacaaatgag tatccaataa agggtagata ttattggctt atgtagcaaa ctagtggtta  97680
acaccttcag gtatgcttct caactgtttt gaataaccga agctgaactg aatttgctag  97740
aagtaggtct gtttgttctt tattttttat tttttatttt tttgagacag agtcttgctc  97800
tgtcgctcag gctggagtgc agtggcgcga tcttatctca ttgcaacatc cacctcccgg  97860
gttcacgcca ttctcctgcc tcagcctccc tagtagctgg gactacaggc gcccaccacc  97920
atgcccagct actttttttt tttttttttt tttttttagt agagacgggg tttcaccgtg  97980
ttagccagga tggtcttgat ctcctgacct cgtgatctgc ctgcctcggc ctcccaaagt  98040
gctgggatta caggcgtgag ccactgacac tgcgcccagc cagtaggttt gctcttaaaa  98100
ggcctgaccc tgaacaggaa cattccattc tttggatgct gtatttaaga tgctatgtca  98160
gacatctcta tgcaggatct caccatgata ggcaaatctc caccacaatt agctttacta  98220
ctggcttcct taatctctct ctggcctatc ttgaggtcta aaccctggaa ggagattgta  98280
```

```
tgaattatat ttcctcattg ctcctgcaat ccttagagag atgacatttt cataaggatg  98340
catctacact aactctggcc ctttctctag agtaaagaag tgaccagatc acctttcata  98400
catactagac tggttttata ttgtgatatg atttccaaac ccaggaaggc tctgtgtgcc  98460
tctcatcact caccactact accatccacc cttgcacaca cacacgtgaa ccctccctcc  98520
tggcttgctg acacaatctg tctaattgga aatccatttc tgtgcttgat gactttgttc  98580
cctataaaaa tacgaattat ctttgaagga aaagcaatca ttaacctttg tgtgtaggag  98640
acagtattaa agtaatagaa agagaaaagc actcaagatt caagaaagag gcattcaaga  98700
ttattagatc ccaaatcttt cctctcttgc aagaagagtt tgccatggtc attaaagcca  98760
tggcactggg tgaggtcatc atccatgtgg tgactattgc tagagaggaa aactctggaa  98820
tctaatggtc tcaaatgcct ttttccctcc tctgtaacca agattctact caagttccct  98880
gatctacaat aacaggatgg catttgagcc attcattcat tcattcatgc attcagcaaa  98940
tcctgaccac cctctcacca tggtcaggta ttgttttaag agcaggggac acagtagtga  99000
acaaaacaaa atccctactc ccacaaagct tatatccaag ccaaagagac aggtaatcag  99060
caaataaaca caaaggttgt aataggttgt caaggagtaa gggatttcaa gaataaaaat  99120
aaaatagggt aaagagatgg agaatgccag gaatgctagt ttagatagag tatttaagga  99180
tgttctttct gaggctgcaa tggttgaata gagacttgaa aacagtgagt gaggcgacag  99240
ctgggcagct agtagaacat tccaggtacg ggactggcaa atgccaaggt cataaggtag  99300
aagtttgctc aaagtgtttg aggaaaataa aagaagcctg tatggttgca ataaagagat  99360
cgctggagag gcatccaaag gccaaaccat atagggcatt gtaggtgatc ataacgactt  99420
ttctgtatat tccaagcgag atatgaaacc actggagagt tccagaagga aagtgacaag  99480
atctgacctt atttagaaaa atcacttggg ccgatatacc tagaacagat caccagggag  99540
ccagagggaa agcaggacag ccagcgagga gctgttgccg tagctcagga gagagatatt  99600
ggtggcttag atgaacaagg aaggtagtag tcaaagaggc aagaaacaga tatgtgatat  99660
atgttgaagg atgggatgta gggtttaggt tccatgccat gaaaaaagta aaaaatgact  99720
ctaaaattgg ttatagcaaa ggagaatgcc atttactgag atgtagaacc atggagaagg  99780
ttggaggagg gacagcaagt ctgttctgga catgtgaagt tggcattgtc tatgagatat  99840
ccagggttca tgttgagcag gcagttgtat acacacagct gggcttcaga ggaagagtca  99900
aggttagaga gacttccgtt tgtggtcatc actgtctgca tggccattaa agccatggca  99960
ctggcaccat gtggtgactt gctagaaaag agaagaggag catccaagaa aagacagtga 100020
gagggaacag ccagggttgt cggaggagta tctggaaagc atggtaacat gtaagccaaa 100080
ctgtaaaatt gctccaagga gggagtgagc aaaagtcgct gagaggttca gatggcgttt 100140
ttaatctcta ctatttatta ctgaattaaa ggagatgaac acctgaaacc atgtattaaa 100200
gtaccttgtg ctacaggtca agtaccagaa atcttgacca aaaatagctt aagcaataaa 100260
agcattcatg atgtcacata atataattct ctgagaagag taattctgag ggccgggcac 100320
agtggctcat ccctgtaatc ccagcacttt aggaggccga ggcaggtgga tcacttgagg 100380
ccaggagatc tagacaagcc tggccaatat ggcaaaaccc tatctataca aaaattagct 100440
ggttggggtg gtgtgtgcct gtaatcccag ctacccagga tgctgaggca caagaattgt 100500
ttgaacccag gagtttgcag tcagccgaga tcacatcaca gcaccccagc ctgggtgaca 100560
gagcgagagt ctgtctcaag ataaaaataa aaataaaaat atataaaaaa agagtaatcc 100620
tgaggttggt tatctcattg gctcaaacat atcaaggacc aagatttctt catctttggg 100680
```

ctctgccacc ctgttggcca ggtgtggtgg ctcatgcctg taatcccagc actttgggaa 100740
gccaaggcag gaggatccct tgagtgcagg agtttgagac cagcctgggc aacacaggga 100800
gaccctgtct ctaaaaagat aaaaacaaaa gaaaaaacgg ggggactgct gtagctccag 100860
atatcacatc ttctcacacc aatgtccaga ggtggaataa agggaatagc ctttcattgt 100920
gtctctttct aagagtgaag aaactttacc agcaacctcc tgcataatta tcttttcaac 100980
gaacccagaa ctgtaccatg cacccatgtc tacgacaatc ctggaaggca gaatgataga 101040
aatcgatatc acactttagg gctggggaag agcccagggc ctctcaaagg acatggctgc 101100
tctgaggaag gtggaagaag tcagggttct gtaagcaaga aagaagactt aaaagggtag 101160
ttcttggttc aacaactgat accatctgca acacaagcat ttgggcattc taaacatgcc 101220
tatctttctt ccacagcaat gatacaaata taggaagtta tgaataaata ttcattatct 101280
ctcagccaag aggacaaggt tttccttttc aggctagtgt ttgagcaacc attgaatgct 101340
tatgcatgtc gtagaatctg tgggttcaaa gaggccttga aggtccatgt atcctcaata 101400
taaaatcccc atgacttctt gtattagaaa agatcccagc aagacataca ggacacactc 101460
agattatcct aatgtaacag gaactcagag gatttgatgc caggactagc tacaagtgag 101520
gccagggctt ggcaaacacc aagggcaatg cagtggccag ggctagtgtc agggaaacct 101580
ccctcaccat gcctaggagg cagaagaggg ctccaagcgt ggggccccca acaggagtca 101640
agaccattgg ttgagggaca tagccaagcc acagtggcct tgtacggatg ggagaggcag 101700
gggaaaatgt ccagacttta cttccttctc cactcaactg gaagccaaag ggcagaggag 101760
ccgcccagtg gaataactgc aggtcagact ctggggtgca gagcagggga gaagagggtg 101820
gagatggcac cggaggagca aatggaagac acccagtcct ccccatggtg ggggccagcc 101880
actcctcagg ctgctcattt cccctggcca gttctgactg ctggaaagtt cccagtcaat 101940
ccagggtcca tgcaaaacag gtctaactct tcacttacat gaaaatactt tagatagagg 102000
acaacagccc acacacctca cagccaagtg gtggagtgaa caaccttgag atgttagttt 102060
agttccttgg ccccagggta cccagtgtct gatggaattg gaaagctaag gtctccatac 102120
atcttcccct tggcatgttg tttctcagct ggaggtaatt gcatccccca caagacactg 102180
gcaatgaata gagacatttt tcactgtcaa aaatggtgga aggcatgcaa ctgacatcta 102240
gagggtagag accagggatg atgcaaaaca tcctataatg cacaaggcag cccccaccat 102300
gaagaatgat ctggccccaa atgtcaatag gccaaggatg agaatcctgc ccaggcagga 102360
gctgagcctg gacaaggctg tagctgcaag acctttcccg ggagccaccc acgatgtttc 102420
tctgggacat ctttgttttc aaggtgagct aatgctgaaa tctgtgtttt caaggtaaga 102480
taacgcaaaa cagtgctaga gtccttgaag aactggaggg aaggaataag cagcaatgga 102540
gtttcagggg tgcggggagc gggaggagat gagagctgtt tgtttgcagt gggaatggca 102600
attgttgaat ttccccttgc ctggccccgg cttctcaact aatgcaaggg ggagccctga 102660
gccacccttg atatcctgcg agccatcctc acatcacaac atcagctttc gcaggcaagc 102720
atgtaaacaa gaagaccagc cacgagaaac ataagaaaga aataaaagtt gtttggtctt 102780
ctgtcaggaa cagattgttg gaatattcca accccagtcc aaaaagaaca accaacaata 102840
acaaccggga gaccgcagcc cacgctgaga cacacgaagc cttcgctttt cccggtgccg 102900
cggaccgttt ccaggagaac gcgccgctgg catcgtcctc tgtttttgcc atggcctggg 102960
gagctctagt gtttgtccaa gcacccgcat tagggccaag aaatatgaaa atgtcatctg 103020

```
tgagcatgaa tcaggagcaa gtgaacttct catctgctga aagtcagcag gtgtgagtat 103080
tctgacaaac atctgcagtc ctgcagcaat tcctcattta tttggcatca acagatcagc 103140
tggaaatatc atattttaag tgaatcttcc agatagctca agttcaccct attaaagaat 103200
atccttaatg atgtagcctt ttagggtgaa gacaactttc caaaaggtat ctattgcctt 103260
tacttcaatc aagtatattg acaatatttc tatttttaa ctggctcaga ataatgagta 103320
taatgtaata ataaaaataa taagatgtct gcagacctag gggtagtttg cccagacatt 103380
aaatgaaccc agatcagaac ctttttcccc ctgctttttt tttttaactc tttatcctcc 103440
ctttgtgtag ctgtcagctg ctactcttta cttacatctc ccgacctgtc catctgtaat 103500
ccctgccttc tagtaattgc cgctgtgggc taggacagtg gttctgaatg ttggcagcat 103560
gctgaaatct cctgggtccc atctccagaa ttgtgttttc actggcctag gcaagaggac 103620
agtttgcaac tccccaggtg actgtgttga gtagccaagg ctgagaacca ctgagatggg 103680
aaatccagta tcttatctgt tagaattgtg cacaaaataa gagttaatat gatctgagag 103740
attttcctac aaataagctt tagtgtataa acctttggca tgtattttga gctcttcgaa 103800
tctgcaactt tctcattctt agctgtacct cagcaatgtg acctcaagct aggagagagg 103860
tagaaaggac cagtggttaa gtgtttgggg tctagagctc aattacctag gttcaaacct 103920
caactctgtg gcctcgagca agtatcttaa cctttttgaa caccagcctc atctataagt 103980
gttggaagga ctcagtgagt cagtgcacag agagggctgg ggacagggtc tggcacgtca 104040
caacactcag cacagtcagc gttacaggca gggtctggca gggtacagaa ttcgcttcag 104100
atgaacaagg aggagaggca gaggtgcgaa ctgggaaaag agcgcaattc aaggctactg 104160
tggttcccag aggctggcga gtgagaagct tgactagcct ggacaggaag cgggaggggga 104220
agaagatgtg ttatgagatc ccagggaaag ctgaggctgt ggagagaagc agggaggcag 104280
cagagaggaa gcacccgact cccattctcc ctccagcctc cgacctcttg caggagcctc 104340
cctcccgctg gctggatcca gtgagaagcc agggagtgga aaagaagtgg ccctcaggct 104400
cagcttctca agaggcaagg caaggcaaag gaagaaagag aatgaatctg ggtgggtggg 104460
aggcaggcaa atggagaaga accagccgag ttagctatta ctaatcattc cgtagctggg 104520
aagtcaccaa agaaagtccc tattgcccta gagtgggtga acgctacaca acatccgctg 104580
tagaatcaga aagagaattg cccctcaagt tcccacatgc tggaagaaat gtgcctccac 104640
cacagacctt tagcaccaaa ctgagatggt tcaacactgc tatgggcaaa agtccaattt 104700
tttaagatgt cctagcctcc ttgagaatct cagggctgag ggcaacgtgc ctcatccctg 104760
tggactagtt cgcgctgctc tctgagcctt ttctcaccag ctggcctctg tctcttttcc 104820
accccctgcc catgcctgtc agaactcaga cctcctagct cacttccttt gctaattgaa 104880
acacattcct gagccccatt tgtaacatgc tttggaattt cttcctccac cacttcccca 104940
cccccaaacg ccacctctct cttctcactc atgaatgttg accttttgtc taataaaagc 105000
ttcattcttc caacctccca ctattgactt aagtagccat tcttggctgt gtttacattt 105060
gctctccaaa accatagtct cactacctat caagtactca gtggtgtaag tagaggcaga 105120
aaccctttc ttccagcagc ttccatttta agtgtaagga caagagacat tgctcagagt 105180
ggctggtggc tttcccagtg gatgtctttg cagcgtgata gttccgcccc atgctttgcc 105240
actgcaccat attacaaatg aaaattagtc acttccagat gcaccccccg ggcatcagag 105300
ccctcttgta ctgtgctggt acacttgctt cgctgccttg gaaactctgc agtgactcta 105360
ttttcatttc catcactagt ttgtttgttt gtttgtttgt ttgtttccag atcctgtaac 105420
```

caaagagcta ttcctttgcc aggatctaat tgaactattc atccttgttc ctccattatg 105480
ttccttccaa attcctttga atccctcttt cccatcacat atgcattatg ctataataat 105540
ggccactatt tggctctgtt ttcccttgga agcctggcac atgttactac tgtgctctcc 105600
tgagtaaaga gagaaggtgg aaccaatcct gttcccctct ggtactcaga tgcccttctg 105660
caaaagcatc agaatcaggg aaccaggacc tccagaaaga gctgggtttg aagttaaaaa 105720
aaatcctaat gaggtttgac ttggcagaat tttaagcact gatttgggtt caggtgggcc 105780
aaaagcgtga gtagcagcaa cagcagcacc ctctgtgtac ccactccctg caaacccctg 105840
ttctaggccc taggaattcc atcaatccct accctcaagg aacttacatt ttagataagg 105900
agagaagact cagcatgtgt gcgcgtgcgc acacacacgt gcacacacac atgcacgcac 105960
acacacacgt gcacaggtgc acacacacgc atgcacacat acatgcacac acacacagag 106020
ccaataatgc aggctagcat agaatgaatg ccaattaagt agtagctaaa taataataat 106080
taacttgcat ttaaaaatct gtaacacagg catttctctt aatcaagact cattttctcc 106140
caggtaattt ccattttaat tggtattggt ggaggtttta attagatttc ttaatctatc 106200
tctgtttctg tttgcacaac tgaaagatgt ctcccacttc caaatctagc gtattgtttg 106260
aaattttgaa tttatgacat ctccacaaat ttactataga ttgatccatc agtatctaat 106320
gatgtcttga gatgatttct tatgattaaa acactttaaa gtagtgatta tctaaagtag 106380
aatctaactt cccgtttgag gaggttgaaa catgtgcttc ctatcttcgg ttctcatttt 106440
ttttaatgtg ggtgctgctt tagcaaagcc aataactaca agaacatcct cccccagttt 106500
gagtagatgt gtcaccagaa aagcaaaagt ccaatgctga gtgatttgag tggcttggaa 106560
gaatttccca gcttgcagct tatactgaac gagcattaat acaagtaaac cattaactca 106620
tcagtcacac ctgctctgtt tgctctgtgc ttgtttctat cctagcaccc ttgacaaagt 106680
gctgagcttg ctgcctgtgg gcatgtcggc ctccttgcta gaccattcac tagctgagaa 106740
catgcaggag gtcttttaaa aaaaattttg tatatatata tatgtgtgtg tgtgtgtgtg 106800
tgtatgtatg tattttaatt gacaaataag aaatgcgtat attttatgat gtacagcatg 106860
atcttttgaa tgtttgtgca atggctaaat caagctaatt aacatatgca ttagctgaca 106920
tatatcattt ttttagggta aaaatattta aaatccactc tcttagcaat tttcgagtat 106980
gcaatacttt actattaact atagtcacca tgacacacaa tagattctct gaacttactc 107040
ctcctaactg aaattttgta tccttttact aacatttcct caatccctgt acctcctctc 107100
cccaacctta gcctctcata accacctttc tactctctac ttctatgagt tccacttttt 107160
tacagcctgc aagtaagtga gatcgtgttg tatttgtctt tctgtgtctg gtttattccc 107220
ctgagcaaaa tgtcctccag gttcacccat gttgtcacaa atgccaagat ggcctttttt 107280
gaggatatgt agtattctac tatctatatg tcctgcgttt tctttattca tctacattta 107340
ttcatttatc cattggacac ttaggttgat tccataactt ggctcttgtc aatgctgcta 107400
caatgaatat gggggtgcag agagctcttt gacacactga tttcatttct ttagatttgt 107460
acctagaagt gtgtatatat ctagaccaga atggaattgc tgggtcatat ggtagtccta 107520
tttttaattt tttgaggaat ttccctactg tttttcataa ggactgtact agtgtacatt 107580
ttccccagcc gtgtgtaagg gttcttttat tcacatcttc accaacacac atcattggtt 107640
ttttcatgct ttattttttg gtaatagcaa ttctaacagg tctgaggtca tatattattg 107700
tgatgcagta ggtattattc agcttggtac agtgagtaca gcagagagta cagttcccaa 107760

```
cagagagtac agtgctctgt gcccagcagg cccagaagtg gattaacgag ttgattgaat 107820
aactgattag tgggaaataa ggaaagcatt aatactccca gagagcaagg atagacctag 107880
gggtgcttgt gagaaaccaa ggttgatcta cagcattcac agcctggtga aaggggccca 107940
gagtgtggca ccagctgtag ccctgtctgc actgagggcc aggtgagtga gatgtgactg 108000
ggtacccctt ccaggtccag ggaagaatct gaagagtggg gcccacatca cccttcagaa 108060
cataagacat ggacactccc tgatcacagg gacagcccag gtcatttagc cctatcccat 108120
accccttat aacaaaatac tctattatta cttccgtaaa acttggaaat tgagatatgt 108180
gcaaatgagg gtatgttcca aaaagctcct aacaaatact aactccaatt ctcatctggt 108240
tcttgggctt gacatagaga gggagagaga gtggaaaaag gatttggtct caaaacaact 108300
tttggatttt gcctggaaac agtatctcgt agcatgttca ttgcagcctt tggctgaatt 108360
ctttcattag aaagaggaaa agcacatttg gatgttgacg tgacattcag gtaggcaaca 108420
tttctttgct cgacttggga aaatgctaat gaagaagaaa ccaatcctat aaaaagaggt 108480
cagagtacgt caaagtacct gtccaccccc atagtcgttt tccttaatct tgacatctga 108540
atcacttgct gtcgggtgaa cacaggaatt ttccagggaa caatctcata ttgagtgagg 108600
ctctactcac ggttgcccta catgtcatgg gtgtccattt cggccttcca ttgtatgaac 108660
aatgcccagg gtaattcgga tcttgataac attgactcac aacctcaaat aaatgaagtc 108720
atatcaagcc actggcaaga cggaatctgc cggccggaaa gggagtagaa ggctagacca 108780
caggcgggga ctgtgtggag ggcaacacag gtgaacgcac acagataggc gcagtccccg 108840
gccgttcgca cctcagcatc ggtggcactt gtcatgattc aggttgccct tgctttcagc 108900
aaattcaacc cttttgaatg cttgtttttta tagaaactaa attagagagg gattattcat 108960
ttacaaacaa attgttcatt ttaaccagag tcttaagtaa ctgatacctc tgtgctagtt 109020
ataatttttt taatctcaac ttggatacac attttcaaga atatatctat taggtaaagt 109080
acactcacat aaggaaaagt agatggttaa ttgcctggct atttaattcc caatatcata 109140
atcttggaca ctcctttcaa taaaccttca cctagccaat tcccaagaaa tcacttcctc 109200
aagtgagtta aactgggcaa cggttaagca ataggagtgt cttttttca gatgccagca 109260
cagagccact tgtccctgtt aatcacgaag actggaaaac aagcagagct atgtgacgga 109320
tatattcacc agaccctatc tctgtgggag gcggtgtttt ggcacagaca ggctgatgat 109380
ttcagggtca agagggaagt gattaatcaa actgggaaga agacagagga aaatccagca 109440
aacagctatg aagaacatat aaaaacaaca accacccaat atctgtatgg gtaaacaacg 109500
ctccgtttgc acactggaga atgcaatgaa gtgtgaccag gatgaagccg aaaacaaaga 109560
aatgatgctt ccaactgcgg ctcccaggca tggcttttct ttctgcacct tggagactcc 109620
tctgcagctc cattctcatc ccacacctcc agggtctgtg cacaccaagg caggtggaag 109680
gggaggcaag gaactgagca atctgaggtt aggtggggga aaggaaacac accttctact 109740
attagtgcaa aacgagaatt ttcccagtta ccgatcttga aataaattca tcagatgata 109800
gcgttctcct tcttcttttg ccccttcttt tgctcacaca tcctacctta atttgaaaca 109860
ttgcaatgaa agagaaatgt aaaaagcaaa tctagaccaa gctgcgttca aatgtgcatg 109920
tagccagaaa ccttaaaagt agaaggtgat catttttgttt tgtttgaatt ttttaaaaag 109980
tataacatct gtcaggtact gactgtgaat tctacatctt gtactgagtc gcccctctct 110040
tctatggaac attagaaagc aagaggaact accatttgtg atagacgaag acagatttgc 110100
aggtggaggg agtgacaaga cctgatttgt tttctgcaca taatgagtaa tccttcagac 110160
```

acagagatcc tcatctgcag cacgagagaa aaggtaaacc aagtccccag gctcagcacc 110220
catggaaagg agcagaggga gagagtcctc tgagttggca cacgagttct gcaccgggct 110280
gtcctttgat atgacagctc tcttctgtgg tggggccacc taagaagtgc ttgggaaaat 110340
atcttgatag gagaactaga cggaaacatg ctttcagaga agggatgtgt cttgttgctt 110400
attgtggttt ttcaatacat gagcctagtt tacatagcag gggcccaaat gcagctctgt 110460
ataatattgt catacttcag ctatgtgcgt gtttatcatt tctttaccaa caacagctgg 110520
agaaaatggc tgagattgga gaggagggag cagaggtaga gaggaagtca aaaccttgga 110580
atggatgaca taccacttcc ccaatgaatg aagctgcaga ttcagccaca tgtagttgat 110640
gtcgccatgt caagactgca tttttccttc caaacacaga agtatggggt aaacttaatg 110700
caggactatg aagatgaagc cattgaggcc caagacttta tcttgatttc ttcaattcct 110760
tggatatgtt tactccctcc ccacactggg cccttgtagc tgcttagact gaacctactg 110820
gcccttctct tgctggaaag ttgccctcca agaagtgcaa gagctcagat tgcacctgct 110880
aactgttaag accagacttg gccaggctac cagatctttc tgcaacaagg ccagcttcac 110940
actgcctgag cagacctttc tgttctgcca aaggcagctg aagcagggaa aatggatcag 111000
caaagggatc tgggccaggc gcagtggctc atttctctaa cctcagcact ttgagaggcc 111060
aaggtgggag gatcacttga ggccaggagt tcaagaccag cctgggcaac aaaatgagac 111120
cgcatttcta caaaacaata aggttaaaaa aaattaatca ggtgtggtgg caactgtggt 111180
gccaactctt gagacactaa atcgggagga tcacttgagc ccaggagatg gaggctggag 111240
tgagctatga tagcaccact gtattccagc ctggaagata gagtgagacc ctgtctcaaa 111300
aaaagtaaat aaaggaatct gaacttgaag aatgggccaa aaaagagtga tacttgactg 111360
cggttcctct ttgcctgtgc cgtcacctgg gattggaatt ctgcatttcc cacccccaat 111420
tcccttctcc agtcatctaa ctcctctgct tcctccaata ctcagctaag gcattacctc 111480
ctcctagaag ccttccctga aatcctcaag cagttctctt tctttgactt ccctctttgg 111540
agcctcaact gtctctttgg gtttgtctgt cctgctagac tgaacgtaaa taactaatga 111600
gggtatctgc atggaaagaa acagaccctt ctaagtgctg tgttaagtaa cttcactgaa 111660
ccagatgaga gcattagagc agctgctttc tagggttttg ccagctcctg tatgcggacg 111720
tgaggctgct ggggatgttg ctattagtga taaagttaag ggtccaagag gttctttgct 111780
tcacgactac gtcattggag gctgataagc catggccaag tgtgttcaag gtctccagct 111840
gtcataaaag tgtctgcttg tttattttag gtagataagt gttgctatta ttcctgggat 111900
ggtaggaaaa gccgggggca agaaatcact ctgtgaagat atattgagat ccctggaaca 111960
tttaaaaaaa aaaaaaaaaa aggttgaggg gagggagaga aaccacatag cctgcatttg 112020
gtgatactgt aattctagct ccctttaatt acagttaatc actacttact attttgtaat 112080
ctaaggtaat gaacactgta gctttgcttg ctaattgaag ttgacagaat gcgagaaagc 112140
gccctatggc aaaccccttt catcaggaga gtgttttatc tttgtttatc aacaagagag 112200
tggatttttt gtttgtttat tttaaggagt cacactctgt tgcccagact ggagtgcagt 112260
gatgcgatct cggctcactg caacctctgc ctcctgggtt caagcaattc ttctgcctca 112320
gcctccagaa tagctgagag attataggca cgcaccacca cacccggcta atttttgtac 112380
ttttagcaga gtcagggttt ctccatgttg gccaggctgt gctacaactc ctgacctcag 112440
gtgatccacc cgccttggcc ttccaaagtg ctaggattca ggcatgagcc accgcatccg 112500
cccaagagtg tttgtttgtt tgtttgtttg tttgtttttt aatggtttac tctaggttta 112560
attcagagga agtaagagat tattctgcag aacacccttg ggtatttaac ctggcacaac 112620
tcaattaata agtgatccat tttactatta caaactaaat ttatctttgg aaataatgac 112680
agaccgaaac aacccagaaa ctacatatat ctattttgta tgaattaaaa aggaaagaaa 112740
tcaccagaaa gaaaaaaaaa gagttattta attgagtgca tggccccata agggcaattg 112800
gaaacctgta tttaagtttg tatgcaattt tgtgtatgca ttttctggaa agaaaagtca 112860
tactttattc agatacccaa ggaggtctgt gatatcccct ctgccaatct caacttagat 112920
attagtgttt agtgaatgaa atagtccata aactagattg actataaatc tggtaataat 112980
gttgtaaaat aaaggttttc cacgctctac aaaagaaaac caaaacaaat agcatagcta 113040
tagttctctc aatcctcatc cccaaattct ctgcagctcc ctaaatagcc taagacacca 113100
gagaaagtca gaaatttatt gtcacagcag ctagaatgac ctgtcaccta accagacaaa 113160
gtccagagca gaactgaagg agcagaagtt cttagaaggt ttaccttgca ctgccatcac 113220
tcacttccag cccaaaacct ttaacaggta ctttgtttgt agtgaatggc ttaacttcac 113280
tgaattgcag ttaacctcaa acgtttgggt tttttgttaa atgttttaag acgagaggaa 113340
aatagcactt ttacgtaata agaaatttca gatacttgac ctctctaagt tcacaaattc 113400
ccattttaat tttcattttt actgaaattt cttacagaga agtaaaatcc ctcttcctaa 113460
tttcaagctg atttaaatac ctctgaaacc aggttaaaac ctaggatatg atatagttct 113520
cccatttggg ccagttgaaa taaatataaa tttagccctt tttccccaaa tattggttgt 113580
gtgtgtgtgt gtgtgtgtgt gtctgtgtgt gtgtgtgtgt gtgatggagc ttcgttcttg 113640
ttgcccaggc tggagtgcag tggcccaatc tcggctcact gcaacctccg cctcctgggt 113700
tcaagtgatt ctcctgcctc agcctcccaa gtagctggga ttacaggtgc ctgccatcac 113760
gccaggctaa tttttgtatt tttagtagag acagggtttc accatggtgg ccaggctggt 113820
ctcaaactcc tgacctcagg tgatctgccc gcttcggcct cccaaagtgc tgggattaca 113880
ggcacgagcc actgcaccca gctggtaaat tctttattat cattaaaagc caacaatttt 113940
gactcagtct tattctatat atctgttctt tcattcttct tgtatttcaa tgaatgcttc 114000
tataagtata ctgacttcag ccaggagtgg tggctcccgc ctgtaatccc agcactttgg 114060
gaggccaaga caagatcact tgagcccagg aatttgagac cagcctaggt aacatggcga 114120
aaccccgact ctattaaaaa gcaatacaaa agttatgcag tctcggtggc gcatgcctgt 114180
agtcccagct actagggaga gtaaggaggg agaatcgcct gagcctgggc agttgaggct 114240
gcagcaagcc gagatcgcgc cactgcactc cagcctgggc gacagagtgg ggccctgtct 114300
gaaacaaaat aaaagtatat tatagatgcc gtttttacct tgactcactg acatccagtt 114360
tcagagccag caaagctgag gcccaactct gctgtggtct aaatctgttg tagggtgaag 114420
cctgagggtc agtttggtgc cccctttac ttttctctac ttaaattcaa tctattctta 114480
cggcataata cttagaaata aactttctat tataagcctt agatataata ttcaaaggta 114540
attagtttat tggagaactg gagaaaggcc attttttaaa cagtttattg gagaactgga 114600
gaaaggccat ttttctcccc cagacaagac ccgtatctcc acaggcattg acaatagctt 114660
cctaattttt ttttcttact agctgattag tgctatgtct aatgaattgc ccataccctt 114720
gttccctagg attgttgttg aaaatatatg cagcaatcag catatgtatt tagttgaaaa 114780
ccaatgtctc caacagcctt aaaagcccag ctttctcttc taatatcaaa atattctatt 114840
ttactaataa accatttctt aagccatgta aaataaagtc taagtacaaa tcttaaggca 114900

```
ttatgaaaag atacttggga actacatccc tgcagccaag gaagtggtgg tttttttttt 114960
tttttcaaag acatctgacc ttatcaaagc ttcagaccaa gaattcagtt catcagttca 115020
tctgctatct aataagcaca agagccattt gtccttcaca tgataaggtc atggtacatt 115080
acaagccact tgcaggtttt gttttcttga aaggacacat ttgcagggag cactgccaga 115140
gagaaacgac tggctgaaat caaatagtcg acatcaaggg atacctattt cagaaaaagc 115200
gattgaaggc agcagccaga aatgctgaga ttttcatatg agggatgttt gtaatcataa 115260
gccagcaggt aattccagca tgtgcagatt ctctttgaca tggtgctata aaaactcttg 115320
ggctaaaagc aaaatctcta cctgacagaa gcaatcctca ctcccatcta ttgatacttt 115380
gctcctgatt cacagcaata aatggtcctt aaagtgaatg agaggagggt aattcattcc 115440
ctacacacac accaagatga gcccagtctt cttgcattaa cttcttgctg aatgcaattg 115500
atccggacca ttggctggtt ttccagagac ttcaaatagc ctgacttggc ttgttcagcc 115560
agtagggttg agatcagaga cccctacatc aaggtcactg aaggtaccat tggaaactac 115620
aactatcctg gcttagactc agaccactgg ttacaacttc ccattcctag gtgacaaata 115680
taaacccata cagtagttga agactaagga ccaataaaaa gcagaaaagt ttttttaat 115740
aataataaat acacctggct aaaaattcca gtggccagaa ggaataaatt tagcatctta 115800
gctttcgttg ctaaaatagg atctgcttcc aggctcactc ttgtaaggga attgtgtata 115860
taatggcttc tttttccaga gtttggggca gggtttctca gcatcagcac tattaacacc 115920
tggggacaaa taattattta ttgtggagtt gccctgtgca ttgtaatacg tttggcagca 115980
tccccagatg ctactagatg ccaatagcac tatgtctccc cctcccccga atccacccaa 116040
gtttgacaat ccaaaatgtc tccagatatg gaaaaatgtt ccctggagta agtgaggggg 116100
gaggggtgca aaatcaccca caggtgagaa ccactgcttt agggcattat ttgtttatta 116160
attgtataaa tgtatggggt ccaagagcaa atttgttaca tgcatagatt gcactgagga 116220
caagtcaggg ctttagccta tccatcactt gaataatata cattgtaccc attaagtaat 116280
ttctcttggt cccctccctt cccacccccct ctcccttcca agtctccatt gtcaatcatt 116340
ctactctcta tgtccatgca tacatggttt ttttagctcc cacttatgag tgagaacatg 116400
tggtatttga ctctctgtgt ctggcttgtt tcacttaaga taatggcctc agttccatcc 116460
attttgctgc aaaagacatg attttattct tttttatggc tgaagagtat tccattgcat 116520
ttatatacca cattttcttt acctaatcct ccattgatag acacttaagt ttatcacata 116580
tccttcttat tgtgaatagt gctgtgataa acatgtaaat acagttatct ttagggcatt 116640
atttaataaa cacatttcat ctgtaccaat gacacctctc ccctgattcc ttgctctcca 116700
aaagtacttc cttccaaaag aattgcctcc aaaagaattg ccttttcttc tgtaaaaagg 116760
tgaccagtct tagtttgaac aatttttctg ccaatattac tagtcataag gacaatacat 116820
taattgatcc aattgttctt tcaggataga gaaaagtgct tccatccata catgctggaa 116880
aactttaagc atagatttat tgaaagaaca aaataagtta aagtccagaa aatactgtag 116940
caatattcaa gtcatcgaga aaaccagaaa aaaatgaaaa tttaaaactc atctgaaatc 117000
ttcacctgaa accacacaga aataaccatt gctgatattt ggtgagcgtt tttccactta 117060
tctctccttg tccatataac agatataaag cctggtagac acaaagaagt tcttctgtga 117120
aataacccag gattcattat cccgtagttt catattgaca tttagaataa tgagaggata 117180
ctcatgcaat tttaaacttg aagtatttga tttaattttc cttgaattaa cagattaaaa 117240
```

aatctgaaaa ctgaagaatc tgatgaactt tggacatttc ttcactgcta gagatattag 117300
ttcttaaaag gtccctataa tttaagaaaa tgtgcaaaac ctatagagct ggctgggagc 117360
agtggcttac gcctgtaacc ccagcacttt gggaaggcaa ggctagagga tcacttgagc 117420
ctaggagttt gagaccagcc tgggcaatac agtaagaccc ccatctctta aaaaagaaac 117480
aaacaaacaa acagaaaaac ttaaaagagc tgaagttatt gttattttta aactgtgctt 117540
ttcactgttg actccttgac aggaaagatg aggaagtcag ttaacatatt tttttcaacc 117600
tcttttcttc tcttaccagt atgattagtt atattaaaat acttacttgt gacctttaaa 117660
ttcttttttt cagccttact ccccaaattg tttggtctca gttctgtttt aaacgaatcc 117720
acagcctctc agtttctgag ttctttattt tgattcattt tttatttggc tggattggtt 117780
ttcaagacac actttttatt tgcaaaaaga acccatggat gctgtgttcc ttgaggtttg 117840
attcgttcct aaatatctgc ctcctgcttt cttactcaag gaacaactgg gctagagatt 117900
gaattcttgg ggaccccttc tcttgctcaa tctttataga caccactcca ctatccctgg 117960
tggttcccca agcagtgacc tatgagcgcg ggatgctggg gcatgtggtt cctcacagag 118020
ccctgattct tcctctgggg gcgccatctc actcagactg cagcctgggc atgctcctgt 118080
cacctcgagg aggtgatggg agtccagctt ttgttgggcc ccctctcgcc actgcccagc 118140
ccctgggctc aatctgcatt tccagtgggg aggtagccgg ttgcaaagcc ccttctccat 118200
ctacaagaat ggcagcagag gctgaccctc cttccttgcc ccagacctgc cttccacatc 118260
cggggaactc tgatggttgc cgtttccctt cttccatgaa ggaggctcta ccactgtccc 118320
tattttaaag atgaggacac tgagacatag aggaattaag gaatatgccc gtgttcagat 118380
agctaataag ctcaagtcta gacttgaacc taagaagact aagagatgct ctgatatcta 118440
catggattat tgtgagagaa atggtctcta tcttgactaa ggtttgcaag gatgtaggct 118500
tacagaagca tacattaaaa tttgggttag gactaagaac aaacttcctt tcttgagagc 118560
aacagggctc agtctaccaa aagaggttat aagtaccctg tgtaaatgtc ccagacaaaa 118620
atggcaccta tgcacatgtg acctcatggc acctatccac gtgtgacacc cttccagcca 118680
accaaacaat gacctcatga tgtcaaaggc caggaatgtg aattgggaag gcgaaaataa 118740
cagcttgctt tcactttcca agcacaagcc agccagccca agacgtttct ctctgccatg 118800
tgctccctgc agttcaagag ggccatccat gcgccagaca gattaaacac taaaggaatt 118860
ctagacgatc actcctggga gggttttttt ccactacttt ctaatccaat gaagcctggg 118920
ctggcaaagg cagttgaatt gagagtggct aaatatgcag agtccttgga ggttagaata 118980
cagtctgtct accaagagaa ggcattttgc cttcagtctg tctggatttc taatatctac 119040
tgcagactat taatcatgaa ggccagactc ttgaacctct ttgagttgtt tcacatttaa 119100
tcagaatcct ccccccttaca cacacaaaaa agctacaaaa tcctgcctgg ttatctgatt 119160
taaatgaatt ttaacattca aacaatggtt tatctggaac atatcccctg catcgaacgt 119220
atatttaata gctttgaaat aaagtcaaac aaaaccaaaa atgcaattac tatgcatgtc 119280
atgaaatcat cagaattaaa aattagccaa ggtcatattg ttcatttcct ttagatttcc 119340
tgttaaaaca ctggttaccc cagattttca ccatcaggaa atgggaaaaa aattgaataa 119400
ctcattttct ataagacaat ttccatcaaa ttgtattggg tgagaatttg gcccagaatt 119460
tacactttaa tgtatgattt tgcattttaa atgtcatctg attttatttg tgattttcac 119520
attaagcaga tgtcataatt tacctgaatt ccatgaatag ctctgttcat ccacataccc 119580
attttccatg tatttaactg agctttaact tattttattc ttttaatgaa tgtatactgt 119640
gtttaactca gacttttcta ttttggcttt ctgagatgtg aggatggaaa tgcttttctc 119700
taagaaccct attctgggat agggaagcca aattggaaat gtggagccac actgatatac 119760
agcttccaga atagtcatat ttccccgttc caaccacaca taaattccta aacttgcttc 119820
acacagagaa tctgggaagt gaacaaagcc tatgttttcc ctcttctact ctccaaagtg 119880
tgggttgtgt gttggcacct taggacagga agggaattta gaccgcatgc tcttgattgc 119940
acagtctggg agggtatggg gtggtaagga gagcaaatgt tcagctaggc cagtagaatg 120000
ttgccaccaa tctgtcacta acgcagctgc caaaattttc acattgccga gaaagtaagt 120060
ctttaaagca aaggctcttt gtgccttctt tttggaagtt tcttgctaat ttcctcctct 120120
gcttccctgg cgatctgaga gctagagctt ttgtaccatc aactctcagc aaatagaagc 120180
tgggccagca ggctgcaaag caaagggtct cattaaacca cagccctttg caagtcaggt 120240
ccgggcacat gtttggcatc aattttctac actggggcat attccaaaat acataaggct 120300
ctcaattttt ctgtttcttt aaaagaaatt ctccaaagtc agataaagtt aaggaatttg 120360
aaaggtgttt aaggtggagg tttccactag gaataattat tccaaggagc tgagttccaa 120420
atttgacatc ctcagggtaa gacgagaatc taacacatca tagcaataat gactgtctgg 120480
tggtctgcaa gcttcaccgc tgggccgaag tgctctttca ctgcacacag actttttagtt 120540 gtttgggaat tttagcagag caaaaacaag gggaagagag aaaataaggt aaaaacaagg 120600
ttcaagttgt cacaacagcc atatattctg gattttccat gatccgcatc catataatct 120660
ctctgattgt tcccataaag gtagtcatac tcactagaat tagaaaagtt aaaagcataa 120720
acttggtata gtttataaca ggtaagacac aactctattg ttctttgaga gcaatgattg 120780
tgccatattt atcttcgtgt ttctaatgac ttgcacatga caaagagctc aatttatgtt 120840
gaatgaatga attgaaacat aaatatgcta atgaaaatca acagaaatat gggaggatag 120900
ttattgtatt aagcattatt gttttacctc tatgactgat tttaacatac actaagaatg 120960
caaagacata ggttctaatt gtggttctgc agaataccag ggagaaagtt acttatcctc 121020
caaagactca gttttgccat atagaaaatg gagttaataa cttccctgac ttagcttatg 121080
ttatggagtt gttatgtaaa ccacctgaga cactgaatgt gaaaacgctt gataatcgga 121140
aaagatgcgt accaatgtac attttcatca ttatcgttat tattaccaat catcacggct 121200
ctggtactca gggatgctca gtcctctcaa atcttgcaaa aagaaaactg ctgggagcca 121260
caaaacatct tgtgccacat gtgagcttac tttccaaaat ggcttcgttt ttatagtcat 121320
taaaacacaa ctcaaaacct gtcattcttt gtccctagtg agccaaccag gacatgatca 121380
aatgtggaga attatggagc atgaatccca ggaagaattc ttttacaaca cacacacaca 121440
cacacacaca cacaggctca cacacgtgct cacacataca tgctcacaca caatatcaca 121500
catcctttca gcactgagaa tggttaatag taggtgtgaa gactcaccca cagaaaactg 121560
agaaatagtg tgtgactatt tctgtgacta acacactttt tatatcatct tcctcttcaa 121620
taccatcctt accccagatg tccaggatct tcaagttact taggacccag catacatgtt 121680
gctaaacttc taccacttct gtaagtcatt taattcaagc ccattcactc aatgcccaga 121740
actggagtga caacgggtgg gatgagaagt catcaccttc ttcatcacca tctttgtgat 121800
cttcatcatt tcatgaacac ttactctgta gctttacatt catcatctct gtctattgtg 121860
acaacatctt atgaaatata tactattaac cccattttgc agatgggcaa gtcgagactc 121920
agaatgatta attttcccaa aggcacacac cctaatgtga cagactctgg atttgaaacc 121980

-continued

```
aattccacct gattctaaag accatgtttt taaccacctc actgtaatgc tgagtgttct 122040
taatcacagg aaatctttgg tgtgctagga cagaggtttg caaggccttc cgggagcttc 122100
tcaatgtaca ttctctactc tgtttatttt tgtctgtata ccaacatata tttttgaacc 122160
ctttttttata tatggccaat gatgctaggc ctggaagaat attaaaaaca attatttcta 122220
taatgtaagt gactaccagt tatttaattt ccgttttttg ggttatttgt attttaaaag 122280
aaaggctata tgctataagc caagtgaatg aatccctaat ggtacgattt ctgacactga 122340
gactagcaga tggagaagga tctttgtttc tgtggtgggg tgtgtgtctg tgtgtgtgtg 122400
tgtgtgtgtg tgttaagggc gcagtcaagc actgcactac tcgtaccata ccatgcagac 122460
aaccatctaa tctgatctct caaaaggttt gacagtattg gcatcattct caatatcctc 122520
atcctacacg ttaaaattgc taattaatat tagtatttgg ttgctttatc ttaaaacaat 122580
acctacctct gttaatagga aaattagaaa ttatatctat tgttcctaaa gatacaattt 122640
gtttctctaa ctccaaggga agtgaatgaa tatgtttcag actatacttg tctgtgtatt 122700
atttgttttt gtaaggtggt tttttctttt gcttcaaatt gagagcatac aaacaaaatt 122760
ccactgtata agcagtcaat tttggtaata ataacacatg cctagagcac tcagattaaa 122820
ttattacaca tactaataaa attattcaca gtagtactcc ttggtaatgt tggtattagg 122880
gaacaggata gaacccatct tcaaagtcaa ccctattact tcaagccttt gcagggtcct 122940
gctgtttcca aggatacaat ccaatgctta atttacagga atccgaaatc atttgctgtg 123000
ttaaaaactt gagattagcc cttgctgccc ccttccaggt tggcctttgg aagcgaaagg 123060
tctttaagct taagtaaact ggagaatatt tctgagtaag caggctccag gtggagggta 123120
cactccaaga taccttcact tgccaaaaca acactccctg caaggttatc agcgaaaagg 123180
cagtagaaag agccctcctg ctgccagaag gtcttgtttt gcaaggcttc tcagcctgcc 123240
tgcagccatt gggtgaggag aggaaaggac acctcacctg gcagagcagc acaaaggtca 123300
ggcatgtttc cctcctgacc tggaagctgg gtcctgctcc ttcacatgaa ctgtccaggg 123360
cttggtcata tacccaggtc cccctcagtc ctgcccagag tgactccact ggtctcccca 123420
gaaaacacca acagcagaga gaaatgaagt gtgtctgttt tctggtttca tattgcagct 123480
cctcttgctc ttcttaggac agaaataaca tctgcaatgc cagagacctg tgaagtaata 123540
aacaaccttt cccccagctc ttgacaagca ttaccttgct ttgaggtgca atcagttctg 123600
acaagtttat ggctttgtgt ccttcaaccc aatggacatt accctctggg ggagtttaat 123660
gacccctctc agcttcacac tcacttgaag gaaagagcta gaagtcagta atgatgtgtt 123720
atgacttgca tggcttcagg tagttcagaa cctgcaacct gtagttcaga ttacaggaga 123780
agaactcaga cgataaattg gcttccaaag aaggccaaat agaaaaaaaa aaggcttctt 123840
cagaccaata gctgagtgac ctgaaattta aatgcaaaaa atgcattaaa acccacaaaa 123900
ccacttcctt taaaattctt gataccaaac atgttacagc attaagtgaa ccttaatcta 123960
agcaaaattc agagaagagc attcacacct ttgatagaag agccagccag ccagggtgct 124020
ggggctcagc tcttgagaaa aatgttgatg taaaagcctt ggtggcctgg ttcagcccct 124080
gagcctccct ggtaagcaca tggcaggctc agaacatcca taactgaatg ctctgagccc 124140
tgtaaaaatg cagttacaat gggaaatcaa ctcttaagta tgctatggga tgctgtgata 124200
aaatttgagt ttctctacct tctgtttgca ctttggttca tttagaaaag agtccataat 124260
tgtgtgcttc aagagtgcaa ttccatggct gtaacagaat agagtcctct ttcttctggc 124320
ctttgcctct ttggggatat tccaactctg tggaaggtga tcatttgcga ttatgatcag 124380
```

ttatttatat ttgactgtaa atgaaaactt cagagtcagt ttcaaaaaac aagagatgga 124440
cataaggaca tgtgcttatg agtaggggac aaataactag agacaagaaa taaaaagaga 124500
caagatatga gacaagataa cctttgatgc cgtactgcac acacacacac acacacacac 124560
acacacacac acagaatcta cattgtttct gtcactctgc ggggctgctg gaaggcagaa 124620
atgagaagcc tcggccctca tcttgtttag agttttgcct gggccaggct cttctgctgc 124680
attggaattc aactttgcaa atctcagtgt ttccaggttg acctcgggag aaaggggacc 124740
ccagaaaaaa ttagaacaaa aaggaacaag taaggagcag tgtctagaat gggaacactg 124800
acaaaaagaa gcaaagtcag aacacatggt ctatttgggg ggctgttaga cagacctgga 124860
ctaggctaat tccagggttg cctccatgta ctcacgggcc ctcagaaggc actcttccct 124920
ctcttccctc tccagatcct tgtcttccca ttagatcaat gaggatggag gactacacca 124980
gggacaccca actaggggca attttgcctc ccaggggtta tttgccaatg tgtagagata 125040
tttttggctg tcaaaactga aggtggtggg tgctactggc atctaatgtg tgcaggccac 125100
ggctgttgtg aaacatcctg aaatgcacag gatactctcc aacagcaaag aattatccag 125160
cccagaatgt caatcatgcc aaagttgagg aaccctggct ccaccatttg aaggatctga 125220
tgcaggtgat cgatggtccc ccagaagagt attggtctgg gaccaagagt ccaatggcca 125280
tactttacat ttttccaggg cctgagtgcc aaagtgacct acaatcctta taaatgttac 125340
cctgttttct ggcattcatg agcattggag gttgaaaaat gattctctaa gagaggcttg 125400
gcctgcagtc aagttgaaag gtgagtgaga gtgggtcagc ctacaaatat gccatccaca 125460
tggggctgct ctgagtttgc acaaaggaca gaatgtcacc taaatcaatt cacatctact 125520
gatacaaaca gcctactgca aaggctctat tgaatccagg gtttgtaata agtatatcag 125580
aattcgaccg ggcagggtgg ctcacacctg taatcccagc actttgggag gtcaaagcag 125640
gagaatcgct tgaggccagg agtttgagac caacctgggc aacatggcga aaccctgtct 125700
ctacaaaaac aaatataaga attagccaag cacggtggca cgcacctgta gtcccagcta 125760
ctcaggaggc tgaggtggga ggatcacttg agccggaagg tccacactct agcctgggtg 125820
acagagtgag acctgtctca aaaaaataaa taaataaaaa ttaaatacta ataaattctg 125880
tgaaagagat accacctacg cttcttggta attgtttggt gaatacagcc aacaagagca 125940
gaggcgcctc tgtggtgtta gagtgggctg gagtgtttcc acaagtttgc caaatattac 126000
agaaatatcc tgccctcctg ctgcacatac acctggcagg agaggaacca atgggagaag 126060
gtctcgccgg gaagattcca gccagatggg ggccctgcct tggcaggtgc ttggcatggg 126120
aaaggtggtt ctgaagcacc aaggcaggtg gcttgtgaat ctgcctacat tcccctaact 126180
ctctgaggct tgaaatatcc cctcagggct ccagagagtt gctgttgttc agttatgatg 126240
ccccatgccc taccagcctc tagcaaaaac catgcatagt gacttgggaa attcttttca 126300
ctttgctggg ccaagaccca gatgctctgt gggcatgctg atgggggcct agtggtgtta 126360
ctcctgtatt cctccgtagc aaaaaaatag tattaggaga gatacaggga gatcaggaga 126420
atacagcgtc ccttcaactt ctgcccaaat ttctgcagta gcctcctaac cagtttcctt 126480
atagctctct ggttcccttc caatctctcc cctcctatgc agccagaggg attccttcac 126540
actgaaagct aatttgttac actcctgctt aaatacataa agtgattcca tagtgctcag 126600
ggattaaggg aaaaatcctt aacagatctc aaaaggcctc gcatggctcc agcggctatg 126660
tggatccatg caaggccttt tggggtctgt taaggaattt tctgcctctc aagcctaaca 126720

```
tcccaccatg cgccaagctt gctttcattt ccttggatgc cccaagcttc cttctgccac 126780
ggggccttca cacatgctgt ttcagctacc ttagatcttc tcctcccagg cccccaccac 126840
ctcttgtcac cagactaatt ctattctcct cagtccttac ctctctcaca aggccctggc 126900
caacctccct caccagatca tgcctcatac accacctatc atggcaacgc gaatttcttt 126960
tacgtagttc tttacaaaat tgcagtttta cattaattta tgcattggaa ttcaataaat 127020
atctactgaa taaacaaatg aatgaatgaa tcaccccctt ctggggtgga acagagaatc 127080
cctccgacca cacattctta cttccatctc tttggtggtt ctgtcctctc agcatggtta 127140
gctgttgatt tgtatctctg cccataagat tcttcctttc tggccaatcc cattcatcca 127200
ctcatttctc catgaaccct tctctcatct cctactcctc acagaactta tttgtctcac 127260
tctatgaatc ctgttgcatt ttctctattt ttccacactt tgccttgaat agcatcagct 127320
gtagacatgc tagtcttccc tttggggctc tgaactcctt gagaaaagag actcaaccca 127380
acatattgtt ctgcaaagca gcatgtactt aataaatatt tgttgaactg aaataccact 127440
tgtgaaagct caggtgatag gaataatcgc aggtggcaac tttaagatca caccaaaaca 127500
ccaatgccac tttcattcca cccactccga cttctaagag aggatgtaga atgtagctgg 127560
gaagagggtc tctctccatg gggagagagc agctagaaat gctgtgagag ttttctaatt 127620
agcagtaagt taccaccacc tttggggccc agtgggattt ctcctcttgc tccagatggc 127680
tgtcatggca gtaactattt ctctgcatgt aagatggtca gatttagcaa ataaaaatac 127740
agggttttag gtacagttta cactgtttgg gtgacaggtg cagcaaaatc tcagaaatca 127800
ccaccaaaga atgtatttat gtaaccaaaa actacctgtt ccccaaaaat tattgaaata 127860
aaagtttaaa aatagaaata tttaattttt aaaaatacag ggctcccagt tatatttaag 127920
cttcagcttc agaaaaacag ccaggcttgg tggctcacac ctgtaatccc gggaggctga 127980
ggtgggcaga tcatgaggtt gggagttcaa gaccagcctg gccaatatgg cgaaacccca 128040
tctctactaa aaatacaaaa attagccggg catggtggca cacacctgta atcccagcta 128100
ctcaggagtt tgaggcagaa gaattgcttg agcccaggag gcagagattg cagtgagctg 128160
agatcatgcc actgtactcc agcctgggtg acagagcgag actccatctc agaaaaaaaa 128220
aagaaagaaa agtttcagat aaacaacaaa tacatttttg cacaaatata acccaaatat 128280
ttcatggcat gtacttctac taaaaagttg ctcatagttt atctgaaatt caaatgtaat 128340
tggccatcgt gtattttatc tgtaatttca tgcttttagc ataagcttga agatgccata 128400
atattaattg gtggctccaa atgaaaattc atttaaaaaa aaataccagt acaaaatgac 128460
cagacgtgtg caactccttc tcactgtatc cttgtttgtc tgcctgtcta taatatcact 128520
gcctgagtca ttattgtctt agagggtggg tgctggatct attttattct ttttatagaa 128580
tcctgatgtt gcattcacat atgcacttaa agtatatttg tcttgctgcc tgtgatgtcc 128640
agaagaagga atggactttg gtaatagttt ttataatgtt cccacagaag atttaaattc 128700
caaaatgata ccatagtttc ccacacttaa aattttacat ttcaaaaaac accataaaat 128760
ttaaacgtgg aaactagttt tgaacatttg aaataagtta acataaaagt tcaggttttc 128820
attcccatgc ggtgtgagtt tgtcctgggg cacggggttg tgcagggaaa gaaaaggcaa 128880
atattctcca gcaattttcc tggagatgta tgacttttca agcaagagga aataaaagtg 128940
aagaatgaga catatccccg atcaaatttt accttcagaa atattaactg ctacagtaca 129000
cttactcccc gcaacctcaa tggaggaggc cagattccta caagcgggga ggccttgtct 129060
gatttcatta tatcttttcc tcctttgcaa tcctgcaaag tgatactttc tctttttat 129120
```

caacatgggt tgtaagttca acgactgcgc acattcatga aagtgccaaa gagatgggaa 129180
cctgttagga ctaaaatcca agcgttttct tttgaccgta ccctgatcct tgtctagatg 129240
ttcttaaaaa actatgacct gactttttta tgactcagat gtttgtaaga cccctagatc 129300
attaagacat atttaaacat tctcgtgccc ctactcctct cccacaagat aatgttttgt 129360
tcttaggcaa ctgccaggaa agcattaaaa acatctagca caagcccaat tttcccaaaa 129420
gaatgatttc ttgtttgaag tttaggagaa aaaaaaaata cattcctatc acttccattt 129480
ctgtgtctaa tttttattta tttattttta gaatatgtaa agtatgtatt ttcttagaat 129540
agttaggccc tggggcatac aaccaattta ctcacaaaca aaccctatat ttaagagaca 129600
gagttgtttt ttttttctgg gaaaatgaaa ctgcaggcta ggaattcatt tctgtcctct 129660
atttgtcatt ttcaactttg attaggataa taatgctttg cttgtgcaga aggctctata 129720
taactaaata gtgtaagtga catggaccta agatgtctat ttcctaccag ctcctttctg 129780
ctctctacag ggtttctttg accatggaag ggggtgcttc caggaggcat gggaggtagc 129840
tgtgggctgt gttaatttgt ttaaaggatg gagagccata gagaattcta ttaacataga 129900
tcttgctgaa gcattcaaaa taagcagaga taatacatga gttactgtga aatcgggacg 129960
tgagagctgg ttccgatatt gcaataggaa actactattc ttttgcttga ctggcatcct 130020
cttagaccct ccaataactc ttctcaattt ttatgttcat ctgtattctc agctcccagt 130080
gagccagaaa gttcatgaca tgctcaggct ggtagaaaat gagaatacca gtcagctctc 130140
cagagggctc tgctggcata gctaagagcc ccaggacaga catgaaatga agatctggct 130200
gagagagcac tacagcgccc agctagaaga tattaacaca agctctgatt cacatgggac 130260
agcaaaatat aatctgtgtg tgacaggaat cgacacagcc ttcaaccctg aggtggagcg 130320
aaagcaccca gatatgcttt tgcattgatg ggaagtgcaa gcagaaggtg aggggagaat 130380
tttgcccatc actcaccatc cccccccaca cacacataca tagagtcatg ccaaagcatg 130440
aagcagcaca gaatccccag cattcagcca tccctggcac tgagccacag agaaattagt 130500
caaaggctct gagggcagct agagcacaaa gggtcatttg tttttagaaa caccagaaaa 130560
aggacaatat tctccagcta aaccttgcca gctccttgtt ttgctttgtt ttcctcttgt 130620
agctctgatt ctaaatccct gaagtggttg aacactgtgt ctgaggccag aagctttcgt 130680
gggtcactag aaaagagcct agtgaggggg aggaactgga ctggaacgtg gaaagctgga 130740
atcgggtctg acctgccctg ccgccttggc aaatcactcc tacaggtaat gagtgggcct 130800
cagctttctc acaaccaaaa ctgagatcct gatgtgagtc ccgctcacct tagagaggag 130860
agagaaaacc atgaccgtga ccgaggaaga tgcctcagga cataacttct gcacagggga 130920
ggttgtcaat ttcctctgca gtatggattt atgctcctca cctaaccagc ctggactcca 130980
gtatccctat ctgtttaata ttaagctctc tgaaatgtct ccaccatagg tatctcatta 131040
gtagaggaca agagacaaag gtgatttaat caaaacagcc accaccccga cagcaaaaca 131100
catttactga ttcctagaac cactatcttt cctgaaatgt tagtatgggg ttgaccctat 131160
tggttacatt tgaattgact tttccatgtt gagagaatta aggtcaagag aatgaactaa 131220
cagccagcca gtttttatac aacaacattt ttgtattctt tccattgtag gttatatttc 131280
tttaaagctc aaattaaaca gccacttatc ctatacccca tcatctcttt aagtctcctt 131340
acagcagaaa aattctggag acattttcaa aggtggaaaa tccaggccca gtacctagag 131400
aaattaaaat atggaacatt ggctcaaagt tcataattaa aggtagtaag gaatttgcag 131460

```
gtgtgtagtt ttatcccgaa gtcagtaaaa agaatcattt taatgttgtt aatcagtggt 131520
tcagcctggg accttgttaa attgatttgc aaatgggaac tttgaaacat cctggagtgg 131580
ccaagtgtaa aggaatgaga gacgggatgt ggggctctgc gcctaagcca cagtacattt 131640
ccagctcctt tatcccaaag gaacagtcat tgtcaagctc aaaagccagg tctggactca 131700
gcttacaggt gtctcctggg gacctgggga ggagcgattc ccactgggtg aatgtcagca 131760
gagaatggta tgccggcaaa gggacaccag agaactctct ggtcgtagga cgggcagcaa 131820
gactgcttcg gtagattcag gacatgattc tgggcagtta gcagcctctc tcccctgctg 131880
tgtgttaaga acacttgagg atgttttccc ttagcattta tgatgctgag gaaaagagat 131940
tttggaaact accttgacaa agaaattaat ggagggtgac atggggattc cagcaaggcc 132000
aacatacaat tgcctcattt tcatggtatg tcaaattaga tttaggtttt ggctactgtg 132060
cttgtcatgg gggctctaac tctcacccag ggccagcatc tcacaaaatt ttatgacttt 132120
acactgactt tgacctccaa ggacaagggc cagtggggag aaagaccagc agaggctcat 132180
tcctcctcta gtctcaacgt ctctctccct ccctctttct ggaacttgtg ctcctgaggt 132240
ggatgtctga ctgtgtcttt ggccacagcc agccatttgc acatctgttc ctgtggagtg 132300
acaggcagtg gggagctcca ccgcccactt caggacccag acagccatgg tccaggcact 132360
gctgtgggct ggagaaagct ggaaaggacc tgcctgtggc aggaatctct gggccccttg 132420
accatgatct ccacactcac cacgtgtgta ccaggagggc agatccagac acaggagcca 132480
gaaggaagcc cacgcgagcc aacagaacat aacctctggg caggaagagg gaaatgcact 132540
ctattgccca gtaccctagc atgactacct accatgagca gaggtctatc caaacaggca 132600
gaaaaaacct ggcacatgta catttatcaa acagttatgg agcatctact gtacatattt 132660
acctagtagg tacttgtggc caacactagc agtcatcctc taatacccat tctcctcttc 132720
cttagtcatg aaatgaccac ctagaataga gactacacct cccagcatcc cttgcagcta 132780
gctgtgacca tgtgaccaag atctggctaa tgggatgaga atggaggttc taggagcacc 132840
tttcagggag gaggcacttt tttcacctaa ttcttctttc ctgctggctg gaagatgtta 132900
tttagaagtg atgtctagaa tttgagccac cttggacctt gtactgagga tttcaaagca 132960
caagagagga gaaacctggg tctctacaga ctttatagag ccctgaacca acccaggaat 133020
tctaacaaat aagaagaaaa ttaacttctt tttaaactca ttcatctagg gtttttctgt 133080
tactcacagt caaacttaac cctattggac tcaatatata tttgttttat ttaggccttc 133140
aactgattgg atgaggccca ccaacattat gaagggcaat ctgctttact caaagtccat 133200
tggtttaaat gtaagtctcc tcccaaaaaa ccctcgcaga aacatccaaa ataatgtctg 133260
accaaatacg tgggcattgc agcccagtca cgttgacata tgaaattacc catcatgggg 133320
atgaaaactg gtgagtcact ggcatatgaa tagctggcat gactgtggac tctggggaga 133380
gagaagagaa ggagaaggca gggcctaagg aacatcacta ttcaatgatc agatggagga 133440
gagggcaggt agctggcaaa ggagacagct gacacttcat caagtcctca gataccagta 133500
ctgtagggag agccgtgtgc aggtagcaga gccatcccag ggccaaggtg gggcctcagt 133560
ttcccatcga gcaagtttcc agaaccaagt gagatcaggg tagcactggt gtgctggggg 133620
cttagtgcca atcagtgctt gaccattctg gatgggcctg gccttgggga cgtgtcaggc 133680
caaaggctcc gatgccttct acaatgaaga atggagggcc acagaagcca ggaccctgag 133740
cagccagcag aacagccaag ccccttccct gtccagctgt tctccaagac cagaagatgt 133800
aatgcctatt gccgttttct gtacaacatc aattttctta ttaggatact tttggggaac 133860
```

cagtttgaga atatatagaa ctgcaatttt gttcaaaggc agtaacaagg ttataagcat 133920
gaggtttgaa gccaggtggg ccttggttag atccttgctg tgatcctgag caaggcagtc 133980
actccctgag catcaggttc catatgtagg attactaacc cctccctgat tcaccattac 134040
ggagaagaga tggcgcactt agctgtatct ggcacatgac ttctacatgg taaaggcttt 134100
cctttctttc tttctttttt ttttccttct caaatctatt gtttttattt tttttaagta 134160
agcagtggta tatatgtcat ctttttaaat gtttcttttg ggaagatctt atagaaaaat 134220
ggcaccctga aactttcagc tctatatccc aaaaattgtc tttcaagagt taaaaaactc 134280
tttaaaatga agagcttttt ttaactcttt atgagtttta aaaaaaccct taaaaatgaa 134340
gataatatac ctggcctaaa tcaaaataat ctgaaaaata gatgtgtccc agtggaaagc 134400
ctacaaagga ataatctccc atcttcatgg gaccttcttt ctcctttctt tctaaaagcc 134460
ttctaaagca tcaccaacac accccaaatt ttgcttttct tttctatttt attaccattt 134520
tttggctgtt atcactccat gttcccttgc atgtgttaaa tgtatacatg tgttcatgcg 134580
actgaagtca tcttttgaaa tacatacaaa aatgtaaata gccaatctcg tgtttgtgtt 134640
agcctttgaa atcaggctga aaataaaaat gcatgaagtc agttataaat tgctattgcc 134700
aaacagaaat gagatgagta tttgccagag gtctggggcc tggggggaaa tggggagtga 134760
tggctgatgg gcatggtgtt tctttctgga gtgatgaaaa agttctggaa ttagatagtg 134820
atgatgttgc tatagctctg tgactatcct ataaaacacc gaagagtaca ctttaaaatt 134880
gtgaatttta tgtaggtgaa ttatgtccca ataaaaacaa atttctatcg cttgggtcaa 134940
atagtggatc gcctacttct aaggtcaagt gttatgaaag gcggggcagc attagggatt 135000
catacatggc agacaatggc accaggactc cgtgttgaac tagcagaact gactttgagc 135060
atagtacaaa ttcaggaaaa aggactcatc tagagaggct ggcgtcaatt ttaggaggac 135120
agacttgagc tgagtatgca gggaggaaag aatggactgg aagagcaaag taaaagacat 135180
tccaaagagg aattcagaag gagggagaga tcatgatgct ctctttactt ggttactgtt 135240
ttaaactttc atttcatgtg gcagtgtttt caaggggaga tgggaagatt ggacttctag 135300
gcaagggagt tgggagcaca aatcttgttt ggctgggcag ggaagagcca cattagagtg 135360
tcccttcaca agcagccttt atcttgatgt gggaggttgc agggcagtcg tctgaagccc 135420
tggagccatg aacagtcaca tgtcgttcat tctgatgcgt ctgaactcct gcatcctaag 135480
tcacgtaact ggaggcaacg agagcctgtt ggataggaaa catgtcgact ggcccagcct 135540
ttgcagcctt tcctttgtaa gagatgtcta agctctgttt gaaagaaatg aggtttcttt 135600
gttttaaaga aatagaatac tgcaagggag agggagagtt tcccgggctg ccatcttgtt 135660
ttctgtgggt gggaagtgaa aaacctctca tttttggtaa gctgagcaaa gcccaaaagc 135720
aggagcaaaa tcagtccaca ctcgagcttc aaatgccact gtgaaaattc gaggcaggct 135780
tcattggtta aaccgcagcc tgtcagggag gcttcagcaa aaatgctggc atgagatctt 135840
gattcttcta tgataggcca caggacagtg gccgtactgc cctgccaggt aactggtggg 135900
gcccggggcc tgggggacca cgtcgtgatg gttcattcct gggccctggg atccatctgc 135960
ctttgcctgt cactggaacc catgacagca gtggactgag cctgtcaggg aggatgagag 136020
agatggaagc agcccaggaa ctctctcaac ctgaggcaag ttgtgcctct tcccggctgc 136080
cctgtgccag gccccgagcc agtacagaaa tggcacttag gttgatatct tacattcagt 136140
ccattttgct ggaatgttct gtaagctccc tcttggaatt ctgggtccat gacattcttt 136200

```
tatcctttgc tattaacatt atcattgtgt tagcagtata gctcagtatg actgctattt 136260
aaacatccat ccccatccct gcccgctccc ccacccgaaa aaaatactgt ctgcactgaa 136320
aagaagtggt ttggcatagt gaaagttttt aaacatccat tttccagatg gatatccttg 136380
ttaaatttaa aaagaaaaaa aaaaactaaa ccatgtggaa tgctcctaag tgaatattat 136440
tgtttactag acttattcca tcttatggca ttttatgaca aaatatcagc aagctcataa 136500
agagggcttt ttttaaggtc cataatcttt ctaaccataa caaaagggtg gtaaatatat 136560
tgtacaagag cacgatggaa aaatgtgcta aagtatttcc acaaatcaaa tgtagcactt 136620
tggcattggc tctaaagcat taaatttagt aaattagaac cagatgattt taaaatagaa 136680
acttacataa ctttacggtg tgattttttt cccccaacgc aagtttatct tcctgcagcc 136740
gcgttggctg ctactgtaat aggtatttaa gaagtagggc agcctctagg tattattcat 136800
ctttgtagct cccaaggtgc ctagcattat attgggcaat tagtaagtat tggtggatgg 136860
gtgaatgaaa tctcagcagg gattaacaag tactagttaa ctggcaagga aatgtaatat 136920
aaatatttat acagatctac aggtagacaa aacactgccg ctatcacaca cataatagtg 136980
aaaatatggg ttgcttttcc tttcattgtt aaagctgtgg attaaaatca atgaacctga 137040
aataaaaggg tggatctgct tcgcctttgg gtcaccatgc ttcaaaccac catcaccctg 137100
gaatgttcct aatacataag tctcatttct atttctgcca tcatagcagc cacagaaaat 137160
gctccttttg gtcatgtctc cctctcctcc cacacacaag ttcacaatgt agctaatacc 137220
ttaaagataa gctgggagtt caacacagca tattgactga gtgcctataa tctccaagac 137280
cctgtatgtg ctgccacagg gggtgcaaag gaataaggta tagtctttgc cttctaggaa 137340
aatactttcc agtagagggt tagtcagcac actgtcattg catgtaaaag aaatctaact 137400
tatactaggt tagtcaggaa ggtgtattta tggccttctg aactgagttg tctaagagta 137460
gacttcaggc atggctagat ccagaggcac agacaacagg attagggttc tctccatctc 137520
tccactctaa atgcctttgc ttctttttgc acatggactc attctctctt gctattgact 137580
ctctctacaa ggagaaaaac atattcacca ccgagcaaac atttacagtc tatgatccaa 137640
agacagagaa gttgtctctc tcccaggctt catatacaaa tctcaaaaag atcttggatt 137700
gactctgagt tacatgtcaa gttctcagat taattactgt agaaaagagg atgtattcta 137760
tgaccaatca ggcctgagtg gtggttggga ctctcccttt gtggatgaat gaaaaggagg 137820
cgatttatgt cttaaatatt gatatttaaa tattgatgtg ccttggcagc tgattggatg 137880
tgggaagtag gtgggagaaa gaaataaaag atcagtctga ggttttgatt ctaggtgact 137940
ggtagggaca taaatagaaa gagaatggtt taaaacagac actgttttaa agggaattta 138000
tcattcatag gtgtattaat cagggttctc caggacatgt gtgtatctat gtgtgtgtgt 138060
gcgtgcacac acgtgtgtgt gtgtgtgtaa agagaaagag agtaaaagat tggtttgttt 138120
tcaaggagtt gtctccaagt ccaaaatctg cagggtagac ccacagcatg tggaccctgg 138180
gaagagctga tgttgcagct tgagtctgaa ggctggtgga acagaattcc ctcttcttca 138240
gggaacctca gtctcttttc cctgaaggcc ttcatctgat tagatgaggc ccacccacat 138300
ggtggagggt atctacttta ctcaaagtct actgatttaa atgttatctc ctctttaaaa 138360
caccttcaca gcaacgtcta gactagtgtt tgatcaaata tctgggtagc atgcatggcc 138420
tatccaggtt gacacataaa attaatcatc ccaatatttg actataagga gcttatgaca 138480
tgcctctgga atatttaggt gcagtagaaa atgagggctt ggaactcaga acacaggttg 138540
ggagatgtga ttgtcatcag agtagacgtc attggagagc atgagataga taagggagaa 138600
```

```
aatacacaag gaaaaggagc tgagaatgga accttgaaga aaggctcctg aaaagaagac 138660
tgaaacacat tggcaagaga agtagaagaa ccagaagagc ccactgcttt ggaaaccgaa 138720
ggagttgatt tcataacagg ggaaataaca aggagtttca ggagttgagg ggagatcata 138780
gagttggcag gcagagaaga gtccccggct tggacaatgg aggctggggg ttcccctgga 138840
gcaggactcc tcaaaatgtg ttctgcagac ctgcaccagg ccacacactg gacaggccca 138900
ccaacaggta ggtgcagaaa ttgagagcta gtgcttagaa gctctgacag ccattagaca 138960
agagtgattt tttatcagct gaattcaatt atcatcatga tcatcatcat catcatcaag 139020
gcttgtattt tgccagtctt tttcatttct tttttctagt aatttcaaca ctactcctat 139080
tctatgcatc aatggctttg atggttattg atggaacagg ggtcagaagc agatgcctgg 139140
aggactgagc aggaggccag gatgctggac cacccactct ctggtcatgg caagtgaaag 139200
atagagggca cttggtcagt gttggggaag gagaggtggc aaagggaaga tcctgaagac 139260
ccagagaatg ttgtttgtgg ctcatatttg ctcatccaca gtaacaaaat gtaaaaatct 139320
ggagtatttt gatagctcac tcagcagcac agcctgattg gagttggcct gagtgatatg 139380
tattctttta cccacttggc atgactcttt gtagattcaa ttgctgaaac atgcatgcct 139440
ttgctcatgg gacacagcca tggatttcac tgggagtgtc ttgtaatatg tggtatatgc 139500
tctaaatctc tttctaaaat ctgaaatatt ctgaattcca caagctcatc tggcctccag 139560
gtttttgaac aaggaactgt gaatctgttt ttagggtgag gaaggccaga acttacttgc 139620
agagagcagg gtgggaaaga ttagggggca catcagagag gggatggtta gggagctgag 139680
tcccagagtg ggcttgagag gagagaaaaa aaatgcacag agctgtctgg ataaaaagga 139740
aagacagttt tttttttttg cctggtgacc agaactgcac aggtgatgac ttttgaaaat 139800
gtagagtgat tttaagatgg caaaatgaaa actgggggaa gacatggcct ctatcagcta 139860
gggccaggag ggcacagcct ttcttcttgt cactactctc cacccctcct aagaccagaa 139920
gctccaaaag caggttagag catgaatcag gagaactgca tgccctgggt tcaagaacac 139980
ccttgcaaca ctcccttgtc tacatcgtca agtctgaaat cacagggtgc caggccttca 140040
gcaagttaag agaacttata cttagtgcct gtaaagctca ggggtaccag tgagcgagac 140100
ttcaagtctt gtgcatgctc attgccagac ccccttttggc tttttgtata aagaagagag 140160
ctgctcttta tttccgggct cagtgggcag aaaggaatgc tccgtccata ctccgttcgg 140220
caagtcaagg gtggacactg gtgtctttat caccacccag tcctcggccc acactggcaa 140280
ggcattcctc tagcagacaa aataaaagat tgctgatagc tggagcactt tgtttgcttt 140340
ctaaaacgag tcaaactctt caaaagcttg gcttgaaccg tgcagggtgt gctgtgttcc 140400
cgccacattc ctctcacccg cctctccacc aggccttgta ttatccggat tcctttcatg 140460
cgctcacgag cgccagctgg cggctgcttg ggctggccgg acaggccaga ggctctgggc 140520
ccggggcctg ctggacattg gccggcctca gctgatgagg gcagcggggc acgggaggga 140580
ggccttcttg gagggctggg tcagctgggc tcttttaagg cacaaggggg agaaaatgca 140640
tctccaaccc ctgaagaaat gaggtaccct gggcattact agtggccatt tggtgtttaa 140700
aacactccct tctcccccat tgtgtactgt ccctacctcc gcccccggag ctatgctgga 140760
tggctggtgt ggaagatggc ttccggaggc cagtgtgcgc tggagaatgg caaagctcgg 140820
aagtagattg gaaacagaaa atccagccca tctaggaagc tagggcacac aatccataag 140880
ccttttctgc ttagtccaac tagacaatag caagacgtgg agaggggaag agggctacaa 140940
```

agtcgcatca tatcacatga tgtcatgcca tggcaagtag gaaagatcat gtcttatacc 141000
acatgacatc acatagaaag tgtatgccag agaagtcagg aagacttttc aaatgtaaga 141060
acatatagag gaagcacaaa ggttagcaag aagaagacct gatgcctttg ctccccttca 141120
tttaataggt agtatgcacc aagatgattg tgtttgggca gtgcctccgg aaagaggaga 141180
cggccactct catttcagcc atgagagtcc attcctgttt atttgatgtt ggcagatcac 141240
ttcaaccttt gtaaaaatcc acagtgtgaa gtttctatca gcagaaaaga tttccatgac 141300
agtttcatat aacaagttgt ttatttggac aaactaaagc atgtaataac agaacacctc 141360
acggctagag aaaacaggag agagaggctt tgccaggcag cctgcacaat tttactatta 141420
aactcctttt gttccactga actctatgcc tttacctagc tggggacaca taaatagtag 141480
aaatgtgaac cttgcacaat tatggagata agcctaaatc tttatgcatt tctaattttt 141540
cttatcactt cacctttaag ttaattcatc caagtctttc atgtaaagaa aatgctaaaa 141600
tggagcgtca caattgcttg tcacatttca ctagagtcga gtgaatttat ttaacaccta 141660
atttaatctg tcaacgtttt tcaattcttt gaagaaaaaa aggtagtaat taagtattcc 141720
aaagttataa taacactaaa catcaaaact tcacaatcgc acagtttttt aaacatcaag 141780
ttaagatatt agccatagtc actccactta aggtggtctg gctaggtttt tagtagcacg 141840
gtagtgacac ggttttacgt gttctatttc atggtttatc aagaactaag aggggcctaa 141900
gacatcccat tttagcgctt caccccttggg ataattaaaa gccacctcaa agagatggaa 141960
ggaagcagga agagggctca gtaggagtgg tggttgtaag ggctgtaca gtgacagcct 142020
gctcaagctc agctaagtgg taagaggcac caggtcctcg tcaagtcttc acagtgtgga 142080
gacccaccgc gtcgctgtaa cctagaagat ctagagaaac tgcttccatt ctctgctgcc 142140
tagcgcccca cccaccccag gcagcttgtc cttgagagcg aaatgagtta ggagggaacc 142200
aaatgagaag aaattcaggg atcacgagtc aaggagcttt tttagaagac actaccctcc 142260
acctccatct gcagaaacaa atttcttttt tttttttttt ttttttgaga tgaagtctcg 142320
ctctgtcccc aggctggagt gcagtggctc gatcttggct cactgaaatc tccgcctccc 142380
gggttcaagc gattctcctg tctcatcgtc ccaagtagct aggactacag gtgtgcacca 142440
ccatgcccag ctaatttttg tatttttagt agagatgggg tttcaccatg ttggccagga 142500
tggtctcaat ctccttacct catgatccac ctgcctcagc ctcccaaagt gctgggatta 142560
caggtgtgag ccaccgtgcc tggcctatta ttttttttaa tacgaactta acaagtcttt 142620
cagaaaatag aatgtattcc taggacactg ttgctaacga ggtagttcgg ggtaaggtcg 142680
ggtagccttc atgaggtctc ttgtgccaaa atattagtgg agggaaagtg aatgaaagcc 142740
ctatttcaca gtatataaag aatcaagcat taaaactctt ttgggctttt ctctaataat 142800
agactttcat tcattccaag agcttgacca gttcaacaga taaaagaggt ttattgcctt 142860
gaagtgagag gagctcattc ccttgccttc tgagaagtgg cttatttgtc cccctgttga 142920
attcagtgaa ggcagtgtgc acagacaaga cacaggcttt gagaggacaa aagatggggt 142980
tcagtcacct acataagtgc aaaatgggct acaacaaaag aaaagacaga accctcttct 143040
ataaattgct caaaatctca ttgcggaaaa gaaactctca caaaagaaac catgtaaggg 143100
aataccaagc actaaatggt gtgttatata cataaaactg actagagagc atatgcagat 143160
tttttttatt tttatttttt tagagacagg gtctcactct gtctcccagg ctgcagtgca 143220
gtggcacaaa catggcacac tgcagcgttg acctcctggg ctcaagtgat cctccccccct 143280
cagcctccta agtaactgag actataggca tgcaccacca cacctggtta attttttttta 143340

```
atttttattt ctgtagagtt ggagtcttgc tatattgccc aggctggtct caaactcctg 143400
ggctcaagca atcctcctgc cttggccaac caaagtgcta ggattacaag tgtgagctac 143460
cgcacacagc catgaagatc actttaaacg ggtagattcc atagcctcat actaagccta 143520
ctgcggctca tacttaaagg agagaggcct aagcatttct aattgtttct taagggaaat 143580
tggatttggg aagcatagac ttaggccaca ggtgacggga gtccagagat acagaggaag 143640
attggaggga ggagagcaac aatggagaga tttttctagg aaaggtttta taaagaagat 143700
ggggtacaag cgggaggcac gataggatgt aggtaagcag agccacgaag tggggcagag 143760
tgatgaaaga agaactacat acgcacaggc tccaacgtgc acgtgagtaa ggggtgtgtg 143820
catttgtatt tacacggctg catcagccct cctcacaact caagaacaat acctgtttct 143880
cagttgagct tagtcccacg agggtggaga ctcgacctta ttgagcggac aaacatgtgc 143940
tcagataacg aagtgcatta attcattcat tcatatgaag agaatggcag caatatagct 144000
ccatggtcag ggccacacag actcagaaac cagaaagcct gggttcataa acaaaatggg 144060
ccatcaccct gtaagttggc gcatgctgta gaacttctcc agtcttggtt ttgtgaagtg 144120
taaagtaaga acaatacaag ctacctcaca gggctgttac gtgagatgaa tattaaatgg 144180
actcctgctt gtaaacatct ggcacagggc ctggcacctc ggagggtttc ggtgaaggct 144240
gaatgaacca agagtcagtt gtattgaagg agaaaactct caatggctgg tctttgagga 144300
ggtttctgga gacttgtaaa agactggaaa agttgctgcc tccaattatt tttgaaataa 144360
gcttggtata tgtagattgt ttttaaaaac taatgtcaaa ctagaaatga taaaacatgg 144420
ccctagaatg gttccttttt aggactgggc ttgttcctct ggtctagcac tcactcagct 144480
tccagattgt tcccctgtag atgtggaaag atctatactt tattctgaac tcaggcatag 144540
atgtaccttg cactaatcta gagtgtgggt cggcaaactt ctagagacaa ccaaataata 144600
ctttttcttc ttcggctttg ggggctttgc catctctgtg gcatgtgctc agagtctgcc 144660
attacagctc aaaagacatc cctacatgaa tagggatggc tgtgttccaa taaaatttta 144720
tttatagaca tcgaaatttg aatttcacat cattttcatg tctcatcttt ggtttttttc 144780
ccaaccactt aaaaatgtaa aagctattct tggctcatag atgcagaact agcaacaggc 144840
cttgagttgg ttctgaaaag gtgcatccta acaccatttt aaataaatgg aaaactcact 144900
gctaaactca aacacacggg ggaatatgtc ttccctgttc ccttcctggg caccaaacag 144960
aacctcatga taaacatacg ttctttgaag ttacatttat cttcttactc attgatgctg 145020
caagcattta tgcacctcta aggtatacaa caggacaggg gacacagatg aacaagatac 145080
caccctgttc cccaagaaca cacatcggag ctggggaaac agacatcaac aaatcattat 145140
gagacaacgt ggaaagccct tataataggg ccgtgttcca gtacaatggg ggcatagtga 145200
agggagggag gaattagttc tgaaagggcg aggtgggcag ggtgggggtt gtagacaagg 145260
atacacaaaa gggttagtgt tgaggccaaa cttgacagca gaagagtgaa ggggggtcat 145320
tctcagcaaa ggggcctgcc tgtgcaagtc aggaaggtgc aagtccgtct tggaatcagt 145380
aagttcccgg caaccccaca ctcccaagta tggctagagg gtgggatggg ggtcggcggt 145440
agagggagaa agaaagggtg ggttcagatg gtggtccatg ccaaagtgtc cagattttgc 145500
ttgttaagcc attgaagtgt cactagaggt ttttaaacac ggtagtaatg tgatcgactc 145560
tgtattccag gaattaaaca cgtagtgagc aacgtggaag atagatgaca gcagtgagag 145620
agttaggcaa agaaactaaa aagaaatcat tagaatagac cagaccaaga gattcagggg 145680
```

cctgacctca ccaccaattg ctgttataac tcaaactggt ggggccctgt gtgaggcact 145740
caatctctct gagcgacaga cagctctgcc ctctctatga gtggctggat taggtgattt 145800
ccaaagtcat ttcctgccct cacatgctct tcactctttg cccttcactc ttagagagca 145860
gtcacgtggg ttcattccaa gttgtcaaca gaagtatttc ttctttctag cctcctcttg 145920 atttttgct gtatttatgc cagtgcccag ttgcagctgg aaaatcatta gaatggcatc 145980
cggtgccatt tccctcactc ctgcctgcac aagcatctgg aaggaagagt gcttggttga 146040
agagcaggca ggcggcaagg atgacaggag gggatgccca ccggagtgct ggcaagtgca 146100
ggaagtggaa ccggaggccc agagttctag ccaatttcag gagggtctct atgggaatcc 146160
tagggctgct gcataaatca attacatagc ccagtttaaa catcattttt gcatctgata 146220
gtaataaatg aggaagggaa ttgtttctgt attcactgag acaatttgtg tttccctgaa 146280
gagttttaag ggcaacatac taaatgacac taataaagta acaactatct gcattattta 146340
agctgcatta agaccagagc tcaatatttt aactagtagc ctgctgtcct tgagtgttta 146400
acaaaccgga gagaaacaga ttactccctg gtcaaaacac tgcagaggct tcatgtcaca 146460
ctcaggaaaa aaatccaagc tccctaccac ctacctctct gagctcatcc tctccatcca 146520
gccctgtgta ccccacgcta agcacactag acagcttgct gcgcttagac acactaagct 146580
cgtgcctact gcgggccctt cccctgggtc acttctgtcc ggaatgctca tcccctagat 146640
ctctgagtgg ctggatccct gaaactattc agatttctgc ttaaatatca tctcctcaga 146700
ggagcttccc tgaccacttt atctaaaata atacacctcc tgtcccaccc tggtctgttt 146760
tcctccagca attttccctg cttaattttt cttcatagca tttatcactg caaatcatat 146820
tatacattca tttaattatt ttcctcaact ctcactagac tgtaagctcc atgaagatgg 146880
gaactttgtc tgggctactg ctgtatcctc ccctcctaga aaggtacctg gcacatgcta 146940
ggtgctctag tgataacagt tcagtgagaa agctgcctta tgaaagaatg gcacacagag 147000
aaggggttcc tccaacttct tctgaatgcc taccacactt atcaacagta gtctaatatt 147060
aatactagtt ataattaata caataattaa ataataatct atagaatata gcaataatgt 147120
cataaaatat taacaaaata tcataaatct gatattaatt aaaataataa ctaataacaa 147180
cagtaataag aacaagcaac catttaaggt cttacaatgt aacaagtact attaaattct 147240
atccacatta tcttatttaa tcctcattat gaggctagca ggtattatta ttttctctat 147300
ttcatactga aggacatcaa aattaagaag ttcaactggc caggcacagt ggcccacgcc 147360
tgtaatccca gcactttggg agactgaagc aggtagatca cctgaggtca ggagttcgag 147420
accagcctgg ccaatctggt gaaaccccgt ctctactaaa aatacaaaaa attagccagg 147480
tatggtggca gacacatgta atcccagcta ctcgggaggc tgagggaatt gcttgaacca 147540
gagatgcggg gattgcagtg agccgatatt gcaccactgc actccagcct gggcaacaag 147600
aatgaaactt tgtctcaaaa aaaaaaaaaa aaaaaattaa aaatgttttg aggttccagc 147660
acaggtttac ctgattccaa cacccttgtg ctttccttta ggcagctaac tatatactga 147720
cccaagcctt cttgaaatga acttcgggta gattacatgt gtcttactta ccttacagga 147780
cagaaacagg aaagcaggag ggccactagc tagagaatga aattacaaaa aaaccccagc 147840
acaaacttta ggaaactgtt tgaaaacatt aaaataggat gggacagcac tcacttactc 147900
aatgatattc atcaaacaaa acagaaaaag gattcagctt gaccacttag gaagccaaag 147960
gaatgttatc tagatctctt ggaggccgca agactcatct tacagatggg aagggctttg 148020
aatcattgtc ctcctttatc caggtagaca ccaaaaacaa tttcctgcaa actaacgact 148080
ctccggtcag tctgcaggat tcttaaggag atcgttacaa tgcaatatgc tgcgtgctta 148140
atttgtgttc agaaaggcct tgcacaatca ctcaggctta tttttgctct aaggacaaat 148200
gaggagaagc aaggcctaat acaggctgga acaggtatgt caacctcatt aggatggcct 148260
ggggggtcat gtccctggaa tcagtgccac actgaactgc aaactaacct gccaaccctg 148320
tatctggaaa ccacttttgt aggacagctg ttctctcatt ccttttgctt agatcataaa 148380
agtagagttt tcatccattg ggaatttgtg tgttagacgc gaagggaatc agattctgat 148440
ccaacttggt caggaaaaaa aaaaataagg gctgattttt ccatccaagt catgtagtct 148500
ggttggagtg catcccactc agggacagct attgtctgga ttcaccgagt ctcagtcttg 148560
cccgggaaaa aggaattttt cgcctcactg ctctgtccgt gagaagagtt gcagaaggtg 148620
accatttctg ttttctgggt gattctcttt ctctatagaa atcctaaaat ggaaccttta 148680
tagaaattat gttctgtgct tcgctggaga gagactggtc tttttaacca ggctcatcaa 148740
acagtgggca ttttcgttct cctggataat aagtgttggt gggttaatgg gtcatcctca 148800
ggacagaggt cagaaggaaa aacactgcag tgttcaaagc tggagctaga aatgccagcc 148860
gtcaaagaac acagaactca gtggacggtg atgatgtata gggcgtgcac tggccaaccc 148920
catccgagag gtcacatcta acctttatcc tcagcaaagc cactgaaggt cgctcaatat 148980
gtgtgacccg caactctgag gccctggtga gaagctgtcc aggaaaacgc tggtgcgtgt 149040
gctagagggt tccttttcac taagggagaa ttgtcttcca gctccttgca gactgacatc 149100
gcaaagtact ttgaacgttg aaaagaacaa aaaaagcaaa cagtcacaca cacacaaaaa 149160
gtaggcggga ggagggggaa agaaaaaggg acagagagag agagaggtat cagcaggggt 149220
ggttagtaaa aaggggcccg gagacagaaa accttttgtt cccggagttc gtttcatgta 149280
gagattgtga ggtgaatggc tttgaaacga aatgggttta tgaaggagtt gctaggtcac 149340
aggaagcgcg actgtcagac tgcttttgtg aattcagttt ctttaaaatt tgggttaatc 149400
ttaaaaagaa tgtatctcct tttcctgttc tttctctttc tgtcttcttt tttggcgggg 149460
gcgggaggac agagtaaggt tcaggacggt tccccacttt ctgttttatt ttccaccgtc 149520
tgataaagca aaaagaagcg atcacattac aagttctttg tcagtttttc agaattaggg 149580
gtgggcaggg cctgagcatt accttgtccc actagccaat ggcggggcgg catgcaaatg 149640
aggtccgcga tcagcctgcc tcagtcacaa cagtgagctc agagacttga gggaggcgct 149700
gcgactgaca agcggctctg cccgggacct tctcgctttc atctagcgct gcactcaatg 149760
gaggggcggg caccgcagtg cttaatgctg tcttaactag tgtaggaaaa cggctcaacc 149820
caccgctgcc gaaatgaagt ataaggtaag agagtgcctt ttacaggtta ccttgcaagc 149880
tgaaagctgt gcctgcgggt gtgtgcttgt gtatgcgtgt tccttactgt cagtcccttg 149940
tgtgtcccgg agagttctaa gatgagtctc ggtcactgag gttgacatgc aagcagacaa 150000
gcaagcagag acccggtctt tgagacccac tccaggggtt cacagtacac ccgagtccat 150060
ctgctctgaa agttgccggg gaaatacctc ggtgagaagt taagacttgg agccgcttca 150120
cagcagccac tggagatcag agggtgtctg acttgaatcg cggcaggcat tggctcaagt 150180
ctccttggct tccccaggcc tggcttccac tgccctgggg aactgtaatg agaggaatga 150240
ggactgcata gtctgtctca gactggctct tagtgcaaag ttttccagac tttgctttaa 150300
tcgtttggtc tcggaaggag tatgccatat gcacttttgg tgggagaaat taaaagccca 150360
gattacacag ctgaggatgg aaaattttga catccttatg ttatattgga tgtaggaata 150420
aataagtatg agccatttct tgaaaacatt tttattggag tttgaatggg gtgagagtgc 150480
gaaggctcag gctggctcat tgtgcctgaa agcttacaga gtgtcatagt catagtactt 150540
cagcagcatt attttccaat gcattttaca ccattgtttg tggatttttc ttgccaaaag 150600
gatttttgac ttgctccgta tattcccccc tcccctttttt cttttaagtc actcccatct 150660
aaggaggcaa gcagcttcca ggggacacaa agaaagcaga ctgcaatgaa ttggacatga 150720
atttttcttg aatgatgaat agacatgagt gctagtgcta ctattttatt ttatgctatt 150780
ttaaacaaaa gtgttattat taagatggat ttgggcaagg gtgctaggct tgtggattga 150840
caatttatat taactgtaca ctagctggaa gctacttcgc tttttttcta aatttttctg 150900
gtccatcctt ttttgatgta aggttgtaaa tacttggtct aactgatagc cactgactag 150960
cctcagtaat aaagcttttg ttcaaaaact atgaatctta ttcaaaagct ttaagtctaa 151020
atgtcaaaag tctttatagt aatgcctacg ttaccactgt ctgaagacac aggtatcagc 151080
tatttctgtt tcatcagctt tctattatct tcatcagtag ggaagatcag aggaaagggt 151140
catcctgaag actattaata tttgacttta ggatgcaacc agaaacaaat ccctctactt 151200
ggcaggaaag ttatcttcct taaagtggct caccccatat ttccttattt agaacaatga 151260
taggaccaga tattactcag cctggagtga cttttttgct cctcctttcc ctgttgttga 151320
ataagaactg gcttgcagaa aaaagagaaa gtatgttcat atgtctatta ttggaaagta 151380
taaatggctg aaattaacat tgagtgctat aatctagaaa gtgacgaaag cgacaaagtc 151440
tcaagtcact tttattcaat gatctcatcg tggttagctt tactctttat ggaaagaaaa 151500
tctaaaggca actgataaag tgactgacag cgtaaactgc gattggcatt catggagaaa 151560
cctgcttctc cactgggcct tactggtgtt gaacaccttg ccaaatgatg taaatacatg 151620
atttttatta ccttgtaggc accttcacca gcaaaaaagc taacttctcc gaccgaacac 151680
atgacttatg ccctatgatg actattaaat caaccaatag ctgaagaaat ccactttcct 151740
tttttataaa gttttctttc tctctagtta ataatgaaca actttacttc aggaaaggat 151800
tttgttattg taagtagagg agagacacaa aagtaatgaa gtaacattaa ttgagactta 151860
ctgtgacaac acaagattgt catattcaac tctcccaata gctctacaag gtgggtatta 151920
tttttatact caatttcaaa tgacacagag aggctaagta atttatctaa tgccacacag 151980
ctagaaagtg gtgagctggg attagaacta aggcgatctg gctccagaac tcatgacttt 152040
aaccactatt aagagaaaga gaaagagcta tcgttgacct ctctaaaata tggccagtgt 152100
tttcttctcc cagaaagttt aagactattt catcccaagt attcctgcag gataatttct 152160
ttttaagata gtaactctac aaagcaaaat gaagtgcatg tttggcagtt atttgtttaa 152220
ttcgagccac ttaggtagta aaaccagata attattagat ggtaaaatcc cagagacagg 152280
aattatctct aaaatactac gttgctctat gcactgtaaa tttagcacaa accttaaaat 152340
gtttactgaa agacttatga atcaggccct ataagattgt cgttgttaac ctgattatct 152400
ggtttggctg ccccagggat cacaactacg gaacaacaaa ccttcactta ttttgcactt 152460
aatatacata gcttcaggcc aggcagcaag gtacttgcag taatcctgag aactgtggaa 152520
tgtaagctat tactccggac agacatttct ggttagcact tatctaatct gtctttattt 152580
ccctgtatgt ttttatttgt ccacaggaag gttgcagtca ctgtcatacg tacttaattt 152640
tccatttctc ttagaaggga ttcagtctgt ggttatgtga tagtaaatta cgggggcttc 152700
atttattaag aattttctac aaaatcccct tcatatacag agcatgttct taattgggcg 152760
ggggctggcg gggttaggtg attgcctcga tggccttggt ttgcttaccc agtgaaggct 152820

```
ccctcctgag ggtctggagg tgtatggttg tgctgtttcc caggagggtg atggaagggt 152880
ctctgcgcag ctgtgtttga gcagaagccc ccgagacccc accccgtttg tgcctgccag 152940
gcccgaggcc ccgcccacct caggcccagc ccgggcgggg gctcagcggc cccttggcct 153000
ggctgctaat ggctgagcag agacgctttt gtggctttgc caaatttctg agcccttacg 153060
tgcctacatt aaaattctaa attatttatc tcgtctacca tgcaacaaat tcattcttta 153120
acgttttgac tgaagaaaaa ttacagacgg aacttacaat gccattaaga aaggtgcatt 153180
ctgaaagtca gagtcctgtg ttctggttga atggggtagg tcagggaaag gagaacctgt 153240
gtgccgtgaa acgctttgga aaggactttg aaagtattcg tatttcctca agcaagaccg 153300
aggaaaataa tgacagagga tctttaattt agtcaatatg gtcatgcata agctattaaa 153360
ttcccaatta tttccttgct ttgatatttt ggtttaaaat gctttatttt tctctgtatg 153420
atttttgcaa ccaatccaaa tgtaggactc ctgtcctttt cctttttaaa ccttgtatga 153480
gatctatgga tttaaaatca ctaaaacatg ctttgaaaaa tatcaacttg gttatttatg 153540
tatttatgca tttatttatt tatttagtaa acccatttgc agagctaaat ggcttaccta 153600
cacagagata aaagccttta gagtactgaa ggtgcctgat aataccaaat ttagcaagtt 153660
gtacagtgcg taacatgcca aggattcctt tagcatcctt tccttgctgg gatacacgtc 153720
agtccctgtt ctcagaattc agtggttccc tgtctctccc ttcactccag tcttctgaaa 153780
aaaacacctt cctctccact tttctttttt tcttttttg agatcaagtc tcactctgtc 153840
gcccaggctg gagtgcagtg gtgccacctc agctcactgc gacctctgcc tcctgggttc 153900
aagtgattct cctgtctcgg cctcctgagt agctgggatt acaggtgccc accaccatgc 153960
ctggataagt tttgtatttt tagtagagat gggtttcact gtgttggtca ggctggtctc 154020
gaactcttga cctcaggtga tccacctgcc tcagcctccc aaagtgctgg gattacaggt 154080
gtgagccacc gcacccggcc tttttgcaaa ttctctccca ctttcgtgct tttatgacct 154140
cattggttct ccttttatct tcttcttctt cttttcaggc tttccttacg cttctttaat 154200
actgacttcc gtagatctta cttccaaccc cctactcccc agccccccac ccgcacctat 154260
ctactgccgc ccccttgcct cccacacaca gatgtgacac ttttaatgca cattctgtag 154320
ccctcatttt tccttctcct tagactctgc tatgggaaat cttggtccct cactgccccc 154380
attcatctgc ctctctgttt gcgtttacat gacttgagtg gcctgtcagt cccgctagta 154440
aagtctcctc atccatccac tctgtttaaa caatcaaact ctgaaacctg tgtctcctgg 154500
accatcctat aatccctaaa ataggctgtt atgcttttca cctctgccct actctgttag 154560
cactacctta cttattgacc tctttcaatc aaatcgttat ctaaaggata cctgtaactc 154620
agataggttg cctactgggc ctgtttagtt ttaagtaaac cccactgaat atgagagacc 154680
caccctctat ttgtatgtag aggcagattg atcgaaaagt ccttgaataa aaaacatgat 154740
ctagggtctg tgaagttttg agggggccaa gacttggtgt tttatgctct tgtgttagag 154800
acatgataga gcatgggctt tgaagaaagg catttctgtt ccttatggct tatagctctg 154860
gaccttaggc aagttaagct ctctaagcct cattttacag cattgtctgt aaaataggga 154920
taagaataac tgcctcatac tattcgaaga cctgggataa tatatgaatg aagtacttac 154980
tatggctctt ggcatatagt aagcagacaa tgcaagctgg ctccagctct ctttgtatgg 155040
tagatgctca atagatgttg aaaggatggt atgtactcaa gacttggtga cagaattatg 155100
tcaaaatccc agttactagg ttgagatggt tgaatattgt tgagtattct gtgggcctgg 155160
```

-continued atgtgtattg taagcatagg gccctaacag catatgaccc cacttgctaa tatactaatg 155220
acttgattcc ttcattattg ttcattggac tcagtattcc tgaaattaca agactttgct 155280
catagaagac aaaatgtata cacaaatagc catttaagag gatcttaata ctatatggca 155340
tagtaaaaaa acaacaacaa caacaaaaaa catgggcttt gtttcagatc ccacttttgt 155400
tactttctaa cagtatagtt ttatgctagc tactttaaac cttcttttcc tcatttatca 155460
aatgagaata atacctgtct tgtcagatag ttataggata taatatatga caattgtcct 155520
ttctagcaga tattaggcat ttaataaatg gcagctatta tatgatgtta tatacacata 155580
cccacaaaga tatacagata tatagatatg gaatttttat atagataaaa gtgtttaaag 155640
gagacattca ctagaattgt ttacccataa cagaaatatc agtgaggaag agaaagtcgt 155700
caattcaaaa aaccaaagat aaaatccaaa gaatgtaagt tgggagtaca tgagaagttc 155760
agggtgaact ctcttatcca attgcagtca attagaatga cataaatgta aagtaagagg 155820
tcttggttgt ctatgtttag atcattttag ggtcagaaag aaatctgaac aaattggttt 155880
gaaatgccaa ccactaggac caaggcaata ctctgcaaga acatataggc tgaattacca 155940
ggacttctcg ccaagacaaa tgaaacaggg ccattgggaa gaaatactat atttctaact 156000
taaaatgcca gagagtaact gacggtttcc taggtgatag atggttgcaa agagtacggg 156060
catgaaaagg ggacacacac acacaaaaaa aaaccctgtt tatactttgc caacaacacc 156120
cccctccatc ttatttactt tgaacattcc agccatctct ctgcagtaat tcctgctggc 156180
taatgaggat tccacacagc tagggaacat gacagcctgc aaaggattat tttcctgaac 156240
aatctgcatt ttaagataag tcaccttgtt ggtaaccttt tgtacccttc attggaaagg 156300
gtgactctct ttgaagacag tttgaccaaa caatgagatc taggtgaatt tgaggaagat 156360
agaacgggca ctccagaaat atggatagtg gtggagctga cagcagtttt tcatggttga 156420
cgtagggagt ggaggcagct gtcatggaga tattaaagtt gccagtggaa tgttttccaa 156480
tacatattcc tgggccccac aatggactat taaatcccag ttattcttta aaaaaaaaaa 156540
aaaaaaaagg ccgggcgcgg tggctcacac ctgtaatccc agcactttgg gaggccgagg 156600
caggcggatc acgaggtcag gagatccaga ccatcatggc taacacggtg aaaccccgtc 156660
tctactaaaa atacaaaaaa ttagctgggc atggtggtgg tcacctgtaa tcccagctac 156720
ttgggaggct aaggcaggag aatggcttga acccgggagg cggagcttgc agtgagccga 156780
gattgcacca ctgcactcca gcctgggcga cagagtgaga ctgtctcaaa aacaaaacaa 156840
acaaacaaat aaacaaacaa acaaaacagc tagtctcttt ctccctaatc ccctcactaa 156900
ccactactag tgcttctggt gcttacacgg tgtctaagta ggtagttcat gatccttatt 156960
caaaggctgg atccagtgat ttgtaagtgt catgtttctt tgcaaatctc agtcttgcga 157020
attagaattc cccctgatat gtctaacata tcaaggtaat agttatatga tgttactaaa 157080
aatgtccctc acatgaaatg ttatgtttat gcccacagga aacaaagatt tagcaacaaa 157140
tatgtaaaag tgaaaccatt tcaagcaaca aaaatatttg atagcccttt tgaaattaat 157200
ttgaattcct ttttttactg tgtgtatgtg tggttggggg gcagggggggc ggtggatgga 157260
ttaattatct gtgaaaccca gtagaaagtt gcagtaacca aaacacgtgt aaagttcaga 157320
tttgaaccag atctcctgtc tacttcttaa ggcattgtgc atttagatag tatatgtcat 157380
tcatgttttt cctaggtttt attggtcagg cagaaacact gtgctatctc ttggtaacta 157440
tgagttagcc ttaatctcag tgattcatga cagtccactt gttttcctta atttaatgcc 157500
tcactcccac aggagatgag gctaactgag gactcatcta gaggactctt taagaatgag 157560
ctgggctttt ctgcccccca acaccctccg cctcccaaaa taaccataac aggcaaagcc 157620
agcacacaga aaatggcagt aagtggactt ctagacactc cagctacttc tgagtcttca 157680
gtgtcaggac acatcagtca tctgtcgatg agattttttt tttcttttcc ttttgttctt 157740
tcgttcttgt tactagtcac tgtggcatga ctgagagttt ggcaggaaat gggttcgtgg 157800
acctgtggta cagtcgcact accacagcag cattggccta gcaaaatgtt gagccctctt 157860
tcccttgcat gctcccctgg ggcagaagtc cagtgctatc tccgcttccc tgaccctctc 157920
cactcagagc ccagcatgac aagcacacct ttaaatgggt tcaaggaagg gaatagcaga 157980
aatgaacgca gcccgacagc ctcctttctc ttgataaccc ctgtcactgt ggagctggac 158040
ttctaggcta tctcacagag gcccagaggc actggaatcg atctcatttc cttacagaca 158100
tcaccttgtc aattagagaa cacataacgt tgattgaatt taagattctt atcagtgcct 158160
agctcttttt ctcccaaatc cgaaattcag ccatggcaga tccataatca agaaatatac 158220
ttacattccc atcctttgtt gttggtttca aaaatatttc ttttttgtga gtatgtatcc 158280
atgttttaca aaccaaaaaa atgggacata tggtctgaca aagggaagga tatttgaacc 158340
tggggactgc ctgggagagt ccggaagcac atggtcactc tagagactgt catcaagggc 158400
tgctcctgag attaatccac tgtcgaaggc attatcccat ctcccttaca gcagcctttt 158460
gcaggaaact gtctaagatg ttgtgctttt tttttcattg acttgtaaat aacaaggtgc 158520
tctctttcct tttctttgca gaaataggca tctttagaaa taaagccatg cccattttga 158580
aataagaact tgtttggaac acctgagagt gttaagcagt gcgggggatt tgcatccaat 158640
tgttcttgct ttaaacctgg catgggcgct ctcgcctcat agcccgcagc acctgaatca 158700
agcctcctgc ctcccttatt aagatcttaa ttacagactc agcttagttc attgctgaag 158760
ggaaagaatt tcatttctct gaagtgtgtc tgtttttttgg tgtggcaggt gtaatcatga 158820
taagatcatt tctgggtttt ttgttttgtt ggtttttttt tcctagagga agtttttttt 158880
tccaagggga ggagtacagt tcttaagaca caatttcatg agctcatctt ggcgcagtaa 158940
taataactgt gctttgattt tatagagact ctttttcctg aagaaatcag agcatttgga 159000
gtaaataatc tcatgattcc tcatattttt ataaagaaga acatgtctat taatatttat 159060
tttgcagaca gggaaacaga ggcacaaaag gcagagattt gatggtcatt agtcttcaaa 159120
tgtgaagtct gaagctagac cctcctaatt cagtctggtg tccattcctc tatccagggt 159180
ttctcaacct tggcactatt gacacttagg gccaggtcat tctttgtggt gggggctgtc 159240
ctgtacactg taggatgttt agcaacatcc ctggccactc tacccactag atgccagtaa 159300
cacacgtgtg catgcatgtg cacatgcaca cacacacaca gtgacaacca aaaaatgcca 159360
ctaaacattg cccgtaccca gaggggacaa aaatcctcct agttgagaag cagtggtcta 159420
atctcttcta ctccttctcc ttaaaaataa ctgccctact caaaaatacc cccatagaac 159480
tgactgccat aattttatca ttactgatat tgagcttaat gtaacaggtc ctaaccaaaa 159540
agcaacttcc tcttacaggc ctagccccag tttgtttcag tgaataccac aaaatactaa 159600
gaagcgcaga gtttcattca agtcaaatgt aaaacccatc aaaccatctc taaggcaact 159660
ttaaagtatt tctctggctt ctctctctac aatatgtacc tcatcatgga acatgcattt 159720
agagctgggt ctttaagaaa gctattttat tctcataaac tggtgtataa catgtgcgtg 159780
taagagcttg tctctccacc tcggcactga acaatttcac aatgaaggtt ttttgttccc 159840
tttgctcctg ccaccttttc cctgtcttct aactaagaag ctgcagcttc aaaaactctt 159900

```
ccttgagaca gcttagtggc tgcattgctg acagtgtatg actgtaaaca cctctcagcc 159960
aagtgtgtga atctgttttc taaaactctc tgaggacctc acaagtgaag tagataatac 160020
caatcaggca ccaaatccag gtcaagtgac atctaaaaga gttccaggga gggttgcatc 160080
ctatttacat caactcggtt ctggctggga gatggacaac agttgccagg atgtgtatgc 160140
atttgtattg gtgggtttag atataacctt gggctgcata gcttggtgaa ggaagataag 160200
atagacagga atggaaaaat aggaacctct ttttcttctt tcaaacacct tatcagatgt 160260
tataacttgt gcattttgac tttgagaaat gacatcattt ttggaagtat attgtaatat 160320
agtagattgg ggtctcctac tccattaaaa cttaattctt atttctcttc cctgagtacc 160380
tggatgttag agggatttgt ctagacaggc agatagatat gatccagtgc caacactgta 160440
atgctggctg aaatccagat ggttgtttta ttgttaataa aatctatctt gtgggtgggt 160500
gggtgtcagg ccttcatcat tatatggtgc ctgtcagatt tatctacaga cagaaccctg 160560
aaaacagctt gtgcctgccc cgcatttttg accccttgcc aagatactgt actgaaatct 160620
atcaaaatca ggcaacctgg gacaaatgct tcgagattcc aaggcttaat agcaacagtg 160680
ctgacttcta agatggagaa gattctcagg aagggcatcc ttgtccggtg gggaaaaatt 160740
ctagattaag aggtgaacca gatgctagct ctggctctgc cgctaatctg agaccctctg 160800
ggctgtaaaa taaggagatt gggttagaat ggttccttct tactctgaaa ttctactcta 160860
atcaactctg gtcaaggtat gggtgacttc tggttctaat acctataaaa aacctaggtg 160920
ttcttccccc ttcttttttt ctttttcttt ttcttttttt ttttttatga cagagtctcg 160980
ctctgtcacc caggctggag tgcaatggcg tgatctcagc tcactgcaac ctccgcctcc 161040
caggttcaag caattctcct gcctcagcct cccgagtaac tgaaactgca ggtgcacacc 161100
tccatgcctg gctaattttt tgtattttag tagagacggg gtttcaccat gttgcccagg 161160
ctggtcgcaa actcctgagc tcaggcaatc tgcccacctc agcctcccaa agtgctggga 161220
ttacaggtgt gagccaccgt gcgcggcctc caccttcttt aagattctca ggagttgctt 161280
cggtaaaccc aaagaccaca gatgagtgaa aaagaactca gcagtcaaat tcatcttcca 161340
ccgtgggcca ggaaataata gaagttgact gtgacattgc acgtatacac acatatatgc 161400
aaatctgcct actaactctt tgccctaaga ttttgttggt tacatagtaa acaaatccta 161460
gcatatgaat gtgtctgtcc agcacgaacc ctaaatcaag caagaataga tggcattcat 161520
tcaagtatgg ggaaggagag gaacccagct tttgaggaac ccctttgtaa ttgcacagct 161580
atgctgtcca tatcatgtta ccaaatctgg tcagagagag atttctttct gagatccaaa 161640
tatccaaatt tgcagtgagc atcagatctt ttcaccagtc ctcaaaaagt aacttcactt 161700
tggtatatga gccaccaaaa tagtgctggg ttccaaatga tccttcatca gacaggattg 161760
gccagtgtgg aagagatgtt aagattccaa gccctggatc tacaaccaca cacagggcgc 161820
tgccccacag cacatccagg gagtattaac agcttctctt gccatgtcaa agagtacctt 161880
cgggaggcaa gtatttaatg tcacatttct caaaccttct cccactcaga catgctcaaa 161940
agagaatgct atagctaaag ttcacaaagc tggaaaatct aagaaaactt gaggactcgg 162000
ggcaaagtga atgacgtcaa gattcggcgg gggggtccaa gatactccta taagctttgt 162060
aactgtcata ggggtctaga agaagcactt cccagaaaat aaaaattact gcctgaaatg 162120
cagtctgggt gccacaggag gccttgtggg aaatgttgaa cacctctcag cagtgggcag 162180
aaggatgcca gggattagtg ggacaaagtg gggtcctgct tttgcctttc tgtgagctcc 162240
attcagctca cctagtgaaa agtgtgtcag aacacagtcg acaaatagta ctgggaaaaa 162300
```

attagcatat cttatattat atcataactt atcatatctt ctgtctcctg tattgaaagc 162360
ttcatgcctg tgacttcata atctcaagag gaaccaactc aaaaaattcg acattccaga 162420
tcttcagatg caagaaccta agtgtaaacc aagtattctg agaattaaaa tcctgacact 162480
tacagatatc catgttttct gactatggct gtttccttct ctggggaaag cccacatccc 162540
cctctatccc aaaggtgatg gtgggaagga aaggagaaat gtagccaaaa tggtttgcag 162600
ttctcagacc aaagccggtt ttcgtcagta tgcacaaaag cacgtgagcc tttctttctc 162660
ttccctgttg tgccctgaga ctgaccttga caatgttcat ccctcagctg cctgccttag 162720
gactgacttc cttgatgatg gccatttcct tgaatgtgtc tgtttctcag ggtctgtcct 162780
ctgcatgcat gcatttgcgc atgcaggcat gcaaacccac aagagtccag gctaaagttt 162840
tgggggattg ggtacaggaa aatcatgtca ttgagaatgg ggcaaccctg aggccatggc 162900
aggatcccct gcatgacaaa tatagaatga agtaaaaata atcagaggaa gccgggccat 162960
tgatgatgct atcagtctta gtggggtgat acaccagaca ttctgtctca tttctcttca 163020
aacgaccgca tgagtggtca tggaaactac aagtcacacc tctccgtatt tggaaaagca 163080
gatcgtttct ctgacatagg agtaataagc tttcttgaca ttttgatagc agtgagggaa 163140
gggaaaaaag gcagggagga gttggaggtg gggtgagggg tagaagccgt catgtgtcct 163200
agagctctct gtaccagcgt tctggtcaac tgtacagtat tttcttccca ctcctcaggc 163260
atagcttggg aaccaggaac agcagaaccc aagtggtctg gcaaagtgtt tgaatggtgc 163320
tctgtcacct agtgccaaaa gcagattgct acactgaagg gagaaaggct cttaaaagag 163380
accattgtgt ttaatctcac tggatggtc agttcctctt ggccttcctg tttgctccgt 163440
agttgcgaac actagtttca ggggggtcag gctcccgatc tgcgtcatta tcctgtttaa 163500
atagggaggg gcaggccctt tcctgctgtc tgtctcccat agtctctggc tgtgaggctt 163560
gagtgacttg gacatgacat ttctctttct ggttcattca ttttccccac ttccatctga 163620
aaattctaac caaatgtctt gctgaattct ctaagtacaa caatttcacc ctccctgcag 163680
acaatgagga aatcagagtc cagaatccat ttcaacttag caaacattta ctgagtctat 163740
attttgtttc ggatactggg gtaaagttct ggaaatgcaa aaggaatttg catctctgaa 163800
cttaaggagt tcacagtctt gaacagggca atccaagttg tactgtaaag aaatagtatg 163860
atcgagaact gggaaaggaa acagcctttg aatagatacc cattctggtt aaatggaaga 163920
tgggtttcga gggaggaagg aatttaatgc aggaaagcca attgggaagc aatttctgtg 163980
ctacagaaaa aaaaaaaaaa aaagttgctg aagacctgaa tgaagggtgg cagtgaggtg 164040
gaaagcaggg ccccagatgg gttgcaggtc atgaagagac acagcaaacc tctgcggctc 164100
ttactgcaca gctgtgtgca tgctgttaac caagcaaagc aaagcaggag aaaaaggtgt 164160
ttgcacttgc ttttagagag gaagatgccc attagactgg atataaggga ctggaatgca 164220
gaagaaatat ccagcgaaga ctatggcttt aggaattatc tgtgtgttca gatgccatcc 164280
tcctgtagag cgtaagcaca tagctgagaa gaggaaagtg caaaggacaa atctctttgg 164340
aacatgatca ctttagggat gggaaaaaga tttagtctcc agtggagaat aaggatgaga 164400
gtggtcaaga gaagacagag aacgaaaaag tggtatcgtg gaggccagaa gaagacagtt 164460
tcaaggaagc ttgggctggg gatcaaggct agaggctgct gcaatcaggg ttccctcaga 164520
tagggctcat gatcctaaat gctgatttgc aatcctgatt agagccacag cttgtgttgc 164580
acctgtattt cacttgacta aattctgtcc taattctaga cctgaagaca agaggcctga 164640
attcctgtct cagctctaag actttcttgc caggtgagct ggcaaatcat taacttcttg 164700
aggctcattt ttttcttttg taaagtgaaa gggttggacg gtaattgttt aaagttcctt 164760
ctggctttca agttctgtgc cctaactgtt ttggtgtttt gccaagctct agctgcactg 164820
ctaactgcca gcctttggag actaaccatc caagtgaata tagagttaca tagctctctt 164880
atctctcctt gatttgtttc tgtgttgacc ttccctaccc tggagataaa tatccaaggg 164940
ggtgagtggg caggagaaag agtacatctt gagtagatta aactgcctct ctggggtttt 165000
tctaagatag cagatcatca gcttctgact ttgtggctca aggaatcaca cctttgcact 165060
gaaggagagg atccctccac ttccttgcca gaagaattca ttcttgattt tcctattacg 165120
actgatgtgc acttttgaat gagatggttt atggtccagc tgaaattcat ttggctgtta 165180
tggtcttact gaaaccttgc accaacacca aatcttttcg aaagtccaac tcctgcctca 165240
tgccttttcc tacctgctga tgtattatct gtgttggaat ctgatgacat ttatccataa 165300
tttatcaagt agtatcatta ttaatatgtt gtctcagaag ttcccttgaa tgcaaccaat 165360
ggtttcacta ttgctgtttg taggcagata ctcaacaaga ggttgcagtg acaagaactc 165420
attcataatt cagaaatata ctgctttaag ataacagttc ttctgaaatg taatcctgag 165480
caagataaat atcagatagg tacaaaacat atataatagc atcattggaa taggaccaag 165540
cctggactgc aaatggaaag gaggcaaggc ggggagggag cctgaagccc aagggccatc 165600
tagcaaatta aataaaacat caccatagct taccaaagac cgggaaacta aggcccaaag 165660
ggatgctgtt gcctggcaaa gtaacacagc tagaacctaa gaccgcaaat atccaattta 165720
ttccatagac acaaaaagaa gaaccgctcc tcttcagaac tttatcatat aatggaactg 165780
agcccagtaa caaggatgct gcgtggctga gctaaggtag cttaaagttc tggaaagagg 165840
attaaactga aagaacgcaa ttctctttcc atcgctgcca atagtgtggt cttgggcaaa 165900
tgataaactt caaatctatt tcctcatctg tgacacaagg gcattgtgtc caggtgatct 165960
ctaaaggtcc ctggagccgt aagcttcggt ttaggagagt ggctggatgt agacattggc 166020
tctctgtagc ttgcgcagat attaaataac tcatactcct gttcggccaa ggctgagaat 166080
atgtatcggt gtgtgaatag gctggtgccg gggtcctggc tactaacagc actgacaagc 166140
tgtgcctgaa acctaatctc tatgggcact gaggaggact gctgggaagt cctgacaacc 166200
agtcaggagg actcacctgc ggtgcccaca ttagcccaga ctgtggggct ctgagagttt 166260
cccccaagaa gcagctcaca ggccagtgta gaaacattag ccagctgctc accaggtggt 166320
aagaaggtta ctggggcagg agacaaagaa cgcccaggac gactctcgca cggggatttc 166380
tatctgcctc tgatcaagca tgctccggtg ctccacttca gtgcctcatg gtgctcttgg 166440
agttggaagt ggcccaattc cgaatgcctt gagctgattt atgctgatta gatctgtagc 166500
cctttgcctt tctactgttt tctgtttctc ttctttccct tctttgtagc cagtataatt 166560
gcacagctac caaccctcag ctcccataca actagcccga ctctgttgct tctgatttca 166620
tgtgggggct tcccgattgc tgaatgggcc cagaagaaag ggacagacag aggccagagt 166680
ggtcagctat ctcctcactt aataatctca gtacagctct ggtggagtca tttcctggag 166740
gtcattttag taaaaggacc agaatcttgt cctctgtaac tctatgactt ctcttgtaaa 166800
atacagaata cccaaaagat gggagaagag aaacagagac aattttagga ttatgacacc 166860
atccttaaat ggttccatga acaggggaaa ctgctgcctg attttttctt tatgtatgtg 166920
aacttttcat tgttagatga aacccagcgc ctcctggaat attaactacc cagtgaaacc 166980
ttcccctgaa atatgcactc ctcagtttcc ctttagcttc cctggccgct cacctctctg 167040
tgtctcacac ttcctggatc tcataactgt caagaaaaag gacttcaacc ttattcttga 167100
agagtatcac aaagcttcct gaggactgtc ctctatggct ttatctcttt taattgccct 167160
ggctaagagg aacctggctc acagcagcag aactggaccc gtcccaacta ctgaatagag 167220
ggcagatccc ttccattgca cagccctcca gagcggaaaa cacacaggac ccgtggcaat 167280
ggggctagca caaggggacg cgagtagtgc aagtcagctg caaagaaatg aaaagcacga 167340
ggctgaatga tcaagtccac gttgctagag aagaaaatag acagcaaaag ctcagacaat 167400
gacagccgaa aatcccacga atatgtcatg gtataaaata aagtcatgaa cctgccccat 167460
ccaatccgta atcctttctt ccataaatga gccccacctc aatgacatta agtgcatcca 167520
aacatcttaa caaagcatta gagttcactt ttagtgttcc gagggcttgt gctgaatcaa 167580
caacgtcccc gacttcgctg tgctctggga agggggcaga catgcgggaa tggctgcccg 167640
cgtgctggga aactttacta atgccaagaa atgaaatctt ccgagccttt gaaaggcctc 167700
caagaatgtc agcacgtact gcctgcccac tctctgctga atgcctactt tggctgtctg 167760
cttagtactg aatgtgccag acaggccttc atacaaagac ggagagtgtg ttgggcccat 167820
gaaaggggaa ggcacagctt ttctgatgtg aatggtgaga ttcaagaagt aggtgacgaa 167880
aggggagggc gaggaggggc cctcaggaaa ggtatgcata aaagaccgag agagaagagt 167940
tggcatccac ctatgtgtta ataaatttgt tgtcaaagct ggagatgtat atggctgctg 168000
gcctatgctc cacgcttgat ggcatgtcta catgccttgc ttgtggattc tctctggatc 168060
caaggctcct gtcatctgag aacaagaatt tctaagccct gccaaggcat atatatgtgt 168120
acttctattg gcttttcaac tccaaatata aatgctattt gtactgtgtg ttatttggga 168180
tttttctttt actcttttca cctccaatat agaacaatat tgagaaatgt tcattgtcga 168240
acatctgaat atctcgggat tttttttcc ttaagctcac tttgaaaaag gaagaaaaat 168300
gttttgtata gtgaaccatg ctctaactct gtaacactgc tactcataat tccttggcac 168360
ggcatatcct gctagaggaa agaactcttc tggtgttttg agcttttcca aggaggcagt 168420
ctgatgtcac tggtggcaga tgcagtgtat atgtatctgt cttttgtctg caccatctgt 168480
ttttctcctt acagtctatt gttcagattt atgcttctct ctttccagga agtgtgcctt 168540
tccataagag cacgggcctt aggtgataaa gggaccgacc caatattcta acacggtttc 168600
cttctcttcc ttccctccta gaatcttatg gcaagggcct tatatgacaa tgtcccagag 168660
tgtgccgagg aactggcctt tcgcaaggga gacatcctga ccgtcataga gcagaacaca 168720
gggggactgg aaggatggtg gctgtgctca ttacacggtc ggcaaggcat tgtcccaggc 168780
aaccgggtga agcttctgat tggtcccatg caggagactg cctccagtca cgagcagcct 168840
gcctctggac tgatgcagca gacctttggc caacagaagc tctatcaagt gccaaaccca 168900
caggctgctc cccgagacac catctaccaa gtgccacctt cctaccaaaa tcagggaatt 168960
taccaagtcc ccactggcca cggcacccaa gaacaagagg tatatcaggt gccaccatca 169020
gtgcagagaa gcattggggg aaccagtggg ccccacgtgg gtaaaaaggt gagtaaatga 169080
ctaactaaat ttttgttcct acttattttt ttttcccatt acacttggag catttggaaa 169140
tgttcccaaa ttaataactt gaagctgcca agaagtagat ataaccaata ccttagctca 169200
ggcatcatgt ttgcatgatt ttgccattca tccatcattc agcaaaactt ctttgaacta 169260
ccatgtgctg agtacagttg atttccagcc ctcctaagtt cctgtgtcat cctgggttac 169320
atgggttatt aaactgtttc tctccatctt tctcatatat cagcttctaa gccttcactc 169380
tgtgctcaga tcgtttccta tcttttctgt ttcttcattg agtggaacaa acaccaaatc 169440
tcgtacaagc ctgatgatgc aacaaggatc ctcccttggc caaaagctga atcatgacct 169500
cagtggcctg gctggacaag gaacccaccc aaagtagcga gagtgaggaa gctgggagta 169560
tgtcatgctg accaactcgt tctatagagt tatcagctta gtttgactca tttaaaaatg 169620
cacagatact agtggaattg gaatgaagcc atcctcctgt ccttcaagtc attcttataa 169680
taatgcctga ggcagtgggt gaaaacagtg gagcttggat atttaggaag gaattaattt 169740
aaaaatacag tgtggggagc tctgcaacac cctgtgtaat cccaaatact ttagcaattt 169800
gaggtcaata gaaattcact aattgaacaa tgaatgttga gcatctaata tatttttgat 169860
gcttgtgata cagtgattaa ttaaagataa acaaagccct ggtgatgctt acattgccgt 169920
gggggagaca gaagcaacca agagaatgct aggtagggac acgtgttatc aggaaaataa 169980
tgtcagtgga ctgatcgggg gtaacaccca caaccaaggt gatgcttatg tgagcatcac 170040
aaaggaggga ttttctcttt catttgctgg caaattccaa tgggtcctac aaggtttggt 170100
attaggaatg aacaaattta actggataag aagatatccc tgaattacaa gaggaaagat 170160
gcaattacat accagaaaga gcttgttgac ccttagaaca ctaactatag atgtgtcctg 170220
ccccaagtaa atctaatatg aagtctgatt ttacaaacct ctgtaaatta gggaatatct 170280
atttgatgta ttagaatcct ctgttgaaaa aacaaaggat tcctttaaac aatgaaagca 170340
ctaatgcatt tttgggtaca tggaaagagg cagcctagag accctgtgga gagcccttag 170400
tgtttggctg gggaggtgcc agggccaccc tcctgccctc cccatcctgg ccatgtcacc 170460
accccagacc ctgaccctgt gtgggtagat tcctttaaac aacaaagcac taatgcattt 170520
ttaaatcacc tttgatataa aaagtatgtt ttacaaaata cttctcaaga gcacgcgtgt 170580
ggcatgaact gagcgtaggt tcgttaagag ggattcctca agggtggtgc acagctttta 170640
gacttgtact gcccacgaca acgatgctgc ctagaggtga taaactgact tgtggctttt 170700
cagtcttcct tgtcctagga attgtagatt caaagggaaa acaaaacctg gcttctatct 170760
ccagagggga aaaataacag ttgaaaggtg taactataaa taagtaactt cactcattct 170820
tagtcctggt tgtttgcacc ttaaaaatag ctctcccaca tctgagccag tgtgaggcag 170880
aaggggaggc cagagcagga aatgcttggc tgggaggtgg tgggctctaa actttcatca 170940
cagttgactt tggcaggaag gtagcgtgtt ttccttttta gacccaacct tttcagctcc 171000
aagtcagaga agcctaagcc ttcagacttc ttccccttgt atctgctggg actgccctgc 171060
aggctttccc catggctccc cgtccttcca gagggcagag atacggactc atcttccctt 171120
ggattgatgt caaagggctg gggtgctggg gtgaccctcg ggcactcaca ttccatgttt 171180
tgttttgctt tttttaagtc tacactcagt agaacatttt ctgtttagca aaaggtagat 171240
gagtcctgca ggaggaaatc aacttctgaa aatgacctgt gccagccctt ccaggagttg 171300
cagccagggc tgaagagtag gccgtgccta aagcatcaca cagtcagggt ctggggtagt 171360
gacatggcca ggatggggag ggcaagaggg tggccctggc accttccctg ccaaatacca 171420
agggcttctc cacagtatcc tgatcctggg tctctaggct gcctctctcc atgtacccca 171480
gagcagtggt tcacatccat gggagtgtgg ttgcctcttc ctttcttttc actcccttcc 171540
tcacttctct tttctatctc tctctctctc tctctctctc tccccccatc cctccctcct 171600
tccctctccc tcccttcctc ccttccttcc tttctttcat agtggagatg gcttagctgc 171660
taggaggtga ttttagcctt ccaggcaatt gcaactgctt taaaaaacat ctgtcaacat 171720
cttcctgggt ataggatatt ctcagtgggt gggaatcatt ctaatgactt aagcctaggc 171780

```
cctaagagat aatcccagca cactggggat caggcgtggc tttttcattt ttctgagttt 171840
gcattttagt agttttactg actggcttaa taaagcaatt tgctcatttt ctctttaaat 171900
ttttcatctg taagataata tgagcccaga actagatatg cctggtagtt taagctatgg 171960
tctttaaaag ctcttgaata agaaaataag gaggcagtgg aatcttattc tgagccaccg 172020
gggtggggtt taaaaatgtt aatgggcata gaatcaccca gagaggtagg gcagtgagtt 172080
taaatgcaga ttcccaggtc tttccctcag agaaattaat ccagtaggtc tggttggggg 172140
cccaggaatc tgcatcttat tgagctcctt gcatagtttt gtgggtggtg gcctaggact 172200
agactttgag aaacactgta aagggaccat gaaggggctg ggacatgctc caatctgatt 172260
atgatttggg actttccata gttcaaaatt ccccttgatat tgctacagac tgtgggcttc 172320
cgaagtttta cccagcactg cttttttcta ctaatgaatc acttaaggaa aaaaaaaaga 172380
cagtgaattc tgccttctat cacttcaact ttgctctctt ggaaactcca acctctaccc 172440
accctcttgc atcccctcca cactaactga cattcatcac atattaaatc agcatttaga 172500
gaaagaaata tagtcataaa atccccaccc ttttaggaaa caagcagaca gtgtgagaat 172560
tgtggagaga gtaaggcctt cagggttcag ctgatgctgg gttgtttctc catagctgta 172620
tatcctttgg taagttactg accatctcta cgccttggtt tcttcatctg tttaatggga 172680
atgatactaa ctacttcata ggctgtcgtg agaattaaac agaagcatac atagaaagtc 172740
cctggctcag tgcttagcat ggcaggggct taaaagaatg cattcctctc accttgcgtt 172800
tcctttctca gagtttattt cctactacat cagccctgtt gtgtttctta cgacacaccg 172860
aaggtacaag tgctttcttg ctaacacata tgctgtgttt tttgagtgtg tggctttctc 172920
tttggttctg caagaattct gcaaagggtg gaaaaaaact ctccaagtta tctgaaaacc 172980
atatacgctg acacctttac ttaatttcat tggtcttttt cactctgtgt tttgtgcaca 173040
gggccgtttt atccattagg cgttgtaggc aatatgccca gtgcctataa gaatgtttgg 173100
gagctgaata aaagatcttt tgactccaaa atatgaaaca caaaaactgc aaaatagaaa 173160
ttaataaaca tttaggtcaa tgtctaggaa accatatcat gtctgcccca ttaattgttt 173220
tatttagggc ttataactat ttcatcatat tagaaaacag tatgtaggtt atatttttct 173280
cactttgcaa agatttctaa atatgcatca tggttgccaa gaacccacag gcaatcctaa 173340
attaaataag ttactcatag tcgaataatt tgaaaaactg aattataaag gaagaaaaaa 173400
agttttcaat ttttaacagc aaaaattcta cttaatatgg gattatggtt tggggtaaat 173460
gaaatctaca aatgttcaaa accaaaagcc taaaaagatc taaaatagtc tcatttctct 173520
gcttcaaaga tcagtgaaat tgctacctga gttcatccat ttcacagttg atctgcatgg 173580
gaaattatat gtgcttctct gatttttctt tggatgtgtc gcttttattc taactgctgg 173640
aactatttgt tgtacctctt tctgaagatc agtttggggc taaattacaa gctccatcag 173700
cacaggggcc atggctgcct cctgactgct gtaggctgag cacttggtag agcatcagcc 173760
cacagatagc agcccagtga accaatgaac aggtggaagc aagaatcaaa gtgttaaatg 173820
agagttaacc tttaattaac tgaaaggtgg ttctgatctt atcacacatc caccctcaca 173880
cgctgctgct cgaatcccat ggttcagctc attaccatct ggtatgagag gtgtcagatt 173940
atatacagtc atttccctcg ctgaaggacc ttccagaatg tcactgcctg tgtcctgtaa 174000
gggtaactat tcatatacaa tcaatgagca ccttgatgca aagcatgagt gatgtaaaga 174060
agggcttatc tgagagttta acttctgtgc attttgccca atttagacaa gattagttaa 174120
```

ctcctctgtg gtcacctaag gaggaaaact aggctttttt tttttttttt tgagtcaggg 174180
tctcgctctg tcacccatgc tgaagtgcgg tggtgccatc tcggctcact gcaacttctg 174240
gctcctgggt tcaagcgatt ctcattcctc agcctgccca gtagctggga ctataggcat 174300
gcgctaccaa gcctggctaa tttttgtgct tttagtagag acggggtttt gccatgttgg 174360
ccaggctggt cttgaactcc tggcctcagg tgatatgccc gcttcaggtt cccaaagtgc 174420
tgggataata ggcatgagcc actgcgcctg gcctaacttt ttctactgag gggcagaact 174480
tcctttgcat atgttatgat ttacctagaa tgcctttccc ttctattttc cctgtgaact 174540
cctatccatt ctttaaaacc cactccaagg ttcatccccc tcatgaagct tcctctctgc 174600
aacccagcag tttctccctt ccctatggtc ccagaatgtg ttgtatattc cattgatctc 174660
aagggcttct taaaaatgga atggtctgcc attgcaatgt gtgtgatggt ctggactggg 174720
gtaagtattg ctttgaggtg gcacttggaa aactgaagta atattcagat ttaccaagat 174780
cctatgacat catctttaag gaccattttc taccttccaa aatgggtcac ggccaaatgt 174840
tggcaggaaa tgattcaaag gttttagcca ggtcttccag gcccattcct gaaaggtaat 174900
gtaagaaaca gaaatagatt agctacaatg tttgtacctt cctagacact gagtcatcac 174960
aaattacaca catacacgta catacacata cacatacaca cacacagaca cccataagct 175020
gttggctaag gaacaaggac ttcccttatt ggaatttgag gcattgtgca atctggttgc 175080
ccagagcgac actcagatac tagccaacta agtgctatat attagcagca tgacttgtct 175140
aacaacaagc aaaaaatagg tttagaggaa atgaaagctt ccagaaaagt taaattctga 175200
cttcacctca ctttctcctg ttccttgcct atacacacac aaaatacgta cacacccaaa 175260
aaatactcct agggcagagg gtacttcggt ttcctcattt ataaatcaat aaagtacaac 175320
tatgttccag aattgtacat ttctacataa agataatcct aatgtatatg aattgtttgc 175380
ctcgatacat gggttttggg gctatgcaga gaactgtact tgccatctaa aatgtcaccc 175440
ctgaagtttc aagatacatt ttaatattac acaaaactgg aggtcattca gctcttgaag 175500
ggcaggactt tatgagctca ctttgaaaat gagaagttat cttttctcag acaagtcacc 175560
cgagccaaag caatgagcaa actctaacac ccctccttaa aaattaacaa aggtcctttt 175620
tgtttggcca gtgccaaagc cttcaaactc agttgcactt cgttctaaat tttatagata 175680
atgcatattt ctaagagtgc attagtaact tcttataaac ccacaccaaa gcaaacagag 175740
gttaaccctc ctttttcaat gatttcatgc taaatgactg tgcttatcag agtgaagagg 175800
taagagactg ctttaatatg atgtctggct aagtaggaga acactgtgag agagagaaaa 175860
cagaataaat ttatttattt aatttcatga taaacaatat tcgttgaaca catctttttt 175920
tttatttttg agatggagtt tcactcttgt tgtccaggct ggaatgcaat ggcgcaatct 175980
tggctcactg caacctccgc ctcccaggtt caagcgattc tcctgtctcc gcctcccaag 176040
tagctgggat tacaggtgcc caccaccttg cccggctaat tttgtattt ttagtagaga 176100
cggggtttca tcatattggt caggctggtc tcaaactcct gatctcaggt gatctgccca 176160
cctcggcctc ccaaagtgct gggattacag acatgagcca tcacgcccgg cctggttgta 176220
caaatcttta aaaaaagact tgcttgacta cattgtgcaa aatgcagaac tagaaactgt 176280
cagcaatcaa aagcacttca ttctaactag ctgtgcctta aacgttgtca agataacttc 176340
tagagagatg tgctgctcct gtttaaagtg tgtcagtgcc actcacatag gacaatgtgt 176400
gttcctcaaa agtcggatgt aggtcgggcg cagtggcgca tgcctgtaat tccagcactt 176460
tggaaggccg aagtgggtag atcacctgag gtcaggagtt tgcaaccagt ctgactgata 176520
ccatgaaacc ccgtctccac taaatacaaa aaaattagcc aggcatggtg gtgcatgcct 176580
gttaatccga gttacttcgg aggctgagac aggagaatcg cttgtacctg ggaggcagag 176640
gttgcagtga gctgagatca cgccattgca ctccagcctg ggcaacaaga gcaaaactct 176700
gtctcaaaaa aaaaaaaaag taggatgtaa ctccagtaac atttgaagag tgccaaggag 176760
tcctctcttt aaagggatcc tacagtatat cagtttttttg aagcaaagaa gcctttagca 176820
atgccacaat cgcctctgat ttatttgatt aatttttgta atacttggtt ttcttaaagc 176880
atggcacact taaaccagtt atttattgga atagtttttg ttttcaaagt cactaccaat 176940
tgaatgtgca gccttcactg gtgtcattac cccatgcttc cgtctcattt tgcaagatag 177000
tgttagaact aaagtggggg tgaccccaag gcgccttgag ccttggctcc atgttaggga 177060
tcccatagag gtactaccac ctgatcctct ccacagcctc gtgaggtgca cctcacagca 177120
tttgctgttc agaggaggga actgaggtct gagaaggaaa ttcacttgct gaagttaact 177180
tgctgcctcc agtgagaggc aggattgata tttgagccca cgtctgtctg actccaatgc 177240
taatgatttt tacatcccgg ctgaaggatg atattgccaa gcccttaaag aagaaggcat 177300
atttggacac ctcattagca atttgggcgc taaatcatac cctgttggcc aggaagaatt 177360
aaagttgctg cccagggctc ccacctcagg tccagggagt agcctcaata ctgagggaat 177420
ctgaattaag gagcttggaa gttcccccca cctagctgta gtgggcagtt tcagagtggg 177480
ctgatccagg agtcctgacc aggtcagtag ggtgatgtct agactccagt accactgaga 177540
atgttgctat gttggctttc tctgccacac agaaaagtct tttctttcct tttcttttct 177600
ttctttcttt cttttttttt tttttttttg agacggaccc tccctctgtt gaccaggctg 177660
gagtgcagtg gcacaatctc ggctcaccac aacctccgcc tcctgggttc aagtgattct 177720
cctgccttag cctcccgagt agctgggact atgggtgcgc actaccatgc ctggctaatt 177780
tttgtatttt tagtagagac aaagtttcac tacgttggca aggctggtct caaactcctg 177840
acctcgtgat ctgcccacct cggcctccca aagtgctggg attataggcg tgagccacca 177900
cgcctggcct aagactgtct ttccaaatga cttcaaattc cttcaaatgg gtaacttcat 177960
ttaaccaggt gggggcacct cccaaaacac aagttaccca gctttcaagt tgtggctctc 178020
atataaggaa gtaactttct ttgagagtat ttacttgtga aattataaaa gtagtaaatt 178080
tctggaaaat gtctaacatg tattgctagc gtaggccgca gggcattgag aaacgtatac 178140
cgctgcactg ctggcccagc taaccaaggg tctccttcac ttctttgtca ttaatagcct 178200
gagtaactaa ctccacttta gttccctcaa ctgtgaaatg gcaagtgatg ctagattatc 178260
tctaatgatc tttgctaaaa ttttatgatc cagatatcct tatctgattc tttctcagaa 178320
tcactttaac agtttaataa aaacggcctg acatcaagag tttttttttt tttaaagaaa 178380
agatactcaa gcattgatta taaatttcaa cttgaccctt aagtttttgc aaatctttcc 178440
tactcttcct ttaggatcca gcccaccatc ccatccagaa ccacagtgcc ctttggaaga 178500
cagagctatg ccaaaagaca gcaggagcag gcagggacac aaggaggcag ggactggagt 178560
gtgctgagcc agtgagaatc agtgtttgac agacctgggt cctgtaccca aaaaaacttc 178620
cagagttccc cattaaggag cactctcatc cctgttttgt taccaagagc taagaaagca 178680
cttcatcctg gaactcattg ttttctgccc attttcccct atgtaatcct cttggatttt 178740
gcagacgttt taggcctgtt gtctctggac acgacaacca ccttcagagc tggcaccgag 178800
ttctgccttg tgagtggttt gccccatcag ccactgcatc ccttcttcca actaaacctg 178860

-continued

```
agcgttctcc tctttaggaa gaaatgatac caatcggcat ttgggtccca aaattctcat 178920
ctctcacctc ctcttcacag tccctttccc cttagggcag tctgtgggca tctctctaaa 178980
atccatttcc caatctagat gtagcgctca gagtcctgtt gaatttattt ggacatcaaa 179040
agagccacaa tacttgtgct tttttatagt tttctttcaa agaacatttc agtccatgag 179100
acagaaaaaa aatggctttg ctgtatccaa cttgtcacag gcttgtattt ggcattgttc 179160
tgagaaagac ctcaaccact cgtgaaaccc agacgtcatt tcccgtcgtg ttctttcatg 179220
ttaaatgctt ctagctgctc gctggtgctt ggtcactcta taactaaata ttgctttagc 179280
actggctaca caaagagctt cctgaaagca gcagggggga catgctaggg gcttaacaat 179340
aggggcactg tttccattga gcgggtttgc tgcccaacgc tgtgtcaaat gaaagtgacc 179400
caggagcacc actgctccac ttctgagctt ccacttgtga ctttttcctc actggggaaa 179460
gaagctggct gtgatttaga tgtggctagc aaaaggttta gttctggcat aaaatcaggc 179520
atcagaacga ctttgaaaga aagtaattca ccttcaaaaa tacatgggga aaaaacttca 179580
tgagcaccag agaagcattt ggaagagtta accttggaca tggcttacga gggtgtattt 179640
ttaaggccag actcagtttt cattatattg ttgctatgca agtaaataaa tgagctcact 179700
gctacaccca agctgggcag aatgaattta cagagaatta ataaatccag ggtaggcaac 179760
atgtggcttt tcttctggtc atagagaagc aactagtact cttggatttt aagcaggcaa 179820
acctctgtag ctttacagtt tctgaaaatt ggatcccagt tctaatgggc aggcagtgat 179880
aatggtaatg tttcttttcc taaggttttc tttaaaggga agggatcaaa tagttcattt 179940
aagacaaaga ggttattata aagtctaata aatactgtgg tagctctgtt aatgcttttc 180000
aagggcattt aagtgaaaga agccctttcc aacaggcagt tttggaaagc taaacactct 180060
tgttaattca tgaaacgcaa agagagataa tataaataaa tcaggggctg gggaggaatt 180120
agagatagac aggaagcagt caaattttac ttcccacata tgccaagaaa agtgcaaata 180180
catggctgtt acttagtaaa acctactttt aaattcagag aatcgtaggt actatgaatg 180240
gtgaggttat aaatctgtaa tcattacagc acggggacac tttttaactt ctcatcaatt 180300
acccattgtt atttcctgag cacatcctgg gttacctagc tcctgactag gcattaggga 180360
aggacacaag aagctgactc cacacattag tactctacta aattcatggg taaactccac 180420
tggtcaataa tcaagtcact atctctatat tggaggcaaa ggattgcaca attcaggcta 180480
tttgtaatgt tgctttggat tgtagagact tagactcaga ggaatcacgg gacatagaat 180540
ctagaacagg tctgtgtccc atcattctct taaaagaaaa cctttcaagt aatatttctt 180600
attatctttt aaaatcttgt taaaatgaca aaatatatat atatttgtaa tttttaaaat 180660
tttgatgcat acaaagatag acatagatag atagataatg tagaagtata aataataata 180720
agtcactaga gcatgactaa ctagtgaagt tacccagtct cctctccatc ccatctctct 180780
gtctcccatc cactctaccc aactcttcct ttcaaagagt aggatttttc tgcttcgttt 180840
ttttactgct ttgttcttac ttagggttgc tggaagcaca tggaaggagg gaagtagtca 180900
aaacaagaca gtgttgtgag gggagagatg agaagtcatg ataagtaggt gggtgggtga 180960
cccacagggc tggcatcaga aggaaacata gcaaaacatg atggatatga ggcttgctgt 181020
ggggaggggg attggccttt gtgagtggca gccgtctgct cccttcccgc ttcccttagt 181080
gctccattga gctagcagca tgcagctgag aagttgaagt tctgaccaca tggcctctgc 181140
tgccgctgct ctgccccatc ccaggcacct agccagctct gcattaagga ggtgaagtgg 181200
atgcccaagg aaagaagtgc ccccaaggag acttgctgag accttgaaca agtgacacaa 181260
```

tgtgagcaga acttgtcttg acagaaaatg ctttgtctct aggtgttcca gagagatggg 181320
caagtgtcct atttcttagt gagagcctct aaacaaacca gcttgtgaac ctccactgaa 181380
aagatctcat ctgatgagca ttttaataaa gtgtcctgag tttggaggct tgccgtcttt 181440
ctcttggata aatatcttca tctcctagac ttggaaaaac acattttctc ctggggtttc 181500
ccattggcgt gtcttgagct gctctggtga taaccgtaat aatgccaata ctgatacgaa 181560
cagcagaaaa cagtaacccc aagaactcta cagatgatca tcaaggacca ctgtctctta 181620
ccatttgctg ctttggtttg aaattctcac tgcctcgtag atctcatttt gagcactata 181680
cattcctaaa gattgatttc tttctatctg acttaaattt aggaatgatt aaatcttcat 181740
ttctcccatg atttgatcct aaaacatttt gaaaggaaac agccttgaga tctgtgatta 181800
ctaagacata cataacattc ttatcacatt agaaagcaag aattgactgt tgcttgtctt 181860
gttcctgttg tcttgtcccc tgaattcctg tttatctttg attgtatgtg ggacattgta 181920
ttttcagtac atttgtagaa ataatgtgaa gcctataaag atgttctctg cctccagaga 181980
gaattttgtt tccttctgcc agcctcatag gcaagcatac atctgattcc atgctttgag 182040
ctgttctggc aaccctgatg tcttcagcct gtgcaagggt gggtttactt ccagttaatc 182100
cttattttgg atacagtcct tagggttcca acccaaagtc gggggtggtt tggggtccct 182160
gccttggtga gccctatagt ccaatgttcc ccccttaccca aagaagctgt agaaaaccca 182220
gcacagcctc ccaggcacca gtttcagatc agcaaaaaat agcaaatgcc cccaggcttg 182280
aaaagcaatc tcacctctat taactcttct cccaaagttt gacctagtaa ttctttatta 182340
tccttgaact cttgacacta ttaagaagat cttttcggct gggcgcagtg gctcacgcct 182400
gtaatcccag cactttcgga ggccgaggcg ggcggatcac gaggtcagga gatcgagatc 182460
gtcctggcta acacggtaaa accccgtctc tactaaaaat acaaaaaatt agctgggcac 182520
ggtggcgggc gcagtgggcg ggtgcctgta gtcccagcta ctcggaaggc tgaggcagga 182580
gaatggcgtg aactcaggag gcggagcttg cggtgagccg agatctcacc actgcactcc 182640
agcctgggcg acagagtaag actctgtctc aaaaaaaaaa aaaaaaaaaa aaaaaaaaaa 182700
aaaaaaaaaa agatctttcc tagcttttct tcattttttt aagttgtctt cagcaagatg 182760
gttaatctca attacctagt ccatgatttc tggaagtcaa agtcaaaagg taaaatctat 182820
atagcctagg tgacaattac aataacaata acaatagcta aggcttatta tggctttatg 182880
ccaggtactt tatgcacttg atctcattta atactcatat agcctatgag ggaagtataa 182940
tttccatttt acctatgaga aaacaggctt agaatggaac ctttgttctc atagcttgtg 183000
agtggtagaa ccgggattta gatccagctc tgcctgagtc cagcttctgt ttgtcaatta 183060
cttccctctt cagacctaat tcttccaata agcaacagaa aaagacccag tggggccatg 183120
gcctctggca cacagcttct cataaacgag cctatcacac atccccagaa ctaaagcaat 183180
cgtatgttcc ttctgatgtt gaggtaaaaa gcagggtttg ttttggtttc ccttttccaa 183240
aacactcccc cacatgtttc tggcttgtgg ttaagaagaa cccaggtgtt catgtcacat 183300
acgagctcaa ctggggaaaa ggaaaccatc cagcagccct ccttgcctgc caatagtggc 183360
ttcacccaac ttggggtgca ttcttctaca gtttctgatt tctcaacttc acctaacatt 183420
cccttgcctt cttggatccc tctcttgccc aacactacca tgcatggctg atagggcact 183480
gttctgcccc atatcccatg ggttctactt aacccagagc tggcttacct ggaaaccaag 183540
cttattctgt agtggcagac ctcacgccat cttgcttaat agccttcagt tttcctttag 183600
ttgattaatg tatcactcaa tagattatgc aagacctact ctgctaggca ctgtactagg 183660
ccctgtggtt tatatttaaa tgaagaggga atgatctctg actttaaaat gctggaagaa 183720
gagatgagat gcatcaagac cgtcaaacca caagtgataa gtgctgtcag agatgtgtgg 183780
atcactggct cagggagttc caaggataga gacatattat ctgtttggga agggcttggt 183840
gggggaaagg cattcagccg ggccttgaaa atcaattaaa gtttgaatat gaggaaagaa 183900
agaagagcat ctcagacaag gacatggcat ggatgaaggc acagaggtat gggcgtgcag 183960
ggcatctgtg gaaatggaca gctcagttct cgccgaggga gggagttggt gcagagcctg 184020
ggggccctgc cttcagaaga tttccaagag gaaggagggc aaaaatacac agatgaaggc 184080
aaagactggc agcccggagg ccaaagacgc gtttagtttg gccaagacac tgtttttaaa 184140
atttaagtca attttgaaaa ccaggtttca cataaaattc caaatttctg gcttctgaaa 184200
acgtgaaaga tctggcaaca cagggcgcaa tgtcttccct ctttcggtag aaggagttct 184260
gtctccccgg caccaaagcc tggcttgttt cttccctaca ccctgcttgc tcggtccgtg 184320
agcatctgag tataggaccc ttgctctgct atgggtacca gctcagggaa cacagatgca 184380
gaaacatcag aaagagtccc aagggcctct catccaactt gctgactgtc atcatgctgg 184440
ttctcagacc tccctatctc tctctgctat ccaaacacag accctcctct ttaaaatttc 184500
agcatacatg gctttcaaaa ttatgaggca tgaaagtgtc aaaagcatct ccagaaactc 184560
atgccgccag gatctgagac tcaaaacagt gtggatcaaa caccatcaaa gtgtggggtg 184620
gggcaattcg agtttgtttc cttgttttta tgtaagcaga ttaattagag aactaacata 184680
acgccagtct ttgggctttt gatcctatcc tgccaggacc cagacttgga gatgtattaa 184740
atggattctt ccttttctaa atggaagaat ctgcccttct cggcttcata gctcttctca 184800
aagtctctgt cttggaccct cccgttagtt actgagaatg gtatactaac atctgagaaa 184860
ggttggattc ctcctaggga cagaaaatcc acatatggaa agtgcaaatc ctgtgccggg 184920
taatcacgaa agcagttgca gtagcattgg atcatagagc cccaggagac ctcacaattc 184980 agccccccttc ctggcaacac taatgaatta agaggtcagt ttggtaattc caaaggctaa 185040
gcctttgtaa ctataaataa atgcacagaa tgaaaggaat gtagaaaaaa aaaaaagcaa 185100
acagaggggg aaaggaaatg aaaaacctga cttgatttca ttgagaaaat tagtttaaaa 185160
atgtcctttg tgtagcaatt cctttaatgc ctcaccgaac aaatgcctag gagaattctt 185220
ccaaacttga ggtcccctta accagacctt ggtgtgcgtc ttcagctgaa attcagcagt 185280
tctgggaggt ggaatgagga gagatcgttg gaaggttttt gtgtacttat gtcacgcagc 185340
aagaaaaagc cttaatgaac cacaaaactg gagactttgt aaggtacagc tcagtcagca 185400
cttttcctcc gaggagagga cacacaattg gcatgaaagt gacccaagca acaggtcgag 185460
gcagagaatg tccaaaagta gaagacttcg agctccctga tcttccacac gtcacaatgc 185520
ggattgctgc actggacttg gcatttaaat gggaccagca ttttgcatcc tggtcccatt 185580
taaatgccat ttgtggacca acgtgaatta gatggtaatg tcaggaaggc tggaatcggt 185640
ggtggcgggc ggggggtgct gtattcggtt ggcgtttccc ccctgtggtt ttcaccatct 185700
gtttctttga atgcataaac aaggaaaatg actggtttgg aatgcagagt tttaaaaaac 185760
cagaagacca caggcatcct ctaaatgaga aagagagagc aagttggggt tctgtgacat 185820
ttgtcaggaa gtgaaatgtt aaataccggg aagcattagc gctttctgcc agggaagatc 185880
cacaaaggca aggaaacact ttagcggtga acctgccttc cttttctgag gtcgtgctat 185940
gtgtttatat gtcacctagt gctattttca gacaccaacg ccacccactc tagctcccaa 186000
tccccttctg ggttttttgt ttgtttgttt gttttgtttt gttttgagac agagtctctc 186060
tctgtcaccc aggctggagt gcagtggaac gatcttggct cactgcaagc tcctcctccc 186120
aggttcacgc cattctcctg cctcagcctc ccaagtagct gggactacag gcgcccacca 186180
ccacacctgg ctaattttgt gtatttttag tagagatggg gtttcactgt gttagccagg 186240
atggtctcga tctcctgacc tcgtgatccg cgatccttgc cctcccaaag cgctgggatt 186300
acaagcgtga gccaccacgc ccagcctgtt tgtttgattg tttgtttgtt ttttgagacg 186360
gagtttcact ctttttgcct aggctggagt gcagtggcaa gatctcagcc cactgcaacc 186420
tccgcctctc gaattcaagt gattctcctg cctcagcctc ccgagtagct gggattacag 186480
gcacatgtca ccacacccgg ctaattttat atttttagta aagacggagt ttcaccatgt 186540
tggccaggct ggtctccaac tcctgacctt aggtgattct cccgccttgg cctcccaaag 186600
tgctgggatt acaggcatga gccactgcgc ccgacatgcc cgcttctgtt ttttaaacga 186660
aagatgaaca gttaagctgg acttagcctt ggttttccat tagcattatt gctaagttgg 186720
caaccttgga taaaatccac tcttggaaac ttttaagctg aacaaaagct gcactatgag 186780
caggtgctat gataaagcca agacagcgct ctaagtagag gggctgatga aatagactaa 186840
ggggagatct tcatttctct cctggacaat agcgagtaaa aaaaaaaaaa caatcatata 186900
agggcattag gaacacattg tgtttttctt tagcaaaggg catcctgctt tgaaaaggaa 186960
ggtttgctat gcacaataca gtggccattc tataaagtgg ttccgtatgc tccatgccaa 187020
cagacctcaa agcaataggt tcctttttta aacccaagac agtggagaga cttgatggaa 187080
attttgagtg catactaatc tcttttactt cgttgcaaga aacaatcagt tgtaagcact 187140
agggattaaa agccaaattg aactcaggca ttttgagagc gcctggggag aaggcattgg 187200
tgcatttggc tgagttccac ccatttcagc ataagatgga cgtggagcat ttttcacata 187260
gttctgtagg cagcctgacg ccagagtttt cacttcagag aaaggataaa agttgacggt 187320
ttcttaggga acaaccaact cttcctcatt tgcaatgtct gttctcctca aagatgtcgt 187380
gggcaacgct tgagatgggc actcaatgac tcaaagggtg gggggttaggc agaaacaaga 187440
ccctgggcat ttagaagccc ttggacgatt acatatattt caaaatgagt taagttcaaa 187500
taattttttg ctggtgctta gcacaccaat gaagtatgta gatatgaaaa caggaggctg 187560
ctaggtaaga ttcattttat tggcactggt tccagatgcc agcatcgtga tgaacgctat 187620
ttgacttctg atatcccttg acgtaggtac tgttggggat gttttctttc ctggtggaaa 187680
tgggaaaatg attagagacc agaggtcagg agacctgaat tctgttcctg gtgcctccct 187740
gactcagtat tttgtttgtt tgatacgtta gaatgaaagc tcccagaggt ttctaaggac 187800
agcacagttt gagcattggc tttgtaaaag tactctggtg acctgtggaa ttacagttat 187860
aatcatcata ataatgtcca atgaagaggc atactgagga aggcatgaga ggaattttaa 187920
gtggctaaac tctatttgca ttattcattt tacaaattgt ttcagagcct taaagcaaat 187980
ttcagtatgc ggtactttag atgcaaaatg ctcctctagg actttcataa gttacacaca 188040
agtatccctt aaagtatatt tcagaaatat gcttgcagtg catcaactct atctgatgaa 188100
ctttgagatg atcacaatta agggtgatag agatatttta gggatttttt ttctcattgg 188160
gattcaagag ggatttaaaa gtttactaac ctgggccaga tgcagtggct cacacctgta 188220
atccctgcac ttttgggggc tgaggtgggt ggatcacctg aggtcaggag tttgagacca 188280
gccaacatga tgaaaccctg tctctactaa aaatacaaaa aattagctgg gcatggtggc 188340
gtgcacctgt aatctcaact actcaggagg ctgaggcagg aaaatcactt gaacccggga 188400
ggcagaggtt gctgtaagct gagattgtgc cactgtactc cagcctgggg agcaagagca 188460
aaactccatt tcaaaaaaaa aaaaaaaagt ttactaacgt ggtgtctact tgtctccttc 188520
ctgttatgtc ttctttcttt ggtttctttc tatcttttta tgagggagag ttgagggatg 188580
agtgcttagt taggaggcaa ggagattcaa ggactcaggc ttggaaattt acacctctgt 188640
gccttctctc ccacaggtga taaccccgt gaggacaggc catggctacg tatacgagta 188700
cccatccaga taccaaaagg acgtctatga tatccctcct tctcatacca ctcaaggggt 188760
gcgtaccaga acatggtcac aagaggagaa gcgcttctaa gggtagcatt ccttcagggc 188820
tgtagagaaa agggagttca caaattatgc attaatatat gtcatatgaa gctttgttta 188880
ggttgtctac ccagtagcca ctttagccaa tgctatttaa attatgtttt ctggatttgc 188940
tttatcagga aatcctagta tttcacccaa gagagcttat gttcttctac aattttgctt 189000
cagaaagtag atttttcttt tttcttttt tttttttaa gacagaatct cactttgttg 189060
cccaggctgg agtgcagtgg ctctatctca gctcactgca acctccacct cccaggctca 189120
agcaactctc ctgcccctgc ctcagcttcc caagtagctg ggactacagg cacacacacc 189180
accatacctg actaattttt gtatttgta gggacaggct tttgccatgg tggccaggct 189240
ggttttgaac tcctaactgc aagtggtctg cccacctcgg ccttccaaag tgctgggatt 189300
acaggtgtga gccacggccc ccagctggaa agtagaaaat ttaaactaca ctttaaagta 189360
cagacagcgt agatatttca cataagatct tttttttttt tttttttttt ttttttgaga 189420
cagagtcttg ttctgtcacc aggctgggag tgcagtggca cgatctcagc tcactgcaac 189480
ctctgcctcc cgggttcagg cgattctcct gtctcagcct cccaagtagc tgggactaca 189540
ggtgtgcacc accacaccca gctaattttt gtatttttag tagagatggg gttttaccat 189600
gttggccagg atggtctcga tttcttgacc ttgtgatctg cccacctcag cctcccaaag 189660
tgctgggatt acaggcgtga gccaccgtgc ctggccaaaa tcatttttat attaaatgta 189720
agttaaaaac cataaaatgt attaaaaaaa aaggcaataa atctgttata acatggagca 189780
ctgccaaaga tcaagcttgt acataacctg gtaaataaat ccataattaa gtgcttagga 189840
gcataaaaaa tgaccaagta taagacattt ccattctggg taactcacgg gtttctcttc 189900
aggtatacga catccctccc tcatcagcaa aaggccctgt gttttcagtt ccagtgggag 189960
agataaaacc tcaaggggtg tatgacatcc cgcctacaaa aggggtgagt gagtgactac 190020
aaagcagcaa aaaggagtgt gtgtgtgtgt ctgtgtgtcg gggggtgcag ggttgggagg 190080
gtgggtaagt agttcactcg aataaaacaa gaaaggcaaa cccaaaaggg gaaaatgtag 190140
tcttggtgag agtaaaggaa ggaagcaaaa aaggaaaggc actaattaaa gatagctcta 190200
gggatttcat attgagaagc cccaactaaa aaacactagg tggccaataa ggataaccct 190260
ttggcaggga agataattag ttcagtttgg caagtactaa tatatatttg tagagggttt 190320
gttttgtttt gttacatttt gtttgagaca gggtctcgct ctgtcaccca ggctggagtg 190380
cagtggcgca accacagctc attgcagtct ttacttccca ggctcaagca atcctcccac 190440
ctcaggctcc caagtagctg ggaccacagg tgcacgccac catgactgga taaattttat 190500
tttttgtaga gacggtgtct ccctatgttg cccaggcttg ttttgaacat atgggcttaa 190560
atgatcctac taccttggcc tcccaaagtg ctgagattac aggctgagcc gcgcctggcc 190620
tgtagagggt ttgacagttt cctcagtgtg tatgtttgag tgaactcgtt tgactcactc 190680
tgttacccta tggggtatgc ctgcacagga ggcacagtaa tccctacttt acagacaagg 190740
ggactgtgtt tcagacgcct atgcagctca ttcagcatca cacagctggt gtgataacca 190800
aaaagaccgg gggagaactc tggtcttact ctgcctctcg gcacagatca gcagagaaag 190860
gatacccagg aggtggtcag aaacacagga ctggaaacac agggtgagca atttagccag 190920
gagggttgta catacgagtc tgcaccaaga acgtggggtt ggacacactt ggcaaaggac 190980
aagggaagtg acagcagaat aacggggaac cttggaagtg cctaacattg gggcggggga 191040
gggcgaccga aaaagtgcca gcaaatagga ctgagcacat gggaccacag gttcccatga 191100
gccaactcaa taaatagcat ttcgctttct acttgctttg caggtatatg ccattccgcc 191160
ctctgcttgc cgggatgaag cagggcttag ggaaaaagac tatgacttcc cccctcccat 191220
gagacaagct ggaaggccgg acctcagacc ggagggggtt tatgacattc ctccaacctg 191280
caccaagcca gcagggaagg accttcatgt aaaatacaac tgtgacattc caggagctgc 191340
agaaccggtg gctcgaaggc accagagcct gtccccgaat cacccacccc cgcaactcgg 191400
acagtcagtg ggctctcaga acgacgcata tgatgtcccc cgaggcgttc agtttcttga 191460
gccaccagca gaaaccagtg agaaagcaaa cccccaggaa agggatggtg tttatgatgt 191520
ccctctgcat aacccgccag atgctaaagg ctctcgggac ttggtggatg ggatcaaccg 191580
attgtctttc tccagtacag gcagcacccg gagtaacatg tccacgtctt ccacctcctc 191640
caaggagtcc tcactgtcag cctccccagc tcaggacaaa aggctcttcc tggatccaga 191700
cacagctatt gagagacttc agcggctcca gcaggccctt gagatgggtg tctccagcct 191760
aatggcactg gtcactaccg actggcggtg ttacggatat atggaaagac acatcaatga 191820
aatacgcaca gcagtggaca aggtggagct gttcctgaag gagtacctcc actttgtcaa 191880
gggagctgtt gcaaatgctg cctgcctccc ggaactcatc ctccacaaca agatgaagcg 191940
ggagctgcaa cgagttgaag actcccacca gatcctgagt caaaccagcc atgacttaaa 192000
tgagtgcagc tggtccctga atatcttggc catcaacaag ccccagaaca agtgtgacga 192060
tctggaccgg tttgtgatgg tggcaaagac ggtgcccgat gacgccaagc agctcaccac 192120
aaccatcaac accaacgcag aggccctctt cagacccggc cctggcagct tgcatctgaa 192180
gaatgggccg gagagcatca tgaactcaac ggagtaccca cacggtggct cccagggaca 192240
gctgctgcat cctggtgacc acaaggccca ggcccacaac aaggcactgc ccccaggcct 192300
gagcaaggag caggcccctg actgtagcag cagtgatggt tctgagagga gctggatgga 192360
tgactacgat tacgtccacc tacaggtaaa acagcggaac tcataaaaca cctacactca 192420
ctcacatgca gggagcctga gaaagatgcc tataaggatg tcgggttgga ctgccaaagg 192480
agagaacata attaatgtta atctacatgg ttcacaaatt ggagggagtg tcgtagagta 192540
gtaagaacgc tgggctgaga gtcctgagta ctcactcaga tctagccctt tctctgacgt 192600
ttactgtgtg accaacttat tcaacctcct tgggccttaa tttcctcatt tgcaaaatga 192660
atggggtaag ggttggatt agatcccgtt gatatacctc aggtaagagg agactcacca 192720
agtaggataa taggccctct aataataata ccagctccac ttctatttgt gttttatgta 192780
tagttccatg caatatttta tttgaaaaaa aagttttcgt cattaagaaa aagaatagaa 192840
gacctttgca ccagagaatt tctaaggccc ctgctagccc tactctgtgt atgtgtgtgt 192900
ataattgctt taaaacttag ccccatctca gacttaccta gaggaccact gggcattagc 192960
tagctgtcct aggagcttaa tctgtgtatg ggacattgga tagtcacagt tggcctccta 193020
caattgggaa ttctaccaag ctccaagttg acctgggatt ccgacagctt tcccttccac 193080
tttgagggat taaaacattc tactggctgg gcgcagtggc tcacgcctgt aatcccagca 193140
ctttgggagg ctgaagcagg tggatcacaa ggtcaggagt tcaagaccag cctggccaat 193200
atggtgaaac cccatctcta ctaaaagtac gaaaattagc caggcatggt gatgcacgcc 193260
tgtagtccca gctacttggg aggccgaggc agaagaatca cttgaacctg ggaggcggag 193320
gttgcagtga gctaagatcg tgccactgga ctccagcctg ggcgacagag cgagactctg 193380
tctcagaaaa aaaaaaaaaa atctaccaag atccattgtt taggactagg cttactatct 193440
tattctgcca ttcttttaat ttgactgaga gtcacagatt atactgagaa ctacgtaact 193500
attatgccaa attccctcaa gcgcaagaaa gtgtggcaag gagaactgag ccccacctga 193560
tgctgaggaa ggaagtggag agagagagga tggaggcatt gaacattcat cttactggtt 193620
gtctgaccct gcacagtggg aactactgcc ttggagcaga aatctataga tgatttgagg 193680
gaactagaag tgagaggtgg accacattta gacctgcatt tgggggttta caggttcaca 193740
tataatctat gagaaaagaa cccagagact ataaaaagaa cattatatat gagatttgaa 193800
gggaatcatg agtagctctc cgaaaatttt aaggtgcccc agaaagctgg caccctatat 193860
ggcaatgggc tttatttttc tgccacccct gtcgtctagg gttcacagtg cctcactggg 193920
catttgagat gttgccaagg cagtggaaaa taaagagtat ttactcatcc gtcaatgaaa 193980
ttgttagcat aagtgaatca cagtgatgac ataatatgtt ctttatgttg aaaattaaca 194040
gggtaaggag gagtttgaga ggcaacagaa agagctattg gaaaaagaga atatcatgaa 194100
acagaacaag atgcagctgg aacatcatca ggtaagttca atcagagcaa aaactgcttg 194160
gcattggaaa gatttcccac ctagcactaa ggaaaggtat cacttcaaga gattatgatt 194220
ttgattcttc cagctcactg gcaggaatca gctccaaagc acggaatggg gtttaaaagc 194280
aaagagaagg tttatgacct tgttagttca actgggtgta cctgggttcc atctaaacgg 194340
caattttttt aaaggctaaa cctgcatatc taacatatga ggactatttg ggttaaggca 194400
tttggtctca agaaacaaga cccattcaag ctagcctaag caagcaggtt tatagtaaag 194460
ccacagtagg ggaattcagt aacagaaagt gaagatagag ccaggtctgg ggagaactag 194520
aactgtaaat tatctctcct tcttgtagtt cctttgcttc tttctatcag tctacttcac 194580
tctcacctat tttctggttt tctctaatta tctactcatt tggctcccct gtaactttgc 194640
agaacccata aatggccact cagaacttct atagatggct tttcatctcg gcttcctctt 194700
ccgatggtta gctcccttct cttgttcatc agattcccaa gaaagagtct gattgggcca 194760
cgttgattgg gccatttctc tttctctctc tctctctctc tttctgtctc tacctcgcta 194820
tttgtctctc tttcgccagc aacacaagcc tatggtttgc ctggccttgg tccaatctaa 194880
aggtaggaga gcagaattca atgttttcaa catatatcca ggcctatcta ctgaggactt 194940
tgggcagggc atgttcattc aaaagctggg tatgagtagg ggagataatg acgactattg 195000
ctagaacaag ggcatacaaa taaagagaga tggattgagg atttatttac aagcctttta 195060
agatgaaatg aagtgaaatg gcatgtaatg acatgaaatg gcatgctata tttaggaaat 195120
ctgagttcta atcctttctg gccaaccaac tatgtcaagt caggtaacct ccccgagctt 195180
cagttacttc cctataaaat gggaaagtac ccccccccatc taatgacatg atatattgat 195240
gaacatattt gcataaagcc taagatatat aaaatataat ccattatgat taaatacctt 195300
ggaatatcac cttgtaccta tttatgtttg ccttggcatc tggcaaggta agactgcagg 195360
gctttgggga acttgtagaa accatagcaa tcgctaagaa gaaaacagat tctagaaaag 195420
taaagctgtt gaaggctggg cacggtggct cacacctgta atcccagcac tttgggaggc 195480
cgagacgggc ggatcatgag gtcaggagat cgagaccatc ctggctaaca caatgaaacc 195540
ccgtctcact aaaaatacaa aaaattagcc aggcatggtg gcgggcgcct gtagtcccag 195600
ctacttggga ggctgaggca ggagaatggt gtgaacctgg gaggcggagc ttgcagtgag 195660
ccaagatcgt gccactgcac tccagcctgg gtgacagagc aagactctgt ctcaaaaaaa 195720
aagaaaagta aagtaaagct ggctgtgcat ctctcagaga agctggggaa gctgggtgag 195780
gtgatcactg ctccagctca tccctacgtc caggtgggag attaactgag tctgaagctc 195840
aggtcacaga tagtccttat ctgcagaaga gaggtctctc ttgagtctta gtggaatccc 195900
tagaaattat tataattgca atttaaataa tacaccattt ggtagcaatg aggaaagaag 195960
gaagaaagcc agcacctgat gcatctgact ctgggtaaaa ccccctcttt ttaacagctc 196020
tgggggacta aatattatga tgcacaattc ccattcagac tgccttagaa actttttttc 196080
cttaagtgct catatattta tatgcattaa tcttcctgta gtgctggatc ataacatgtc 196140
tatcaatctt gacagaaaga gtaggataaa cagaaagggg tcatgaatgg tcatttcatc 196200
tgagcatcct gagatagtcg aggctttctc cgagaaggag caaactgtca gtgacttact 196260
tgacaaggag gtcactacat ttggttttcc cttgccaccc ctcaacatta ataaacattt 196320
acatagagcc tactacatac caaactatta taagcatttt gtaaacgtta actcatttaa 196380
cctccataaa ggtgtaggta acagggctgc ggtttaaaca ctatgctacc ttctagccag 196440
agggtacaag agaccagtag tccaatcata gaaggtctga gcttgaggat catctttccc 196500
aacgtctaca ttttacaatt taggaaagca aggcagcttg acccaggctt tacagctcac 196560
atgcatctga cagttactag cgactaaaat ccctgtcttt taactccaag gcctagtgaa 196620
tttccattgc aacacactcc cttgctctaa tgagatctgc tttcgtcttc cttgcagctg 196680
agccagttcc agctgttgga acaagagatt acaaagcccg tggagaatga catctcgaag 196740
tggaagccct ctcagagcct acccaccaca aacagtggcg tgagtgctca ggatcggcag 196800
ttgctgtgct tctactatga ccaatgtgag acccatttca tttcccttct caacgccatt 196860
gacgcactct tcagttgtgt cagctcagcc cagccccccgc gaatcttcgt ggcacacagc 196920
aagtttgtca tcctcagtgc acacaaactg gtgttcattg gagacacgct gacacggcag 196980
gtgactgccc aggacattcg caacaaagtc atgaactcca gcaaccagct ctgcgagcag 197040
ctcaagacca tagtcatggc aaccaagatg gccgccctcc attaccccag caccacggcc 197100
ctgcaggaaa tggtgcacca agtgacagac ctttctagaa atgcccagct gttcaagcgc 197160
tctttgctgg agatggcaac gttctgagaa gaaaaaaaag aggaagggga ctgcgttaac 197220
ggttactaag gaaaactgga aatactgtct ggtttttgta aatgttatct atttttgtag 197280
atattttata taaaaatgaa atattttaac attttatggg tcagtcaact ttcagaaatt 197340
cagggagctg gagagggaaa tcttttttttt tccccctgag tggttcttat gtatacatag 197400
aagtatctga gacataaact gtacagaaaa cttgtccacg tgcttttgta tgcccatgta 197460
ttcatgtttg tttgtagatg tttgtctgat gcatttcatt aaaaaaaaaa ccatgaatta 197520
cgaagcacct tagtaagcac cttctaatgc tgcatttttt ttgttgttgt taaaaacata 197580
ccagctggtt ataatattgt tctccacgtc cttgtgatga ttctgagcct ggcactccca 197640
aatctgggaa gcatagttta tttgcaagtg ttcaccttcc aaatcatgag gcatagcatg 197700
acttattctt gtttggaaaa ctcttttcaa aactgaccat cttaaacaca tgatggccaa 197760
gtgcccaaaa gccctcttgc ggagcaaatt tcagaatata tatgtggatc caagctctga 197820

```
tagttcaggt gctggaggga agagagacct gtgtgtttag aggccaggac cacagttagg 197880

attgggttgt ttcaatactg agagacagct acaataaaag gagagcaatt gcctccctgg 197940

ggctgttcaa tcttctgcat ttgtgagtgg ttcagtcatg aggttttcca aaagatgttt 198000

ttagagttgt aaaaaccata tttgcagcaa agatttacaa aggcgtatca gactatgatt 198060

gttcaccaaa ataggggaat ggtttgatcc gccagttgca agtagaggcc tttctgactc 198120

ttaatattca ctttggtgct actaccccca ttacctgagg gaaactggcc aggtccttga 198180

tcatggaact atagagctac caggacatat cctgctctct aagggaattt attgctatct 198240

tgcaccttct ttaaaactca catatgcaga cctgacactc aagagtggct agctacacag 198300

agtccatcta atttttgcaa cttcctgtgg ccagtgtgta taaccccttc cactatctca 198360

cagatagtca cagcgtccat tccatagtct gtctcctcac atctgttagt attgacacag 198420

cacagacacc acaagccatc aggttcttca tggggcaggt gaaatacttc taccccatgg 198480

gtaaatgtat tcacatatta ccaagagaag aagcacatta tctatgatct tttggcccag 198540

ttcttattta gcatttttat tccagcctac ttggaaacat gtttttattt gcaatatatg 198600

cctgactgaa ttaagcttgc ttgttttaaa caaccaaatc attggaacag aaaaggattt 198660

aaaaaacaag aatgcatgat ctcagagtga ttaaaaaaaa atcagtggaa ataaatgatc 198720

atagaaggtg cttttcaaaa caactgctat tataattctc aaagtcctac tctgccaaaa 198780

gaagattaaa agtcatacat tacattacaa ggaaatgttc atgtgggaag agggttgctg 198840

aaaatcaaca acgcttgaag ttaaaaagtg tgtctttgta gatttcattg tataatgtgt 198900

atttcttagg agatggctga cttgattgat ctacgctaag tggagacatt tcacattttt 198960

aaaaccaaat gttcaatctg tattactctt tgccgtcttg tatgtagagg ctatttttaa 199020

atcattaaat ttttagatct ctgttttcat a                                199051
```

<210> SEQ ID NO 5
<211> LENGTH: 4550
<212> TYPE: DNA
<213> ORGANISM: Homo sapiens

<400> SEQUENCE: 5

```
acaacagtga gctcagagac ttgagggagg cgctgcgact gacaagcggc tctgcccggg     60

accttctcgc tttcatctag cgctgcactc aatggagggg cggcaccgc agtgcttaat    120

gctgtcttaa ctagtgtagg aaaacggctc aacccaccgc tgccgaaatg aagtataaga    180

atcttatggc aagggcctta tatgacaatg tcccagagtg tgccgaggaa ctggcctttc    240

gcaagggaga catcctgacc gtcatagagc agaacacagg gggactggaa ggatggtggc    300

tgtgctcatt acacggtcgg caaggcattg tcccaggcaa ccgggtgaag cttctgattg    360

gtcccatgca ggagactgcc tccagtcacg agcagcctgc ctctggactg atgcagcaga    420

cctttggcca acagaagctc tatcaagtgc caaacccaca ggctgctccc cgagacacca    480

tctaccaagt gccaccttcc taccaaaatc agggaattta ccaagtcccc actggccacg    540

gcacccaaga acaagaggta tatcaggtgc caccatcagt gcagagaagc attgggggaa    600

ccagtgggcc ccacgtgggt aaaaaggtga taacccccgt gaggacaggc catggctacg    660

tatacgagta cccatccaga taccaaaagg acgtctatga tatccctcct tctcatacca    720

ctcaaggggt atacgacatc cctccctcat cagcaaaagg ccctgtgttt tcagttccag    780

tgggagagat aaaacctcaa ggggtgtatg acatcccgcc tacaaaaggg gtatatgcca    840

ttccgccctc tgcttgccgg gatgaagcag ggcttaggga aaaagactat gacttccccc    900
```

```
ctcccatgag acaagctgga aggccggacc tcagaccgga gggggtttat gacattcctc    960
caacctgcac caagccagca gggaaggacc ttcatgtaaa atacaactgt gacattccag   1020
gagctgcaga accggtggct cgaaggcacc agagcctgtc cccgaatcac ccaccccgc   1080
aactcggaca gtcagtgggc tctcagaacg acgcatatga tgtcccccga ggcgttcagt   1140
ttcttgagcc accagcagaa accagtgaga aagcaaaccc ccaggaaagg gatggtgttt   1200
atgatgtccc tctgcataac ccgccagatg ctaaaggctc tcgggacttg gtggatggga   1260
tcaaccgatt gtctttctcc agtacaggca gcacccggag taacatgtcc acgtcttcca   1320
cctcctccaa ggagtcctca ctgtcagcct ccccagctca ggacaaaagg ctcttcctgg   1380
atccagacac agctattgag agacttcagc ggctccagca ggcccttgag atgggtgtct   1440
ccagcctaat ggcactggtc actaccgact ggcggtgtta cggatatatg gaaagacaca   1500
tcaatgaaat acgcacagca gtggacaagg tggagctgtt cctgaaggag tacctccact   1560
ttgtcaaggg agctgttgca aatgctgcct gcctcccgga actcatcctc cacaacaaga   1620
tgaagcggga gctgcaacga gttgaagact cccaccagat cctgagtcaa accagccatg   1680
acttaaatga gtgcagctgg tccctgaata tcttggccat caacaagccc cagaacaagt   1740
gtgacgatct ggaccggttt gtgatggtgg caaagacggt gcccgatgac gccaagcagc   1800
tcaccacaac catcaacacc aacgcagagg ccctcttcag acccggccct ggcagcttgc   1860
atctgaagaa tgggccggag agcatcatga actcaacgga gtacccacac ggtggctccc   1920
agggacagct gctgcatcct ggtgaccaca aggcccaggc ccacaacaag gcactgcccc   1980
caggcctgag caaggagcag gcccctgact gtagcagcag tgatggttct gagaggagct   2040
ggatggatga ctacgattac gtccacctac agggtaagga ggagtttgag aggcaacaga   2100
aagagctatt ggaaaaagag aatatcatga aacagaacaa gatgcagctg gaacatcatc   2160
agctgagcca gttccagctg ttggaacaag agattacaaa gcccgtggag aatgacatct   2220
cgaagtggaa gccctctcag agcctaccca ccacaaacag tggcgtgagt gctcaggatc   2280
ggcagttgct gtgcttctac tatgaccaat gtgagaccca tttcatttcc cttctcaacg   2340
ccattgacgc actcttcagt tgtgtcagct cagcccagcc cccgcgaatc ttcgtggcac   2400
acagcaagtt tgtcatcctc agtgcacaca aactggtgtt cattggagac acgctgacac   2460
ggcaggtgac tgcccaggac attcgcaaca aagtcatgaa ctccagcaac cagctctgcg   2520
agcagctcaa gaccatagtc atggcaacca agatggccgc cctccattac cccagcacca   2580
cggccctgca ggaaatggtg caccaagtga cagacctttc tagaaatgcc cagctgttca   2640
agcgctcttt gctggagatg gcaacgttct gagaagaaaa aaaagaggaa ggggactgcg   2700
ttaacggtta ctaaggaaaa ctggaaatac tgtctggttt ttgtaaatgt tatctatttt   2760
tgtagatatt ttatataaaa atgaaatatt ttaacatttt atgggtcagt caactttcag   2820
aaattcaggg agctggagag ggaaatcttt tttttcccc ctgagtggtt cttatgtata   2880
catagaagta tctgagacat aaactgtaca gaaaacttgt ccacgtgctt ttgtatgccc   2940
atgtattcat gtttgtttgt agatgtttgt ctgatgcatt tcattaaaaa aaaaaccatg   3000
aattacgaag caccttagta agcaccttct aatgctgcat ttttttgtt gttgttaaaa   3060
acataccagc tggttataat attgttctcc acgtccttgt gatgattctg agcctggcac   3120
tcccaaatct gggaagcata gtttatttgc aagtgttcac cttccaaatc atgaggcata   3180
gcatgactta ttcttgtttg gaaaactctt ttcaaaactg accatcttaa acacatgatg   3240
```

-continued gccaagtgcc caaaagccct cttgcggagc aaatttcaga atatatatgt ggatccaagc 3300
tctgatagtt caggtgctgg agggaagaga gacctgtgtg tttagaggcc aggaccacag 3360
ttaggattgg gttgtttcaa tactgagaga cagctacaat aaaaggagag caattgcctc 3420
cctggggctg ttcaatcttc tgcatttgtg agtggttcag tcatgaggtt ttccaaaaga 3480
tgtttttaga gttgtaaaaa ccatatttgc agcaaagatt tacaaaggcg tatcagacta 3540
tgattgttca ccaaaatagg ggaatggttt gatccgccag ttgcaagtag aggcctttct 3600
gactcttaat attcactttg gtgctactac ccccattacc tgagggaaac tggccaggtc 3660
cttgatcatg gaactataga gctaccagga catatcctgc tctctaaggg aatttattgc 3720
tatcttgcac cttctttaaa actcacatat gcagacctga cactcaagag tggctagcta 3780
cacagagtcc atctaatttt tgcaacttcc tgtggccagt gtgtataacc ccttccacta 3840
tctcacagat agtcacagcg tccattccat agtctgtctc ctcacatctg ttagtattga 3900
cacagcacag acaccacaag ccatcaggtt cttcatgggg caggtgaaat acttctaccc 3960
catgggtaaa tgtattcaca tattaccaag agaagaagca cattatctat gatcttttgg 4020
cccagttctt atttagcatt tttattccag cctacttgga aacatgtttt tatttgcaat 4080
atatgcctga ctgaattaag cttgcttgtt ttaaacaacc aaatcattgg aacagaaaag 4140
gatttaaaaa acaagaatgc atgatctcag agtgattaaa aaaaaatcag tggaaataaa 4200
tgatcataga aggtgctttt caaaacaact gctattataa ttctcaaagt cctactctgc 4260
caaaagaaga ttaaaagtca tacattacat tacaaggaaa tgttcatgtg ggaagagggt 4320
tgctgaaaat caacaacgct tgaagttaaa aagtgtgtct ttgtagattt cattgtataa 4380
tgtgtatttc ttaggagatg gctgacttga ttgatctacg ctaagtggag acatttcaca 4440
tttttaaaac caaatgttca atctgtatta ctctttgccg tcttgtatgt agaggctatt 4500
tttaaatcat taaattttta gatctctgtt ttcataaaaa aaaaaaaaaa 4550

<210> SEQ ID NO 6
<211> LENGTH: 1329
<212> TYPE: DNA
<213> ORGANISM: Homo sapiens

<400> SEQUENCE: 6
acaacagtga gctcagagac ttgagggagg cgctgcgact gacaagcggc tctgcccggg 60
accttctcgc tttcatctag cgctgcactc aatggagggg cgggcaccgc agtgcttaat 120
gctgtcttaa ctagtgtagg aaaacggctc aacccaccgc tgccgaaatg aagtataaga 180
atcttatggc aagggcctta tatgacaatg tcccagagtg tgccgaggaa ctggcctttc 240
gcaagggaga catcctgacc gtcatagagc agaacacagg ggactggaa ggatggtggc 300 tgtgctcatt acacggtcgg caaggcattg tcccaggcaa ccgggtgaag cttctgattg 360
gtcccatgca ggagactgcc tccagtcacg agcagcctgc ctctggactg atgcagcaga 420
cctttggcca acagaagctc tatcaagtgc caaacccaca ggctgctccc cgagacacca 480
tctaccaagt gccaccttcc taccaaaatc agggaattta ccaagtcccc actggccacg 540
gcacccaaga acaagaggta tatcaggtgc caccatcagt gcagagaagc attgggggaa 600
ccagtgggcc ccacgtgggt aaaaaggtgt tccagagaga tgggcaagtg tcctatttct 660
tagtgagagc ctctaaacaa accagcttgt gaacctccac tgaaaagatc tcatctgatg 720
agcattttaa taaagtgtcc tgagtttgga ggcttgccgt ctttctcttg gataaatatc 780
ttcatctcct agacttggaa aaacacattt tctcctgggg tttcccattg gcgtgtcttg 840
agctgctctg gtgataaccg taataatgcc aatactgata cgaacagcag aaaacagtaa 900
ccccaagaac tctacagatg atcatcaagg accactgtct cttaccattt gctgctttgg 960
tttgaaattc tcactgcctc gtagatctca ttttgagcac tatacattcc taaagattga 1020
tttctttcta tctgacttaa atttaggaat gattaaatct tcatttctcc catgatttga 1080
tcctaaaaca ttttgaaagg aaacagcctt gagatctgtg attactaaga catacataac 1140
attcttatca cattagaaag caagaattga ctgttgcttg tcttgttcct gttgtcttgt 1200
cccctgaatt cctgtttatc tttgattgta tgtgggacat tgtattttca gtacatttgt 1260
agaaataatg tgaagcctat aaagatgttc tctgcctcca aaaaaaaaaa aaaaaaaaaa 1320
aaaaaaaaa 1329

<210> SEQ ID NO 7
<211> LENGTH: 4745
<212> TYPE: DNA
<213> ORGANISM: Homo sapiens

<400> SEQUENCE: 7
acacatacat atgccactca catccgacgt gtgtggttgc tcagtaggga aatgcttaca 60
gctgcctcta gaagcaagtc cgctcgctgc atggagaggg aaacatgagc atgcagcagg 120
actagctgtc acctcccgcc cgcctgccca gagagggcca gagcgtcggg gaggcaagat 180
gatccaccag cggttccatc ctacacttgg attcagtaag ctgtgaggtc cgtaatgtca 240
gacactggca aacatcatat gttcttcaag tagagttatg aaaacgaaga aactggtcag 300
aagagtaaaa cgccggaatt gtcctttcca acatccagag ctgcatcatt ccttggggca 360
aaatgtggac aaggaatctt atggcaaggg ccttatatga caatgtccca gagtgtgccg 420
aggaactggc ctttcgcaag ggagacatcc tgaccgtcat agagcagaac acagggggac 480
tggaaggatg gtggctgtgc tcattacacg gtcggcaagg cattgtccca ggcaaccggg 540
tgaagcttct gattggtccc atgcaggaga ctgcctccag tcacgagcag cctgcctctg 600
gactgatgca gcagaccttt ggccaacaga agctctatca agtgccaaac ccacaggctg 660
ctccccgaga caccatctac caagtgccac cttcctacca aaatcaggga atttaccaag 720
tccccactgg ccacggcacc caagaacaag aggtatatca ggtgccacca tcagtgcaga 780
gaagcattgg gggaaccagt gggccccacg tgggtaaaaa ggtgataacc cccgtgagga 840
caggccatgg ctacgtatac gagtacccat ccagatacca aaaggacgtc tatgatatcc 900
ctccttctca taccactcaa ggggtatacg acatccctcc ctcatcagca aaaggccctg 960
tgttttcagt tccagtggga gagataaaac ctcaaggggt gtatgacatc ccgcctacaa 1020
aaggggtata tgccattccg ccctctgctt gccgggatga agcagggctt agggaaaaag 1080
actatgactt ccccccctccc atgagacaag ctggaaggcc ggacctcaga ccggaggggg 1140
tttatgacat tcctccaacc tgcaccaagc cagcagggaa ggaccttcat gtaaaataca 1200
actgtgacat tccaggagct gcagaaccgg tggctcgaag gcaccagagc ctgtccccga 1260
atcacccacc cccgcaactc ggacagtcag tgggctctca gaacgacgca tatgatgtcc 1320
cccgaggcgt tcagtttctt gagccaccag cagaaaccag tgagaaagca aacccccagg 1380
aaagggatgg tgtttatgat gtccctctgc ataacccgcc agatgctaaa ggctctcggg 1440
acttggtgga tgggatcaac cgattgtctt tctccagtac aggcagcacc cggagtaaca 1500
tgtccacgtc ttccacctcc tccaaggagt cctcactgtc agcctcccca gctcaggaca 1560

-continued

```
aaaggctctt cctggatcca gacacagcta ttgagagact tcagcggctc cagcaggccc   1620
ttgagatggg tgtctccagc ctaatggcac tggtcactac cgactggcgg tgttacggat   1680
atatggaaag acacatcaat gaaatacgca cagcagtgga caaggtggag ctgttcctga   1740
aggagtacct ccactttgtc aagggagctg ttgcaaatgc tgcctgcctc ccggaactca   1800
tcctccacaa caagatgaag cgggagctgc aacgagttga agactcccac cagatcctga   1860
gtcaaaccag ccatgactta aatgagtgca gctggtccct gaatatcttg gccatcaaca   1920
agccccagaa caagtgtgac gatctggacc ggtttgtgat ggtggcaaag acggtgcccg   1980
atgacgccaa gcagctcacc acaaccatca acaccaacgc agaggccctc ttcagacccg   2040
gccctggcag cttgcatctg aagaatgggc cggagagcat catgaactca acggagtacc   2100
cacacggtgg ctcccaggga cagctgctgc atcctggtga ccacaaggcc caggcccaca   2160
acaaggcact gcccccaggc ctgagcaagg agcaggcccc tgactgtagc agcagtgatg   2220
gttctgagag gagctggatg gatgactacg attacgtcca cctacagggt aaggaggagt   2280
ttgagaggca acagaaagag ctattggaaa aagagaatat catgaaacag aacaagatgc   2340
agctggaaca tcatcagctg agccagttcc agctgttgga acaagagatt acaaagcccg   2400
tggagaatga catctcgaag tggaagccct ctcagagcct acccaccaca aacagtggcg   2460
tgagtgctca ggatcggcag ttgctgtgct tctactatga ccaatgtgag acccatttca   2520
tttcccttct caacgccatt gacgcactct tcagttgtgt cagctcagcc cagcccccgc   2580
gaatcttcgt ggcacacagc aagtttgtca tcctcagtgc acacaaactg gtgttcattg   2640
gagacacgct gacacggcag gtgactgccc aggacattcg caacaaagtc atgaactcca   2700
gcaaccagct ctgcgagcag ctcaagacca tagtcatggc aaccaagatg gccgccctcc   2760
attaccccag caccacggcc ctgcaggaaa tggtgcacca agtgacagac ctttctagaa   2820
atgcccagct gttcaagcgc tctttgctgg agatggcaac gttctgagaa gaaaaaaaag   2880
aggaagggga ctgcgttaac ggttactaag gaaaactgga aatactgtct ggtttttgta   2940
aatgttatct atttttgtag atattttata taaaaatgaa atattttaac attttatggg   3000
tcagtcaact ttcagaaatt cagggagctg gagagggaaa tctttttttt tccccctgag   3060
tggttcttat gtatacatag aagtatctga gacataaact gtacagaaaa cttgtccacg   3120
tgcttttgta tgcccatgta ttcatgtttg tttgtagatg tttgtctgat gcatttcatt   3180
aaaaaaaaaa ccatgaatta cgaagcacct tagtaagcac cttctaatgc tgcatttttt   3240
ttgttgttgt taaaaacata ccagctggtt ataatattgt tctccacgtc cttgtgatga   3300
ttctgagcct ggcactccca aatctgggaa gcatagttta tttgcaagtg ttcaccttcc   3360
aaatcatgag gcatagcatg acttattctt gtttggaaaa ctcttttcaa aactgaccat   3420
cttaaacaca tgatggccaa gtgcccaaaa gccctcttgc ggagcaaatt tcagaatata   3480
tatgtggatc caagctctga tagttcaggt gctggaggga agagagacct gtgtgtttag   3540
aggccaggac cacagttagg attgggttgt ttcaatactg agagacagct acaataaaag   3600
gagagcaatt gcctccctgg ggctgttcaa tcttctgcat ttgtgagtgg ttcagtcatg   3660
aggttttcca aaagatgttt ttagagttgt aaaaaccata tttgcagcaa agatttacaa   3720
aggcgtatca gactatgatt gttcaccaaa ataggggaat ggtttgatcc gccagttgca   3780
agtagaggcc tttctgactc ttaatattca ctttggtgct actacccccca ttacctgagg   3840
gaaactggcc aggtccttga tcatggaact atagagctac caggacatat cctgctctct   3900
aagggaattt attgctatct tgcaccttct ttaaaactca catatgcaga cctgacactc   3960
```

```
aagagtggct agctacacag agtccatcta atttttgcaa cttcctgtgg ccagtgtgta   4020
taaccccttc cactatctca cagatagtca cagcgtccat tccatagtct gtctcctcac   4080
atctgttagt attgacacag cacagacacc acaagccatc aggttcttca tggggcaggt   4140
gaaatacttc taccccatgg gtaaatgtat tcacatatta ccaagagaag aagcacatta   4200
tctatgatct tttggcccag ttcttattta gcatttttat tccagcctac ttggaaacat   4260
gtttttattt gcaatatatg cctgactgaa ttaagcttgc ttgttttaaa caaccaaatc   4320
attggaacag aaaaggattt aaaaaacaag aatgcatgat ctcagagtga ttaaaaaaaa   4380
atcagtggaa ataaatgatc atagaaggtg cttttcaaaa caactgctat tataattctc   4440
aaagtcctac tctgccaaaa gaagattaaa agtcatacat tacattacaa ggaaatgttc   4500
atgtgggaag agggttgctg aaaatcaaca acgcttgaag ttaaaaagtg tgtctttgta   4560
gatttcattg tataatgtgt atttcttagg agatggctga cttgattgat ctacgctaag   4620
tggagacatt tcacattttt aaaaccaaat gttcaatctg tattactctt tgccgtcttg   4680
tatgtagagg ctatttttaa atcattaaat ttttagatct ctgttttcat aaaaaaaaaa   4740
aaaaa                                                               4745
```

<210> SEQ ID NO 8
<211> LENGTH: 4103
<212> TYPE: DNA
<213> ORGANISM: Homo sapiens

<400> SEQUENCE: 8

```
acaacagtga gctcagagac ttgagggagg cgctgcgact gacaagcggc tctgcccggg     60
accttctcgc tttcatctag cgctgcactc aatggagggg cgggcaccgc agtgcttaat    120
gctgtcttaa ctagtgtagg aaaacggctc aacccaccgc tgccgaaatg aagtataagg    180
tgataacccc cgtgaggaca ggccatggct acgtatacga gtacccatcc agataccaaa    240
aggacgtcta tgatatccct ccttctcata ccactcaagg ggtatacgac atccctccct    300
catcagcaaa aggccctgtg ttttcagttc cagtgggaga gataaaacct caaggggtgt    360
atgacatccc gcctacaaaa ggggtatatg ccattccgcc ctctgcttgc cgggatgaag    420
cagggcttag ggaaaaagac tatgacttcc cccctcccat gagacaagct ggaaggccgg    480
acctcagacc ggaggggggtt tatgacattc ctccaacctg caccaagcca gcagggaagg    540
accttcatgt aaaatacaac tgtgacattc caggagctgc agaaccggtg gctcgaaggc    600
accagagcct gtccccgaat cacccacccc cgcaactcgg acagtcagtg ggctctcaga    660
acgacgcata tgatgtcccc cgaggcgttc agtttcttga gccaccagca gaaaccagtg    720
agaaagcaaa cccccaggaa agggatggtg tttatgatgt ccctctgcat aacccgccag    780
atgctaaagg ctctcgggac ttggtggatg ggatcaaccg attgtctttc tccagtacag    840
gcagcacccg gagtaacatg tccacgtctt ccacctcctc caaggagtcc tcactgtcag    900
cctccccagc tcaggacaaa aggctcttcc tggatccaga cacagctatt gagagacttc    960
agcggctcca gcaggccctt gagatgggtg tctccagcct aatggcactg gtcactaccg   1020
actggcggtg ttacggatat atggaaagac acatcaatga aatacgcaca gcagtggaca   1080
aggtggagct gttcctgaag gagtacctcc actttgtcaa gggagctgtt gcaaatgctg   1140
cctgcctccc ggaactcatc ctccacaaca agatgaagcg ggagctgcaa cgagttgaag   1200
actcccacca gatcctgagt caaaccagcc atgacttaaa tgagtgcagc tggtccctga   1260
```

```
atatcttggc catcaacaag ccccagaaca agtgtgacga tctggaccgg tttgtgatgg   1320
tggcaaagac ggtgcccgat gacgccaagc agctcaccac aaccatcaac accaacgcag   1380
aggccctctt cagacccggc cctggcagct tgcatctgaa gaatgggccg gagagcatca   1440
tgaactcaac ggagtaccca cacggtggct cccagggaca gctgctgcat cctggtgacc   1500
acaaggccca ggcccacaac aaggcactgc ccccaggcct gagcaaggag caggcccctg   1560
actgtagcag cagtgatggt tctgagagga gctggatgga tgactacgat tacgtccacc   1620
tacagggtaa ggaggagttt gagaggcaac agaaagagct attggaaaaa gagaatatca   1680
tgaaacagaa caagatgcag ctggaacatc atcagctgag ccagttccag ctgttggaac   1740
aagagattac aaagcccgtg gagaatgaca tctcgaagtg gaagccctct cagagcctac   1800
ccaccacaaa cagtggcgtg agtgctcagg atcggcagtt gctgtgcttc tactatgacc   1860
aatgtgagac ccatttcatt tcccttctca acgccattga cgcactcttc agttgtgtca   1920
gctcagccca gcccccgcga atcttcgtgg cacacagcaa gtttgtcatc ctcagtgcac   1980
acaaactggt gttcattgga gacacgctga cacggcaggt gactgcccag gacattcgca   2040
acaaagtcat gaactccagc aaccagctct gcgagcagct caagaccata gtcatggcaa   2100
ccaagatggc cgccctccat taccccagca ccacggccct gcaggaaatg gtgcaccaag   2160
tgacagacct ttctagaaat gcccagctgt tcaagcgctc tttgctggag atggcaacgt   2220
tctgagaaga aaaaaaagag gaaggggact gcgttaacgg ttactaagga aaactggaaa   2280
tactgtctgg tttttgtaaa tgttatctat ttttgtagat attttatata aaaatgaaat   2340
attttaacat tttatgggtc agtcaacttt cagaaattca gggagctgga gagggaaatc   2400
tttttttttc cccctgagtg gttcttatgt atacatagaa gtatctgaga cataaactgt   2460
acagaaaact tgtccacgtg cttttgtatg cccatgtatt catgtttgtt tgtagatgtt   2520
tgtctgatgc atttcattaa aaaaaaaacc atgaattacg aagcacctta gtaagcacct   2580
tctaatgctg catttttttt gttgttgtta aaaacatacc agctggttat aatattgttc   2640
tccacgtcct tgtgatgatt ctgagcctgg cactcccaaa tctgggaagc atagtttatt   2700
tgcaagtgtt caccttccaa atcatgaggc atagcatgac ttattcttgt ttggaaaact   2760
cttttcaaaa ctgaccatct taaacacatg atggccaagt gcccaaaagc cctcttgcgg   2820
agcaaatttc agaatatata tgtggatcca agctctgata gttcaggtgc tggagggaag   2880
agagacctgt gtgtttagag gccaggacca cagttaggat tgggttgttt caatactgag   2940
agacagctac aataaaagga gagcaattgc ctccctgggg ctgttcaatc ttctgcattt   3000
gtgagtggtt cagtcatgag gttttccaaa agatgttttt agagttgtaa aaaccatatt   3060
tgcagcaaag atttacaaag gcgtatcaga ctatgattgt tcaccaaaat aggggaatgg   3120
tttgatccgc cagttgcaag tagaggcctt tctgactctt aatattcact ttggtgctac   3180
tacccccatt acctgaggga aactggccag gtccttgatc atggaactat agagctacca   3240
ggacatatcc tgctctctaa gggaatttat tgctatcttg caccttcttt aaaactcaca   3300
tatgcagacc tgacactcaa gagtggctag ctacacagag tccatctaat tttgcaact    3360
tcctgtggcc agtgtgtata accccttcca ctatctcaca gatagtcaca gcgtccattc   3420
catagtctgt ctcctcacat ctgttagtat tgacacagca cagacaccac aagccatcag   3480
gttcttcatg gggcaggtga aatacttcta ccccatgggt aaatgtattc acatattacc   3540
aagagaagaa gcacattatc tatgatcttt tggcccagtt cttatttagc atttttattc   3600
cagcctactt ggaaacatgt ttttatttgc aatatatgcc tgactgaatt aagcttgctt   3660
```

```
gttttaaaca accaaatcat tggaacagaa aaggatttaa aaaacaagaa tgcatgatct   3720

cagagtgatt aaaaaaaaat cagtggaaat aaatgatcat agaaggtgct tttcaaaaca   3780

actgctatta taattctcaa agtcctactc tgccaaaaga agattaaaag tcatacatta   3840

cattacaagg aaatgttcat gtgggaagag ggttgctgaa aatcaacaac gcttgaagtt   3900

aaaaagtgtg tctttgtaga tttcattgta taatgtgtat ttcttaggag atggctgact   3960

tgattgatct acgctaagtg gagacatttc acatttttaa aaccaaatgt tcaatctgta   4020

ttactctttg ccgtcttgta tgtagaggct atttttaaat cattaaattt ttagatctct   4080

gttttcataa aaaaaaaaaa aaa                                           4103


<210> SEQ ID NO 9
<211> LENGTH: 834
<212> TYPE: PRT
<213> ORGANISM: Homo sapiens

<400> SEQUENCE: 9

Met Lys Tyr Lys Asn Leu Met Ala Arg Ala Leu Tyr Asp Asn Val Pro
1               5                   10                  15

Glu Cys Ala Glu Glu Leu Ala Phe Arg Lys Gly Asp Ile Leu Thr Val
            20                  25                  30

Ile Glu Gln Asn Thr Gly Gly Leu Glu Gly Trp Trp Leu Cys Ser Leu
        35                  40                  45

His Gly Arg Gln Gly Ile Val Pro Gly Asn Arg Val Lys Leu Leu Ile
    50                  55                  60

Gly Pro Met Gln Glu Thr Ala Ser Ser His Glu Gln Pro Ala Ser Gly
65                  70                  75                  80

Leu Met Gln Gln Thr Phe Gly Gln Gln Lys Leu Tyr Gln Val Pro Asn
                85                  90                  95

Pro Gln Ala Ala Pro Arg Asp Thr Ile Tyr Gln Val Pro Pro Ser Tyr
            100                 105                 110

Gln Asn Gln Gly Ile Tyr Gln Val Pro Thr Gly His Gly Thr Gln Glu
        115                 120                 125

Gln Glu Val Tyr Gln Val Pro Pro Ser Val Gln Arg Ser Ile Gly Gly
    130                 135                 140

Thr Ser Gly Pro His Val Gly Lys Lys Val Ile Thr Pro Val Arg Thr
145                 150                 155                 160

Gly His Gly Tyr Val Tyr Glu Tyr Pro Ser Arg Tyr Gln Lys Asp Val
                165                 170                 175

Tyr Asp Ile Pro Pro Ser His Thr Thr Gln Gly Val Tyr Asp Ile Pro
            180                 185                 190

Pro Ser Ser Ala Lys Gly Pro Val Phe Ser Val Pro Val Gly Glu Ile
        195                 200                 205

Lys Pro Gln Gly Val Tyr Asp Ile Pro Pro Thr Lys Gly Val Tyr Ala
    210                 215                 220

Ile Pro Pro Ser Ala Cys Arg Asp Glu Ala Gly Leu Arg Glu Lys Asp
225                 230                 235                 240

Tyr Asp Phe Pro Pro Pro Met Arg Gln Ala Gly Arg Pro Asp Leu Arg
                245                 250                 255

Pro Glu Gly Val Tyr Asp Ile Pro Pro Thr Cys Thr Lys Pro Ala Gly
            260                 265                 270

Lys Asp Leu His Val Lys Tyr Asn Cys Asp Ile Pro Gly Ala Ala Glu
        275                 280                 285
```

```
Pro Val Ala Arg Arg His Gln Ser Leu Ser Pro Asn His Pro Pro Pro
    290                 295                 300

Gln Leu Gly Gln Ser Val Gly Ser Gln Asn Asp Ala Tyr Asp Val Pro
305                 310                 315                 320

Arg Gly Val Gln Phe Leu Glu Pro Pro Ala Glu Thr Ser Glu Lys Ala
                325                 330                 335

Asn Pro Gln Glu Arg Asp Gly Val Tyr Asp Val Pro Leu His Asn Pro
            340                 345                 350

Pro Asp Ala Lys Gly Ser Arg Asp Leu Val Asp Gly Ile Asn Arg Leu
        355                 360                 365

Ser Phe Ser Ser Thr Gly Ser Thr Arg Ser Asn Met Ser Thr Ser Ser
    370                 375                 380

Thr Ser Ser Lys Glu Ser Ser Leu Ser Ala Ser Pro Ala Gln Asp Lys
385                 390                 395                 400

Arg Leu Phe Leu Asp Pro Asp Thr Ala Ile Glu Arg Leu Gln Arg Leu
                405                 410                 415

Gln Gln Ala Leu Glu Met Gly Val Ser Ser Leu Met Ala Leu Val Thr
            420                 425                 430

Thr Asp Trp Arg Cys Tyr Gly Tyr Met Glu Arg His Ile Asn Glu Ile
        435                 440                 445

Arg Thr Ala Val Asp Lys Val Glu Leu Phe Leu Lys Glu Tyr Leu His
    450                 455                 460

Phe Val Lys Gly Ala Val Ala Asn Ala Ala Cys Leu Pro Glu Leu Ile
465                 470                 475                 480

Leu His Asn Lys Met Lys Arg Glu Leu Gln Arg Val Glu Asp Ser His
                485                 490                 495

Gln Ile Leu Ser Gln Thr Ser His Asp Leu Asn Glu Cys Ser Trp Ser
            500                 505                 510

Leu Asn Ile Leu Ala Ile Asn Lys Pro Gln Asn Lys Cys Asp Asp Leu
        515                 520                 525

Asp Arg Phe Val Met Val Ala Lys Thr Val Pro Asp Asp Ala Lys Gln
    530                 535                 540

Leu Thr Thr Thr Ile Asn Thr Asn Ala Glu Ala Leu Phe Arg Pro Gly
545                 550                 555                 560

Pro Gly Ser Leu His Leu Lys Asn Gly Pro Glu Ser Ile Met Asn Ser
                565                 570                 575

Thr Glu Tyr Pro His Gly Gly Ser Gln Gly Gln Leu Leu His Pro Gly
            580                 585                 590

Asp His Lys Ala Gln Ala His Asn Lys Ala Leu Pro Pro Gly Leu Ser
        595                 600                 605

Lys Glu Gln Ala Pro Asp Cys Ser Ser Ser Asp Gly Ser Glu Arg Ser
    610                 615                 620

Trp Met Asp Asp Tyr Asp Tyr Val His Leu Gln Gly Lys Glu Glu Phe
625                 630                 635                 640

Glu Arg Gln Gln Lys Glu Leu Leu Glu Lys Glu Asn Ile Met Lys Gln
                645                 650                 655

Asn Lys Met Gln Leu Glu His His Gln Leu Ser Gln Phe Gln Leu Leu
            660                 665                 670

Glu Gln Glu Ile Thr Lys Pro Val Glu Asn Asp Ile Ser Lys Trp Lys
        675                 680                 685

Pro Ser Gln Ser Leu Pro Thr Thr Asn Ser Gly Val Ser Ala Gln Asp
    690                 695                 700

Arg Gln Leu Leu Cys Phe Tyr Tyr Asp Gln Cys Glu Thr His Phe Ile
```

```
705                 710                 715                 720

Ser Leu Leu Asn Ala Ile Asp Ala Leu Phe Ser Cys Val Ser Ser Ala
                725                 730                 735

Gln Pro Pro Arg Ile Phe Val Ala His Ser Lys Phe Val Ile Leu Ser
            740                 745                 750

Ala His Lys Leu Val Phe Ile Gly Asp Thr Leu Thr Arg Gln Val Thr
        755                 760                 765

Ala Gln Asp Ile Arg Asn Lys Val Met Asn Ser Ser Asn Gln Leu Cys
    770                 775                 780

Glu Gln Leu Lys Thr Ile Val Met Ala Thr Lys Met Ala Ala Leu His
785                 790                 795                 800

Tyr Pro Ser Thr Thr Ala Leu Gln Glu Met Val His Gln Val Thr Asp
                805                 810                 815

Leu Ser Arg Asn Ala Gln Leu Phe Lys Arg Ser Leu Leu Glu Met Ala
            820                 825                 830

Thr Phe


<210> SEQ ID NO 10
<211> LENGTH: 174
<212> TYPE: PRT
<213> ORGANISM: Homo sapiens

<400> SEQUENCE: 10

Met Lys Tyr Lys Asn Leu Met Ala Arg Ala Leu Tyr Asp Asn Val Pro
1               5                   10                  15

Glu Cys Ala Glu Glu Leu Ala Phe Arg Lys Gly Asp Ile Leu Thr Val
            20                  25                  30

Ile Glu Gln Asn Thr Gly Gly Leu Glu Gly Trp Trp Leu Cys Ser Leu
        35                  40                  45

His Gly Arg Gln Gly Ile Val Pro Gly Asn Arg Val Lys Leu Leu Ile
    50                  55                  60

Gly Pro Met Gln Glu Thr Ala Ser Ser His Glu Gln Pro Ala Ser Gly
65                  70                  75                  80

Leu Met Gln Gln Thr Phe Gly Gln Gln Lys Leu Tyr Gln Val Pro Asn
                85                  90                  95

Pro Gln Ala Ala Pro Arg Asp Thr Ile Tyr Gln Val Pro Pro Ser Tyr
            100                 105                 110

Gln Asn Gln Gly Ile Tyr Gln Val Pro Thr Gly His Gly Thr Gln Glu
        115                 120                 125

Gln Glu Val Tyr Gln Val Pro Pro Ser Val Gln Arg Ser Ile Gly Gly
    130                 135                 140

Thr Ser Gly Pro His Val Gly Lys Lys Val Phe Gln Arg Asp Gly Gln
145                 150                 155                 160

Val Ser Tyr Phe Leu Val Arg Ala Ser Lys Gln Thr Ser Leu
                165                 170


<210> SEQ ID NO 11
<211> LENGTH: 834
<212> TYPE: PRT
<213> ORGANISM: Homo sapiens

<400> SEQUENCE: 11

Met Trp Thr Arg Asn Leu Met Ala Arg Ala Leu Tyr Asp Asn Val Pro
1               5                   10                  15

Glu Cys Ala Glu Glu Leu Ala Phe Arg Lys Gly Asp Ile Leu Thr Val
            20                  25                  30
```

```
Ile Glu Gln Asn Thr Gly Gly Leu Glu Gly Trp Trp Leu Cys Ser Leu
        35                  40                  45

His Gly Arg Gln Gly Ile Val Pro Gly Asn Arg Val Lys Leu Leu Ile
    50                  55                  60

Gly Pro Met Gln Glu Thr Ala Ser Ser His Glu Gln Pro Ala Ser Gly
65                  70                  75                  80

Leu Met Gln Gln Thr Phe Gly Gln Gln Lys Leu Tyr Gln Val Pro Asn
                85                  90                  95

Pro Gln Ala Ala Pro Arg Asp Thr Ile Tyr Gln Val Pro Pro Ser Tyr
            100                 105                 110

Gln Asn Gln Gly Ile Tyr Gln Val Pro Thr Gly His Gly Thr Gln Glu
        115                 120                 125

Gln Glu Val Tyr Gln Val Pro Pro Ser Val Gln Arg Ser Ile Gly Gly
    130                 135                 140

Thr Ser Gly Pro His Val Gly Lys Lys Val Ile Thr Pro Val Arg Thr
145                 150                 155                 160

Gly His Gly Tyr Val Tyr Glu Tyr Pro Ser Arg Tyr Gln Lys Asp Val
                165                 170                 175

Tyr Asp Ile Pro Pro Ser His Thr Thr Gln Gly Val Tyr Asp Ile Pro
            180                 185                 190

Pro Ser Ser Ala Lys Gly Pro Val Phe Ser Val Pro Val Gly Glu Ile
        195                 200                 205

Lys Pro Gln Gly Val Tyr Asp Ile Pro Pro Thr Lys Gly Val Tyr Ala
    210                 215                 220

Ile Pro Pro Ser Ala Cys Arg Asp Glu Ala Gly Leu Arg Glu Lys Asp
225                 230                 235                 240

Tyr Asp Phe Pro Pro Pro Met Arg Gln Ala Gly Arg Pro Asp Leu Arg
                245                 250                 255

Pro Glu Gly Val Tyr Asp Ile Pro Pro Thr Cys Thr Lys Pro Ala Gly
            260                 265                 270

Lys Asp Leu His Val Lys Tyr Asn Cys Asp Ile Pro Gly Ala Ala Glu
        275                 280                 285

Pro Val Ala Arg Arg His Gln Ser Leu Ser Pro Asn His Pro Pro Pro
    290                 295                 300

Gln Leu Gly Gln Ser Val Gly Ser Gln Asn Asp Ala Tyr Asp Val Pro
305                 310                 315                 320

Arg Gly Val Gln Phe Leu Glu Pro Pro Ala Glu Thr Ser Glu Lys Ala
                325                 330                 335

Asn Pro Gln Glu Arg Asp Gly Val Tyr Asp Val Pro Leu His Asn Pro
            340                 345                 350

Pro Asp Ala Lys Gly Ser Arg Asp Leu Val Asp Gly Ile Asn Arg Leu
        355                 360                 365

Ser Phe Ser Ser Thr Gly Ser Thr Arg Ser Asn Met Ser Thr Ser Ser
    370                 375                 380

Thr Ser Ser Lys Glu Ser Ser Leu Ser Ala Ser Pro Ala Gln Asp Lys
385                 390                 395                 400

Arg Leu Phe Leu Asp Pro Asp Thr Ala Ile Glu Arg Leu Gln Arg Leu
                405                 410                 415

Gln Gln Ala Leu Glu Met Gly Val Ser Ser Leu Met Ala Leu Val Thr
            420                 425                 430

Thr Asp Trp Arg Cys Tyr Gly Tyr Met Glu Arg His Ile Asn Glu Ile
        435                 440                 445
```

```
Arg Thr Ala Val Asp Lys Val Glu Leu Phe Leu Lys Glu Tyr Leu His
    450                 455                 460

Phe Val Lys Gly Ala Val Ala Asn Ala Ala Cys Leu Pro Glu Leu Ile
465                 470                 475                 480

Leu His Asn Lys Met Lys Arg Glu Leu Gln Arg Val Glu Asp Ser His
                485                 490                 495

Gln Ile Leu Ser Gln Thr Ser His Asp Leu Asn Glu Cys Ser Trp Ser
            500                 505                 510

Leu Asn Ile Leu Ala Ile Asn Lys Pro Gln Asn Lys Cys Asp Asp Leu
        515                 520                 525

Asp Arg Phe Val Met Val Ala Lys Thr Val Pro Asp Asp Ala Lys Gln
    530                 535                 540

Leu Thr Thr Thr Ile Asn Thr Asn Ala Glu Ala Leu Phe Arg Pro Gly
545                 550                 555                 560

Pro Gly Ser Leu His Leu Lys Asn Gly Pro Glu Ser Ile Met Asn Ser
                565                 570                 575

Thr Glu Tyr Pro His Gly Gly Ser Gln Gly Gln Leu Leu His Pro Gly
            580                 585                 590

Asp His Lys Ala Gln Ala His Asn Lys Ala Leu Pro Pro Gly Leu Ser
        595                 600                 605

Lys Glu Gln Ala Pro Asp Cys Ser Ser Ser Asp Gly Ser Glu Arg Ser
    610                 615                 620

Trp Met Asp Asp Tyr Asp Tyr Val His Leu Gln Gly Lys Glu Glu Phe
625                 630                 635                 640

Glu Arg Gln Gln Lys Glu Leu Leu Glu Lys Glu Asn Ile Met Lys Gln
                645                 650                 655

Asn Lys Met Gln Leu Glu His His Gln Leu Ser Gln Phe Gln Leu Leu
            660                 665                 670

Glu Gln Glu Ile Thr Lys Pro Val Glu Asn Asp Ile Ser Lys Trp Lys
        675                 680                 685

Pro Ser Gln Ser Leu Pro Thr Thr Asn Ser Gly Val Ser Ala Gln Asp
    690                 695                 700

Arg Gln Leu Leu Cys Phe Tyr Tyr Asp Gln Cys Glu Thr His Phe Ile
705                 710                 715                 720

Ser Leu Leu Asn Ala Ile Asp Ala Leu Phe Ser Cys Val Ser Ser Ala
                725                 730                 735

Gln Pro Pro Arg Ile Phe Val Ala His Ser Lys Phe Val Ile Leu Ser
            740                 745                 750

Ala His Lys Leu Val Phe Ile Gly Asp Thr Leu Thr Arg Gln Val Thr
        755                 760                 765

Ala Gln Asp Ile Arg Asn Lys Val Met Asn Ser Ser Asn Gln Leu Cys
    770                 775                 780

Glu Gln Leu Lys Thr Ile Val Met Ala Thr Lys Met Ala Ala Leu His
785                 790                 795                 800

Tyr Pro Ser Thr Thr Ala Leu Gln Glu Met Val His Gln Val Thr Asp
                805                 810                 815

Leu Ser Arg Asn Ala Gln Leu Phe Lys Arg Ser Leu Leu Glu Met Ala
            820                 825                 830

Thr Phe
```

```
<210> SEQ ID NO 12
<211> LENGTH: 685
<212> TYPE: PRT
<213> ORGANISM: Homo sapiens
```

<400> SEQUENCE: 12

```
Met Lys Tyr Lys Val Ile Thr Pro Val Arg Thr Gly His Gly Tyr Val
1               5                   10                  15

Tyr Glu Tyr Pro Ser Arg Tyr Gln Lys Asp Val Tyr Asp Ile Pro Pro
            20                  25                  30

Ser His Thr Thr Gln Gly Val Tyr Asp Ile Pro Pro Ser Ser Ala Lys
        35                  40                  45

Gly Pro Val Phe Ser Val Pro Val Gly Glu Ile Lys Pro Gln Gly Val
    50                  55                  60

Tyr Asp Ile Pro Pro Thr Lys Gly Val Tyr Ala Ile Pro Pro Ser Ala
65                  70                  75                  80

Cys Arg Asp Glu Ala Gly Leu Arg Glu Lys Asp Tyr Asp Phe Pro Pro
                85                  90                  95

Pro Met Arg Gln Ala Gly Arg Pro Asp Leu Arg Pro Glu Gly Val Tyr
            100                 105                 110

Asp Ile Pro Pro Thr Cys Thr Lys Pro Ala Gly Lys Asp Leu His Val
        115                 120                 125

Lys Tyr Asn Cys Asp Ile Pro Gly Ala Ala Glu Pro Val Ala Arg Arg
    130                 135                 140

His Gln Ser Leu Ser Pro Asn His Pro Pro Pro Gln Leu Gly Gln Ser
145                 150                 155                 160

Val Gly Ser Gln Asn Asp Ala Tyr Asp Val Pro Arg Gly Val Gln Phe
                165                 170                 175

Leu Glu Pro Pro Ala Glu Thr Ser Glu Lys Ala Asn Pro Gln Glu Arg
            180                 185                 190

Asp Gly Val Tyr Asp Val Pro Leu His Asn Pro Pro Asp Ala Lys Gly
        195                 200                 205

Ser Arg Asp Leu Val Asp Gly Ile Asn Arg Leu Ser Phe Ser Ser Thr
    210                 215                 220

Gly Ser Thr Arg Ser Asn Met Ser Thr Ser Ser Thr Ser Ser Lys Glu
225                 230                 235                 240

Ser Ser Leu Ser Ala Ser Pro Ala Gln Asp Lys Arg Leu Phe Leu Asp
                245                 250                 255

Pro Asp Thr Ala Ile Glu Arg Leu Gln Arg Leu Gln Gln Ala Leu Glu
            260                 265                 270

Met Gly Val Ser Ser Leu Met Ala Leu Val Thr Thr Asp Trp Arg Cys
        275                 280                 285

Tyr Gly Tyr Met Glu Arg His Ile Asn Glu Ile Arg Thr Ala Val Asp
    290                 295                 300

Lys Val Glu Leu Phe Leu Lys Glu Tyr Leu His Phe Val Lys Gly Ala
305                 310                 315                 320

Val Ala Asn Ala Ala Cys Leu Pro Glu Leu Ile Leu His Asn Lys Met
                325                 330                 335

Lys Arg Glu Leu Gln Arg Val Glu Asp Ser His Gln Ile Leu Ser Gln
            340                 345                 350

Thr Ser His Asp Leu Asn Glu Cys Ser Trp Ser Leu Asn Ile Leu Ala
        355                 360                 365

Ile Asn Lys Pro Gln Asn Lys Cys Asp Asp Leu Asp Arg Phe Val Met
    370                 375                 380

Val Ala Lys Thr Val Pro Asp Asp Ala Lys Gln Leu Thr Thr Thr Ile
385                 390                 395                 400

Asn Thr Asn Ala Glu Ala Leu Phe Arg Pro Gly Pro Gly Ser Leu His
```

```
                405                 410                 415

Leu Lys Asn Gly Pro Glu Ser Ile Met Asn Ser Thr Glu Tyr Pro His
            420                 425                 430

Gly Gly Ser Gln Gly Gln Leu Leu His Pro Gly Asp His Lys Ala Gln
        435                 440                 445

Ala His Asn Lys Ala Leu Pro Pro Gly Leu Ser Lys Glu Gln Ala Pro
    450                 455                 460

Asp Cys Ser Ser Ser Asp Gly Ser Glu Arg Ser Trp Met Asp Asp Tyr
465                 470                 475                 480

Asp Tyr Val His Leu Gln Gly Lys Glu Glu Phe Glu Arg Gln Gln Lys
                485                 490                 495

Glu Leu Leu Glu Lys Glu Asn Ile Met Lys Gln Asn Lys Met Gln Leu
            500                 505                 510

Glu His His Gln Leu Ser Gln Phe Gln Leu Leu Glu Gln Glu Ile Thr
        515                 520                 525

Lys Pro Val Glu Asn Asp Ile Ser Lys Trp Lys Pro Ser Gln Ser Leu
    530                 535                 540

Pro Thr Thr Asn Ser Gly Val Ser Ala Gln Asp Arg Gln Leu Leu Cys
545                 550                 555                 560

Phe Tyr Tyr Asp Gln Cys Glu Thr His Phe Ile Ser Leu Leu Asn Ala
                565                 570                 575

Ile Asp Ala Leu Phe Ser Cys Val Ser Ser Ala Gln Pro Pro Arg Ile
            580                 585                 590

Phe Val Ala His Ser Lys Phe Val Ile Leu Ser Ala His Lys Leu Val
        595                 600                 605

Phe Ile Gly Asp Thr Leu Thr Arg Gln Val Thr Ala Gln Asp Ile Arg
    610                 615                 620

Asn Lys Val Met Asn Ser Ser Asn Gln Leu Cys Glu Gln Leu Lys Thr
625                 630                 635                 640

Ile Val Met Ala Thr Lys Met Ala Ala Leu His Tyr Pro Ser Thr Thr
                645                 650                 655

Ala Leu Gln Glu Met Val His Gln Val Thr Asp Leu Ser Arg Asn Ala
            660                 665                 670

Gln Leu Phe Lys Arg Ser Leu Leu Glu Met Ala Thr Phe
        675                 680                 685


<210> SEQ ID NO 13
<211> LENGTH: 1001
<212> TYPE: DNA
<213> ORGANISM: Homo sapiens

<400> SEQUENCE: 13

tatctccttg gatcagccct gctgtcatct cttcacaact ccctgtcctt gttgctgccc      60

attttgggga atttatttat caactcctgc tgtaaacgat aataataaca atgataacac     120

atattgaata ttttgtgcct aacactgtac actttctcat gtaatcctcc aataaccacg     180

tgagataggt gctattatta tttccattga caggtgaaat aacagatgtt cagagagtta     240

agtaatctat ccaaagtcag acagctagta cctgacaacg catatcagag caagaaattc     300

tagctctcat aacaggcaaa ctcccaaatc acagtatctt aacacaaaaa gagtttattt     360

catgatcaca tcttggcccc tgggaattgg tgactccttc tagtcaggcc atcatgaaac     420

atatgacacc catggcttct gcatggggta atgaaagagg cattgcaaac tttaagggcc     480

tcagcccttc ctgtcacagt tcaatgacaa gaatgagtat tgtgacccct atctacttac     540
```

```
aagggaggat aggacacata ggggaagaca tatctattta gtgagcacta actgtactgc    600

tttaccctag cacccatgct cttatctagc ttaactgtcc ttagttatct atctatctat    660

ctatctatct atctatctat ctatctatct atcatctatc tgcctacagt taactatctt    720

aactgtcctt accaaggccc cagttgcaca ttccctgatg ccaccagggc tctgctgacc    780

tttattacaa ctcctctaca gattcaacag tctgcctttg ctctgctttc ctgctcatct    840

gctttcctgc tcatctgctt tgctcttttt actctttctc cctcccatct ccctttcctc    900

tgcttctcac tgtctttctt ctgcataacc ctactctgtg tgttgagtct tctatcacat    960

ctttctcctg tacgtgcctt ctctgatctt ctttcagttg c                       1001


<210> SEQ ID NO 14
<211> LENGTH: 1001
<212> TYPE: DNA
<213> ORGANISM: Homo sapiens

<400> SEQUENCE: 14

tatctccttg gatcagccct gctgtcatct cttcacaact ccctgtcctt gttgctgccc     60

attttgggga atttatttat caactcctgc tgtaaacgat aataataaca atgataacac    120

atattgaata ttttgtgcct aacactgtac actttctcat gtaatcctcc aataaccacg    180

tgagataggt gctattatta tttccattga caggtgaaat aacagatgtt cagagagtta    240

agtaatctat ccaaagtcag acagctagta cctgacaacg catatcagag caagaaattc    300

tagctctcat aacaggcaaa ctcccaaatc acagtatctt aacacaaaaa gagtttattt    360

catgatcaca tcttggcccc tgggaattgg tgactccttc tagtcaggcc atcatgaaac    420

atatgacacc catggcttct gcatggggta atgaaagagg cattgcaaac tttaagggcc    480

tcagcccttc ctgtcacagt ccaatgacaa gaatgagtat tgtgacccct atctacttac    540

aagggaggat aggacacata ggggaagaca tatctattta gtgagcacta actgtactgc    600

tttaccctag cacccatgct cttatctagc ttaactgtcc ttagttatct atctatctat    660

ctatctatct atctatctat ctatctatct atcatctatc tgcctacagt taactatctt    720

aactgtcctt accaaggccc cagttgcaca ttccctgatg ccaccagggc tctgctgacc    780

tttattacaa ctcctctaca gattcaacag tctgcctttg ctctgctttc ctgctcatct    840

gctttcctgc tcatctgctt tgctcttttt actctttctc cctcccatct ccctttcctc    900

tgcttctcac tgtctttctt ctgcataacc ctactctgtg tgttgagtct tctatcacat    960

ctttctcctg tacgtgcctt ctctgatctt ctttcagttg c                       1001


<210> SEQ ID NO 15
<211> LENGTH: 8718
<212> TYPE: DNA
<213> ORGANISM: Homo sapiens

<400> SEQUENCE: 15

cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcgg gactctttat gcgctgcggc aggatacgcg ctcggcgctg ggacgcgact    180

gcgctcagtt ctctcctctc ggaagctgca gccatgatgg aagtttgaga gttgagccgc    240

tgtgaggcga ggccgggctc aggcgaggga gatgagagac ggcggcggcc gcggcccgga    300

gcccctctca gcgcctgtga gcagccgcgg gggcagcgcc ctcggggagc cggccggcct    360

gcggcggcgg cagcggcggc gtttctcgcc tcctcttcgt cttttctaac cgtgcagcct    420
```

```
cttcctcggc ttctcctgaa agggaaggtg gaagccgtgg gctcgggcgg gagccggctg    480
aggcgcggcg gcggcggcgg cacctcccgc tcctggagcg ggggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt tccatcctgc    960
agaagaagcc ccgccaccag cagcttctgc catctctctc ctccttttc ttcagccaca   1020
ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaatttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt ttttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
```

```
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac atttttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
tttcataaaa gctgaaaatt gttacctaaa atgaaaatca acttcatgtt ttgaagatag   4380
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
```

```
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
aggatacaca aaaataccaa tatgatgtgt acaggataat gcctcatccc aatcagatgt   5460
ccatttgtta ttgtgtttgt taacaaccct ttatctctta gtgttataaa ctccacttaa   5520
aactgattaa agtctcattc ttgtcattgt gtgggtgttt tattaaatga gagtttataa   5580
ttcaaattgc ttaagtccat tgaagtttta attaatgggc agccaaatgt gaatacaaag   5640
ttttcagttt tttttttcc tgctgtcctt caaagcctac tgtttaaaaa aaaaaaaaaa   5700
aaaaaacatg gcctgagagt agagtatctg tctactcatg tttaattaag gaaaaacact   5760
tatttttagg gctttagtca tcacttcata aattgtataa gcacattaaa tagcgttcta   5820
gtcctgaaaa agtccaagat tcttagaaaa ttgtgcatat ttttattatg acagatgttt   5880
gaagataatt ccccagaatg gatttgatac tttagatttc aattttgtgg cttttgtcta   5940
ttattctgta ctctgccatc agcatatgga aagcttcatt tactcatcat gacttgtgcc   6000
atataaaaat tgatatttcg gaatagtcta aaggactttt tgtacttgaa tttaatcatg   6060
ttgtttctaa tattcttaaa agcttgaaga ctaaagcata tcctttcaac aaagcatagt   6120
aaggtaataa gaaagtgtag tttgtacaag tgttaaaaaa ataaagtaga caatgttaca   6180
gtgggactta ttatttcaag tttacatttt ctccatgtaa ttttttaaaa agtaaatgaa   6240
aaaatgtgca ataatgtaaa atatgaagtg tatgtgtaca cacattttat ttttcggtat   6300
cttgggtata cgtatggttg aaaactatac tggagtctaa aagtattcta atttataaga   6360
agacattttg gtgatgtttg aaaaatagaa atgtgctagt tttgttttta tatcatgtcc   6420
tttgtacgtt gtaatatgag ctggcttggt tcagtaaatg ccatcaccat ttccattgag   6480
aatttaaaac tcaccagtgt ttaatatgca ggcttccaaa ggcttatgaa aaaaatcaag   6540
acccttaaat ctagttaatt tgctgctaac atgaaactct ttggttcttt tatttttgcc   6600
agataattag acacacatct aaagcttagt cttaaatggc ttaagtgtag ctattgatta   6660
gtgctgttgc tagttcagaa agaaatgttt gtgaatggaa acaagaatat tcagtccaaa   6720
ctgttgtaag gacagtacct gaaaaccagg aaacaggata atggaaaaag tcttttaaag   6780
atgaaatgtt ggagccaact ttcttataga attaattgta tgtggctata gaaagcctaa   6840
tgattgttgc ttatttttga gagcatatta ttcttttatg accataatct tgctgttttt   6900
ccatcttcca aaagatcttc cttctaatat gtatatcaga atgtgggtag ccagtcagac   6960
aaattcatat tggttggtag ctttaaaaag tttgtaatgt gaagacagga aaggacaaaa   7020
tagtttgctt tggtggtagt actctggttg ttaagctagg tattttgaga ctacttcccc   7080
atcacaacaa caataaaata atcactcata atcctatcac ctggagacat agccatcgtt   7140
aatatgttag tgactataca atcatgtttt cttctgtata tccatgtata ttctttaaaa   7200
atgaaattta tactgtacct gatctcaaag ctttttagct tagtatatct gtcatgaatt   7260
tgtaggatgt tccattgcat cagaaaacgg acagtgattt gattactttc taatgccaca   7320
gatgcagatt acatgtagtt attgagaatc ctttcgaatt cagtggctta atcatgaatg   7380
tctaaatatt gttgacatta ggatgataca tgtaaattaa agttacattt gtttagcata   7440
gacaagctta acattgtaga tgtttctctt caaaaatcat cttaaacatt tgcatttgga   7500
```

-continued

```
attgtgttaa atagaatgtg tgaaacactg tattagtaaa cttcatcacc tttctacttc   7560
cttatagttt gaacttttca gtttttgtag ttcccaaaca gttgctcaat ttagagcaaa   7620
ttaatttaac acctgccaaa aaaaggctgc tgttggctta tcagttgtct ttaaattcaa   7680
atgctcatgt gacttttatc acatcaaaaa atatttcatt aatgattcac ctttagctct   7740
gaaaattacc gcgtttagta attatagtgg gcttataaaa acatgcaact ctttttgata   7800
gttatttgag aattttggtg aaaaatattt agctgagggc agtatagaac ttataaacca   7860
atatattgat atttttaaaa catttttaca tataagtaaa ctgccatctt tgagcataac   7920
tacatttaaa aataaagctg catattttta aatcaagtgt ttaacaagaa tttatatttt   7980
ttatttttta aaattaaaaa taatttatat ttcctctgtt gcatgaggat tctcatctgt   8040
gcttataatg gttagagatt ttatttgtgt ggaatgaagt gaggcttgta gtcatggttc   8100
tagtgtttca gtttgccaag tctgtttact gcagtgaaat tcatcaaatg tttcagtgtg   8160
gttttctgta gcctatcatt tactggctat ttttttatgt acacctttag gatttctgc   8220
ctactctatc cagttgtcca aatgatatcc tacattttac aaatgccctt tcagtttcta   8280
ttttcttttt ccattaaatt gccctcatgt cctaatgtgc agtttgtaag tgtgtgtgtg   8340
tgtgtctgtg tgtgtgtgaa tttgattttc aagagtgcta gacttccaat ttgagagatt   8400
aaataattta attcaggcaa acatttttca ttggaatttc acagttcatt gtaatgaaaa   8460
tgttaatcct ggatgacctt tgacatacag taatgaatct tggatattaa tgaatttgtt   8520
agtagcatct tgatgtgtgt tttaatgagt tattttcaaa gttgtgcatt aaaccaaagt   8580
tggcatactg gaagtgttta tatcaagttc catttggcta ctgatggaca aaaaatagaa   8640
atgccttcct atggagagta tttttccttt aaaaaattaa aaaggttaat tattttgact   8700
aaaaaaaaaa aaaaaaaa                                                 8718
```

<210> SEQ ID NO 16
<211> LENGTH: 8718
<212> TYPE: DNA
<213> ORGANISM: Homo sapiens

<400> SEQUENCE: 16

```
cctcccctcg cccggcgcgg tcccgtccgc ctctcgctcg cctcccgcct cccctcggtc     60
ttccgaggcg cccgggctcc cggcgcggcg gcggaggggg cgggcaggcc ggcgggcggt    120
gatgtggcgg gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cacctcccgc tcctggagcg ggggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
```

```
aagcggcggc agagcgaggg gcatcagcta ccgccaagtc cagagccatt tccatcctgc    960
agaagaagcc ccgccaccag cagcttctgc catctctctc ctcctttttc ttcagccaca   1020
ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaattttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt tttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
```

```
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac attttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
tttcataaaa gctgaaaatt gttacctaaa atgaaaatca acttcatgtt ttgaagatag   4380
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
aggatacaca aaaataccaa tatgatgtgt acaggataat gcctcatccc aatcagatgt   5460
ccatttgtta ttgtgtttgt taacaaccct ttatctctta gtgttataaa ctccacttaa   5520
aactgattaa agtctcattc ttgtcattgt gtgggtgttt tattaaatga gagtttataa   5580
ttcaaattgc ttaagtccat tgaagtttta attaatgggc agccaaatgt gaatacaaag   5640
```

```
ttttcagttt tttttttcc tgctgtcctt caaagcctac tgtttaaaaa aaaaaaaaaa   5700
aaaaaacatg gcctgagagt agagtatctg tctactcatg tttaattaag gaaaaacact   5760
tatttttagg gctttagtca tcacttcata aattgtataa gcacattaaa tagcgttcta   5820
gtcctgaaaa agtccaagat tcttagaaaa ttgtgcatat ttttattatg acagatgttt   5880
gaagataatt ccccagaatg gatttgatac tttagatttc aattttgtgg cttttgtcta   5940
ttattctgta ctctgccatc agcatatgga aagcttcatt tactcatcat gacttgtgcc   6000
atataaaaat tgatatttcg gaatagtcta aaggactttt tgtacttgaa tttaatcatg   6060
ttgtttctaa tattcttaaa agcttgaaga ctaaagcata tcctttcaac aaagcatagt   6120
aaggtaataa gaaagtgtag tttgtacaag tgttaaaaaa ataaagtaga caatgttaca   6180
gtgggactta ttatttcaag tttacatttt ctccatgtaa ttttttaaaa agtaaatgaa   6240
aaaatgtgca ataatgtaaa atatgaagtg tatgtgtaca cacattttat ttttcggtat   6300
cttgggtata cgtatggttg aaaactatac tggagtctaa aagtattcta atttataaga   6360
agacattttg gtgatgtttg aaaaatagaa atgtgctagt tttgtttttta tatcatgtcc   6420
tttgtacgtt gtaatatgag ctggcttggt tcagtaaatg ccatcaccat ttccattgag   6480
aatttaaaac tcaccagtgt ttaatatgca ggcttccaaa ggcttatgaa aaaaatcaag   6540
acccttaaat ctagttaatt tgctgctaac atgaaactct ttggttcttt tatttttgcc   6600
agataattag acacacatct aaagcttagt cttaaatggc ttaagtgtag ctattgatta   6660
gtgctgttgc tagttcagaa agaaatgttt gtgaatggaa acaagaatat tcagtccaaa   6720
ctgttgtaag gacagtacct gaaaaccagg aaacaggata atggaaaaag tcttttaaag   6780
atgaaatgtt ggagccaact ttcttataga attaattgta tgtggctata gaaagcctaa   6840
tgattgttgc ttatttttga gagcatatta ttcttttatg accataatct tgctgttttt   6900
ccatcttcca aaagatcttc cttctaatat gtatatcaga atgtgggtag ccagtcagac   6960
aaattcatat tggttggtag ctttaaaaag tttgtaatgt gaagacagga aaggacaaaa   7020
tagtttgctt tggtggtagt actctggttg ttaagctagg tattttgaga ctacttcccc   7080
atcacaacaa caataaaata atcactcata atcctatcac ctggagacat agccatcgtt   7140
aatatgttag tgactataca atcatgtttt cttctgtata tccatgtata ttctttaaaa   7200
atgaaattta tactgtacct gatctcaaag ctttttagct tagtatatct gtcatgaatt   7260
tgtaggatgt tccattgcat cagaaaacgg acagtgattt gattactttc taatgccaca   7320
gatgcagatt acatgtagtt attgagaatc ctttcgaatt cagtggctta atcatgaatg   7380
tctaaatatt gttgacatta ggatgataca tgtaaattaa agttacattt gtttagcata   7440
gacaagctta acattgtaga tgtttctctt caaaaatcat cttaaacatt tgcatttgga   7500
attgtgttaa atagaatgtg tgaaacactg tattagtaaa cttcatcacc tttctacttc   7560
cttatagttt gaacttttca gtttttgtag ttcccaaaca gttgctcaat ttagagcaaa   7620
ttaatttaac acctgccaaa aaaaggctgc tgttggctta tcagttgtct ttaaattcaa   7680
atgctcatgt gacttttatc acatcaaaaa atatttcatt aatgattcac ctttagctct   7740
gaaaattacc gcgtttagta attatagtgg gcttataaaa acatgcaact ctttttgata   7800
gttatttgag aattttggtg aaaaatattt agctgagggc agtatagaac ttataaacca   7860
atatattgat atttttaaaa catttttaca tataagtaaa ctgccatctt tgagcataac   7920
tacatttaaa aataaagctg catattttta aatcaagtgt ttaacaagaa tttatatttt   7980
```

ttatttttta aaattaaaaa taatttatat ttcctctgtt gcatgaggat tctcatctgt 8040
gcttataatg gttagagatt ttatttgtgt ggaatgaagt gaggcttgta gtcatggttc 8100
tagtgtttca gtttgccaag tctgtttact gcagtgaaat tcatcaaatg tttcagtgtg 8160
gttttctgta gcctatcatt tactggctat ttttttatgt acacctttag gattttctgc 8220
ctactctatc cagttgtcca aatgatatcc tacattttac aaatgccctt tcagtttcta 8280
ttttcttttt ccattaaatt gccctcatgt cctaatgtgc agtttgtaag tgtgtgtgtg 8340
tgtgtctgtg tgtgtgtgaa tttgattttc aagagtgcta gacttccaat ttgagagatt 8400
aaataattta attcaggcaa acatttttca ttggaatttc acagttcatt gtaatgaaaa 8460
tgttaatcct ggatgacctt tgacatacag taatgaatct tggatattaa tgaatttgtt 8520
agtagcatct tgatgtgtgt tttaatgagt tattttcaaa gttgtgcatt aaaccaaagt 8580
tggcatactg gaagtgttta tatcaagttc catttggcta ctgatggaca aaaaatagaa 8640
atgccttcct atggagagta tttttccttt aaaaaattaa aaaggttaat tattttgact 8700
aaaaaaaaaa aaaaaaaa 8718

<210> SEQ ID NO 17
<211> LENGTH: 8833
<212> TYPE: DNA
<213> ORGANISM: Homo sapiens

<400> SEQUENCE: 17
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg ggggggagaa gcggcggcgg 540
cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020
ggctcccaga catgacagcc atcatcaaag agatcgttag cagaaacaaa aggagatatc 1080
aagaggatgg attcgactta gacttgacct atatttatcc aaacattatt gctatgggat 1140
ttcctgcaga aagacttgaa ggcgtataca ggaacaatat tgatgatgta gtaagttgtg 1200
ctgaaagaca ttatgacacc gccaaattta attgcagagt tgcacaatat ccttttgaag 1260
accataaccc accacagcta gaacttatca aaccctttTg tgaagatctt gaccaatggc 1320
taagtgaaga tgacaatcat gttgcagcaa ttcactgtaa agctggaaag ggacgaactg 1380

```
gtgtaatgat atgtgcatat ttattacatc ggggcaaatt tttaaaggca caagaggccc   1440
tagatttcta tggggaagta aggaccagag acaaaaaggc agatcctaca ggaggtattc   1500
cagataaagg cattattgtc ataggagatg gcagctccat ggatgttatt gccccttaag   1560
accttccagt gggacaagat gtataggtgg aagacagtga tattgatgat cctgaccttg   1620
tagaggccaa ggctaaagga gtaactattc ccagtcagag gcgctatgtg tattattata   1680
gctacctgtt aaagaatcat ctggattata gaccagtggc actgttgttt cacaagatga   1740
tgtttgaaac tattccaatg ttcagtggcg gaacttgcaa tcctcagttt gtggtctgcc   1800
agctaaaggt gaagatatat tcctccaatt caggacccac acgacgggaa gacaagttca   1860
tgtactttga gttccctcag ccgttacctg tgtgtggtga tatcaaagta gagttcttcc   1920
acaaacagaa caagatgcta aaaaaggaca aaatgtttca cttttgggta aatacattct   1980
tcataccagg accagaggaa acctcagaaa aagtagaaaa tggaagtcta tgtgatcaag   2040
aaatcgatag catttgcagt atagagcgtg cagataatga caaggaatat ctagtactta   2100
ctttaacaaa aaatgatctt gacaaagcaa ataaagacaa agccaaccga tacttttctc   2160
caaattttaa ggtgaagctg tacttcacaa aaacagtaga ggagccgtca aatccagagg   2220
ctagcagttc aacttctgta acaccagatg ttagtgacaa tgaacctgat cattatagat   2280
attctgacac cactgactct gatccagaga atgaaccttt tgatgaagat cagcatacac   2340
aaattacaaa agtctgaatt tttttttatc aagagggata aaacaccatg aaaataaact   2400
tgaataaact gaaaatggac cttttttttt ttaatggcaa taggacattg tgtcagatta   2460
ccagttatag gaacaattct cttttcctga ccaatcttgt tttaccctat acatccacag   2520
ggttttgaca cttgttgtcc agttgaaaaa aggttgtgta gctgtgtcat gtatatacct   2580
ttttgtgtca aaaggacatt taaaattcaa ttaggattaa taaagatggc actttcccgt   2640
tttattccag ttttataaaa agtggagaca gactgatgtg tatacgtagg aatttttttcc  2700
ttttgtgttc tgtcaccaac tgaagtggct aaagagcttt gtgatatact ggttcacatc   2760
ctaccccttt gcacttgtgg caacagataa gtttgcagtt ggctaagaga ggtttccgaa   2820
gggttttgct acattctaat gcatgtattc gggttagggg aatggaggga atgctcagaa   2880
aggaaataat tttatgctgg actctggacc atataccatc tccagctatt tacacacacc   2940
tttctttagc atgctacagt tattaatctg gacattcgag gaattggccg ctgtcactgc   3000
ttgttgtttg cgcatttttt tttaaagcat attggtgcta gaaaaggcag ctaaaggaag   3060
tgaatctgta ttggggtaca ggaatgaacc ttctgcaaca tcttaagatc cacaaatgaa   3120
gggatataaa aataatgtca taggtaagaa acacagcaac aatgacttaa ccatataaat   3180
gtggaggcta tcaacaaaga atgggcttga aacattataa aaattgacaa tgatttatta   3240
aatatgtttt ctcaattgta acgacttctc catctcctgt gtaatcaagg ccagtgctaa   3300
aattcagatg ctgttagtac ctacatcagt caacaactta cacttatttt actagttttc   3360
aatcataata cctgctgtgg atgcttcatg tgctgcctgc aagcttcttt tttctcatta   3420
aatataaaat attttgtaat gctgcacaga aattttcaat ttgagattct acagtaagcg   3480
tttttttttct ttgaagattt atgatgcact tattcaatag ctgtcagccg ttccaccctt   3540
ttgaccttac acattctatt acaatgaatt ttgcagtttt gcacattttt taaatgtcat   3600
taactgttag ggaattttac ttgaatactg aatacatata atgtttatat taaaaaggac   3660
atttgtgtta aaaaggaaat tagagttgca gtaaactttc aatgctgcac acaaaaaaaa   3720
```

```
gacatttgat ttttcagtag aaattgtcct acatgtgctt tattgatttg ctattgaaag   3780
aatagggttt tttttttttt tttttttttt ttttttaaat gtgcagtgtt gaatcatttc   3840
ttcatagtgc tcccccgagt tgggactagg gcttcaattt cacttcttaa aaaaaatcat   3900
catatatttg atatgcccag actgcatacg attttaagcg gagtacaact actattgtaa   3960
agctaatgtg aagatattat taaaaaggtt tttttttcca gaaatttggt gtcttcaaat   4020
tataccttca ccttgacatt tgaatatcca gccattttgt ttcttaatgg tataaaattc   4080
cattttcaat aacttattgg tgctgaaatt gttcactagc tgtggtctga cctagttaat   4140
ttacaaatac agattgaata ggacctacta gagcagcatt tatagagttt gatggcaaat   4200
agattaggca gaacttcatc taaaatattc ttagtaaata atgttgacac gttttccata   4260
ccttgtcagt ttcattcaac aatttttaaa tttttaacaa agctcttagg atttacacat   4320
ttatatttaa acattgatat atagagtatt gattgattgc tcataagtta aattggtaaa   4380
gttagagaca actattctaa cacctcacca ttgaaattta tatgccacct tgtctttcat   4440
aaaagctgaa aattgttacc taaaatgaaa atcaacttca tgttttgaag atagttataa   4500
atattgttct ttgttacaat ttcgggcacc gcatattaaa acgtaacttt attgttccaa   4560
tatgtaacat ggagggccag gtcataaata atgacattat aatgggcttt tgcactgtta   4620
ttatttttcc tttggaatgt gaaggtctga atgagggttt tgattttgaa tgtttcaatg   4680
tttttgagaa gccttgctta cattttatgg tgtagtcatt ggaaatggaa aaatggcatt   4740
atatatatta tatatataaa tatatattat acatactctc cttactttat ttcagttacc   4800
atccccatag aatttgacaa gaattgctat gactgaaagg ttttcgagtc ctaattaaaa   4860
ctttatttat ggcagtattc ataattagcc tgaaatgcat tctgtaggta atctctgagt   4920
ttctggaata ttttcttaga ctttttggat gtgcagcagc ttacatgtct gaagttactt   4980
gaaggcatca cttttaagaa agcttacagt tgggccctgt accatcccaa gtcctttgta   5040
gctcctcttg aacatgtttg ccatactttt aaaagggtag ttgaataaat agcatcacca   5100
ttctttgctg tggcacaggt tataaactta agtggagttt accggcagca tcaaatgttt   5160
cagctttaaa aaataaaagt agggtacaag tttaatgttt agttctagaa attttgtgca   5220
atatgttcat aacgatggct gtggttgcca caaagtgcct cgtttacctt taaatactgt   5280
taatgtgtca tgcatgcaga tggaagggggt ggaactgtgc actaaagtgg gggctttaac   5340
tgtagtattt ggcagagttg ccttctacct gccagttcaa aagttcaacc tgttttcata   5400
tagaatatat atactaaaaa atttcagtct gttaaacagc cttactctga ttcagcctct   5460
tcagatactc ttgtgctgtg cagcagtggc tctgtgtgta aatgctatgc actgaggata   5520
cacaaaaata ccaatatgat gtgtacagga taatgcctca tcccaatcag atgtccattt   5580
gttattgtgt ttgttaacaa ccctttatct cttagtgtta taaactccac ttaaaactga   5640
ttaaagtctc attcttgtca ttgtgtgggt gttttattaa atgagagttt ataattcaaa   5700
ttgcttaagt ccattgaagt tttaattaat gggcagccaa atgtgaatac aaagttttca   5760
gttttttttt ttcctgctgt ccttcaaagc ctactgttta aaaaaaaaaa aaaaaaaaaa   5820
catggcctga gagtagagta tctgtctact catgtttaat taaggaaaaa cacttatttt   5880
tagggcttta gtcatcactt cataaattgt ataagcacat taaatagcgt tctagtcctg   5940
aaaaagtcca agattcttag aaaattgtgc atatttttat tatgacagat gtttgaagat   6000
aattccccag aatggatttg atactttaga tttcaatttt gtggcttttg tctattattc   6060
tgtactctgc catcagcata tggaaagctt catttactca tcatgacttg tgccatataa   6120
```

```
aaattgatat ttcggaatag tctaaaggac tttttgtact tgaatttaat catgttgttt   6180
ctaatattct taaaagcttg aagactaaag catatccttt caacaaagca tagtaaggta   6240
ataagaaagt gtagtttgta caagtgttaa aaaaataaag tagacaatgt tacagtggga   6300
cttattattt caagtttaca ttttctccat gtaatttttt aaaaagtaaa tgaaaaaatg   6360
tgcaataatg taaaatatga agtgtatgtg tacacacatt ttatttttcg gtatcttggg   6420
tatacgtatg gttgaaaact atactggagt ctaaaagtat tctaatttat aagaagacat   6480
tttggtgatg tttgaaaaat agaaatgtgc tagttttgtt tttatatcat gtcctttgta   6540
cgttgtaata tgagctggct tggttcagta aatgccatca ccatttccat tgagaattta   6600
aaactcacca gtgtttaata tgcaggcttc caaaggctta tgaaaaaaat caagacccctt   6660
aaatctagtt aatttgctgc taacatgaaa ctctttggtt cttttatttt tgccagataa   6720
ttagacacac atctaaagct tagtcttaaa tggcttaagt gtagctattg attagtgctg   6780
ttgctagttc agaaagaaat gtttgtgaat ggaaacaaga atattcagtc caaactgttg   6840
taaggacagt acctgaaaac caggaaacag gataatggaa aaagtctttt aaagatgaaa   6900
tgttggagcc aactttctta tagaattaat tgtatgtggc tatagaaagc ctaatgattg   6960
ttgcttattt ttgagagcat attattcttt tatgaccata atcttgctgt ttttccatct   7020
tccaaaagat cttccttcta atatgtatat cagaatgtgg gtagccagtc agacaaattc   7080
atattggttg gtagctttaa aaagtttgta atgtgaagac aggaaaggac aaaatagttt   7140
gctttggtgg tagtactctg gttgttaagc taggtatttt gagactactt ccccatcaca   7200
acaacaataa aataatcact cataatccta tcacctggag acatagccat cgttaatatg   7260
ttagtgacta tacaatcatg ttttcttctg tatatccatg tatattcttt aaaaatgaaa   7320
tttatactgt acctgatctc aaagcttttt agcttagtat atctgtcatg aatttgtagg   7380
atgttccatt gcatcagaaa acggacagtg atttgattac tttctaatgc cacagatgca   7440
gattacatgt agttattgag aatcctttcg aattcagtgg cttaatcatg aatgtctaaa   7500
tattgttgac attaggatga tacatgtaaa ttaaagttac atttgtttag catagacaag   7560
cttaacattg tagatgtttc tcttcaaaaa tcatcttaaa catttgcatt tggaattgtg   7620
ttaaatagaa tgtgtgaaac actgtattag taaacttcat cacctttcta cttccttata   7680
gtttgaactt ttcagttttt gtagttccca aacagttgct caatttagag caaattaatt   7740
taacacctgc caaaaaaagg ctgctgttgg cttatcagtt gtctttaaat tcaaatgctc   7800
atgtgacttt tatcacatca aaaaatattt cattaatgat tcacctttag ctctgaaaat   7860
taccgcgttt agtaattata gtgggcttat aaaaacatgc aactcttttt gatagttatt   7920
tgagaatttt ggtgaaaaat atttagctga gggcagtata gaacttataa accaatatat   7980
tgatattttt aaaacatttt tacatataag taaactgcca tctttgagca taactacatt   8040
taaaaataaa gctgcatatt tttaaatcaa gtgtttaaca agaatttata ttttttattt   8100
tttaaaatta aaaataattt atatttcctc tgttgcatga ggattctcat ctgtgcttat   8160
aatggttaga gattttattt gtgtggaatg aagtgaggct tgtagtcatg gttctagtgt   8220
ttcagtttgc caagtctgtt tactgcagtg aaattcatca aatgtttcag tgtggttttc   8280
tgtagcctat catttactgg ctattttttt atgtacacct ttaggatttt ctgcctactc   8340
tatccagttg tccaaatgat atcctacatt ttacaaatgc cctttcagtt tctattttct   8400
ttttccatta aattgccctc atgtcctaat gtgcagtttg taagtgtgtg tgtgtgtgtc   8460
```

-continued

```
tgtgtgtgtg tgaatttgat tttcaagagt gctagacttc caatttgaga gattaaataa    8520

tttaattcag gcaaacattt ttcattggaa tttcacagtt cattgtaatg aaaatgttaa    8580

tcctggatga cctttgacat acagtaatga atcttggata ttaatgaatt tgttagtagc    8640

atcttgatgt gtgttttaat gagttatttt caaagttgtg cattaaacca aagttggcat    8700

actggaagtg tttatatcaa gttccatttg gctactgatg gacaaaaaat agaaatgcct    8760

tcctatggag agtatttttc ctttaaaaaa ttaaaaaggt taattatttt gactaaaaaa    8820

aaaaaaaaaa aaa                                                       8833
```

COMPOSITIONS AND METHODS FOR SCREENING AND IDENTIFYING CLINICALLY AGGRESSIVE PROSTATE CANCER

CROSS-REFERENCE TO RELATED APPLICATIONS

This application is a National Stage filing under 35 U.S.C. § 371 of International Patent Application No. PCT/US2017/014362, filed Jan. 20, 2017, which claims the benefit of priority of U.S. Provisional Application No. 62/280,994, filed Jan. 20, 2016, the entireties of which are hereby incorporated herein by reference.

GOVERNMENT RIGHTS

This invention was made with government support under grant number W81XWH-11-1-0379 awarded by the Department of the Army. The government has certain rights in the invention.

BACKGROUND

Prostate cancer is the most common non-skin cancer and second most common cause of cancer mortality in men in the United States. It represents 13.3% of all new cancer cases in the United States. Thanks to the development of new therapeutics, about 99% patients survive five years or more after being diagnosed of prostate cancer, and the mortality rate has been declining steadily over the past decade. The success in managing prostate cancer is ascribed to a great extent to the ability of detecting the cancer at an early stage. It is screened for by testing the amount of prostate-specific antigen (PSA) in a man's blood or by a digital rectal exam (DRE). Abnormalities on these screening tests prompt a biopsy and the screening tests are given to men most commonly over the age of 50 years and especially those at a higher risk of cancer, on a regular basis. Early identification thereby reduces the incidence of advanced prostate cancer and increases the curability by eradicating clinically localized disease. However, some cancer cells have already metastasized prior to radiation or surgery but are not detected at time of the therapy, leading to recurrence of prostate cancer which may become visible on computed tomography scan or bone scans. This is referred to as metastatic prostatic cancer, which can also occur as first presentation (i.e. no prior localized therapy) and is referred to as "de novo" metastatic prostate cancer.

Most metastatic prostate cancer is initially androgen dependent, i.e. prostate cancer cells require androgens for continued proliferation. Androgen deprivation therapy, such as castration by medical or surgical means, leads to rapid regression of cancer. In nearly all cases, however, some cancer cells survive and lead to castration resistant prostate cancer (CRPC). While most recurrent prostate cancer can be readily diagnosed with PSA test, treatment is much more difficult, with a five-year survival rate of about 28% from the time of androgen deprivation therapy.

Therefore, discovery of biomarkers that can predict the prognosis of prostate cancer at an early stage will contribute to early identification of high-risk patients, allowing them to be treated more aggressively before the cancer relapses and/or metastasizes while avoiding overtreatment in those who can be managed with less intense strategies.

Nuclear factor kappa B (NF-κB) is a central regulator of cell survival and proliferation and thus plays an important role in cancer development. The NF-κB signaling pathway regulates gene transcription in response to growth factors, inflammatory factors, etc. Zinc finger protein 36 homolog (ZFP36) encodes the protein tristetraprolin (TTP), which facilitates decay of mRNAs of some genes induced by NF-κB and/or MAP kinases. By this means ZFP36/TTP negatively modulates pro-inflammatory factors such as tumor necrosis factor (TNF) and granulocyte-macrophage colony-stimulating factor (GM-CSF). In light of the important role of inflammation in cancer, the present invention identifies a correlation between prostate cancer progression and the expression of some NF-κB related genes, such as ZFP36, NEDD9 and an SNP rs1910301 risk allele A.

SUMMARY

The present disclosure provides a method of determining the likelihood of increased tumor load of prostate cancer in a subject, the method comprising measuring the expression level of ZFP36 in a sample from the subject, and comparing the measured expression level of ZFP36 in the sample from the subject to the expression level of ZFP36 in a control sample, wherein the likelihood of increased tumor load of prostate cancer is higher if the expression level of ZFP36 in the sample from the subject is lower than the expression level of ZFP36 in the control sample, and wherein the likelihood of increased tumor load of prostate cancer is lower if the expression level of ZFP36 in the sample from the subject is about the same as or higher than the expression level of ZFP36 in the control sample.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the control sample is selected from the group consisting of a normal prostate tissue, a non-lethal prostate cancer, and a prostate cancer cell line.

In some embodiments, the likelihood of increased tumor load of prostate cancer is the likelihood of increased tumor load of prostate cancer within 20 years from the time when the sample is collected. In some embodiments, the likelihood of increased tumor load of prostate cancer is the likelihood of increased tumor load of prostate cancer within 5 years from the time when the sample is collected.

In some embodiments, the expression levels of ZFP36 are mRNA levels. In one embodiment, the expression levels of ZFP36 are measured by a polymerase chain reaction using a first synthetic primer comprising a polynucleotide that hybridizes to the sense strand of a DNA target comprising the sequence of SEQ ID NO: 2 and a second synthetic primer comprising a polynucleotide that hybridizes to the antisense strand of the DNA target. In a particular embodiment, the polymerase chain reaction further comprises a polynucleotide that hybridizes to the sense or antisense strand of the DNA target, wherein the polynucleotide is conjugated to a detectable moiety.

In some embodiments, the expression levels of ZFP36 are protein levels. In a particular embodiment, the expression levels of ZFP36 are measured by immunohistochemistry using an anti-ZFP36 antibody.

The present disclosure provides a method of determining the likelihood of decreased survival of a subject with prostate cancer, the method comprising measuring the expression level of ZFP36 in a sample from the subject, and comparing the measured expression level of ZFP36 in the sample from the subject to the expression level of ZFP36 in a control sample, wherein the likelihood of decreased survival of the subject is higher if the expression level of ZFP36 in the sample from the subject is lower than the expression level of ZFP36 in the control sample.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the control sample is selected from the group consisting of a normal prostate tissue, a non-lethal prostate cancer, and a prostate cancer cell line.

In some embodiments, the likelihood of decreased survival is the likelihood of decreased survival within 20 years from the time when the sample is collected. In some embodiments, the likelihood of decreased survival is the likelihood of decreased survival within 5 years from the time when the sample is collected.

In some embodiments, the expression levels of ZFP36 are mRNA levels. In one embodiment, the expression levels of ZFP36 are measured by a polymerase chain reaction using a first synthetic primer comprising a polynucleotide that hybridizes to the sense strand of a DNA target comprising the sequence of SEQ ID NO: 2 and a second synthetic primer comprising a polynucleotide that hybridizes to the antisense strand of the DNA target. In a particular embodiment, the polymerase chain reaction further comprises a polynucleotide that hybridizes to the sense or antisense strand of the DNA target, wherein the polynucleotide is conjugated to a detectable moiety.

In some embodiments, the expression levels of ZFP36 are protein levels. In a particular embodiment, the expression levels of ZFP36 are measured by immunohistochemistry using an anti-ZFP36 antibody.

The present disclosure provides a method of determining the likelihood of recurrence of prostate cancer in a subject, the method comprising measuring the expression level of ZFP36 in a sample from the subject; and comparing the measured expression level of ZFP36 in the sample from the subject to the expression level of ZFP36 in a control sample, wherein the likelihood of recurrence of prostate cancer is higher if the expression level of ZFP36 in the sample from the subject is lower than the expression level of ZFP36 in the control sample.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the control sample is selected from the group consisting of a normal prostate tissue, a non-lethal prostate cancer, and a prostate cancer cell line.

In some embodiments, the likelihood of recurrence of prostate cancer is the likelihood of recurrence of prostate cancer within 20 years from the time when the sample is collected. In some embodiments, the likelihood of recurrence of prostate cancer is the likelihood of recurrence of prostate cancer within 5 years from the time when the sample is collected.

In some embodiments, the expression levels of ZFP36 are mRNA levels. In one embodiment, wherein the expression levels of ZFP36 are measured by a polymerase chain reaction using a first synthetic primer comprising a polynucleotide that hybridizes to the sense strand of a DNA target comprising the sequence of SEQ ID NO: 2 and a second synthetic primer comprising a polynucleotide that hybridizes to the antisense strand of the DNA target. In a particular embodiment, the polymerase chain reaction further comprises a polynucleotide that hybridizes to the sense or antisense strand of the DNA target, wherein the polynucleotide is conjugated to a detectable moiety.

In some embodiments, the expression levels of ZFP36 are protein levels. In a particular embodiment, the expression levels of ZFP36 are measured by immunohistochemistry using an anti-ZFP36 antibody.

The present disclosure provides a method for treating prostate cancer in a subject with prostate cancer, the method comprising measuring the expression level of ZFP36 in a sample from the subject, comparing the measured expression level of ZFP36 in the sample from the subject to the expression level of ZFP36 in a control sample, and providing a treatment if the expression level of ZFP36 in the sample from the subject is lower than the expression level of ZFP36 in the control sample.

In some embodiments, the sample is from a tumor lesion. In some embodiments, the sample comprises circulating tumor cells. In some embodiments, the prostate cancer is a primary prostate tumor. In some embodiments, the expression levels of ZFP36 are mRNA levels. In some embodiments, the expression levels of ZFP36 are protein levels. In some embodiments, the control sample is selected from the group consisting of a normal prostate tissue, a non-lethal prostate cancer, and a prostate cancer cell line.

In some embodiments, the treatment comprises one or more therapies selected from the group consisting of surgical castration, androgen deprivation therapy, a radiation therapy, an ablation therapy, a chemotherapy, a targeted therapy and an immunotherapy. In some embodiments, the subject is provided with a treatment even if (s)he is identified as a candidate for active surveillance by a method not dependent on the expression level of ZFP36.

The present disclosure provides a method for treating prostate cancer in a subject with prostate cancer, the method comprising measuring the expression level of ZFP36 in a sample from the subject, comparing the measured expression level of ZFP36 in the sample from the subject to the expression level of ZFP36 in a control sample, and monitoring the cancer without providing a treatment if the expression level of ZFP36 in the sample from the subject is about the same as or higher than the expression level of ZFP36 in the control sample.

In some embodiments, the prostate cancer is a primary prostate tumor.

The present disclosure provides a kit comprising a reagent for reverse transcription of an RNA molecule, two or more primers, wherein a first primer comprises a polynucleotide that hybridizes to the sense strand of a DNA target comprising the sequence of SEQ ID NO: 2 and a second primer comprises a polynucleotide that hybridizes to the anti-sense strand of the DNA target, and a reagent for amplification of a DNA sequence.

In some embodiments, the kit further comprises a polynucleotide that hybridizes to the sense or antisense strand of the amplified DNA target, wherein the polynucleotide is conjugated to a detectable moiety.

The present disclosure provides a kit comprising an antibody that is capable of binding to ZFP36 and a reagent for the detection of the antibody.

The present disclosure provides a method of determining the likelihood of increased tumor load of prostate cancer in a subject, the method comprising measuring the expression level of NEDD9 in a sample from the subject, and comparing the measured expression level of NEDD9 in the sample from the subject to the expression level of NEDD9 in a control sample, wherein the likelihood of increased tumor load of prostate cancer is higher if the expression level of NEDD9 in the sample from the subject is higher than the expression level of NEDD9 in the control sample.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the control sample is selected from the group consisting of a normal prostate tissue, a non-lethal prostate cancer, and a prostate cancer cell line.

In some embodiments, the likelihood of increased tumor load of prostate cancer is the likelihood of increased tumor load of prostate cancer within 20 years from the time when the sample is collected. In some embodiments, the likelihood of increased tumor load of prostate cancer is the likelihood of increased tumor load of prostate cancer within 5 years from the time when the sample is collected.

In some embodiments, the expression levels of NEDD9 are mRNA levels. In one embodiment, the expression levels of NEDD9 are measured by a polymerase chain reaction using a first synthetic primer comprising a polynucleotide that hybridizes to the sense strand of a DNA target that comprises a sequence selected from SEQ ID NO: 5, NO: 6, NO: 7 and NO: 8, and a second synthetic primer comprising a polynucleotide that hybridizes to the antisense strand of the DNA target. In a particular embodiment, the polymerase chain reaction further comprises a polynucleotide that hybridizes to the sense or antisense strand of the DNA target, wherein the polynucleotide is conjugated to a detectable moiety.

In some embodiments, the expression levels of NEDD9 are protein levels. In a particular embodiment, the expression levels of NEDD9 are measured by immunohistochemistry using an anti-NEDD9 antibody.

The present disclosure provides a method of determining the likelihood of recurrence of prostate cancer in a subject, the method comprising measuring the expression level of NEDD9 in a sample from the subject, and comparing the measured expression level of NEDD9 in the sample from the subject to the expression level of NEDD9 in a control sample, wherein the likelihood of recurrence of prostate cancer is higher if the expression level of NEDD9 in the sample from the subject is higher than the expression level of NEDD9 in the control sample.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the control sample is selected from the group consisting of a normal prostate tissue, a non-lethal prostate cancer, and a prostate cancer cell line.

In some embodiments, the likelihood of recurrence of prostate cancer is the likelihood of recurrence of prostate cancer within 20 years from the time when the sample is collected. In some embodiments, the likelihood of recurrence of prostate cancer is the likelihood of recurrence of prostate cancer within 5 years from the time when the sample is collected.

In some embodiments, the expression levels of NEDD9 are mRNA levels. In one embodiment, the expression levels of NEDD9 are measured by a polymerase chain reaction using a first synthetic primer comprising a polynucleotide that hybridizes to the sense strand of a DNA target that comprises a sequence selected from SEQ ID NO: 5, NO: 6, NO: 7 and NO: 8, and a second synthetic primer comprising a polynucleotide that hybridizes to the antisense strand of the DNA target. In a particular embodiment, the polymerase chain reaction further comprises a polynucleotide that hybridizes to the sense or antisense strand of the DNA target, wherein the polynucleotide is conjugated to a detectable moiety.

In some embodiments, the expression levels of NEDD9 are protein levels. In a particular embodiment, the expression levels of NEDD9 are measured by immunohistochemistry using an anti-NEDD9 antibody.

The present disclosure provides a method for treating prostate cancer in a subject with prostate cancer, the method comprising measuring the expression level of NEDD9 in a sample from the subject; comparing the measured expression level of NEDD9 in the sample from the subject to the expression level of NEDD9 in a control sample, and providing a treatment if the expression level of NEDD9 in the sample from the subject is higher than the expression level of NEDD9 in the control sample.

In some embodiments, the sample is from a tumor lesion. In some embodiments, the sample comprises circulating tumor cells. In some embodiments, the prostate cancer is a primary prostate tumor. In some embodiments, the expression levels of NEDD9 are mRNA levels. In some embodiments, the expression levels of NEDD9 are protein levels. In some embodiments, the control sample is selected from the group consisting of a normal prostate tissue, a non-lethal prostate cancer, and a prostate cancer cell line.

In some embodiments, the treatment comprises one or more therapies selected from the group consisting of surgical castration, androgen deprivation therapy, a radiation therapy, an ablation therapy, a chemotherapy, a targeted therapy and an immunotherapy. In some embodiments, the subject is provided with a treatment even if (s)he is identified as a candidate for active surveillance by a method not dependent on the expression level of NEDD9.

The present disclosure provides a method for treating prostate cancer in a subject with prostate cancer, the method comprising measuring the expression level of NEDD9 in a sample from the subject, comparing the measured expression level of NEDD9 in the sample from the subject to the expression level of NEDD9 in a control sample, and monitoring the cancer without providing a treatment if the expression level of NEDD9 in the sample from the subject is about the same as or lower than the expression level of NEDD9 in the control sample.

In some embodiments, the prostate cancer is a primary prostate tumor.

The present disclosure provides a kit comprising a reagent for reverse transcription of an RNA molecule, two or more primers, wherein a first primer comprises a polynucleotide that hybridizes to the sense strand of a DNA target that that comprises a sequence selected from SEQ ID NO: 5, NO: 6, NO: 7 and NO: 8, and a second primer comprises a polynucleotide that hybridizes to the anti-sense strand of the DNA target, and a reagent for amplification of a DNA sequence.

In some embodiments, the kit further comprises a polynucleotide that hybridizes to the sense or antisense strand of the amplified DNA target, wherein the polynucleotide is conjugated to a detectable moiety.

The present disclosure provides a kit comprising an antibody that is capable of binding to NEDD9 and a reagent for the detection of the antibody.

The present disclosure provides a method of determining the likelihood of decreased survival of a subject with prostate cancer, the method comprising measuring the genotype of the rs1910301 SNP in a sample from the subject, and comparing the genotype of the rs1910301 SNP in the sample from the subject to the rs1910301 risk allele A, wherein the likelihood of decreased survival of the subject is higher if the risk allele A of the rs1910301 SNP is present in the sample from the subject.

In some embodiments, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the sample is from a somatic or germline tissue.

In some embodiments, the likelihood of decreased survival is the likelihood of decreased survival within 20 years from the time when the sample is collected. In some embodiments, the likelihood of decreased survival is the likelihood of decreased survival within 5 years from the time when the sample is collected. In some embodiments, the genotype of the rs1910301 SNP is measured by sequencing of a genomic DNA comprising the rs1910301 SNP.

In some embodiments, a genomic DNA comprising the rs1910301 SNP is amplified by polymerase chain reaction using a first synthetic primer comprising a polynucleotide that hybridizes to one strand of a genomic DNA target which locates within 50 kilobases from the rs1910301 SNP on the chromosome, and a second synthetic primer comprising a polynucleotide that hybridizes to one strand of a genomic DNA target which locates within 50 kilobases from the rs1910301 SNP on the chromosome, wherein the two primers hybridize to different chains of the genomic DNA, wherein the two primers locate on different sides of the rs1910301 SNP on the chromosome.

In some embodiments, the genotype of the rs1910301 SNP is measured by hybridizing a genomic DNA comprising the rs1910301 SNP with a polynucleotide comprising the rs1910301 SNP site of risk allele A and at least 7 contiguous nucleotides adjacent to the SNP site on each side.

The present disclosure provides a method for treating prostate cancer in a subject with low-grade prostate cancer, the method comprising measuring the genotype of the rs1910301 SNP in a sample from the subject; comparing the genotype of the rs1910301 SNP in the sample from the subject to the rs1910301 risk allele A, and providing a treatment to the subject if the risk allele A of rs1910301 is present in the sample from the subject.

In some embodiments, the sample is from a tumor lesion. In some embodiments, the sample comprises circulating tumor cells. In some embodiments, the prostate cancer is a primary prostate tumor. In some embodiments, the treatment comprises one or more therapies selected from the group consisting of surgical castration, androgen deprivation therapy, a radiation therapy, an ablation therapy, a chemotherapy, a targeted therapy and an immunotherapy. In some embodiments, the subject is provided with a treatment even if (s)he is identified as a candidate for active surveillance by a method not dependent on the genotype of rs1910301.

The present disclosure provides a method for treating prostate cancer in a subject with prostate cancer comprising measuring the genotype of the rs1910301 SNP in a sample from the subject; comparing the genotype of the rs1910301 SNP in the sample from the subject to the rs1910301 risk allele A, and monitoring the cancer without providing a treatment if the risk allele A of rs1910301 is not present in the sample from the subject.

In some embodiments, the prostate cancer is a primary prostate tumor.

The present disclosure provides a kit comprising a polynucleotide comprising the rs1910301 SNP site of risk allele A and at least 7 contiguous nucleotides adjacent to the SNP site on each side, wherein the polynucleotide is conjugated to a detectable moiety.

The present disclosure provides a kit comprising two or more primers, wherein at least one primer comprises a polynucleotide that hybridizes to one strand of a genomic DNA target which locates within 50 kilobases from the rs1910301 SNP on the chromosome, and at least one other primer comprises a polynucleotide that hybridizes to one strand of a genomic DNA target which locates within 50 kilobases from the rs1910301 SNP on the chromosome, wherein the two primers hybridize to different chains of the genomic DNA, wherein the two primers locate on different sides of the rs1910301 SNP on the chromosome, and a reagent for amplification of a DNA sequence.

In some embodiments, the kit further comprises a polynucleotide comprising the rs1910301 risk allele A, wherein the polynucleotide is conjugated to a detectable moiety.

The present disclosure provides a method of determining the likelihood of increased tumor load of prostate cancer in a subject, comprising measuring the expression level of ZFP36 in a first sample from the subject; measuring the expression level of PTEN in a second sample from the subject; comparing the measured expression level of ZFP36 in the first sample to the expression level of ZFP36 in a first control sample; and comparing the measured expression level of PTEN in the second sample to the expression level of PTEN in a second control sample, wherein the likelihood of increased tumor load of prostate cancer is higher if the expression level of ZFP36 in the first sample is lower than the expression level of ZFP36 in the first control sample, and the expression level of PTEN in the second sample is lower than the expression level of PTEN in the second control sample, and wherein the likelihood of increased tumor load of prostate cancer is lower if the expression level of ZFP36 in the first sample is about the same as or higher than the expression level of ZFP36 in the first control sample, and the expression level of PTEN in the second sample is about the same as or higher than the expression level of PTEN in the second control sample.

In some embodiments, the likelihood of increased tumor load of prostate cancer is the likelihood of increased tumor load of prostate cancer within 20 years from the time when the sample is collected. In some embodiments, the likelihood of increased tumor load of prostate cancer is the likelihood of increased tumor load of prostate cancer within 5 years from the time when the sample is collected.

The present disclosure provides a method of determining the likelihood of decreased survival of a subject with prostate cancer, comprising measuring the expression level of ZFP36 in a first sample from the subject; measuring the expression level of PTEN in a second sample from the subject; comparing the measured expression level of ZFP36 in the first sample to the expression level of ZFP36 in a first control sample; and comparing the measured expression level of PTEN in the second sample to the expression level of PTEN in a second control sample, wherein the likelihood of decreased survival of the subject is higher if the expression level of ZFP36 in the first sample is lower than the expression level of ZFP36 in the first control sample, and the expression level of PTEN in the second sample is lower than the expression level of PTEN in the second control sample.

In some embodiments, the likelihood of decreased survival is the likelihood of decreased survival within 20 years from the time when the sample is collected. In some embodiments, the likelihood of decreased survival is the likelihood of decreased survival within 5 years from the time when the sample is collected.

The present disclosure provides a method of determining the likelihood of recurrence of prostate cancer in a subject, comprising measuring the expression level of ZFP36 in a first sample from the subject; measuring the expression level of PTEN in a second sample from the subject; comparing the measured expression level of ZFP36 in the first sample to the expression level of ZFP36 in a first control sample; and comparing the measured expression level of PTEN in the second sample to the expression level of PTEN in a second control sample, wherein the likelihood of recurrence of prostate cancer is higher if the expression level of ZFP36 in the first sample is lower than the expression level of ZFP36 in the first control sample, and the expression level of PTEN in the second sample is lower than the expression level of PTEN in the second control sample.

In some embodiments, the likelihood of recurrence of prostate cancer is the likelihood of recurrence of prostate cancer within 20 years from the time when the sample is collected. In some embodiments, the likelihood of recurrence of prostate cancer is the likelihood of recurrence of prostate cancer within 5 years from the time when the sample is collected.

In some embodiments of the two methods provided supra, the prostate cancer is a primary prostate tumor. In some embodiments, the prostate cancer is metastatic prostate cancer. In some embodiments, the subject is a human.

In some embodiments, the first sample is from a tumor lesion. In some embodiments, the first sample comprises circulating tumor cells. In some embodiments, the second sample is from a tumor lesion. In some embodiments, the second sample comprises circulating tumor cells. In some embodiments, the first sample and the second sample are the same sample. In some embodiments, the first sample and the second sample are different samples.

In some embodiments, the first control sample is selected from the group consisting of a normal prostate tissue, a non-lethal prostate cancer, and a prostate cancer cell line. In some embodiments, the second control sample is selected from the group consisting of a normal prostate tissue, a non-lethal prostate cancer, and a prostate cancer cell line.

In some embodiments, the expression levels of ZFP36 are mRNA levels. In some embodiments, the expression levels of ZFP36 are measured by a polymerase chain reaction using a first synthetic primer comprising a polynucleotide that hybridizes to the sense strand of a DNA target comprising the sequence of SEQ ID NO: 2 and a second synthetic primer comprising a polynucleotide that hybridizes to the antisense strand of the DNA target. In some embodiments, the polymerase chain reaction further comprises a polynucleotide that hybridizes to the sense or antisense strand of the DNA target, wherein the polynucleotide is conjugated to a detectable moiety.

In some embodiments, the expression levels of ZFP36 are protein levels. In some embodiments, the expression levels of ZFP36 are measured by immunohistochemistry using an anti-ZFP36 antibody.

In some embodiments, the expression levels of PTEN are mRNA levels. In some embodiments, the expression levels of PTEN are measured by a polymerase chain reaction using a first synthetic primer comprising a polynucleotide that hybridizes to the sense strand of a DNA target comprising the sequence of SEQ ID NO: 15, 16, or 17, and a second synthetic primer comprising a polynucleotide that hybridizes to the antisense strand of the DNA target. In some embodiments, the polymerase chain reaction further comprises a polynucleotide that hybridizes to the sense or antisense strand of the DNA target, wherein the polynucleotide is conjugated to a detectable moiety.

In some embodiments, the expression levels of PTEN are protein levels. In some embodiments, the expression levels of PTEN are measured by immunohistochemistry using an anti-PTEN antibody.

In some embodiments, the method further comprises providing a treatment if the expression level of ZFP36 in the first sample is lower than the expression level of ZFP36 in the first control sample, and the expression level of PTEN in the second sample is lower than the expression level of PTEN in the second control sample. In some embodiments, the method further comprises monitoring the cancer without providing a treatment if the expression level of ZFP36 in the first sample is about the same as or higher than the expression level of ZFP36 in the first control sample, and the expression level of PTEN in the second sample is lower than the expression level of PTEN in the second control sample.

The present disclosure provides a kit comprising a reagent for reverse transcription of an RNA molecule; two or more primers, wherein a first primer comprises a polynucleotide that hybridizes to the sense strand of a DNA target comprising the sequence of SEQ ID NO: 2, and a second primer comprises a polynucleotide that hybridizes to the anti-sense strand of the DNA target; two or more primers, wherein a first primer comprises a polynucleotide that hybridizes to the sense strand of a DNA target comprising the sequence of SEQ ID NO: 15, 16, or 17, and a second primer comprises a polynucleotide that hybridizes to the anti-sense strand of the DNA target; and a reagent for amplification of a DNA sequence.

In some embodiments, the kit further comprises a polynucleotide that hybridizes to the sense or antisense strand of the amplified DNA target, wherein the polynucleotide is conjugated to a detectable moiety.

The present disclosure provides a kit comprising a first antibody that is capable of binding to ZFP36; a second antibody that is capable of binding to PTEN; a first reagent for the detection of the first antibody; and a second reagent for the detection of the second antibody.

The present disclosure provides a method of measuring the expression level of ZFP36 in a subject having prostate cancer, the method comprising measuring the binding of a first probe in a sample from the subject, wherein the first probe specifically hybridizes to a nucleic acid having the sequence set forth in SEQ ID NO: 2, thereby measuring expression of ZFP36 in the subject.

In some embodiments, the method further comprises amplifying a first target nucleic acid comprising at least 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 nucleotides of SEQ ID NO: 2 by a polymerase chain reaction using (a) a first synthetic primer comprising a polynucleotide that hybridizes to the sense strand of the first target nucleic acid; and (b) a second synthetic primer comprising a polynucleotide that hybridizes to the antisense strand of the first target nucleic acid. In some embodiments, the first probe is conjugated to a detectable moiety.

The present disclosure provides a method of measuring the expression level of ZFP36 in a subject having prostate cancer, the method comprising measuring the binding of a first antibody in a sample from the subject, wherein the first antibody specifically binds to ZFP36, thereby measuring expression of ZFP36 in the subject.

In some embodiments, the expression level of ZFP36 is measured by immunohistochemistry using the first antibody.

In some embodiments, the method further comprises measuring the binding of a second probe in the sample from the subject, wherein the second probe specifically hybridizes to a nucleic acid having the sequence set forth in SEQ ID NO: 15, 16, or 17, thereby measuring expression of PTEN in the subject. In some embodiments, the method further comprising amplifying a second target nucleic acid comprising at least 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 nucleotides of SEQ ID NO: 15, 16, or 17 by a polymerase chain reaction using (a) a third synthetic primer comprising a polynucleotide that hybridizes to the sense strand of the second target nucleic acid; and (b) a fourth synthetic primer comprising a polynucleotide that hybridizes to the antisense strand of the second target nucleic acid. In some embodiments, the second probe is conjugated to a detectable moiety.

In some embodiments, the method further comprises measuring the binding of a second antibody in a sample from the subject, wherein the second antibody specifically binds to PTEN, thereby measuring expression of PTEN in the subject. In some embodiments, the expression level of PTEN is measured by immunohistochemistry using the second antibody.

The present disclosure provides a method of measuring the expression level of NEDD9 in a subject having prostate cancer, the method comprising measuring the binding of a probe in a sample from the subject, wherein the probe specifically hybridizes to a nucleic acid having the sequence set forth in SEQ ID NO: 5, 6, 7, or 8, thereby measuring expression of NEDD9 in the subject. In some embodiments, the method further comprises amplifying a target nucleic acid comprising at least 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 nucleotides of SEQ ID NO: 5, 6, 7, or 8 by a polymerase chain reaction using (a) a first synthetic primer comprising a polynucleotide that hybridizes to the sense strand of the target nucleic acid; and (b) a second synthetic primer comprising a polynucleotide that hybridizes to the antisense strand of the target nucleic acid. In some embodiments, the probe is conjugated to a detectable moiety.

The present disclosure provides a method of measuring the expression level of NEDD9 in a subject having prostate cancer, the method comprising measuring the binding of an antibody in a sample from the subject, wherein the antibody specifically binds to NEDD9, thereby measuring expression of NEDD9 in the subject. In some embodiments, the expression level of NEDD9 is measured by immunohistochemistry using the antibody.

The present disclosure provides a method of measuring the genotype of the rs1910301 SNP in a subject having prostate cancer, the method comprising sequencing of a genomic DNA comprising the rs1910301 SNP.

The present disclosure provides a method of measuring the genotype of the rs1910301 SNP in a subject having prostate cancer, the method comprising hybridizing a genomic DNA comprising the rs1910301 SNP with a polynucleotide comprising the rs1910301 SNP site of risk allele A and at least 7 contiguous nucleotides adjacent to the SNP site on each side.

In some embodiments of the six methods provided supra, the prostate cancer is a primary prostate tumor. In some embodiments, the prostate cancer is metastatic prostate cancer. In some embodiments, the subject is a human. In some embodiments, the sample is from a tumor lesion. In some embodiments, the sample comprises circulating tumor cells. In some embodiments, the sample is from a somatic or germline tissue.

DETAILED DESCRIPTION

Figure 1:
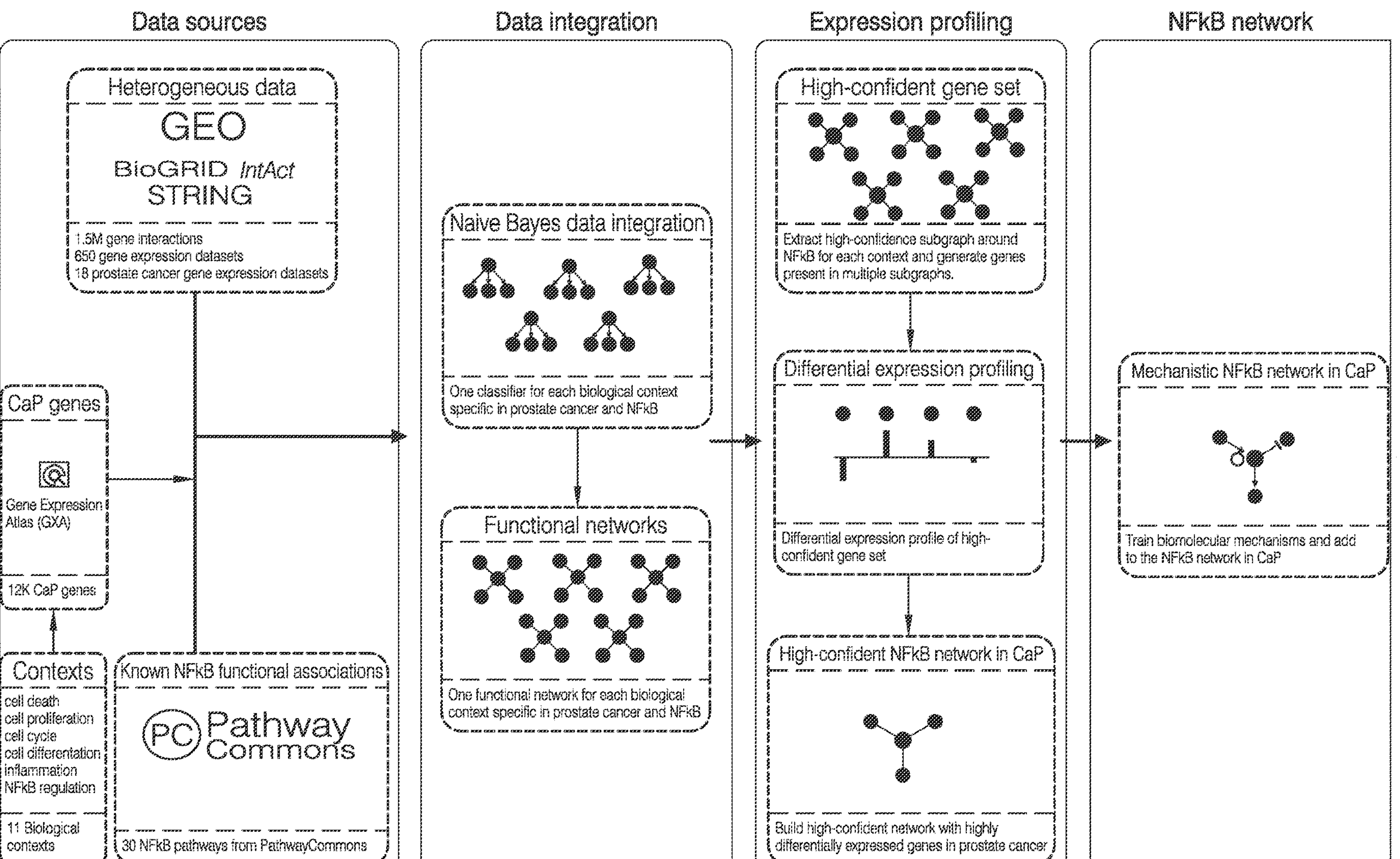
FIG. 1 is a schematic summary of data-mining process. The left columns depict the mining of the 878 publically available databases which lead to the creation of the biological context specific networks. High-confidence subgraphs around the NF-κB gene were identified in each context specific network and assessed by an additional set of hierarchical mechanism-specific learners to create a complete inferred biomolecular pathway. This identified both characterized and novel NF-κB interactors in prostate cancer. A high-confidence NF-κB network was created involving 351 selected NF-κB related genes and 271 of them were in the 6096 gene cDNA-mediated Annealing, Selection, extension, and Ligation (DASL) gene expression database annotated with lethal versus not lethal outcome from Physicians Health Study (PHS) cohort of patients (middle figure of third panel). This was used to refine the gene set to those associated with lethal prostate cancer (31 genes). The 31 genes were then used to define a network of NF-κB cancer promoting genes in prostate cancer (fourth panel).
Figure 2A:
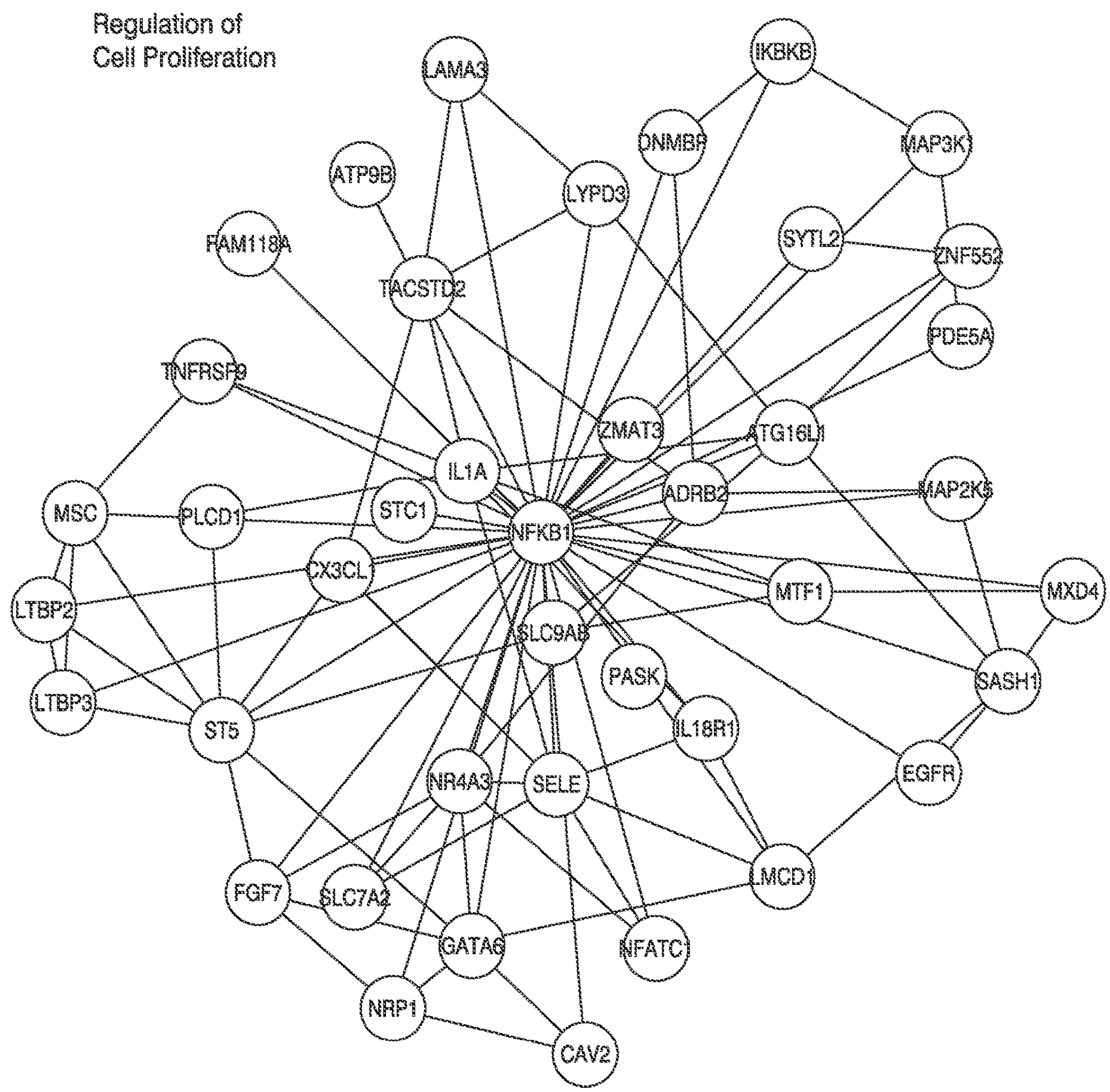
FIG. 2A shows NF-κB networks the biological contexts of regulation of cell proliferation. The intensity of the lines resembles the strength of association—the darker a line is, the stronger the association is between the two molecules connected by the line.
Figure 2B:
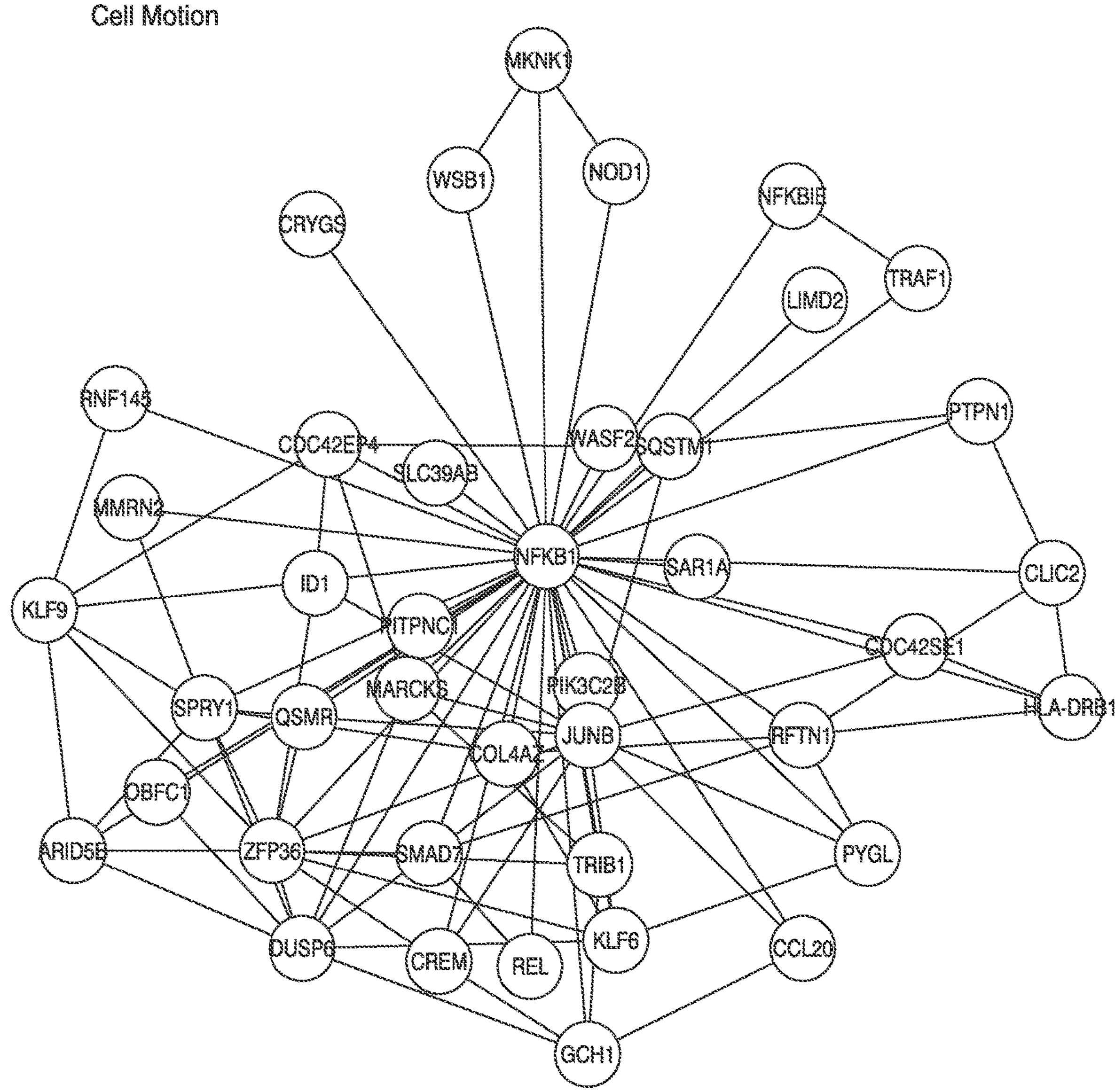
FIG. 2B shows NF-κB networks the biological contexts of regulation of cell motion. The intensity of the lines resembles the strength of association—the darker a line is, the stronger the association is between the two molecules connected by the line.
Figure 2C:
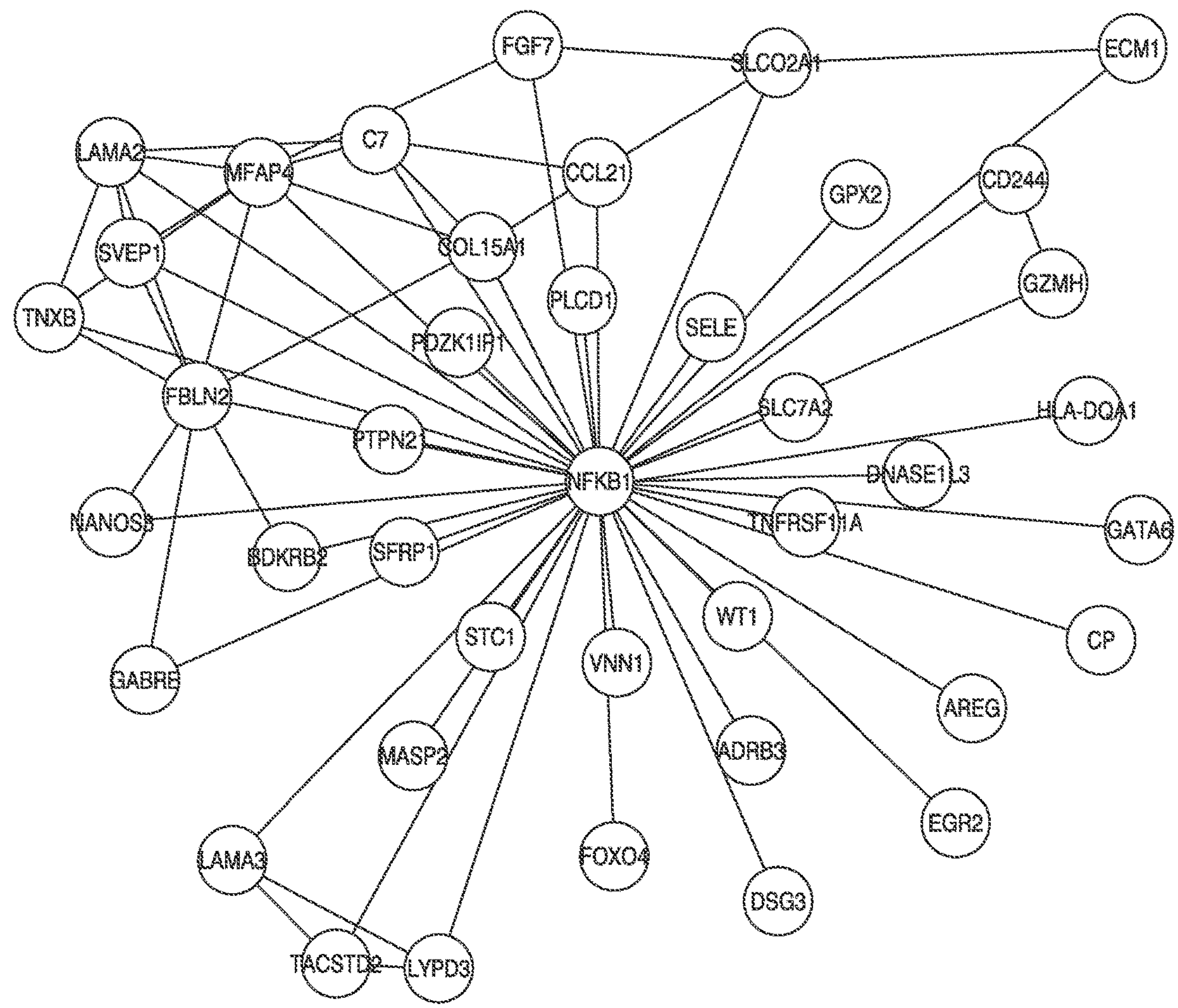
FIG. 2C shows NF-κB networks the biological contexts of cell death. The intensity of the lines resembles the strength of association—the darker a line is, the stronger the association is between the two molecules connected by the line.
Figure 2D:
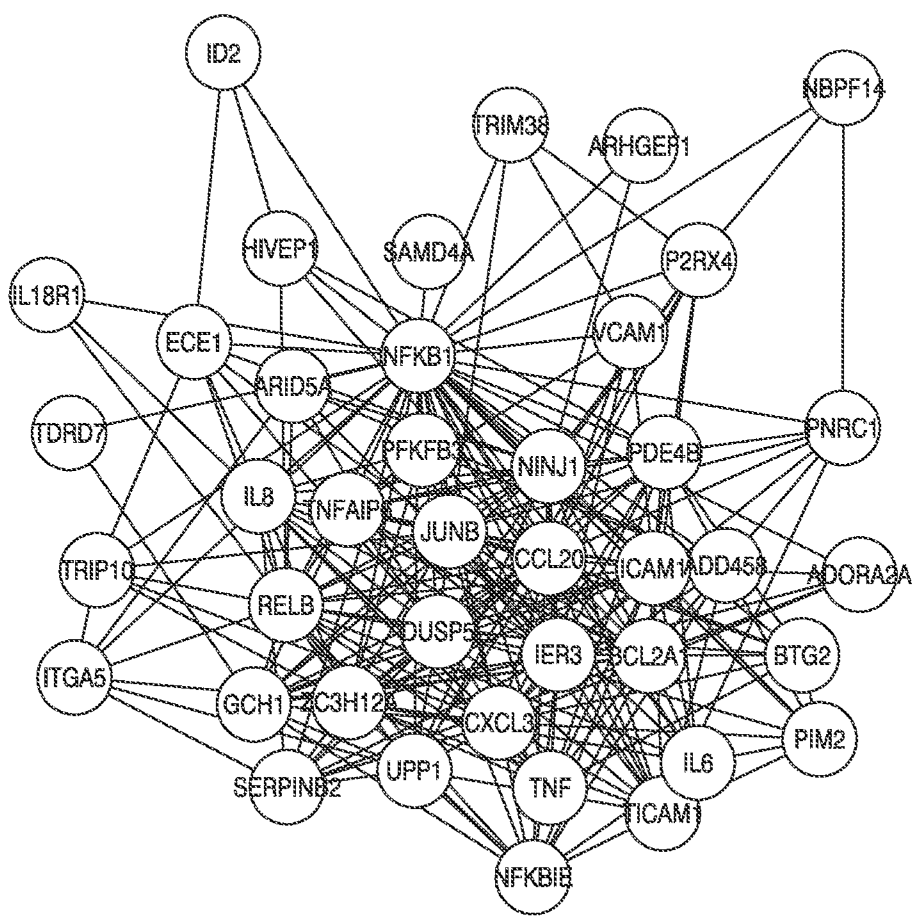
FIG. 2D shows NF-κB networks the biological contexts of positive regulation of NF-κB. The intensity of the lines resembles the strength of association—the darker a line is, the stronger the association is between the two molecules connected by the line.
Figure 3:
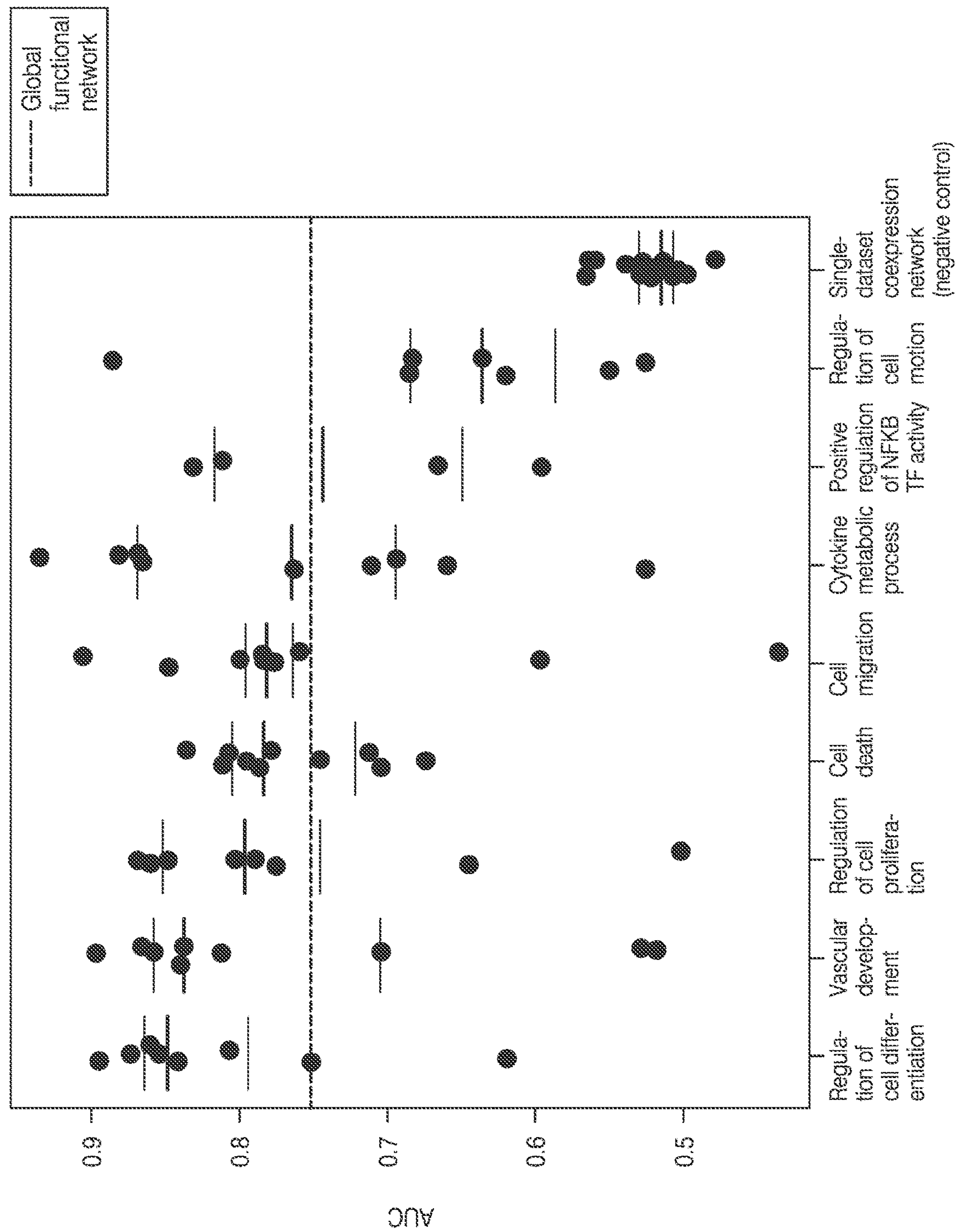
FIG. 3 shows the performance of eight context-specific inferred networks compared with the performance of a non-context-specific global inferred network (dotted horizontal line) and a control of coexpression networks from 18 curated prostate cancer specific single expression datasets.

The present disclosure identifies novel factors associated with prostate cancer progression. A systems biology approach was taken to integrate epidemiological, clinical, pathological and biological data that implicate Nuclear factor kappa B (NF-κB) activation in the development of lethal prostate cancer. A number of NF-κB related genes associated with prostate cancer progression were identified. Among them a lower expression of ZFP36 is strongly associated with a poorer prognosis, including faster cancer cell growth, cancer recurrence and lethality. ZFP36 interacts with NEDD9, another NF-κB related gene whose higher expression is associated with prostate cancer lethality. The expression levels of ZFP36 and NEDD9 are positively correlated. Higher NEDD9 expression is also associated with faster cancer cell growth and cancer recurrence. In addition, the risk allele A of a single nucleotide polymorphism (SNP) rs1910301 is associated with prostate cancer lethality.

In certain embodiments, the expression level of ZFP36 is examined using a sample of prostate cancer that has been removed from a subject by surgery or biopsy. The expression level in the sample from the subject is compared to the level in a control sample. If the ZFP36 level is lower in the sample from the subject, the likelihood of increased tumor load, cancer recurrence and lethality is high, and more aggressive monitoring or treatment of the prostate cancer may be recommended. If the ZFP36 level is about the same or higher in the sample from the subject, the subject is identified to be at a low risk of increased tumor load, cancer recurrence and lethality, in which case no additional monitoring or treatment is needed.

In certain embodiments, the sample is examined while it is scored according to the Gleason pathological grading. In one embodiment, the expression level of ZFP36 is measured by immunohistochemistry. In another embodiment, one or more other tumor antigens (e.g. prostate-specific antigen, PTEN) are examined simultaneously, either by a similar method or by a different method. In some embodiments, a plurality of markers is used to predict prostate cancer prognosis. In certain embodiments, a patient with low grade prostate cancer is identified as a candidate for surgery, radiation or adjuvant therapy such as androgen deprivation therapy rather than a candidate for active surveillance of the localized disease if the expression of ZFP36 is low in the cancer cells, wherein the cancer cells are collected directly from a tumor lesion, from a draining lymph node, or from a body fluid such as blood.

In certain embodiments, the genotype of the SNP rs1910301 is examined using a sample of somatic or germline DNA that has been removed from a subject by swab of buccal mucosa or sample of blood. The genotype of rs1910301 in the sample is measured. If the risk allele A is present, the likelihood of cancer lethality is high and more aggressive monitoring or treatment of the prostate cancer may be recommended. In one embodiment, a man who should be screened for prostate cancer more frequently or starting at an earlier age is identified if he carries the risk allele A. In another embodiment, a patient with low grade prostate cancer is identified as a candidate for surgery, radiation or adjuvant therapy such as androgen deprivation therapy rather than a candidate for active surveillance of his localized disease if he carries the risk allele A. In another embodiment, a patient with low grade prostate cancer is treated with surgery, radiation or adjuvant therapy such as androgen deprivation therapy rather than receiving active surveillance of his localized disease if he carries the risk allele A. If the risk allele A is not detected, the subject is identified to be at a low risk of cancer lethality, in which case less intense monitoring or treatment is needed.

In certain embodiments, the risk assessment based on ZFP36 expression level and/or rs1910301 genotype is followed by a treatment. Where ZFP36 expression level of a sample from a subject is lower than the level of a control sample, and/or if the risk allele A of rs1910301 is present in a sample from a subject, the subject may be treated by an anti-cancer therapy, such as an immunotherapy, a chemotherapy, a targeted therapy, a radiation therapy, an ablation therapy and/or an androgen deprivation therapy rather than receiving an active surveillance of their localized disease even if they are otherwise a candidate for active surveillance by another diagnostic standard.

As used herein, a "subject" within the context of the present invention encompasses, but is not limited to, a mammal, e g a human, a domestic animal or a livestock including a cat, a dog, a cattle and a horse.

"Prostate cancer" encompasses, but is not limited to, a primary prostate tumor, metastatic prostate cancer, prostate adenocarcinoma, and neuroendocrine prostate cancer.

"A primary prostate tumor" encompasses, but is not limited to, a tumor localized in the prostate gland and/or surrounding areas.

"Metastatic prostate cancer" encompasses, but is not limited to, a cancer of prostate origin that spreads to one or more other parts of the body.

"Increased tumor load" encompasses, but is not limited to, an increased number of cancer cells, an increased size of a tumor, and/or an increased amount of cancer in the body. The tumor load may be determined by measuring the tumor size and/or by measuring a tumor antigen. A commonly used tumor antigen for prostate cancer is prostate-specific antigen (PSA).

"Monitoring the cancer" encompasses, but is not limited to, measuring the number of cancer cells, measuring the size of tumor, and/or measuring the amount of cancer in the subject at least once every three months, at least once every six months, at least once a year, or at least once every two years.

"Decreased survival of a subject" encompasses, but is not limited to, shorter time of survival of a subject.

"Recurrence of prostate cancer" means the return of prostate cancer after initial treatment and after a period of time during which the cancer cannot be detected. The initial treatment of prostate cancer encompasses, but is not limited to, an androgen deprivation therapy such as a prostatectomy.

"A sample" encompasses, but is not limited to, a sample from a tumor lesion, a sample from a cancer draining lymph node, a body fluid such as blood, serum, plasma, urine, semen, lymph, and peritoneal fluid.

"Circulating tumor cells" encompass, but are not limited to, cells with a tumor origin in the circulating blood stream. In certain embodiments, the circulating tumor cells are enriched from the blood.

"A tumor lesion" encompasses, but is not limited to, a tissue, organ or structure wherein a prostate tumor or prostate cancer locates. It may be in or attached to a prostate, or at a metastatic site.

"A control sample" encompasses, but is not limited to, a normal prostate tissue obtained from a subject that does not have prostate cancer, wherein the tissue is either fresh or has been preserved in a way that does not significantly affect the abundance of nucleic acids or proteins in the sample. "A control sample" also encompasses a sample that has been determined to have a similar expression level of ZFP36 and/or NEDD9 compared to a normal prostate tissue.

"The expression level of ZFP36" means the amount of ZFP36 mRNA or the amount of ZFP36 protein. The mRNA amount can be measured by polymerase chain reaction (PCR) following reverse transcription, nucleic acid hybridization methods such as microarray, and RNA sequencing methods. The protein amount can be measured by mass spectrometry or by antibody-based methods, such as immunohistochemistry, enzyme-linked immunosorbent assay (ELISA), Western blotting, flow cytometry, and immunoelectron microscopy.

"The expression level of ZFP36 in the sample from the subject is lower than the expression level of ZFP36 in the control sample" means the amount of ZFP36 mRNA or protein is lower than 95%, 90%, 80%, 70%, 60%, 50%, 40%, 30%, 20% or 10% of the expression level of ZFP36 in the control sample.

"The expression level of ZFP36 in the sample from the subject is about the same as or higher than the expression level of ZFP36 in the control sample" means the amount of ZFP36 mRNA or protein is higher than 99%, 100%, 110%, 120%, 130%, 140%, 150%, 200%, 300%, 500% or 1000% of the expression level of ZFP36 in the control sample.

"A non-lethal prostate cancer" means a prostate cancer that does not lead to mortality of the subject who has the cancer within 1, 2, 5, 10, 20, 30, 40 or 50 years.

"Surgical castration" encompasses, but is not limited to, orchiectomy i.e. surgical removal of testicles.

"Androgen deprivation therapy" encompasses, but is not limited to, (1) surgical castration; (2) medical castration e.g. luteinizing hormone-releasing hormone (LHRH) agonists and antagonists, including degarelix, abiraterone, leuprolide, goserelin, triptorelin and histrelin; (3) androgen receptor antagonists including flutamide, bicalutamide, nilutamide, enzalutamide, apalutamide, cyproterone, abiraterone, topilutamide, galeterone, orteronel, BAY1841788, ORM-15341; (4) 5α-reductase inhibitors including finasteride, dutasteride, bexlosteride, izonsteride, turosteride and episteride; and (5) other androgen-suppressing drugs including estrogens, megestrol, chlormadinone, ketoconazole, dexamethasone and prednisone. These compounds can be used in their final non-salt form or in the form of a pharmaceutically acceptable salt, which can be derived from various organic and inorganic acids and bases by procedures known in the art.

"A radiation therapy" encompasses, but is not limited to, localized therapy of prostate cancer by a certain level of radiation from an external beam and/or internal radioactive seeds placed into the prostate.

"An ablation therapy" means a therapy that attacks a tumor by exposing the tumor to higher or lower local temperature than a normal body temperature using a probe. The probe is placed into the tumor and mediates the generation of heat or coldness. Ablation therapies encompass, but are not limited to, radiofrequency therapy, cryotherapy, microwave therapy and focused ultrasound therapy.

"A chemotherapy" means one or more anti-cancer chemical substances. It encompasses, but is not limited to, (1) a mitotic inhibitor e.g. a taxane, an epothilone, a *vinca* alkaloid, an estramustine, (2) an alkylating agent e.g. a nitrogen mustard, a nitrosourea, an alkyl sulfonate, a triazine, an ethylenimine, (3) an antimetabolite, e.g. 5-fluorouracil, 6-mercaptopurine, capecitabine, cytarabine, floxuridine, fludarabine, gemcitabine, hydroxyurea, methotrexate, pemetrexed, (4) an anti-tumor antibiotic e.g. an anthracycline, actinomycin D, bleomycin, mitomycin C, (5) a topoisomerase inhibitor e.g. topotecan, irinotecan, etoposide, teniposide, mitoxantrone, (6) a corticosteroid e.g. prednisone, methylprednisolone, dexamethasone, and (7) other chemotherapy drugs e.g. L-asparaginase, bortezomib.

"A targeted therapy" means a therapy designed to act on a specific molecular target associated with cancer to interfere with tumor growth and progression. In certain embodiments, the specific molecular target is expressed at a higher amount in cancer cells than in most non-cancer cells. In certain embodiments, the specific molecular target is expressed in a different form in cancer cells from the form expressed in most non-cancer cells. For instance, the target expressed in cancer cells may be a transcript variant or a mutation. Targeted therapies for prostate cancer encompass, but are not limited to, angiogenesis inhibitors e.g. thalidomide.

"An immunotherapy" means a therapy designed to use a subject's immune system to treat cancer. It encompasses, but is not limited to, (1) a cancer vaccine e.g. a vaccine containing prostate-specific antigen (PSA), (2) a monoclonal antibody designed to have affinity to cancer cells, and (3) an immune checkpoint inhibitor e.g. an anti-CTLA-4 antibody, an anti-PD-1 antibody, an anti-PD-L1 antibody.

"A method not dependent on the expression level of ZFP36" encompasses, but is not limited to, examination of tumor load, examination of Gleason score, examination of one or more biomarkers. The biomarkers include but are not limited to PTEN.

"An increased frequency" means a higher frequency of prostate cancer screening than the frequency at which a subject not identified to be at risk is screened. It also encompasses using one or more screening method different from the method by which a subject not identified to be at risk is screened.

"An earlier age" means an earlier age than the age at which a subject not identified to be at risk starts to receive prostate cancer screening. In certain embodiments, the age at which a subject not identified to be at risk starts to receive prostate cancer screening is 40, 45, 50, 55, 60, 65, or 70 years of age.

"A method not dependent on the expression level of NEDD9" encompasses, but is not limited to, examination of tumor load, examination of Gleason score, examination of one or more biomarkers. The biomarkers include but are not limited to PTEN.

"A method not dependent on the genotype of rs1910301" encompasses, but is not limited to, examination of tumor load, examination of Gleason score, examination of one or more biomarkers. The biomarkers include but are not limited to PTEN.

"The expression level of NEDD9" means the amount of NEDD9 mRNA or the amount of NEDD9 protein. The mRNA amount can be measured by polymerase chain reaction (PCR) following reverse transcription, nucleic acid hybridization methods such as microarray, and RNA sequencing methods. The protein amount can be measured by mass spectrometry or by antibody-based methods, such as immunohistochemistry, enzyme-linked immunosorbent assay (ELISA), Western blotting, flow cytometry, and immuno-electron microscopy.

"The expression level of NEDD9 in the sample from the subject is lower than the expression level of NEDD9 in the control sample" means the amount of NEDD9 mRNA or protein is lower than 95%, 90%, 80%, 70%, 60%, 50%, 40%, 30%, 20% or 10% of the expression level of NEDD9 in the control sample.

"The expression level of NEDD9 in the sample from the subject is about the same as or higher than the expression level of NEDD9 in the control sample" means the amount of NEDD9 mRNA or protein is higher than 99%, 100%, 110%, 120%, 130%, 140%, 150%, 200%, 300%, 500% or 1000% of the expression level of NEDD9 in the control sample.

"A reagent for reverse transcription of an RNA molecule" encompasses, but is not limited to, a reverse transcriptase, an RNase inhibitor, a primer that hybridizes to an mRNA sequence, a primer that hybridizes to an adenosine oligonucleotide, and a buffer solution that provides a suitable chemical environment for optimum activity, binding kinetics, and stability of the reverse transcriptase. The reagents can be provided in the form of a solution, a concentrated solution, or powder.

"A primer" refers to a short, single-stranded DNA sequence that binds to a target DNA sequence and enables addition of new deoxyribonucleotides by DNA polymerase at the 3' end. In certain embodiments, the forward primer is 18-35, 19-32 or 21-31 nt in length. The nucleotide sequence of the forward primer is not limited, so long as it specifically hybridizes with part of or an entire target site, and its Tm value may be within a range of 50° C. to 72° C., in particular may be within a range of 58° C. to 61° C., and may be within a range of 59° C. to 60° C. The nucleotide sequence of the primer may be manually designed to confirm the Tm value using a primer Tm prediction tool.

"A reagents for amplification of a DNA sequence" includes, but is not limited to, (1) a heat-stable DNA polymerase, (2) deoxynucleotide triphosphates (dNTPs), (3) a buffer solution, providing a suitable chemical environment for optimum activity, binding kinetics, and stability of the DNA polymerase, (4) bivalent cations such as magnesium or manganese ions, and (5) and monovalent cations, such as potassium ions. The reagents can be provided in the form of a solution, a concentrated solution, or powder. The target DNA sequence can be amplified by polymerase chain reaction (PCR). PCR relies on thermal cycling, which consists of cycles of repeated heating and cooling of the reaction for DNA denaturation, annealing and enzymatic elongation of the amplified DNA. First, the strands of the DNA are separated at a high temperature in a process called DNA melting or denaturing. Next, the temperature is lowered, allowing the primers and the strands of DNA to selectively anneal, creating templates for the polymerase to amplify the target DNA. Next, at a working temperature of the DNA polymerase, template-dependent DNA synthesis occurs. These steps are repeated.

"A polynucleotide that hybridizes to the sense or antisense strand of the amplified DNA target, wherein the polynucleotide is conjugated to a detectable moiety" encompasses, but is not limited to, a polynucleotide about 18-35, 19-32 or 21-31 nt in length that can hybridize to a PCR product of DNA target amplification. The detectable moiety encompasses, but is not limited to, a fluorescent agent, a catalyst that catalyzes a luminescent reaction, and a catalyst that catalyzes a colorimetric reaction. The detectable moiety is either exposed or masked upon the binding of the polynucleotide to the PCR product of DNA target amplification.

"A polynucleotide comprising the rs1910301 risk allele A" encompasses, but is not limited to, a polynucleotide about 18-35, 19-32 or 21-31 nt in length that can hybridize to a DNA target comprising rs1910301, wherein the hybridization binding affinity is decreased where the DNA target comprises an allele other than the risk allele A.

"A detectable moiety" encompasses, but is not limited to, a fluorescent agent, a catalyst that catalyzes a luminescent reaction, and a catalyst that catalyzes a colorimetric reaction. The detectable moiety is either exposed or masked upon the hybridization of the polynucleotide to the DNA target.

"An antibody that is capable of binding to ZFP36" encompasses, but is not limited to, an anti-ZFP36 antiserum, an anti-ZFP36 polyclonal antibody, an anti-ZFP36 monoclonal antibody, an antigen-binding fragment of an anti-ZFP36 antibody, a variable fragment of an anti-ZFP36 antibody, and a protein that binds to ZFP36 specifically.

"An antibody that is capable of binding to NEDD9" encompasses, but is not limited to, an anti-NEDD9 antiserum, an anti-NEDD9 polyclonal antibody, an anti-NEDD9 monoclonal antibody, an antigen-binding fragment of an anti-NEDD9 antibody, a variable fragment of an anti-NEDD9 antibody, and a protein that binds to NEDD9 specifically.

"A reagent for the detection of" an antibody encompasses, but is not limited to, a fluorescent agent, a catalyst that catalyzes a luminescent reaction, a catalyst that catalyzes a colorimetric reaction, and an electron-dense agent. The reagents may be linked to the antibody covalently or associated with the antibody noncovalently through an intermolecular interaction or through one or more intermediates. The intermediate includes an agent comprising a moiety that binds to the antibody.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a “nucleic acid” is meant any two or more covalently bonded nucleotides or nucleotide analogs or derivatives. As used herein, this term includes, without limitation, DNA, RNA, and PNA. The term “nucleic acid” may include a modified nucleic acid, and, accordingly, nucleic acid and modified nucleic acid may be used interchangeably.

“Genomic DNA” encompasses, but is not limited to, a chromosomal DNA or a fragment thereof, and a nucleic acid (e.g., DNA) amplified from (e.g., by polymerase chain reaction) a chromosomal DNA or a fragment thereof.

Furthermore, in accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York (herein “Sambrook et al., 1989”); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The present disclosure also provides recombinant expression vectors which include the synthetic, genomic, or cDNA-derived nucleic acid fragments of the invention, i.e. polynucleotides encoding the proteins of the invention. The nucleotide sequence coding for any of the sequences provided herein can be inserted into an appropriate expression vector, i.e., a vector that contains the necessary elements for the transcription and translation of the inserted protein-coding sequence. The necessary transcriptional and translational signals can also be supplied by the native or source gene and/or its flanking regions.

A variety of host vector systems may be utilized to express the recombinant expression vectors of the invention. These include, but are not limited to, mammalian cell systems infected with recombinant virus (e.g., vaccinia virus, adenovirus, retroviruses, etc.); mammalian cell systems transfected with recombinant plasmids; insect cell systems infected with recombinant virus (e.g., baculovirus); microorganisms such as yeast containing yeast expression vectors, or bacteria transformed with recombinant bacteriophage DNA, recombinant plasmid DNA, or cosmid DNA (see, for example, Goeddel, 1990).

Mammalian expression vectors may comprise non-transcribed elements such as origin of replication, a suitable promoter and enhancer linked to the recombinant nucleic acid to be expressed, and other 5' or 3' flanking sequences such as ribosome binding sites, a polyadenylation sequence, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (SV40), and human cytomegalovirus, including the cytomegalovirus immediate-early gene 1 promoter and enhancer (CMV).

The following examples are provided to further elucidate the advantages and features of the present application, but are not intended to limit the scope of the application. The examples are for illustrative purposes only.

EXAMPLES

Example 1: Gene Expression Data Revealed NF-κB Networks in Multiple Biological Contexts To determine whether a set of genes and/or proteins indicative of NF-κB activation were associated with lethal prostate cancer, whole genome expression profiling and analysis of lethal versus non-lethal prostate cancer was performed. Datasets from 18 curated prostate cancer expression datasets, GEO (Barrett et al., 2009), ArrayExpress (Parkinson et al., 2009) and non-condition-specific genomic data such as physical and genetic interactions from BioGRID (Breitkreutz et al., 2008) and IntAct (Kerrien et al., 2007), transcriptional regulatory relationships from Transfac (Matys et al., 2006) and cisRED (Robertson et al., 2006), and miRNA data from miRBase (Griffiths-Jones, 2006) were integrated. NF-κB related genes were enriched and networks were built. This data-mining process is illustrated in FIG. 1.

NF-κB networks were also generated for distinct biological processes. 11 networks were developed and analyzed, among which four are shown in FIGS. 2A, 2B, 2C and 2D. The four networks were built in the biological contexts of regulation of cell proliferation, regulation of cell motion, cell death, and positive regulation of NF-κB.

The ability of the NF-κB context specific networks to predict biomolecular mechanisms in pathway-specific functional relationship networks in prostate cancer was assessed using receiver operating characteristic (ROC) curves. 7 of 8 predictions achieved areas under curve (AUCs) over 0.7 for all specific mechanistic interaction types and over 0.75 for general functional associations, both using 10-fold gene-holdout-based cross-validations. The cell death network included several highest-confidence links between NF-κB and characterized examples such as CCL217 (regulatory), HDAC118 (phosphorylation) and IKBKB19 (physical). This computational method can integrate thousands of experimental results and to identify those data most informative regarding specific putative mechanisms of interaction in pathways surrounding genes of interest in cancer.

Example 2: NF-κB Related Genes were Identified to be Associated with Lethal Prostate Cancer Genes associated with lethal prostate cancer were identified in a database of patients from the Physicians Health Study with clinical annotation connected to gene expression profile data developed from a 6,096 gene DASL platform. 217 of the 351 genes from the context specific networks were on the 6,096 gene DASL. An assessment of the differential gene expression was done of the 217 NF-κB related genes to identify genes associated with lethal prostate cancer. There were 115 PHS patients (83 indolent, 32 lethal). The DASL data was presented as difference between the mean log expression in the lethal group and in the indolent group, and a minus result indicated a lower expression level in the lethal group than in the indolent group. Differential gene expression was inferred using the limma software package linear model for microarray data. An analysis was performed with or without Gleason grade as an additional covariate.

The PHS subset without Gleason grade as a covariate was analyzed first. 186 of the 6096 genes on the DASL platform were differentially expressed between men who underwent a prostatectomy and relapsed and died of prostate cancer (N=32 lethal disease) compared with those who did not relapse after a prostatectomy or had an indolent disease that did not require a prostatectomy (N=83 non-lethal disease). FDR correction was performed using Benjamini-Hochberg method. 19 of these genes were associated with the NF-κB network (Table 1).

TABLE 1

NF-κB related genes differentially expressed in lethal versus indolent prostate cancer identified from the PHS subset when analyzed without Gleason score as a covariate.

| | logFC | t | adj P Val | rank | observed score |
|---|---|---|---|---|---|
| FOSB | −1.22 | −5.53 | 0.00 | 11.00 | −1.00 |
| ZFP36 | −1.07 | −5.46 | 0.00 | 12.00 | −1.00 |
| ATF3 | −0.96 | −5.22 | 0.00 | 15.00 | −1.00 |
| EGR2 | −1.11 | −5.13 | 0.00 | 18.00 | −1.00 |
| JUNB | −0.81 | −4.98 | 0.00 | 25.00 | −1.00 |
| NR4A3 | −1.19 | −4.65 | 0.00 | 35.00 | −1.00 |
| SELE | −0.83 | −4.41 | 0.00 | 46.00 | −1.00 |
| FOSL2 | −0.39 | −4.25 | 0.00 | 52.00 | −1.00 |
| BTG2 | −0.39 | −4.20 | 0.01 | 58.00 | −1.00 |
| HBEGF | −0.65 | −4.11 | 0.01 | 66.00 | −1.00 |
| SFRP1 | −0.79 | −4.01 | 0.01 | 73.00 | −1.00 |
| NEDD9 | −0.48 | −3.85 | 0.01 | 85.00 | −1.00 |
| CXCL2 | −0.81 | −3.80 | 0.01 | 96.00 | −1.00 |
| DUSP5 | −0.76 | −3.72 | 0.02 | 112.00 | −1.00 |
| TRIB1 | −0.35 | −3.64 | 0.02 | 124.00 | −1.00 |
| CX3CL1 | −0.60 | −3.61 | 0.02 | 127.00 | −1.00 |
| IL1B | −0.57 | −3.48 | 0.03 | 143.00 | −1.00 |
| NPR3 | −0.80 | −3.47 | 0.03 | 145.00 | −1.00 |
| CEBPD | −0.53 | −3.46 | 0.03 | 148.00 | −1.00 |

The Swedish subset without Gleason grade as a covariate was also analyzed. 129 genes were differentially expressed at 0.05 FDR level between lethal and indolent subgroups. FDR correction was performed using Benjamini-Hochberg method. 3 genes were found significant in our analysis of the 271 NF-κB gene set (Table 2). Of note, the tissues analyzed from this analysis were obtained by transurethral resection of the prostate (TURP). The patients had a disease arising from the central gland with a different biology to a disease from peripheral portions of the prostate gland. Patients in this data-set were also managed with "watchful waiting" and did not undergo a prostatectomy.

TABLE 2

NF-κB related genes differentially expressed in lethal versus indolent prostate cancer identified from the Swedish subset when analyzed without Gleason Grade as a covariate.

| | logFC | t | adj P Val | rank | observed score |
|---|---|---|---|---|---|
| SLC39A8 | −0.35 | −4.20 | 0.01 | 28.00 | −1.00 |
| SLCO2A1 | 0.30 | 4.13 | 0.01 | 30.00 | 1.00 |
| KLF10 | 0.22 | 3.96 | 0.01 | 41.00 | 1.00 |

The PHS cohort for discovery of a set of cancer-promoting NF-κB related genes was selected for focus because the PHS cohort represented the more commonly ascertained tissue of prostatectomy and transrectal ultrasonography of the prostate (TRUS) biopsy. On account of trying to improve on the prognostic ability of Gleason Score, analysis with Gleason Grade as a covariate in the PHS prostatectomy series was performed. Gleason scores were recoded as "low" (<7), "med" (=7), and "high" (>7). 0 out of 6096 genes represented on a DASL platform were differentially expressed at 0.05 FDR level between lethal and indolent subgroups in this analysis. FDR correction was performed using Benjamini-Hochberg method. When no multiple testing correction was applied, there were 384 differentially expressed genes with p-values below 0.05. 31 of these genes belonged to the NF-κB 271 gene set (Table 3). Of the 19 genes differentially expressed with FDR correction and identified without Gleason as a covariate, 18 overlapped with the 31 differentially expressed genes. The following tumor suppressors to be lost in lethal prostate cancer were identified: CCAAT/enhancer-binding protein delta (CEBPD), dual specificity protein phosphatase 5 (DUSPS), secreted frizzled-related protein 1 (SFRP1), neuron-derived orphan receptor 1 (NOR1, also known as NR4A3) and tristetraprolin (TTP, also known as zinc finger protein 36 homolog or ZFP36).

TABLE 3

NF-κB related genes differentially expressed in lethal versus indolent prostate cancer identified from the PHS subset when analyzed with Gleason Grade as a covariate without applying multiple testing correction.

| | logFC | t | P Value | adj P Val | rank | observed sec |
|---|---|---|---|---|---|---|
| ZFP36 | −0.82 | −3.36 | 0.00 | 0.31 | 20.00 | −1.00 |
| JUNB | −0.68 | −3.34 | 0.00 | 0.31 | 22.00 | −1.00 |
| IL1B | −0.68 | −3.31 | 0.00 | 0.33 | 23.00 | −1.00 |
| FOSB | −0.88 | −3.23 | 0.00 | 0.38 | 24.00 | −1.00 |
| ATF3 | −0.74 | −3.20 | 0.00 | 0.38 | 26.00 | −1.00 |
| KLF6 | −0.76 | −3.17 | 0.00 | 0.38 | 31.00 | −1.00 |
| GPX2 | 0.54 | 3.11 | 0.00 | 0.44 | 33.00 | 1.00 |
| EGR2 | −0.82 | −3.06 | 0.00 | 0.45 | 37.00 | −1.00 |
| NR4A3 | −0.95 | −2.96 | 0.00 | 0.48 | 46.00 | −1.00 |
| OAS2 | 0.62 | 2.93 | 0.00 | 0.50 | 49.00 | 1.00 |
| CEBPD | −0.54 | −2.78 | 0.01 | 0.55 | 70.00 | −1.00 |
| ENPP1 | −0.54 | −2.74 | 0.01 | 0.57 | 76.00 | −1.00 |
| HBEGF | −0.52 | −2.64 | 0.01 | 0.61 | 89.00 | −1.00 |
| CDC42EP4 | −0.53 | −2.58 | 0.01 | 0.61 | 104.00 | −1.00 |
| DUSP6 | −0.55 | −2.57 | 0.01 | 0.61 | 110.00 | −1.00 |
| ITGA5 | −0.69 | −2.55 | 0.01 | 0.61 | 115.00 | −1.00 |
| BTG2 | −0.30 | −2.54 | 0.01 | 0.61 | 122.00 | −1.00 |
| SFRP1 | −0.61 | −2.50 | 0.01 | 0.62 | 134.00 | −1.00 |
| DUSP5 | −0.64 | −2.50 | 0.01 | 0.62 | 136.00 | −1.00 |
| FOSL2 | −0.28 | −2.48 | 0.01 | 0.62 | 144.00 | −1.00 |
| SELE | −0.57 | −2.46 | 0.02 | 0.62 | 149.00 | −1.00 |
| MKNK1 | 0.53 | 2.43 | 0.02 | 0.64 | 156.00 | 1.00 |
| CX3CL1 | −0.50 | −2.43 | 0.02 | 0.65 | 157.00 | −1.00 |
| ARHGEF7 | −0.38 | −2.30 | 0.02 | 0.68 | 209.00 | −1.00 |
| BCL6 | 0.62 | 2.29 | 0.02 | 0.68 | 216.00 | 1.00 |
| TRIB1 | −0.26 | −2.22 | 0.03 | 0.70 | 245.00 | −1.00 |
| IER3 | −0.42 | −2.11 | 0.04 | 0.72 | 314.00 | −1.00 |
| BDKRB2 | 0.43 | 2.05 | 0.04 | 0.74 | 346.00 | 1.00 |
| NEDD9 | −0.32 | −2.04 | 0.04 | 0.76 | 352.00 | −1.00 |
| CXCL2 | −0.53 | −2.00 | 0.05 | 0.77 | 376.00 | −1.00 |
| FOXJ1 | 0.56 | 1.98 | 0.05 | 0.79 | 384.00 | 1.00 |

Figure 4:
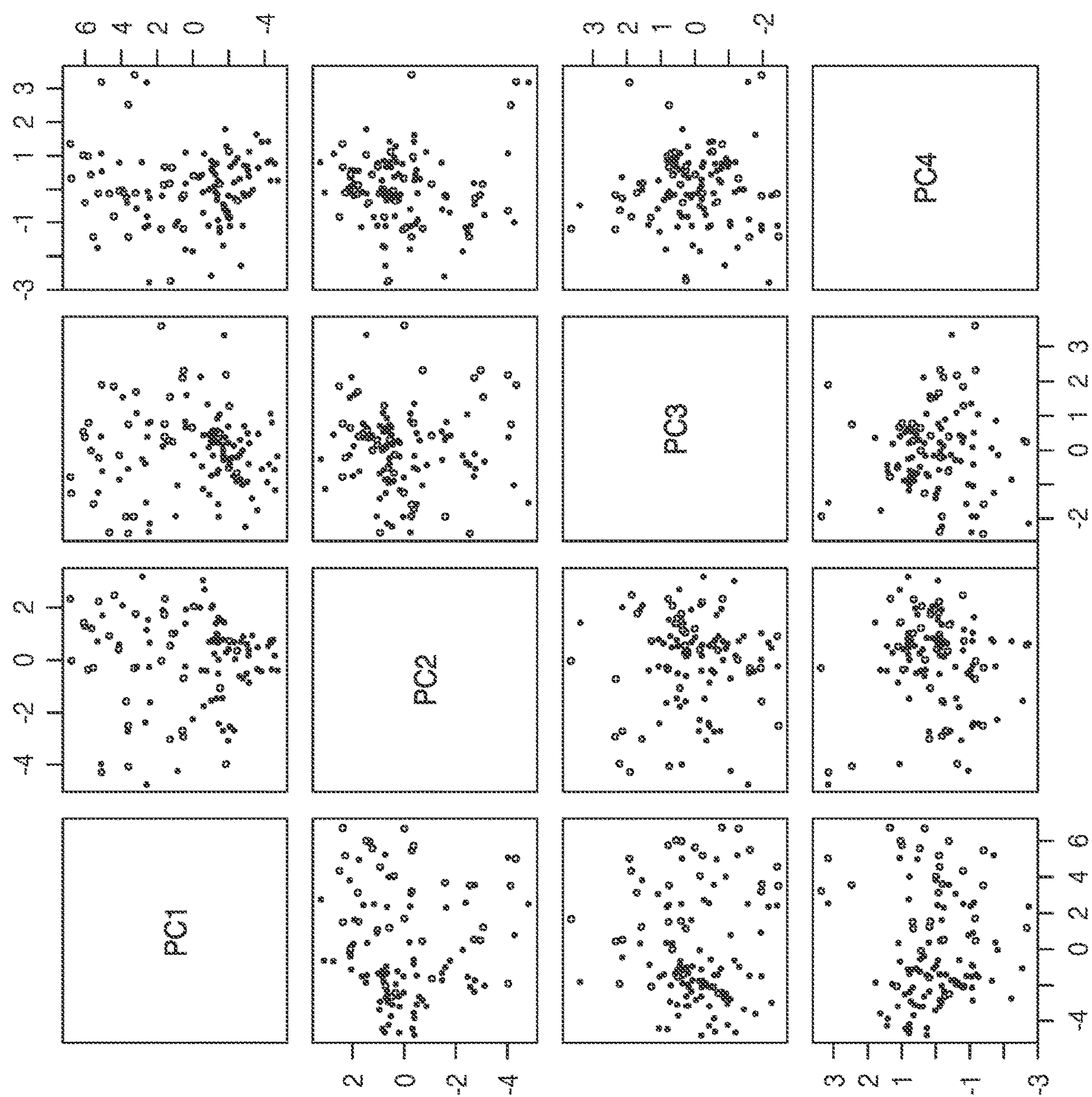
FIG. 4 illustrates Principal Component Analysis (PCA) performed on PHS cases using significant genes from the NF-κB datasets.
Figure 5:
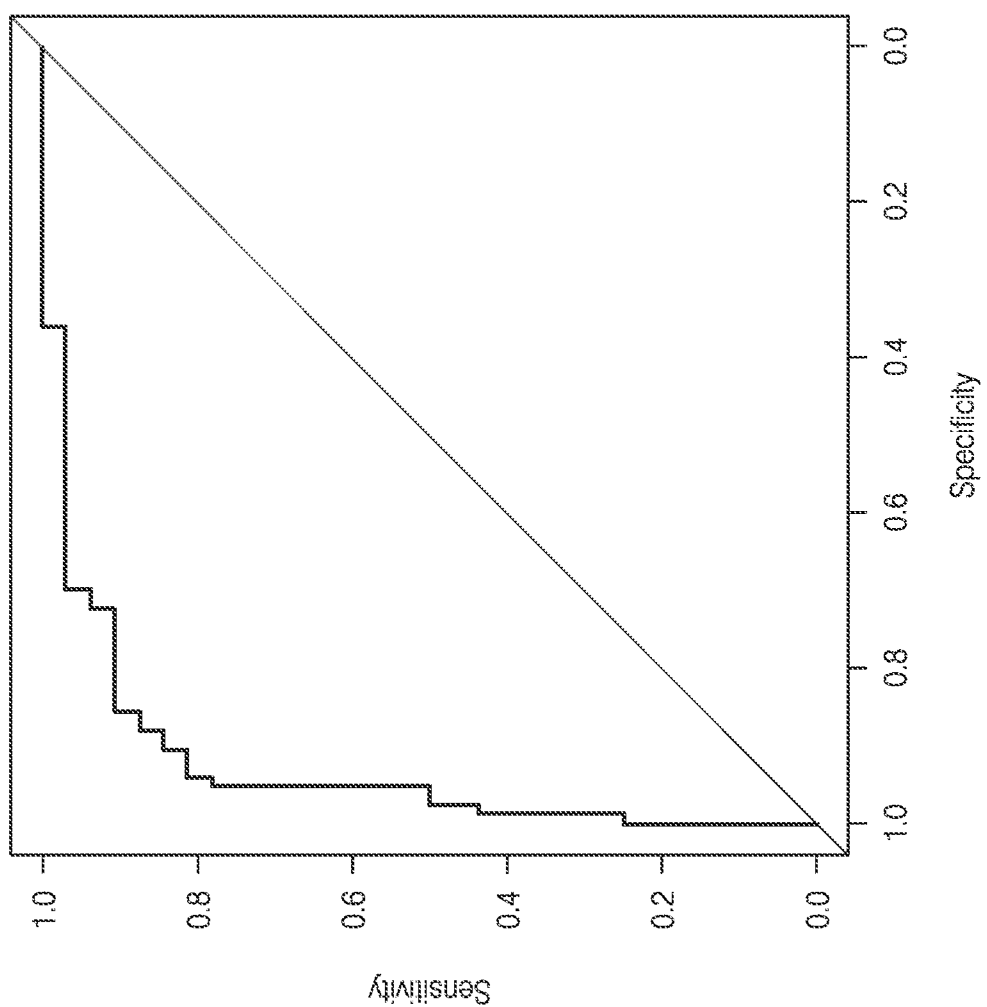
FIG. 5 shows a receiver operating characteristic (ROC) curve for predicting lethal versus indolent prostate cancer from the results of the PCA analysis performed on PHS cases using significant genes from the NF-κB datasets.

Principal Component Analysis (PCA) was performed on PHS cases using significant genes from the NF-κB set. PCA 1, 2, 3 and 4 were developed. Logistic regression of the 4 different PCAs suggested that PCA1 and PCA3 were significantly associated with lethal cancer (FIG. 4 and Table 4). An ROC curve was generated and an AUC of 0.9313 was found for predicting lethal versus indolent prostate cancer (FIG. 5). This curve was subject to over-fitting because the data used to generate PCA were not subject to correction for multiple testing and the data input was selected to be differentially expressed. These "discovery sets" which include ZFP36, NEDD9 and rs1910301 can be tested in publicly available data sets for association with Gleason score and lethality after prostatectomy.

TABLE 4

Principal Component Analysis (PCA) on PHS cases using significant genes from the NF-κB datasets.

| Logistics Regression Deviance Residuals | | | | |
|---|---|---|---|---|
| Min | 1Q | Median | 3Q | Max |
| −2.30 | −0.41 | −0.20 | 0.31 | 2.77 |

Coefficients

| | Estimate | Std Error | z value | Pr (>IzI) |
|---|---|---|---|---|
| Intercept | 0.47 | 0.48 | 0.97 | 0.32 |
| PC1 | 0.41 | 0.12 | 3.55 | 0.0004 |
| PC2 | −0.26 | 0.17 | −1.51 | 0.13 |
| PC3 | 0.64 | 0.25 | 2.56 | 0.01 |
| Gl Low | −18.77 | 1511 | −0.01 | 0.99 |
| Gl Med | −2.92 | 0.71 | −.41 | 4.22e−05 |

Eight novel genes were identified to be significantly downregulated in lethal prostate cancer versus indolent in publically available databases (Sboner et al., 2010; Setlur et al., 2008) that were highly functionally associated with NF-κB in multiple biological contexts (Table 5). All these eight genes were also identified in the PHS study (Table 1).

TABLE 5

List of genes that are significantly downregulated in lethal prostate cancer compared to indolent prostate cancer.

| Gene | logFC | FDR | Biological contexts |
|---|---|---|---|
| ATF3 | −0.96 | 0 | Regulation of cell cycle, Cytokine metabolic process |
| CXCL2 | −0.81 | 0.01 | Vasculature development, Cytokine metabolic process |
| DUSP5 | −0.76 | 0.02 | Positive regulation of NFκB transcription factor activity, Cytokine metabolic process |
| JUNB | −0.81 | 0 | Regulation of cell cycle, Positive regulation of NFκB transcription factor activity, Regulation of cell motion |
| NEDD9 | −0.48 | 0.01 | Vasculature development, Cell migration, Cytokine metabolic process |
| SELE | −0.83 | 0 | Cell death, Regulation of cell proliferation |
| TRIB1 | −0.35 | 0.02 | Vasculature development, Cell migration, Regulation of cell motion, Cytokine metabolic process |
| ZFP36 | −1.07 | 0 | Regulation of cell cycle, Regulation of cell motion, Cytokine metabolic process |

Figure 6:
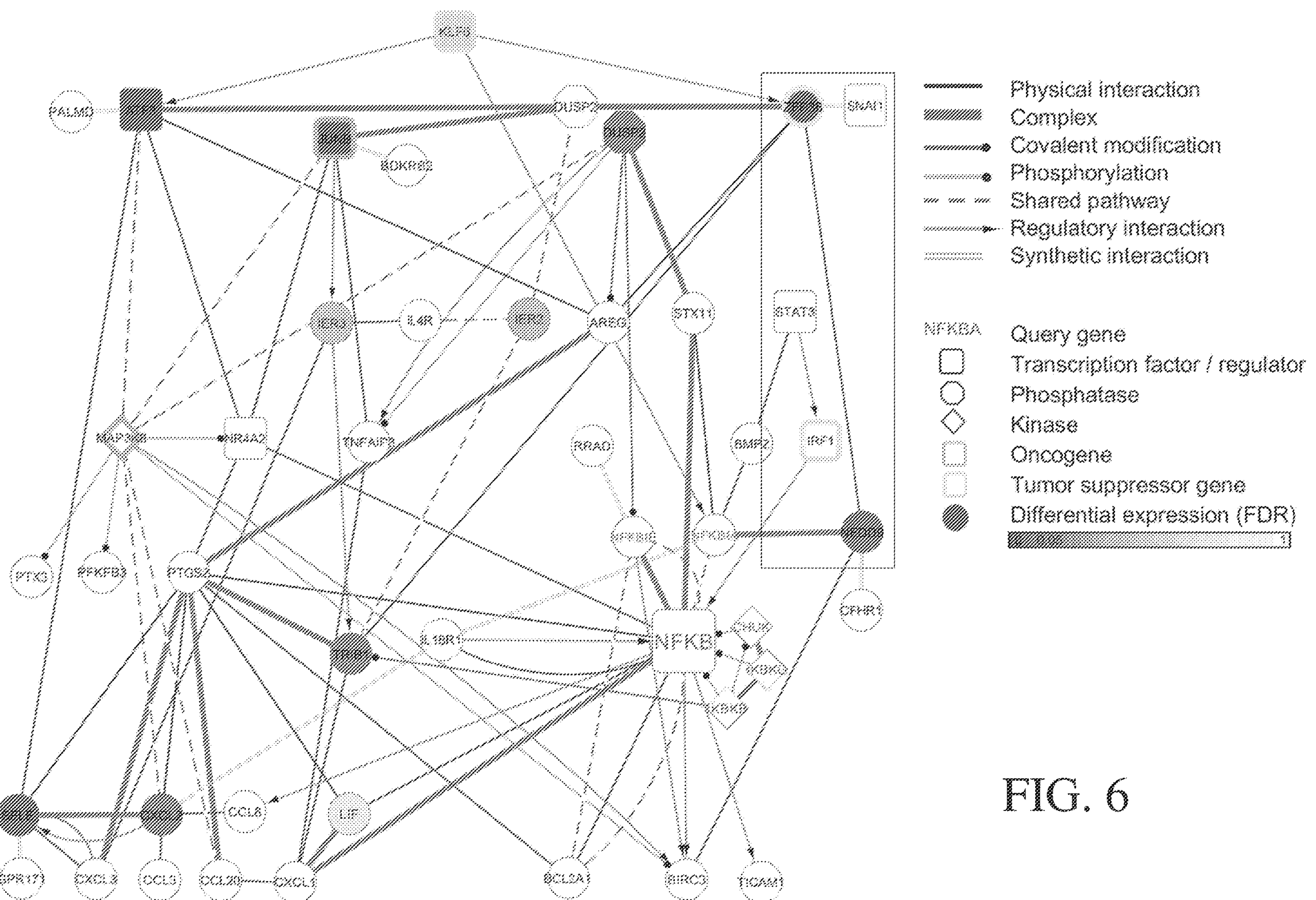
FIG. 6 shows interaction between NF-κB related genes.
Figure 7A:
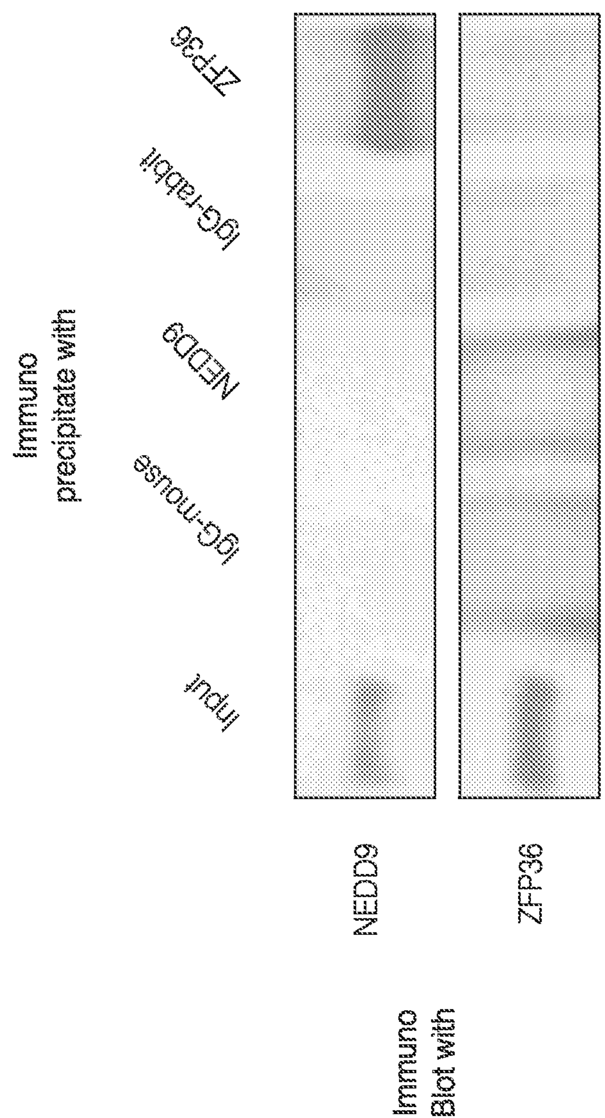
FIG. 7A shows levels of NEDD9 and ZFP36 in immunoprecipitates of LAPC4 cell lysate with anti-NEDD9 or anti-ZFP36 antibody compared to control antibodies for each (IgG-mouse and IgG-rabbit, respectively).
Figure 7B:
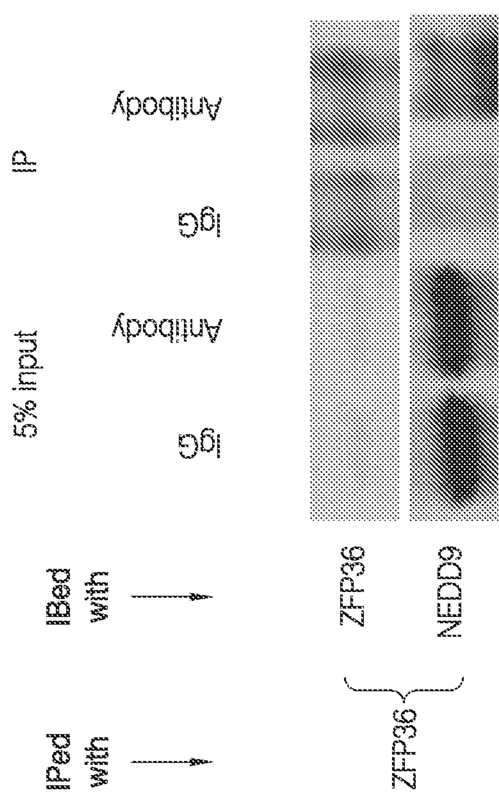
FIG. 7B shows levels of ZFP36 and NEDD9 detected in LAPC4 lysates immunoprecipitated with anti-ZFP36 antibody.

Example 3: Interactions Between NF-κB Related Genes in a Prostate Cancer Network Datasets from 18 curated prostate cancer expression datasets, GEO (Barrett et al., 2009), ArrayExpress (Parkinson et al., 2009) and non-condition-specific genomic data such as physical and genetic interactions from BioGRID (Breitkreutz et al., 2008) and IntAct (Kerrien et al., 2007), transcriptional regulatory relationships from Transfac (Matys et al., 2006) and cisRED (Robertson et al., 2006), and miRNA data from miRBase (Griffiths-Jones, 2006) were integrated to generate an NF-κB related gene interaction map (FIG. 6). Various types of gene interactions were shown. ZFP36 and NEDD9, two of the novel genes we identified to be downregulated in prostate cancer, were predicted to have a physical interaction. The physical interaction between ZFP36 and NEDD9 was confirmed by co-immunoprecipitation experiments (FIG. 7A, B).

Figure 8:
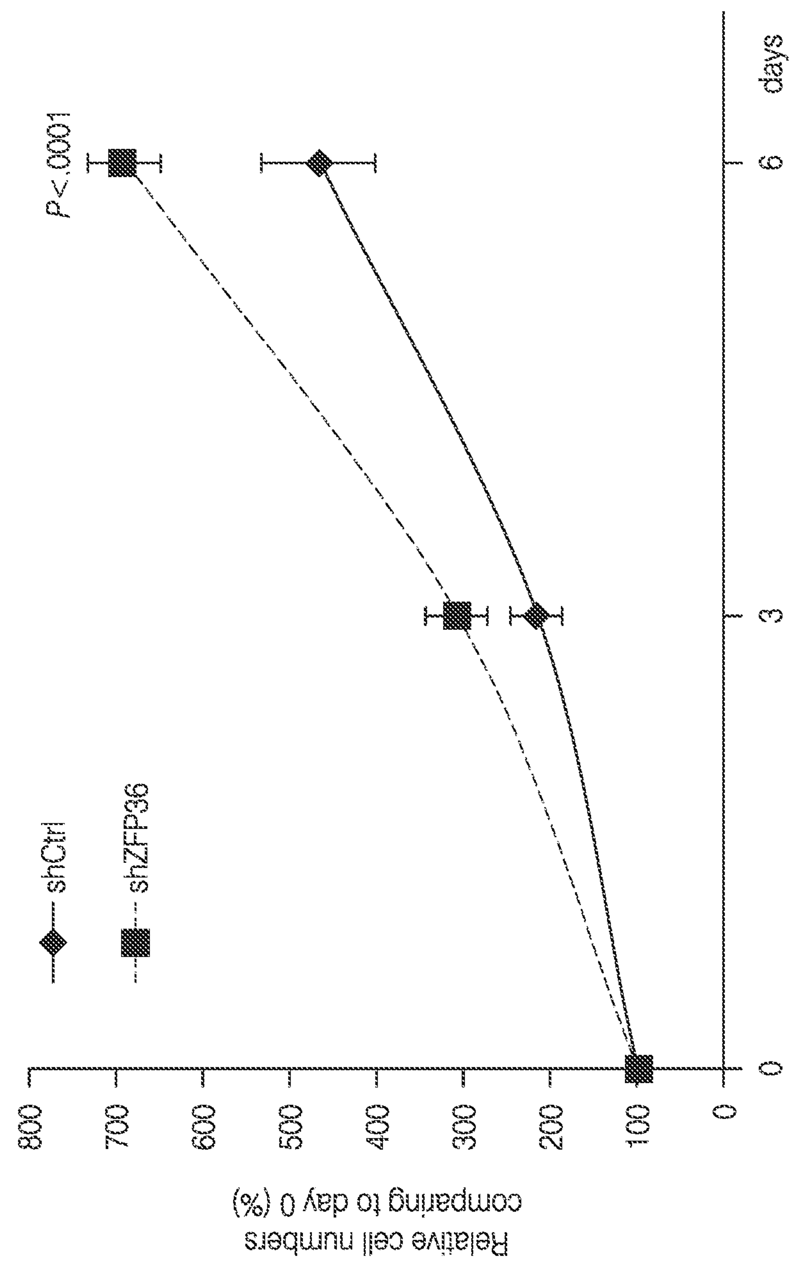
FIG. 8 shows the change in relative cell number (cell growth) over time of RWPE-1 cells expressing ZFP36 shRNA ("shZFP36") or control shRNA ("shCtrl").
Figure 9A:
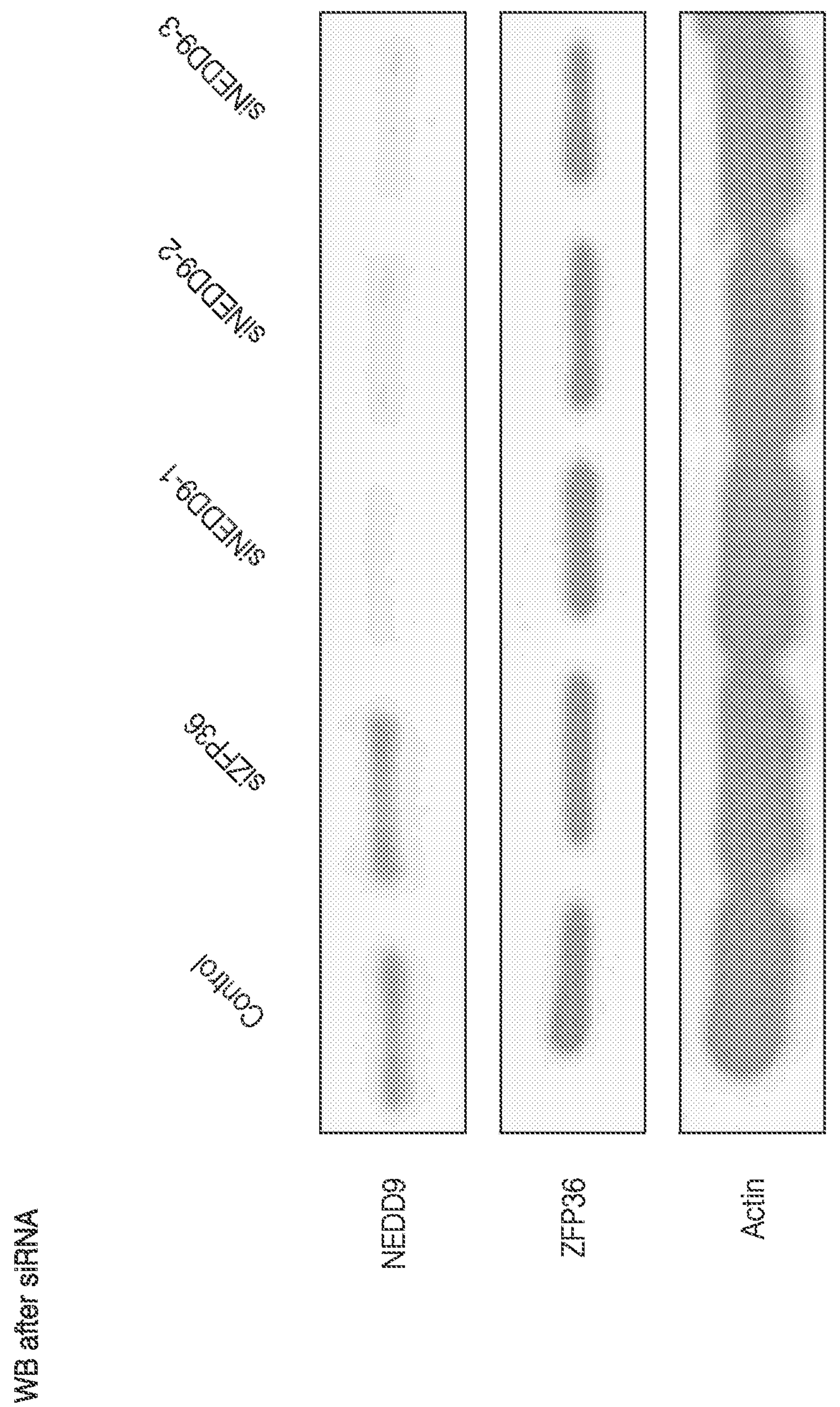
FIG. 9A shows the protein levels of ZFP36 and NEDD9 in lystates of LAPC4 cells transfected with ZFP36 siRNA ("siZFP36"), NEDD9 siRNA (siNEDD9-1, siNEDD9-2 and siNEDD9-3) or control siRNA.
Figure 9B:
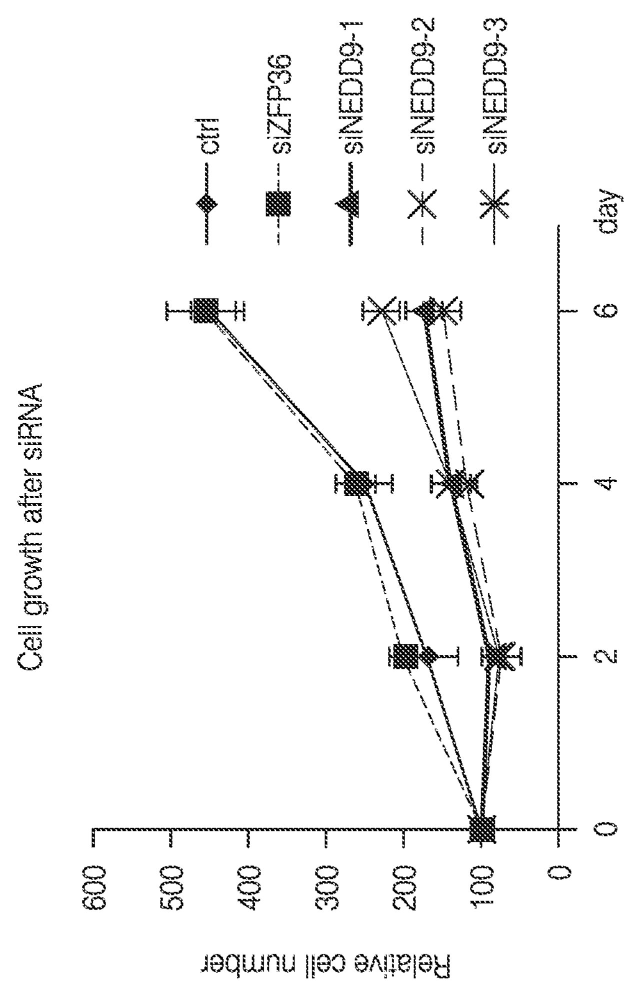
FIG. 9B shows the change in cell growth (relative cell number) over time in cells transfected with ZFP36 siRNA ("siZFP36"), NEDD9 siRNA (siNEDD9-1, siNEDD9-2 and siNEDD9-3) or control siRNA.

Example 4: Association Between NF-κB Related Genes (ZFP36, NEDD9, Etc.) and Prostate Cancer Progression To interrogate the functions of ZFP36 and NEDD9 in prostate cancer cells, knock down of the genes and examination of the increase of cell number, which indicates a combinational effect of cell proliferation and cell death was performed. An shRNA targeting ZFP36 promoted cell growth (FIG. 8), suggesting that ZFP36 was a tumor suppressor. On the other hand, three different NEDD9 siRNAs all reduced cell growth (FIGS. 9A, 9B).

Figure 10:
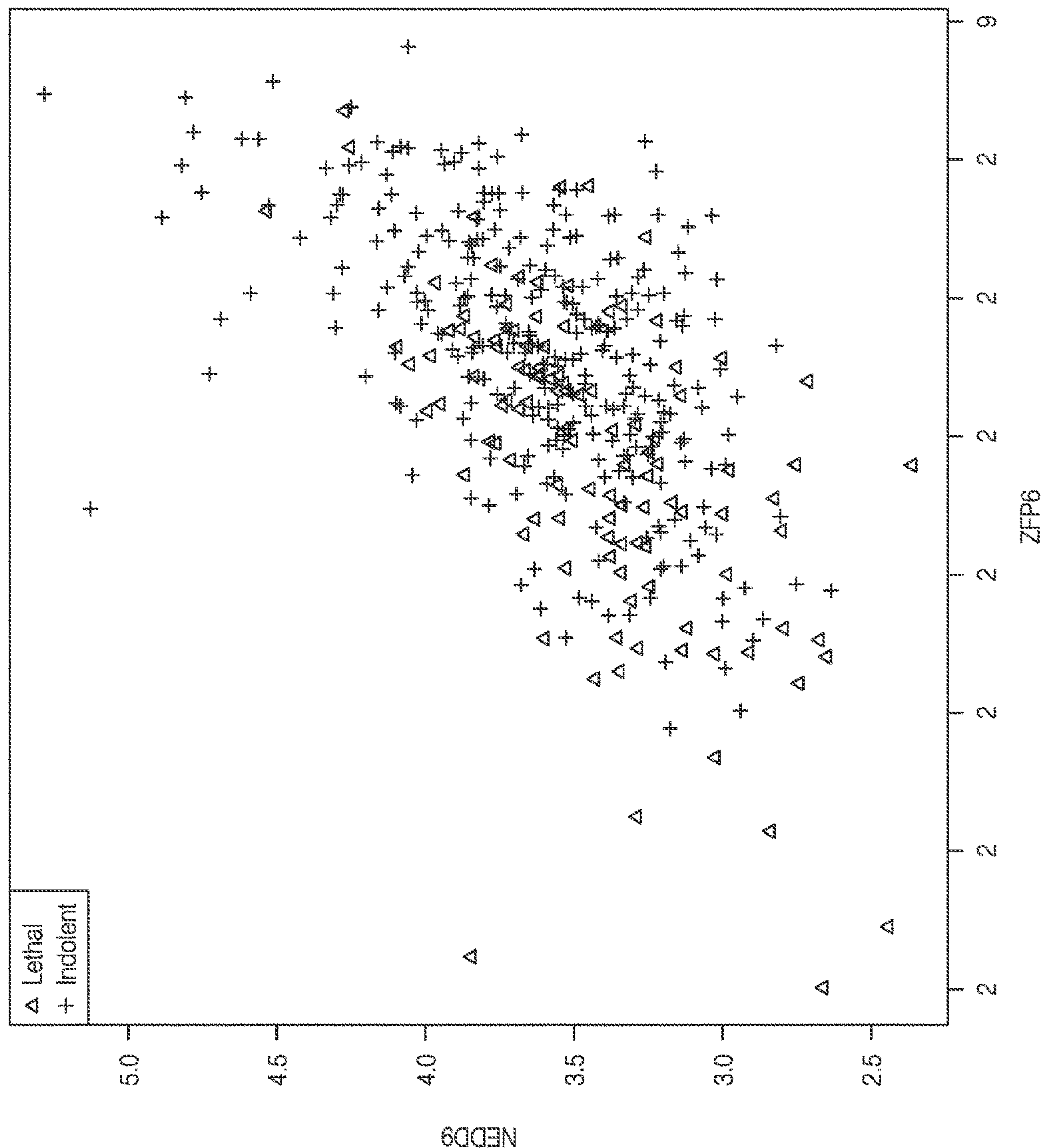
FIG. 10 shows the expression of ZFP36 and NEDD9 in lethal versus indolent prostate cancer in the HPFS/PHS cohort.

ZFP36 and NEDD9 were examined in human samples from the Health Professionals Follow-up Study and the Physician Health Study (HPFS/PHS). As shown in FIG. 10, NEDD9 and ZFP36 expression were fairly well correlated (cor=0.58) and overexpression of both was highly associated with indolent disease. Individually, higher expression levels of ZFP36 and NEDD9 were each associated with indolent prostate cancer ($p=2.4\times10^{-9}$ and $p=7.5\times10^{-5}$, respectively). The expression level of ZFP36 had a particularly strong predictive power. A logistic regression of the HPFS/PHS data adjusted for age at diagnosis, Gleason score, and stage suggested that ZFP36 had a strong protective effect (z value −2.677) from lethal prostate cancer. In contrast Gleason 8 and higher had a z value of 3.735 and was strongly associated with lethal disease. NEDD9 had no association with clinical outcome (Table 6).

TABLE 6

Logistic regression of ZFP36 (denoted as X802862) and NEDD9 (denoted as X8123936) expression in indolent versus lethal prostate cancer in the HPFS/PHS datasets adjusted for age at diagnosis, Gleason score, and stage.
Coefficients:

| | Estimates | Std. Error | z value | Pr(>\|z\|) |
|---|---|---|---|---|
| (Intercept) | −2.51078 | 2.24381 | −1.119 | 0.263147 |
| gleasoncat3 + 4 | 1.70750 | 1.05475 | 1.619 | 0.105478 |
| gleasoncat4 + 3 | 2.97110 | 1.03981 | 2.857 | 0.004272 ** |
| gleasoncat > 7 | 3.87305 | 1.03688 | 3.735 | 0.000187 *** |
| as. factor(cTNM)2 | 0.53529 | 0.46130 | 1.160 | 0.245882 |
| as. factor(cTNM)3 | 3.02168 | 1.05457 | 2.865 | 0.004166 ** |
| agedx | 0.02198 | 0.02230 | 0.985 | 0.324384 |
| X8028652 | −0.45368 | 0.16945 | −2.677 | 0.007421 ** |
| X8123936 | 0.00812 | 0.39913 | 0.020 | 0.983769 |

---
Signif. codes: 0 '*' 0.001 '' 0.01 '*' 0.05 '.' 0.1 ' ' 1

Figure 11:
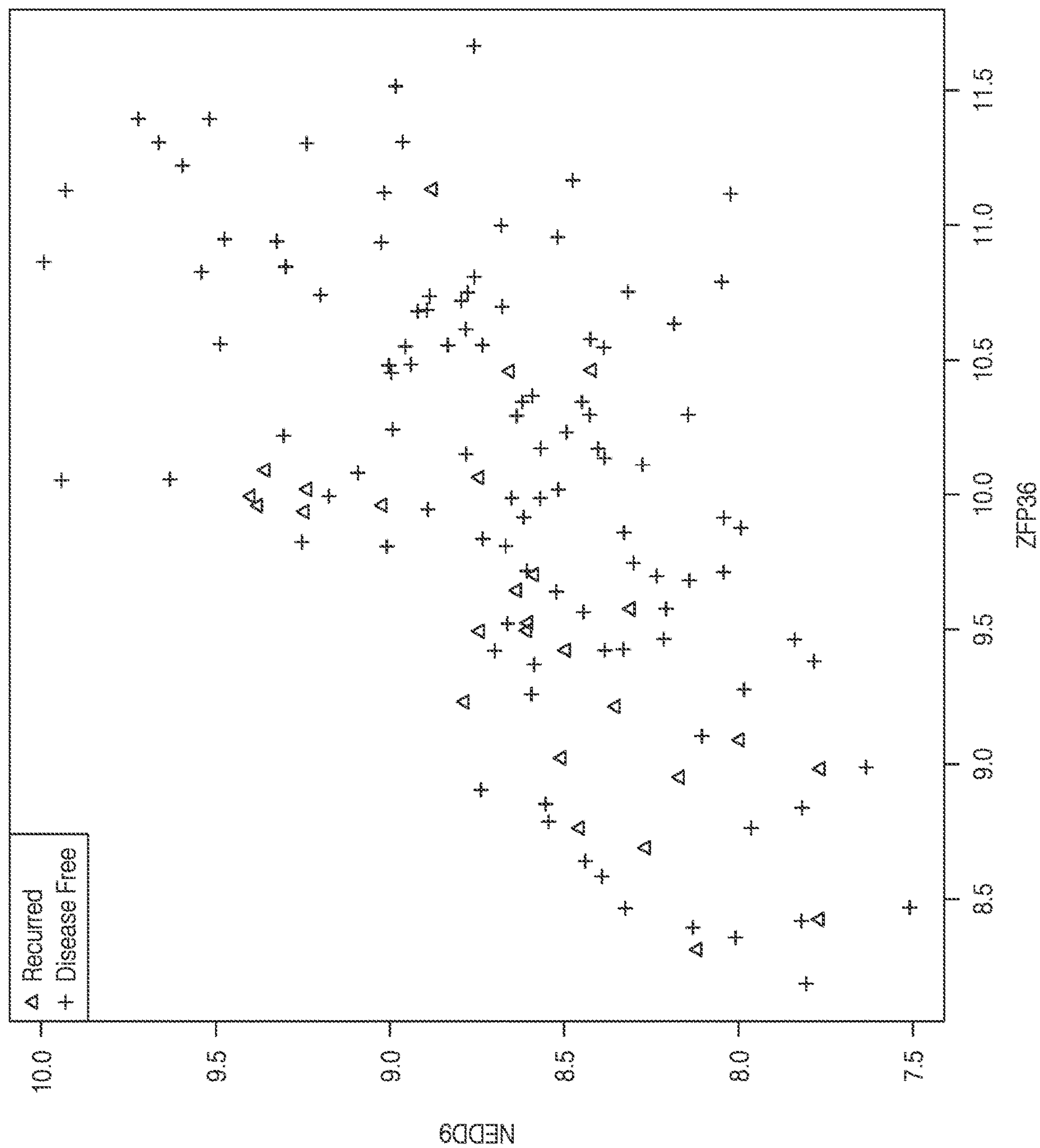
FIG. 11 shows the expression of ZFP36 and NEDD9 in relapsed ("recurred") versus non-relapsed ("disease free") prostate cancer in the Taylor cohort.

Another gene expression profiling dataset (Taylor et al., 2010) was examined using 131 primary tumor samples with mRNA. We observed similar correlation between the two genes (r=0.60). ZFP36 was significantly associated with recurrence in the univariate setting (p<0.001, low expression associated with recurrence), while NEDD9 was not (p=0.65, though in the same negative direction) (FIG. 11). When ZFP36 and NEDD9 were analyzed as part of a logistic regression adjusted for Gleason score, lower ZFP36 expression and higher NEDD9 expression were each significantly associated with recurrence (Table 7).

TABLE 7

Logistic regression of ZFP36 (X802862) and NEDD9 (X8123936) expression in relapsed versus non-relapsed prostate cancer in the Taylor datasets adjusted for Gleason score.

| Variable | Odds Ratio | P value |
|---|---|---|
| ZFP36 | 0.31 (0.12-0.75) | 0.012 |
| NEDD9 | 3.65 (1.05-14.0) | 0.047 |
| Gleason7 | 4.45 (1.10-30.25) | 0.066 |
| Gleason8 | 36.46 (4.84-446.84) | 0.001 |
| Gleason9 | 40.87 (5.36-501.87) | <0.001 |

Figure 12:
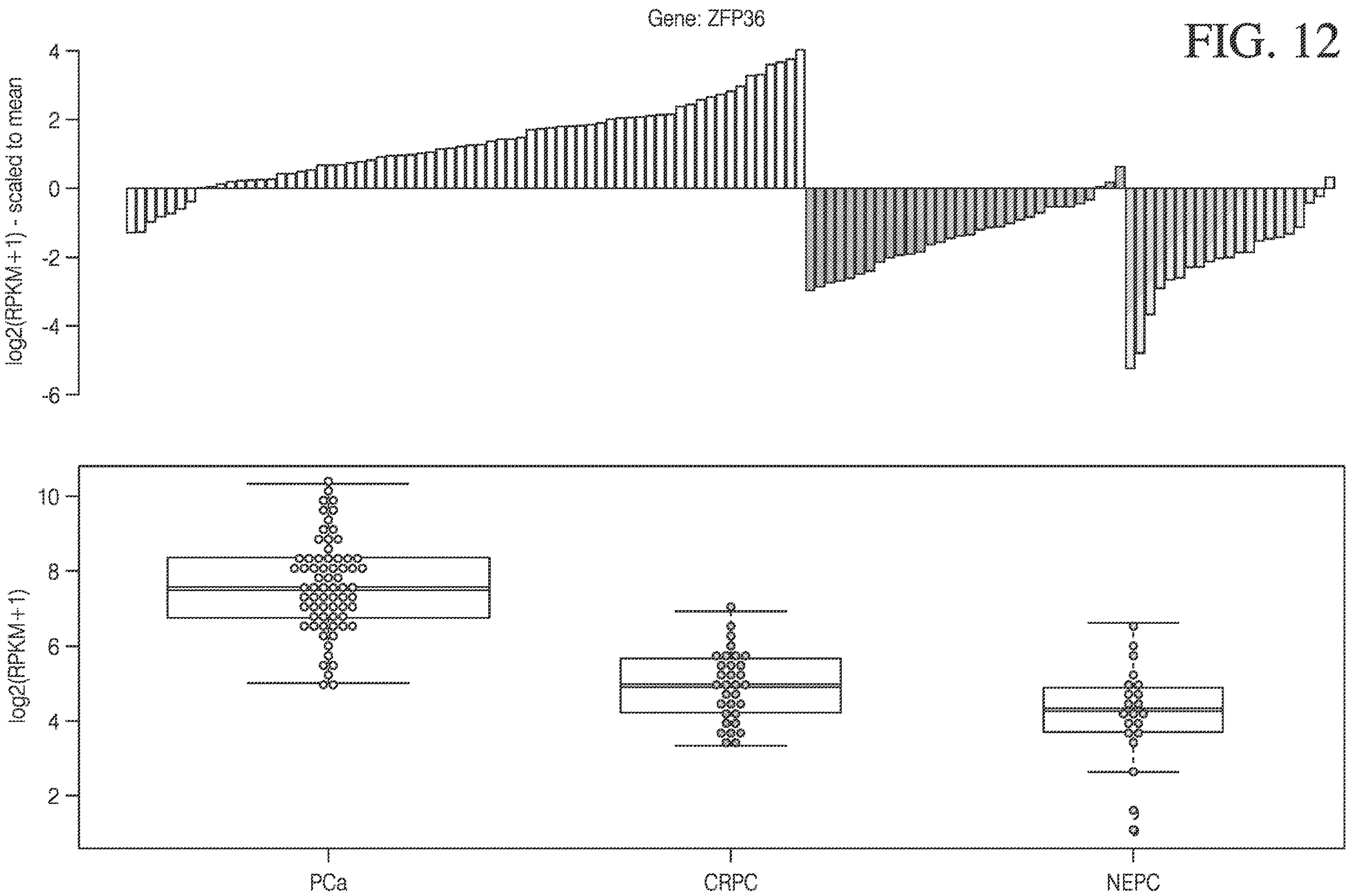
FIG. 12 shows the expression levels of ZFP36 in different types or stages of prostate cancer. (CRPC: castration-resistant prostate cancer (metastatic disease); NEPC: neuroendocrine prostate cancer (metastatic disease); PCa: hormone naive localized prostate cancer).

Expression levels across different types or stages of prostate cancer were analyzed. Lower expression levels of ZFP36 were found in more aggressive types of prostate cancer, such as metastatic castration-resistant prostate cancer (CRPC) and metastatic neuroendocrine prostate cancer (NEPC), than in clinically localized hormone naive prostate cancer (PCa) (FIG. 12).

Example 5: Association Between SNP Rs1910301 and Lethality of Prostate Cancer Using the network approach detailed in FIG. 1, a genome-wide functional association network specific to prostate cancer and the NFκB pathway consisting of 351 genes and 8,154,133 high-confidence functional associations was created. The dense module searching (DMS) method described by Jia et al. was used to identify a candidate subnetwork of interacting genes related to both (i) the NFκB pathway and (ii) to lethal prostate cancer. The method combines a genome-wide association study conducted by the Harvard School of Public Health (HSPH) with a protein-protein interaction network developed by us. The HSPS GWAS was conducted on 196 lethal and 368 indolent cases in the HPFS and PHS for 419,461 SNPs, and the p-value results were used to assign gene weights in the current study. After using the annotation file to assign each SNP on the Affymetrix 5.0 chip to a gene, a single SNP with the lowest p-value was selected to represent each of 16,387 genes. For each SNP-gene pair, the GWAS p-value was used as the gene's weight during DMS. The protein-protein interaction (PPI) network was constructed based on NFκB-based interactions likely to be functionally related to prostate cancer, and included 8,154,133 high-confidence interactions. These interactions provided the connections between genes that were used to form modules.

As a brief summary, the DMS method then iteratively proceeded through four searching steps to identify modules that had genes with low p-values as compared to other modules. Each gene in the PPI was initially assigned as a seed gene and then genes that interacted with the current module gene(s), with an interaction path less than or equal to 2, were identified. For each neighborhood interactor, Zm+1 was calculated after including it in the seed module and it was permanently added to the seed module if Zm+1>1.1*Zm, where Zm was defined as $(\Sigma zi)/k$, k was the number of genes in the module, and $zi=\Phi-1\ (1-Pi)$. These steps were repeated until no more neighborhood nodes could be added to the module. Normalized Zm values, called values, were then calculated by comparing the module to 100,000 modules of the same size that were created by randomly selecting genes. After conducting dense module selection, the modules were ranked and the top 40 modules with the highest ZN values were selected for the subnetwork. The selected subnetwork included 68 genes with 185 interactions, where each gene was weighted by a single SNP in the GWAS study. Of the 68 SNPs used to represent the genes in the selected subnetwork, the top 40 SNPs with a minor allele frequency >0.1 were carried forward for subsequent validation.

Samples were pulled and DNA isolated from 256 Gelb Center patients (low risk/non-lethal prostate cancer cohort) and compared with samples from patients with metastatic disease—(254 ECOG patients). Only one of 40 SNPs was nominally significantly associated with lethal disease in the same direction. In the original HSPH GWAS, the rs1910301 SNP with the risk allele being A had an odd ratio (OR) of 1.40 (p-value=0.02) for lethal disease. In the GC/ECOG cohorts, the rs1910301 risk allele A had an OR of 1.35 (p-value=0.04) for lethal disease. There was a chance of false discovery given only 1 of 40 SNPs tested was nominally significant. However, the likelihood was low because it was reproduced in two independent cohorts with the same ethnic background (Caucasians only). It was also identified via the dense module selection process using NF-κB pathway as the underlying biology.

Example 6: Association Between ZFP36 and PTEN Expression and Prostate Cancer Progression The previous examples show that certain biomarkers, such as the expression levels of NF-κB-related genes and the rs1910301 SNP, are associated with the progression of prostate cancer. This example provides a combination of specific biomarkers that is associated with prostate cancer progression with high accuracy.

Gene expression data was obtained from the Taylor cohort. Gene expression for ZFP36 was quantified from archival surgical tumor tissue using Affymetrix Human Gene 1.0 ST microarrays. Cases (n=113) were men who died of prostate cancer or developed metastatic disease, and controls (n=291) were men who lived at least 8 years after diagnosis and remained metastasis free. A genetically validated PTEN immunohistochemistry (IHC) assay was performed on tissue microarrays (TMAs) for a subset of the men (n=257).

Mean ZFP36 expression was significantly lower in the cases compared to the controls ($p<0.001$), and the crude odds ratio (OR) for lethal disease comparing those with low ZFP36 expression (below the lower quartile) to those with high ZFP36 expression (greater than or equal to the lower quartile) was 3.52 (95% CI: 2.18-5.69; $p<0.001$). The association persisted with adjustment for Gleason category, age at diagnosis, and clinical stage, with an adjusted OR of 1.93 (95% CI: 1.07-3.49; p=0.03). When modeled as a continuous variable in a logistic regression for prognosis, ZFP36 improved the AUC of the clinical factor model (Gleason, age, and clinical stage) from 0.83 (95% CI: 0.79-0.88) to 0.85 (95% CI: 0.81-0.89; p=0.10 for improvement).

Figure 13:
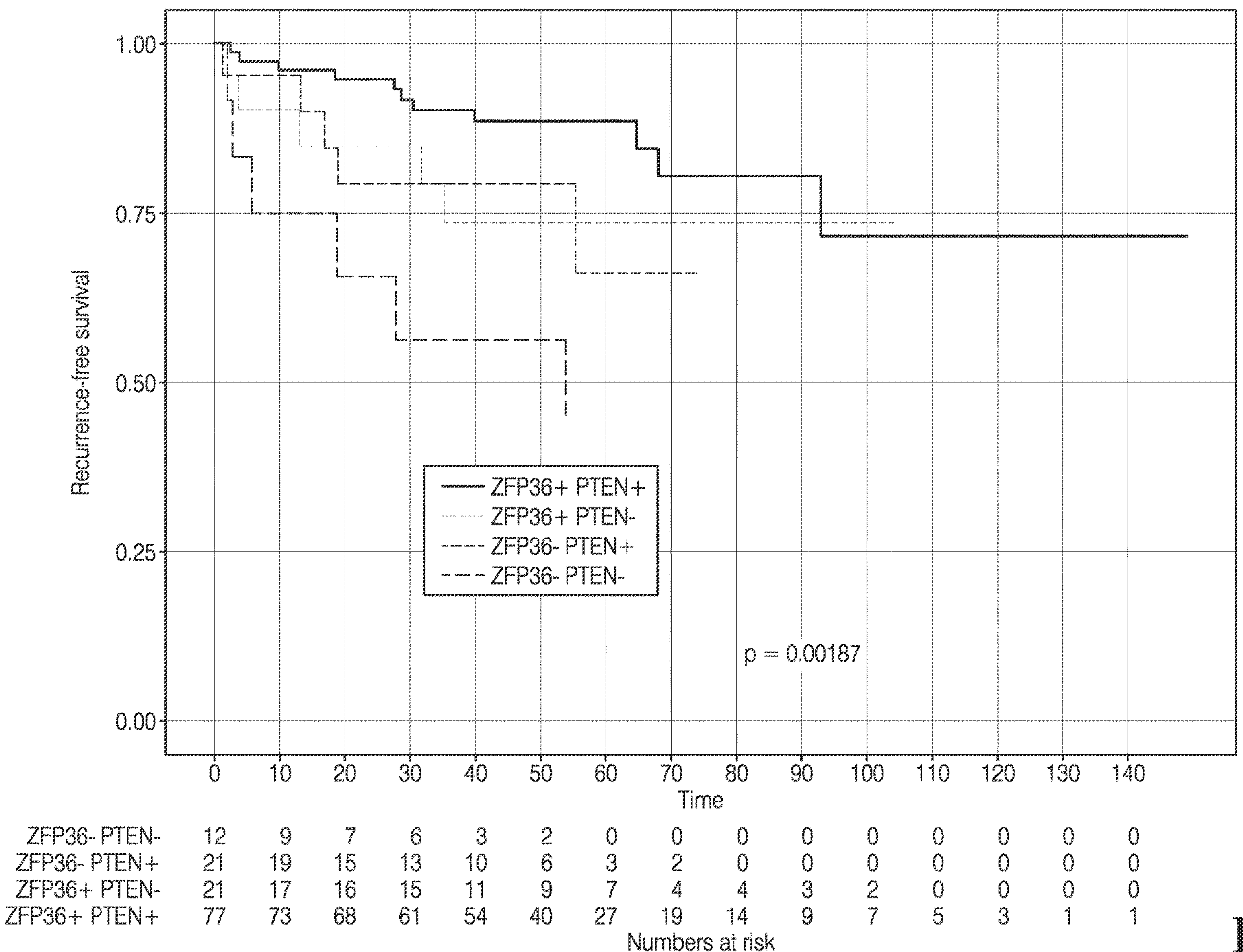
FIG. 13 is a Kaplan-Meier plot of recurrence-free survival of patients with high or low ZFP36 and PTEN levels.

Among the patients with available PTEN staining, independent effects of ZFP36 and PTEN loss were observed. In the logistic regression on lethal disease with both variables included, PTEN negativity conferred an OR of 2.10 (95% CI: 1.11-3.93; p=0.02) and low ZFP36 produced an OR of 2.34 (95% CI: 1.24-4.36; p=0.01). An OR of 4.90 (95% CI: 2.05-11.72) was observed comparing patients with PTEN negativity and low ZFP36 to those with PTEN staining present and high ZFP36. As shown in FIG. 13, patients with double negativity of ZFP36 and PTEN had significantly shorter recurrence-free survival than patients with double positivity of ZFP36 and PTEN.

Among the patients with available PTEN expression levels, an OR of 6.78 (95% CI: 3.04-15.15) was observed comparing patients with low PTEN and low ZFP36 to those with high PTEN and high ZFP36 (Table 8).

TABLE 8

Logistic regression of ZFP36 expression (from gene expression profile data) and PTEN expression (from immunohistochemistry data) in indolent versus lethal prostate cancer in the HPFS/PHS datasets.

$data

| | indolent | lethal | Total |
|---|---|---|---|
| High ZFP36.High PTEN | 126 | 26 | 152 |
| Low ZFP36.High PTEN | 28 | 15 | 43 |
| High ZFP36.Low PTEN | 29 | 14 | 43 |
| Low ZFP36.Low PTEN | 10 | 9 | 19 |
| Total | 193 | 64 | 257 |

$measure

| odds ratio with 95% C.I. | NA estimate | lower | upper |
|---|---|---|---|
| High ZFP36.High PTEN | 1.000000 | NA | NA |
| Low ZFP36.High PTEN | 2.596154 | 1.219006 | 5.529105 |
| High ZFP36.Low PTEN | 2.339523 | 1.088755 | 5.027178 |
| Low ZFP36.Low PTEN | 4.361538 | 1.613223 | 11.791933 |

$p.value

| two-sided | NA midp.exact | fisher.exact | chi.square |
|---|---|---|---|
| High ZFP36.High PTEN | NA | NA | NA |
| Low ZFP36.High PTEN | 0.016697174 | 0.018527222 | 0.011540429 |
| High ZFP36.Low PTEN | 0.035116396 | 0.033257632 | 0.026720498 |
| Low ZFP36.Low PTEN | 0.005724298 | 0.004791046 | 0.002052485 |

The same conclusion is drawn from gene expression data of PTEN. Among the patients with available PTEN gene expression profile data, an OR of 6.78 (95% CI: 3.04-15.15) was observed comparing patients with low PTEN and low ZFP36 to those with high PTEN and high ZFP36 (Table 9).

TABLE 9

Logistic regression of ZFP36 and PTEN expression (both from gene expression profile data) in indolent versus lethal prostate cancer in the HPFS/PHS datasets.

$data

| | indolent | lethal | Total |
|---|---|---|---|
| High ZFP36.High PTEN | 190 | 42 | 232 |
| Low ZFP36.High PTEN | 40 | 31 | 71 |
| High ZFP36.Low PTEN | 49 | 22 | 71 |
| Low ZFP36.Low PTEN | 12 | 18 | 30 |
| Total | 291 | 113 | 404 |

TABLE 9-continued

Logistic regression of ZFP36 and PTEN expression (both from gene expression profile data) in indolent versus lethal prostate cancer in the HPFS/PHS datasets.

$measure

| odds ratio with 95% C.I. | NA estimate | lower | upper |
|---|---|---|---|
| High ZFP36.High PTEN | 1.000000 | NA | NA |
| Low ZFP36.High PTEN | 3.505952 | 1.971084 | 6.236011 |
| High ZFP36.Low PTEN | 2.031098 | 1.110356 | 3.715349 |
| Low ZFP36.Low PTEN | 6.785714 | 3.039112 | 15.151111 |

$p.value

| two-sided | NA midp.exact | fisher.exact | chi.square |
|---|---|---|---|
| High ZFP36.High PTEN | NA | NA | NA |
| Low ZFP36.High PTEN | 2.756779e−05 | 2.733570e−05 | 1.049996e−05 |
| High ZFP36.Low PTEN | 2.497034e−02 | 2.979737e−02 | 1.996293e−02 |
| Low ZFP36.Low PTEN | 3.534299e−06 | 3.112126e−06 | 2.761415e−07 |

In conclusion, loss of the tumor suppressor ZFP36 is prognostic for metastatic or lethal prostate cancer, and a combination of ZFP36 and PTEN expression confers a highly accurate model for predicting cancer prognosis.

Sequence Listing

```
SEQ ID NO: 1 - human ZFP36 genomic sequence

SEQ ID NO: 2 - human ZFP36 mRNA sequence

SEQ ID NO: 3 - human ZFP36 protein sequence

SEQ ID NO: 4 - human NEDD9 genomic sequence

SEQ ID NO: 5 - human NEDD9 mRNA sequence,
transcript variant 1

SEQ ID NO: 6 - human NEDD9 mRNA sequence,
transcript variant 2

SEQ ID NO: 7 - human NEDD9 mRNA sequence,
transcript variant 3

SEQ ID NO: 8 - human NEDD9 mRNA sequence,
transcript variant 4

SEQ ID NO: 9 - human NEDD9 protein sequence,
isoform 1

SEQ ID NO: 10 - human NEDD9 protein sequence,
isoform 2

SEQ ID NO: 11 - human NEDD9 protein sequence,
isoform 3

SEQ ID NO: 12 - human NEDD9 protein sequence,
isoform 4

SEQ ID NO: 13 - DNA sequence flanking human SNP
rs1910301, allele A (SNP site underlined)
TATCTCCTTG GATCAGCCCT GCTGTCATCT CTTCACAACT
CCCTGTCCTT GTTGCTGCCC ATTTTGGGGA ATTTATTTAT
CAACTCCTGC TGTAAACGAT AATAATAACA ATGATAACAC
ATATTGAATA TTTTGTGCCT AACACTGTAC ACTTTCTCAT
GTAATCCTCC AATAACCACG TGAGATAGGT GCTATTATTA
```

-continued

Sequence Listing

```
TTTCCATTGA CAGGTGAAAT AACAGATGTT CAGAGAGTTA
AGTAATCTAT CCAAAGTCAG ACAGCTAGTA CCTGACAACG
CATATCAGAG CAAGAAATTC TAGCTCTCAT AACAGGCAAA
CTCCCAAATC ACAGTATCTT AACACAAAAA GAGTTTATTT
CATGATCACA TCTTGGCCCC TGGGAATTGG TGACTCCTTC
TAGTCAGGCC ATCATGAAAC ATATGACACC CATGGCTTCT
GCATGGGGTA ATGAAAGAGG CATTGCAAAC TTTAAGGGCC
TCAGCCCTTC CTGTCACAGT T CAATGACAAG AATGAGTATT
GTGACCCCTA TCTACTTACA AGGGAGGATA GGACACATAG
GGGAAGACAT ATCTATTTAG TGAGCACTAA CTGTACTGCT
TTACCCTAGC ACCCATGCTC TTATCTAGCT TAACTGTCCT
TAGTTATCTA TCTATCTATC TATCTATCTA TCTATCTATC
TATCTATCTA TCATCTATCT GCCTACAGTT AACTATCTTA
ACTGTCCTTA CCAAGGCCCC AGTTGCACAT TCCCTGATGC
CACCAGGGCT CTGCTGACCT TTATTACAAC TCCTCTACAG
ATTCAACAGT CTGCCTTTGC TCTGCTTTCC TGCTCATCTG
CTTTCCTGCT CATCTGCTTT GCTCTTTTTA CTCTTTCTCC
CTCCCATCTC CCTTTCCTCT GCTTCTCACT GTCTTTCTTC
TGCATAACCC TACTCTGTGT GTTGAGTCTT CTATCACATC
TTTCTCCTGT ACGTGCCTTC TCTGATCTTC TTTCAGTTGC
```

SEQ ID NO: 14 - DNA sequence flanking human SNP rs1910301, allele G (SNP site underlined)

```
TATCTCCTTG GATCAGCCCT GCTGTCATCT CTTCACAACT
CCCTGTCCTT GTTGCTGCCC ATTTTGGGGA ATTTATTTAT
CAACTCCTGC TGTAAACGAT AATAATAACA ATGATAACAC
ATATTGAATA TTTTGTGCCT AACACTGTAC ACTTTCTCAT
GTAATCCTCC AATAACCACG TGAGATAGGT GCTATTATTA
TTTCCATTGA CAGGTGAAAT AACAGATGTT CAGAGAGTTA
AGTAATCTAT CCAAAGTCAG ACAGCTAGTA CCTGACAACG
CATATCAGAG CAAGAAATTC TAGCTCTCAT AACAGGCAAA
CTCCCAAATC ACAGTATCTT AACACAAAAA GAGTTTATTT
CATGATCACA TCTTGGCCCC TGGGAATTGG TGACTCCTTC
TAGTCAGGCC ATCATGAAAC ATATGACACC CATGGCTTCT
GCATGGGGTA ATGAAAGAGG CATTGCAAAC TTTAAGGGCC
TCAGCCCTTC CTGTCACAGT C CAATGACAAG AATGAGTATT
GTGACCCCTA TCTACTTACA AGGGAGGATA GGACACATAG
GGGAAGACAT ATCTATTTAG TGAGCACTAA CTGTACTGCT
TTACCCTAGC ACCCATGCTC TTATCTAGCT TAACTGTCCT
TAGTTATCTA TCTATCTATC TATCTATCTA TCTATCTATC
TATCTATCTA TCATCTATCT GCCTACAGTT AACTATCTTA
ACTGTCCTTA CCAAGGCCCC AGTTGCACAT TCCCTGATGC
CACCAGGGCT CTGCTGACCT TTATTACAAC TCCTCTACAG
ATTCAACAGT CTGCCTTTGC TCTGCTTTCC TGCTCATCTG
CTTTCCTGCT CATCTGCTTT GCTCTTTTTA CTCTTTCTCC
CTCCCATCTC CCTTTCCTCT GCTTCTCACT GTCTTTCTTC
TGCATAACCC TACTCTGTGT GTTGAGTCTT CTATCACATC
TTTCTCCTGT ACGTGCCTTC TCTGATCTTC TTTCAGTTGC
```

SEQ ID NO: 15 - human PTEN mRNA sequence, splice variant 1

SEQ ID NO: 16 - human PTEN mRNA sequence, splice variant 2

SEQ ID NO: 17 - human PTEN mRNA sequence, splice variant 3

The invention claimed is:

1. A method of measuring the expression level of ZFP36 and PTEN in a subject having prostate cancer, the method consisting of:

a. measuring the binding of a first probe in a first sample from the subject, wherein the first probe specifically hybridizes to a nucleic acid having the sequence set forth in SEQ ID NO: 2, thereby measuring expression of ZFP36 in the subject, and b. measuring the binding of a second probe in a second sample from the subject, wherein the second probe specifically hybridizes to a nucleic acid having the sequence set forth in SEQ ID NO: 15, 16, or 17, thereby measuring expression of PTEN in the subject.

2. The method of claim 1, wherein the prostate cancer is a primary prostate tumor or a metastatic prostate cancer.

3. The method of claim 1, wherein the subject is a human.

4. The method of claim 1, wherein the sample is from a tumor lesion or comprises circulating tumor cells.

5. The method of claim 1, wherein the first and second sample are the same sample.

6. The method of claim 1, wherein the expression levels of ZFP36 and PTEN are mRNA levels.

7. A method of treating prostate cancer in a subject, comprising:

a) providing a biological sample from the subject, b) measuring the expression level of a set of biomarkers consisting of ZFP36 and PTEN in the sample, c) detecting decreased expression levels of the set of biomarkers consisting of ZFP36 and PTEN in the sample as compared to the expression level of ZFP36 and PTEN in control subjects without prostate cancer recurrence, and d) treating the subject from step c) with one or more therapies selected from surgical castration, androgen deprivation therapy, a radiation therapy, an ablation therapy, a chemotherapy, a targeted therapy, or an immunotherapy.

8. The method of claim 7, wherein the prostate cancer is a primary prostate tumor or a metastatic prostate cancer.

9. The method of claim 7, wherein the subject is a human.

10. The method of claim 7, wherein the sample is from a tumor lesion or comprises circulating tumor cells.

11. The method of claim 7, wherein the sample for measuring the expression level of ZFP36 and sample for measuring the expression level of PTEN are the same sample.

12. The method of claim 7, wherein the expression levels of ZFP36 and PTEN are mRNA levels.

* * * * *